(12) United States Patent
Luehr et al.

(10) Patent No.: US 10,675,353 B2
(45) Date of Patent: Jun. 9, 2020

(54) PEGYLATED CARFILZOMIB COMPOUNDS

(71) Applicant: AMGEN INC., Thousand Oaks, CA (US)

(72) Inventors: Gary Luehr, Hayward, CA (US); Shabbir T. Anik, San Francisco, CA (US); Ge Peng, Mountain View, CA (US); Irina Dotsenko, San Jose, CA (US); Pasit Phiasivongsa, Brentwood, CA (US); Dante Romanini, Sherman Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/675,134

(22) Filed: Nov. 5, 2019

(65) Prior Publication Data

US 2020/0069808 A1    Mar. 5, 2020

Related U.S. Application Data

(62) Division of application No. 15/602,823, filed on May 23, 2017, now Pat. No. 10,517,954.

(60) Provisional application No. 62/340,926, filed on May 24, 2016, provisional application No. 62/485,812, filed on Apr. 14, 2017.

(51) Int. Cl.
| | |
|---|---|
| *C07D 405/12* | (2006.01) |
| *A61K 38/07* | (2006.01) |
| *A61K 47/60* | (2017.01) |
| *A61K 9/00* | (2006.01) |
| *C08G 65/333* | (2006.01) |

(52) U.S. Cl.
CPC ............ *A61K 47/60* (2017.08); *A61K 9/0019* (2013.01); *A61K 9/0053* (2013.01); *A61K 38/07* (2013.01); *C07D 405/12* (2013.01); *C08G 65/33396* (2013.01); *C08G 2230/00* (2013.01)

(58) Field of Classification Search
CPC . C07D 405/12; A61K 38/07; C08G 65/33396
See application file for complete search history.

(56) References Cited

U.S. PATENT DOCUMENTS

| | | | |
|---|---|---|---|
| 9,315,542 B2 | 4/2016 | Phiasivongsa et al. | |
| 2005/0245435 A1 | 11/2005 | Smyth et al. | |
| 2005/0256324 A1 | 11/2005 | Laidig et al. | |
| 2014/0105921 A1 | 4/2014 | Phiasivongsa et al. | |

FOREIGN PATENT DOCUMENTS

| | | |
|---|---|---|
| CL | 2018002081 A1 | 12/2018 |
| CL | 2018003343 A1 | 1/2019 |
| CL | 2018003319 A1 | 2/2019 |
| CL | 2018003345 A1 | 3/2019 |
| CL | 2018003318 A1 | 4/2019 |
| WO | 9216221 A1 | 10/1992 |
| WO | 2005063777 A1 | 7/2005 |
| WO | 2006017842 A1 | 2/2006 |
| WO | 2006063154 A1 | 6/2006 |
| WO | 2009045497 A1 | 4/2009 |
| WO | 2009152160 A1 | 12/2009 |
| WO | 2010048298 A1 | 4/2010 |

(Continued)

OTHER PUBLICATIONS

"N-Quarternary CFZ Prodrug—Substances Found" *American Chemical Society* (ACS) (2015).

(Continued)

*Primary Examiner* — Rebecca L Anderson
(74) *Attorney, Agent, or Firm* — Joseph F. Reidy; Elsa D. Lemoine

(57) ABSTRACT

The present invention provides a method of treating multiple myeloma using polymeric pegylated carfilzomib compounds, and pharmaceutically acceptable salts thereof, of Formula I Formula I

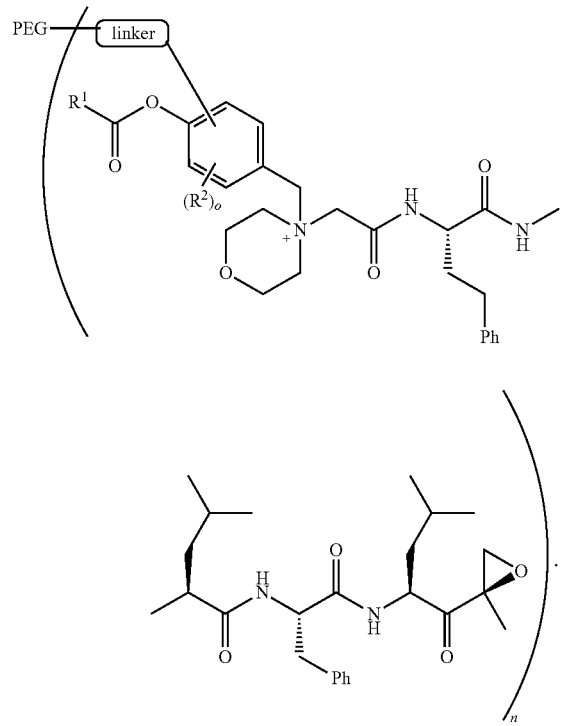

wherein $R^1$, $R^2$, linker, PEG, n and o are as defined herein.

25 Claims, 10 Drawing Sheets

(56) References Cited

FOREIGN PATENT DOCUMENTS

| WO | 2011084846 A1 | 7/2011 |
| WO | 2013169282 A1 | 11/2013 |
| WO | 2014015016 A1 | 1/2014 |
| WO | 2014011695 A2 | 1/2015 |

OTHER PUBLICATIONS

Greenwald, R. B., et al. "Drug Delivery Systems Employing 1,4- or 1,6-Elimination: Poly(ethylene Glycol) Prodrugs of Amine-Containing Compounds" *J. Med. Chem.* 42:3657-3667 (1999).

Myung, J., et al. "The Ubiquitin-Proteasome Pathway and Proteasome Inhibitors" *Med Res Rev.* 21(4): 245-273 (2001).

Phiasivongsa, P., et al. "Preparation of peptide derivatives as prodrugs of peptide epoxyketone protease inhibitors" *American Chemical Society* (ACS) (2015).

Sin, N. et al. "Total Synthesis of the Potent Proteasome Inhibitor Epoxomicin: A Useful Tool for Understanding Proteasome Biology" *Bioorganic & Medicinal Chemistry Letters* 9:2283-2288 (1999).

Oliyai, Reza and Stella, Valentino, *Annual Rev. Pharmacol. Toxicol.* 32:521-544 (1993).

CFZ-Captisol and OP-0059381 in HT-29 cancer xenograft model

PEGYLATED CARFILZOMIB COMPOUNDS

RELATED APPLICATIONS

This application is a divisional of U.S. patent application Ser. No. 15/602,823 filed on May 23, 2017, which claims priority from and the benefit of U.S. Provisional Patent Application 62/340,926 filed on May 24, 2016 and U.S. Provisional Patent Application 62/485,812, filed on Apr. 14, 2017, all of which are hereby incorporated by reference in their entireties and for all purposes as if fully set forth herein.

FIELD OF THE INVENTION

The present invention relates to pegylated carfilzomib compounds, pharmaceutical compositions comprising the compounds, and methods and uses thereof for treating cancer, including hematologic malignancies such as multiple myeloma, and solid tumors.

BACKGROUND OF THE INVENTION

Cancer is one of the most widespread diseases and a leading cause of death worldwide. In the United States alone, cancer is the second leading cause of death, surpassed only by heart disease. Cancer is often characterized by deregulation of normal cellular processes or unregulated cell proliferation.

Multiple myeloma (MM) is a progressive and malignant neoplastic type of cancer originating from plasma cells. It is characterized by abnormal accumulation of malignant plasma cells within bone marrow, and it accounts for approximately 13% of all hematologic cancers (Palumbo and Anderson, 2011). In 2015, about 26,850 new cases were expected to be diagnosed with MM, and about 11,240 people were expected to die from the disease in the United States (ACS, 2015). The incidence of MM has increased steadily due to increased life expectancy of the general population in the United States (Warren et al., 2013). The disease most commonly affects the elderly population, with the median age of incidence around 69 years old (Howlander et al., 2013, ACS, 2015).

The therapeutic goals of management of MM are to provide symptomatic relief, achieve disease control and provide prolonged remissions (Kurtin, 2013). Conventionally, a combination of high dose chemotherapeutic agents (meclphalan, vincristine, cyclophosphamide, doxombicin, liposomal doxombicin, bendamamustine) followed by autologous stem-cell transplantation (ASCT) has been utilized to treat young, treatment-nalve and medically fit patients (less than 65 years of age) (Palumbo et al., 2011). Age, comorbid conditions and geriatric assessment are the major criteria for deciding patients' eligibility to tolerate high-dose therapy (HDT) followed by ASCT (Palumbo et al., 2014). For elderly patients ineligible for HDT and ASCT, melphalan plus prednisone had been the standard therapy for several decades (Palumbo et al., 2011; Rodriguez et al., 2012). During the last decade, treatment algorithm of MM underwent a paradigm change with the introduction of novel immunomodulatory agents (such as thalidomide, lenalidomide, and pomalidomide) and targeted proteasome inhibitors (bortezomib and carfilzomib) (Richardson et al., 2007; Dmoszyńska, 2008; Gupta et al., 2013).

Carfilzomib is a tetrapeptide epoxy ketone proteosome inhibitor that binds selectively and irreversibly to the constitutive proteosome and immunoproteosome. More specifically, the epoxyketone electrophilic warhead binds to the catalytic threonine residue of the 15 subunit of the proteasome protein. CFZ is well tolerated with acceptable toxicity profile. Carfilzomib, polymorphic forms, methods of making, formulations, its use and other carfilzomib attributes are described in US20050245435. US20140105921 and PCT publications WO2006017842. WO2009045497, WO2014169897, WO2013169282. WO2014011695, WO2006063154, WO2014015016, and WO2010048298, each specification of which is hereby incorporated herein by reference in its entirety.

Carfilzomib has shown an encouraging response rate in patients with relapsed and refractory MM and with newly diagnosed patients with MM. To this end, carfilzomib was first approved (as Kyprolis®) for treatment in patients with relapsed and refractory MM in July 2012 as a single agent therapy. More recently Kyprolis was approved in combination with lenalidomide and dexamethasone (July 2015) and in combination with dexamethasone (January 2016) for the treatment of patients with relapsed and refractory MM who have received one to three lines of therapy. The approved treatment regimen for carfilzomib is to administer it to the patient by infusion, either over a short 10 minute period or over a slower, longer 30 minute duration of time. This infusion is to occur for 2 consecutive days per week for three consecutive weeks in a 28 day cycle. Thus, to comply with this treatment schedule, patients need to drive or be driven two times per week on consecutive days to an authorized drug administration center, such as a doctor's office, a clinic or a hospital, where carfilzomib can be properly and safely administered. This may be inconvenient or impractical, or may simply be a burden, to some patients, increasing the likelihood of reduced or decreased compliance with, or even complete non-compliance of, the full and complete course of the prescribed carfilzomib therapeutic regimen.

Carfilzomib is rapidly metabolized and cleared in humans. Carfilzomib, a small tetrapeptide compound, exhibits a short half-life in-vivo of about 60 minutes or less in humans. One mechanism of carfilzomib clearance is via hepatic blood flow, resulting in the relatively brief half-life for carfilzomib. Drug products possessing short half lives or rapid clearance in general tend to exhibit reduced target coverage leading to decreased and/or shortened biological inhibitory activity. To overcome such shortfalls, additional drug is typically administered to provide more drug and prolonged efficacy at the biological site of action. Hence, both the rapid clearance and the twice weekly frequency of dosing of carfilzomib leave room for possible improvements in efficacy, delivery and/or patient compliance.

Carfilzomib, as currently approved (Kyprolis®), is a sterile lyophilized formulation comprising sulfabutylether beta cyclodextrin (SBECD) and a sodium citrate buffer. The lyophilate is reconstituted with sterile water, and infused or injected into the patient. The SBECD excipient acts primarily as a solubilizing additive for carfilzomib, and forms a complex with carfilzomib thereby improving carfilzomib water solubility.

History has revealed that attempts to solve weaknesses of drug products have led to the preparation of alternative forms of these medicinal compounds, including production of pro-drug versions, in attempts to enhance their drug pK and/or PD properties. For instance, Greenwald et al disclose Prodrugs of Amine Containing Compounds (*J. Med. Chem.*, 1999, 42, 3657-3667). WO2005063777 discloses benzyl-phosphate and substituted benzylphosphate prodrugs for the treatment of pulmonary inflammation. WO20090152160 discloses inhaled carbaprotacyclin and prostacyclin prodrugs for the treatment of arterial hypertension. US patent publication no. 20040100225 discloses acyloxymethyl pro-drugs of imatinib (Gleeve®). Also, PCT publication WO2011084846 discloses acyloxymethyl pro-drugs of risperidone. These pro-drug disclosures teach alkyl-acyloxymethyl linked pro-drugs. Another example, US patent application publication no. US20140105921 describes carfilzomib and other epoxyketone proteasome inhibitor pro-drugs having an acyloxymethyl linker connecting the inhibitor to polyethylene glycol units (PEG). However, these carfilzomib pro-drug compounds have been found to release quinone methide byproducts during metabolism in vivo, which may be potentially toxic and may present a safety risk. To this end, it would be desirable to identify alternative forms of carfilzomib and/or alternative ways to deliver the active pharmaceutical ingredient carfilzomib to patients while maintaining or possibly improving the efficacy and/or safety of the currently approved carfilzomib treatments.

BRIEF DESCRIPTION OF THE INVENTION

The present invention provides novel polymeric carfilzomib compounds, i.e., modified structures of carfilomib, that deliver therapeutic anti-cancer benefits to the patient while maintaining comparable or longer carfilzomib plasma concentrations and proteasome exposure. To this end, these polymeric carfilzomib compounds provide proteosomal inhibitory activity comparable to that of the currently approved carfilzomib cyclodextrin IV formulation.

Particularly, the present invention provides pegylated carfilzomib compounds, having improved water solubility, and which are useful to treat various types of cancer, including without limitation, multiple myeloma. More particularly, the pegylated compounds provided herewith maintain or exhibit suitable bioavailability and reduce or completely eliminate the need for solubilizing excipients or agents such as sulfobutylether-β-cyclodextrin. The present invention further provides a method of preparing the pegylated carfilzomib compounds, pharmaceutical compositions comprising the same, and methods of using the compounds and compositions for treating various forms of cancer such as multiple myeloma.

In one aspect of the invention, the pegylated carfilzomib compounds described herein include one or more covalently linked PEG moieties that (i) can confer enhanced solubility, permeability, pharmacokinetics (pK) and/or pharmacodynamics (PD) properties to carfilzomib when compared with the corresponding approved carfilzomib product that does not contain such polymeric moieties; and (ii) can be cleaved or removed in vivo after administration to a subject thereby further providing free carfilzomib, that has proven safety and efficacy capabilities to treat various cancers, including without limitation, multiple myeloma.

The pegylated carfilzomib compounds provided by the present invention further provide potential benefits including, without limitation, extended release allowing for reduced dosing frequency, lower Cmax and, consequently, possibly reduced side effects when compared with the presently approved carfilzomib product. An improved safety profile of the compounds of the invention may also result from enhanced aqueous solubility which could facilitate alternative modes of administration, such as for example subcutaneous administration, from the presently approved infusion mode of administration. A modified pK and/or biodistribution profile for the pegylated carfilzomib compounds of the invention may result in improved efficacy in treating cancers, including without limitation, multiple myeloma and solid tumors. Further, the pegylated carfilzomib compounds of the invention provide formulation options with potentially improved chemical and temperature stability, lower dosing volume and the potential to eliminate a lyophilization step, part of the manufacturing procedure for the currently approved carfilzomib drug product.

DETAILED DESCRIPTION OF THE INVENTION

Figure 1:
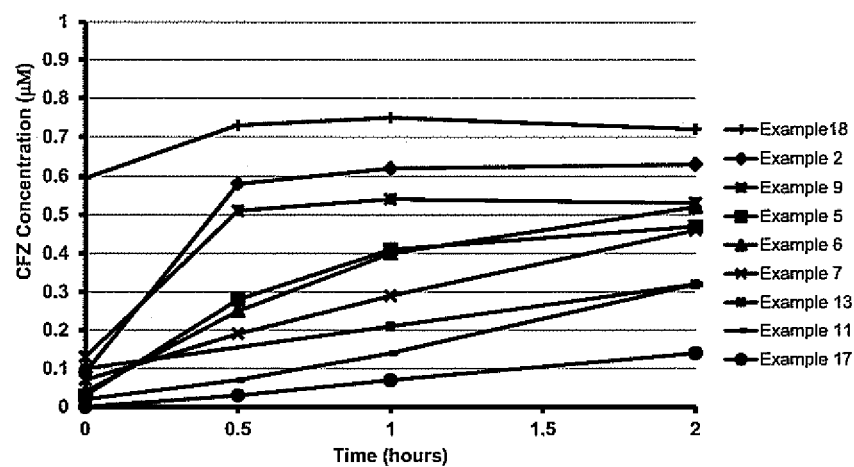
FIG. 1 is a graph of curves generated by rates of conversion of several exemplified pegylated compounds of carfilzomib to free carfilzomib in human plasma (representative of human pK)

The present invention provides novel pegylated carfilzomib compounds, pharmaceutical compositions comprising the compounds, methods of making the compounds, and uses of the compounds and compositions including the compounds for the treatment of cancer, including treatment of hematologic malignancies such as multiple myeloma, lymphoma, leukemia, and treatment of other cancers such as solid tumors. Specifically, the polymeric units of polyethylene glycol (PEG) linked carfilzomib possess various pharmacokinetic (pK) and/or pharmacodynamics (PD) properties comparable to or improved over that of the currently approved IV administered Kyprolis® (carfilzomib).

Carfilzomib is an epoxy ketone protease inhibitor described in U.S. Pat. Nos. 7,417,042 and 7,737,112, among others. The pegylated carfilzomib compounds described in the present invention (i) generally confer enhanced solubility, permeability, pK and/or PD properties relative to free drug carfilzomib not containing such PEG moieties; and (ii) can be cleaved in vivo thereby releasing the freely active drug carfilzomib. In the embodiments presented by the invention, the N-terminal "cap" of the carfilzomib (e.g., the morpholino cap) is converted to a quaternary salt (e.g., by the addition of a N-acyloxyphenylmethyl group). In some embodiments, the quaternary salt contains a PEG moiety. In some embodiments, the pegylated compounds are cleavable by pH change and/or enzymes such as, but not limited to, esterases, cytochrome P450, phosphodiesterase, phosphoamidase, phosphatase, and DT-diaphorase, or any combination thereof. In some embodiments, the PEG is a linear PEG. In some embodiments, the PEG is a bifunctional PEG that can conjugate 1-2 compounds per PEG. In some embodiments, the PEG is a four-arm PEG that can conjugate 1-4 compounds per PEG. In some embodiments, the PEG is an eight-arm PEG with a hexaglycerin core that can conjugate 1-8 compounds per PEG. In some embodiments, the PEG is an eight-arm PEG with a tripentaerythritol core that can conjugate 1-8 compounds per PEG. In some embodiments, the PEG is a branched two-arm PEG. In some embodiments, the PEG is a branched four-arm PEG. In addition, the compounds can further include solubilizers, permeability enhancers, masking agents, macromolecular carriers, targeting moieties, and biologics to improve half-life and disease specificity that are attached directly to the compound or indirectly attached via a spacer moiety.

The terms "aspect" and "embodiment" are used interchangeably herein.

In aspect 1 of the invention, the invention provides a pegylated carfilzomib compound having a structure of formula I

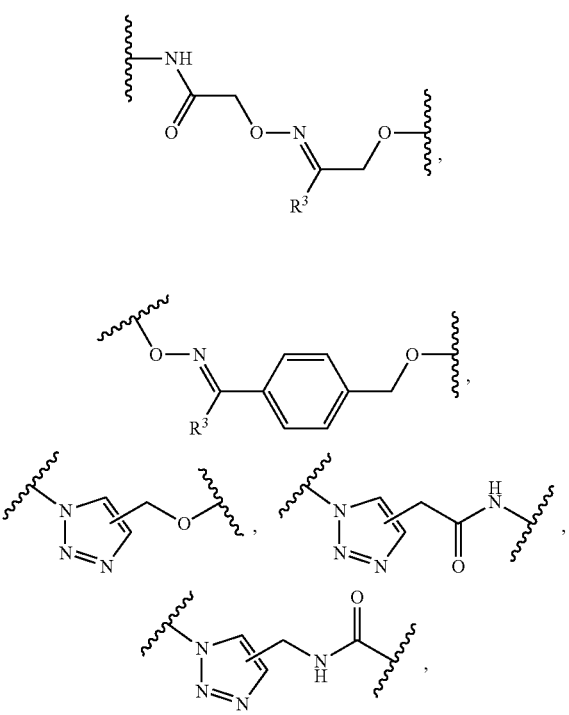

Formula I

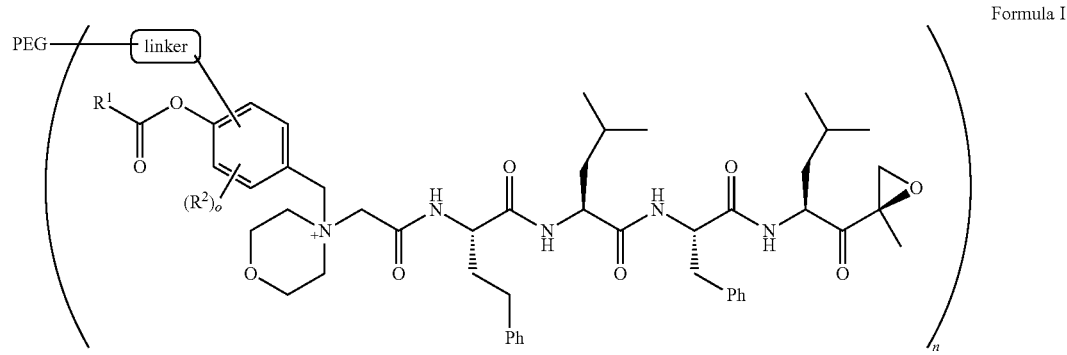

or a pharmaceutically acceptable salt thereof, wherein
R$^1$ is C$_{1-10}$alkyl or C$_{3-7}$cycloalkyl;
each R$^2$, independently, is C$_{1-6}$alkyl, —OCH$_3$ or halogen;
o is an integer selected from 0, 1, 2 or 3;
linker is a moiety having the structure of

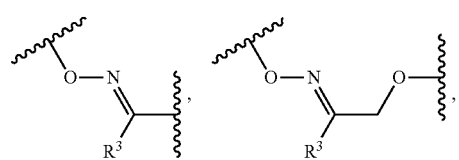

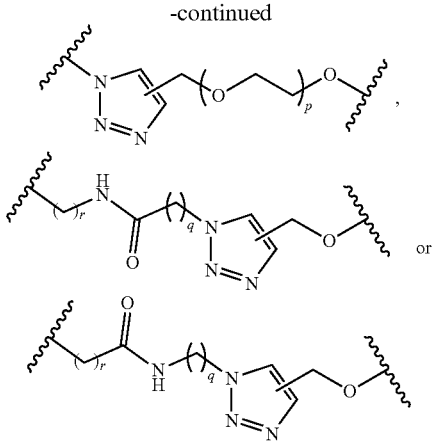

wherein R$^3$ is H or CH$_3$;
n is an integer selected from 1, 2, 3 or 4;

p is an integer selected from 0, 1, 2, 3 or 4;
q is an integer selected from 1, 2, 3, 4, 5, 6, 7, 8 or 9;
r is an integer selected from 0, 1, 2, 3, 4 or 5; and
PEG is a polyethylene glycol polymeric moiety having a molecular weight ranging from about 500 to about 20,000.

In aspect 1a of the invention, the invention provides a pegylated carfilzomib compound having a structure of formula I

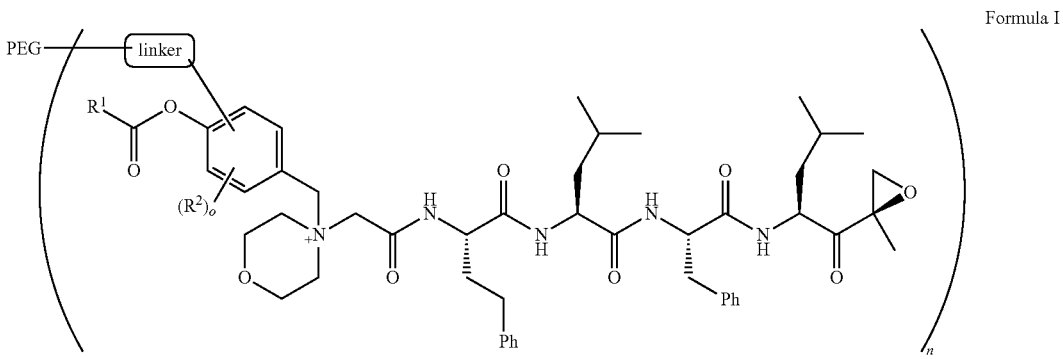

Formula I or a pharmaceutically acceptable salt thereof, wherein
$R^1$ is $C_{1-10}$alkyl or $C_{3-7}$cycloalkyl;
each $R^2$, independently, is $C_{1-6}$alkyl, —$OCH_3$ or halogen;
o is an integer selected from 0, 1, 2 or 3;
linker is a moiety having the structure of

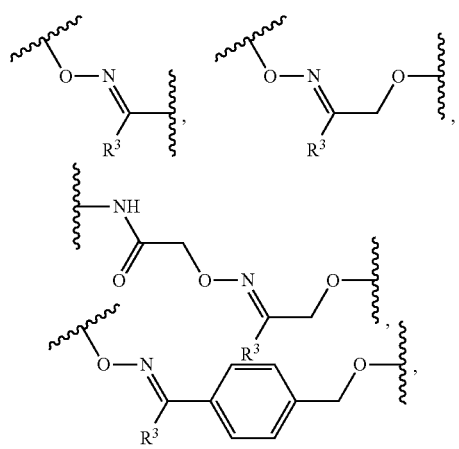

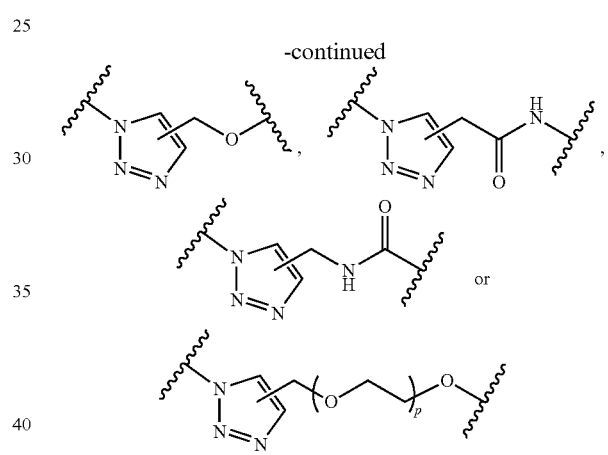

wherein $R^3$ is H or $CH_3$; and
p is an integer selected from 0, 1, 2, 3 or 4
n is an integer selected from 1, 2, 3 or 4; and
PEG is a polyethylene glycol polymeric moiety having a molecular weight ranging from about 500 to about 20,000.

In aspect 2 of the invention, the invention provides the pegylated carfilzomib compound of aspect 1 having a structure of Formula II

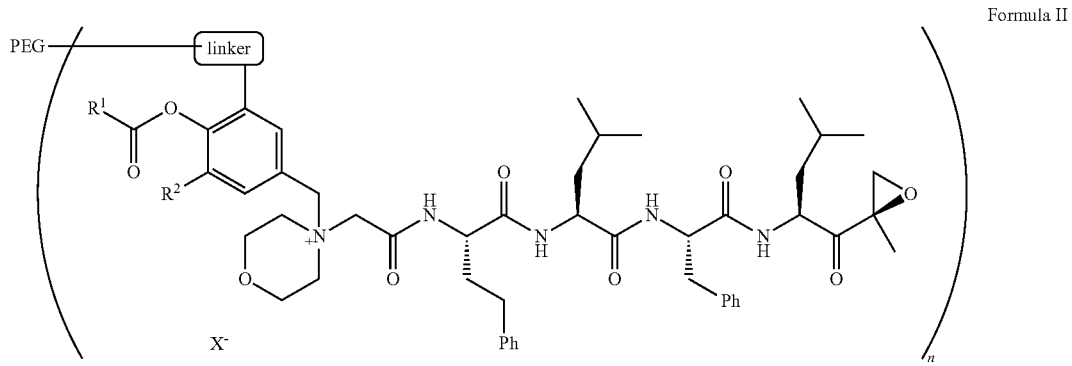

Formula II wherein
R¹ is C₁₋₁₀alkyl or C₃₋₇cycloalkyl;
R² is C₁₋₆alkyl, —OCH₃ or halogen;
linker is a moiety having the structure of

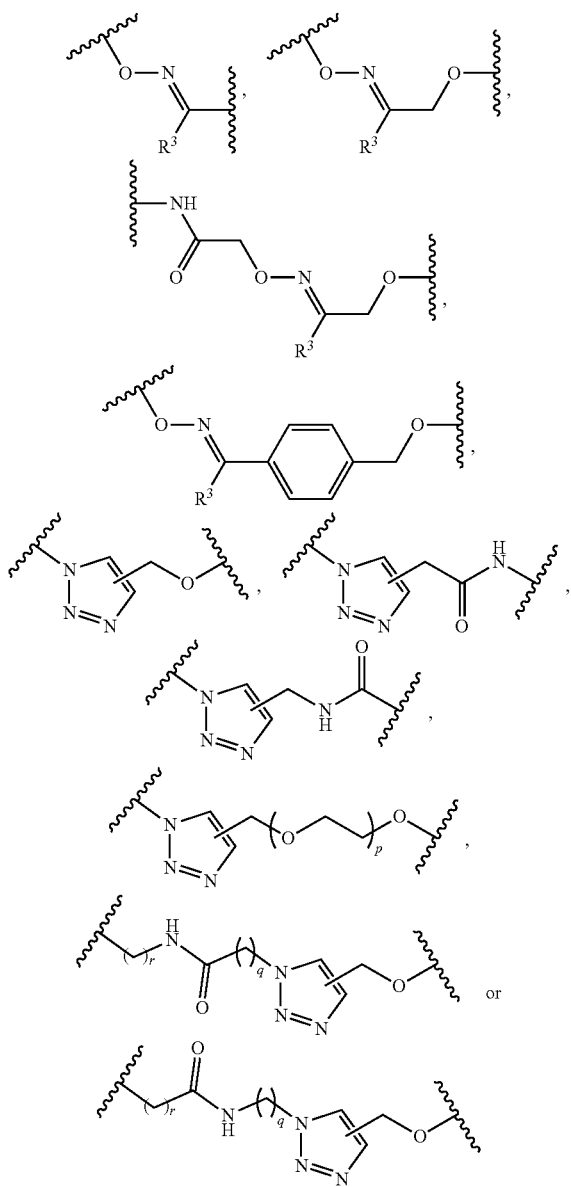

when R³ is H or CH₃;
n is an integer selected from 0, 2, 3 or 4:
p is an integer selected from 0, 1, 2, 3 or 4;
q is an integer selected from 1.2, 3, 4, 5, 6, 7, 8 or 9;
r is an integer selected from 1.2, 3, 4 or 5;
X is a counter ion salt selected from a chloride, a bisulfate, a sulfate, a nitrate, a phosphate, an alky-sulfonate or an aryl-sulfonate; and
PEG is a polyethylene glycol polymeric moiety having a molecular weight ranging from about 2000 to about 20,000.

In aspect 3 of the invention, the invention provides the compound of aspects 1, 1a and 2 wherein R¹ is C₁₋₁₀alkyl.

In aspect 4 of the invention, the invention provides the compound of any one of aspects 1, 1a, 2 and 3 wherein each R², independently, is H, CH₃ or halogen.

In aspect 5 of the invention, the invention provides the compound of any one of aspects 1, 1a, 2, 3 and 4 wherein each R², independently, is H, CH₃, Cl or F.

In aspect 5a of the invention, the invention provides the compound of any one of aspects 1, 1a, 2, 3 and 4 wherein each R², independently, is H, CH₃ or F.

In aspect 6 of the invention, the invention provides the compound of any one of aspects 1, 1a, 2, 3, 4 and 5 wherein the linker is a moiety having the structure of

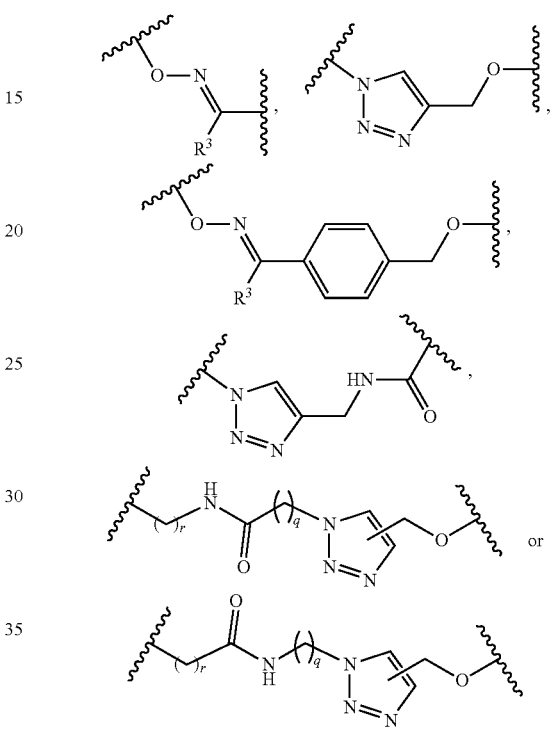

wherein R³ is H or CH₃;
q is an integer selected from 1, 2, 3, 4 or 5; and
r is an integer selected from 0, 1, 2, 3 or 4.

In aspect 6a of the invention, the invention provides the compound of any one of aspects 1, 1a, 2, 3, 4 and 5 wherein the linker is a moiety having the structure of

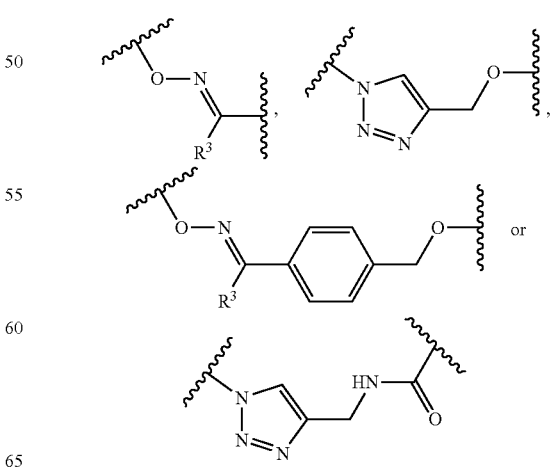

wherein $R^3$ is H or CH$_3$.

In aspect 7 of the invention, the invention provides the compound of any one of aspects 1, 1a, 2, 3, 4, 5 and 7 wherein the linker is

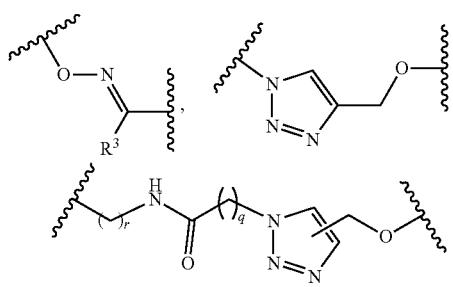

wherein $R^3$ is H or CH$_3$;
q is 4 and
r is 2.

In aspect 7a of the invention, the invention provides the compound of any one of aspects 1, 1a, 2, 3, 4, 5 and 7 wherein the linker is

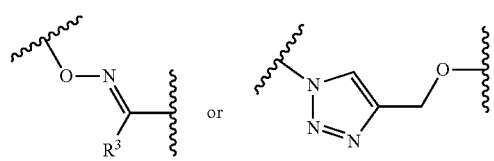

wherein $R^3$ is H or CH$_3$.

In aspect 8 of the invention, the invention provides the the compound of any one of aspects 1, 1a, 2, 3, 4, 6, 6a, 7 and 7a wherein $R^3$ is H.

In aspect 9 of the invention, the invention provides the compound of any one of aspects 1-8 wherein $R^1$ is methyl, ethyl, propyl, isopropyl, butyl, t-butyl, pentyl, hexyl or heptyl.

In aspect 10 of the invention, the invention provides the compound of any one of aspects 1-9 wherein $R^1$ is methyl, ethyl, propyl, isopropyl, butyl, t-butyl, pentyl, hexyl or heptyl; and the linker is

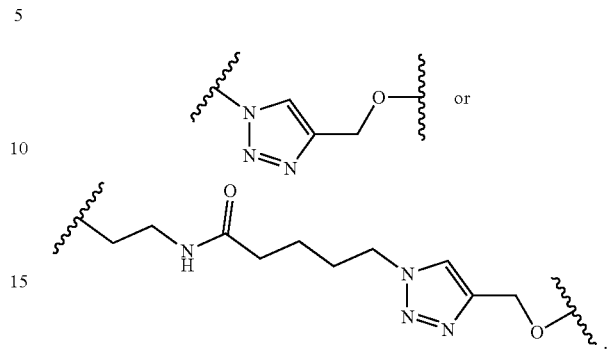

In aspect 10a of the invention, the invention provides the compound of any one of aspects 1-9 wherein $R^1$ is methyl, ethyl, propyl, isopropyl, butyl, t-butyl, pentyl, hexyl or heptyl; and the linker is

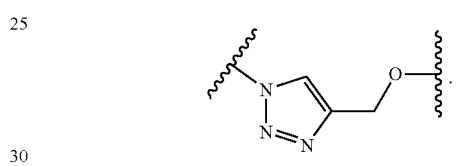

It should be noted that in aspects 1, 1a, 2 and aspects 3-10 that the term "or a pharmaceutically acceptable salt thereof" may include a counter ion salt of the quaternary nitrogen cationic charge, such as that illustrated in formula II of aspect 2, or those illustrated in aspects 11-24 hereinbelow. Further, it should be noted that it is intended that the term "any one of aspects 1-X" also include all sub-aspects of 1-X disclosed herein, including without limitation sub-aspects 1a, 5a, 6a, 7a and 10a.

In aspect 11 of the invention, the invention provides a pegylated carfilzomib compound according to any one of aspects 1-10, having the structure of

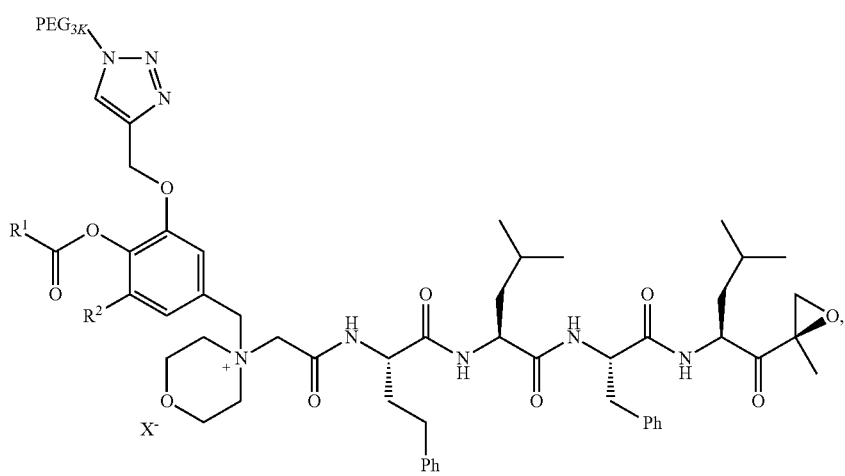

-continued

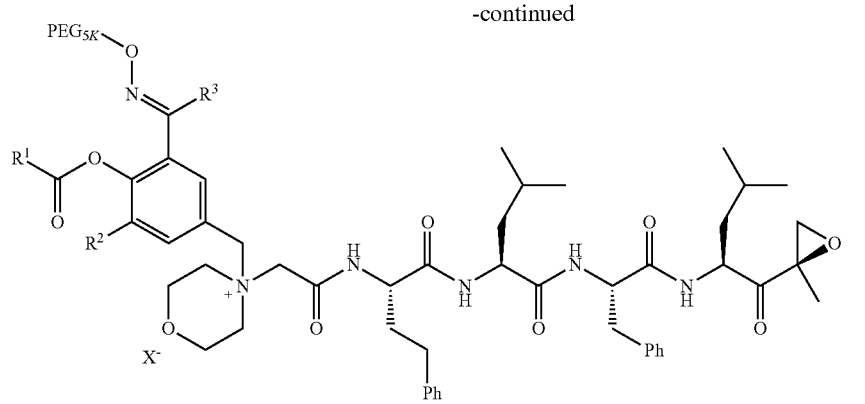

or

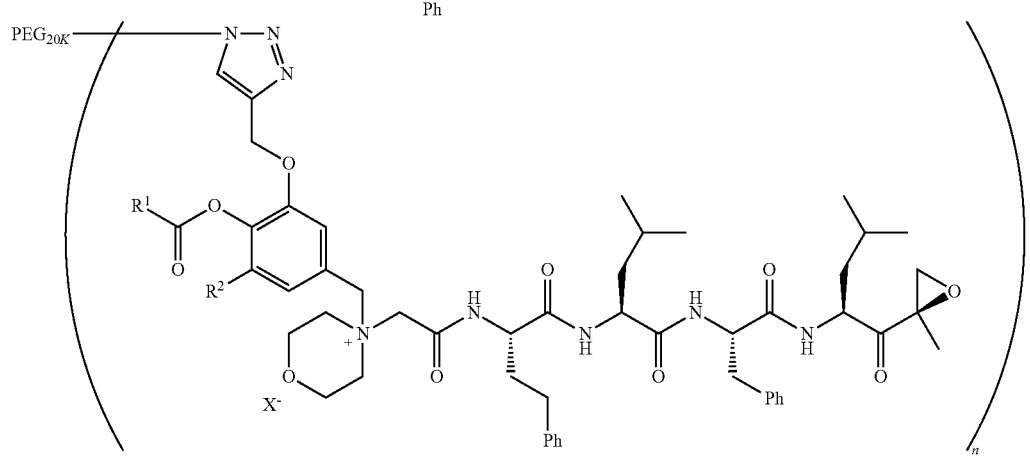

wherein R¹ is $C_{1-10}$alkyl;
R² is $C_{1-6}$alkyl, —$OCH_3$ or halogen;
R³ is H or $CH_3$;
$X^-$ is a counter anion selected from chloride anion and a alkyl-sulfonate anion;
n is 4; and
PEG is a polyethylene glycol polymeric moiety having a molecular weight ranging from about 2000 to about 20,000.

In aspect 12 of the invention, the invention provides the compound of any one of aspects 1-11 wherein the compound is

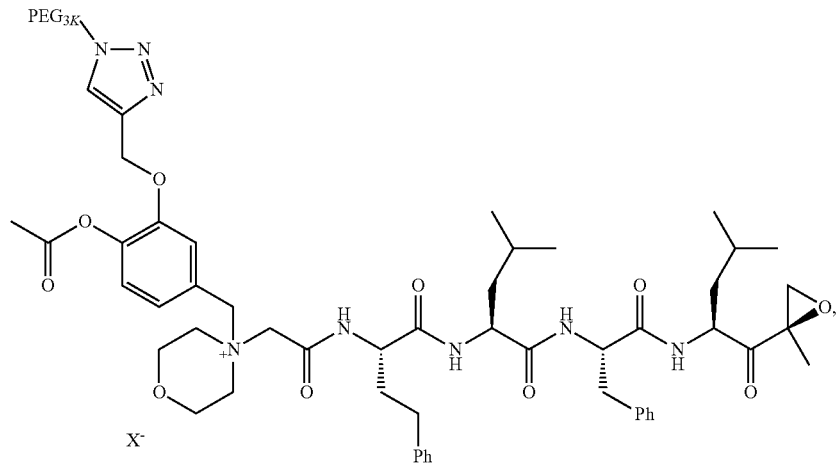

wherein X is a halide, a sulfonate or an alkyl-sulfonate counterion salt.
In aspect 12a of the invention, the invention provides the compound of any one of aspects 1-11 wherein the compound is
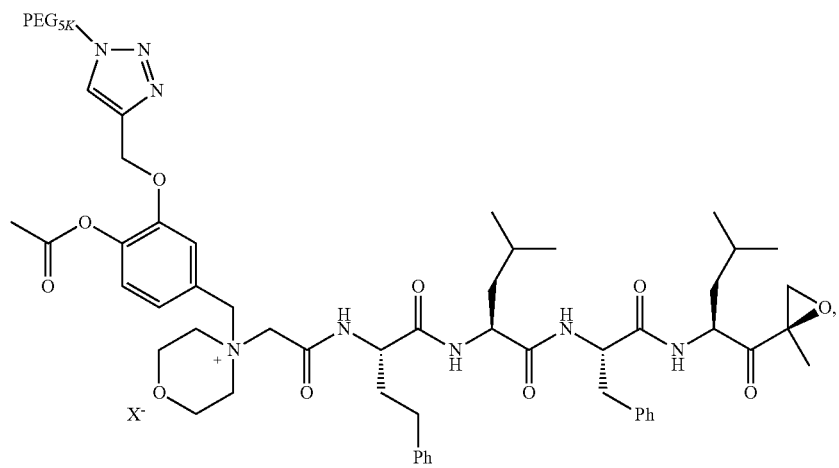
wherein X is a halide, a sulfonate or an alkyl-sulfonate counterion salt.
In aspect 13 of the invention, the invention provides the compound of any one of aspects 1-11 wherein the compound is
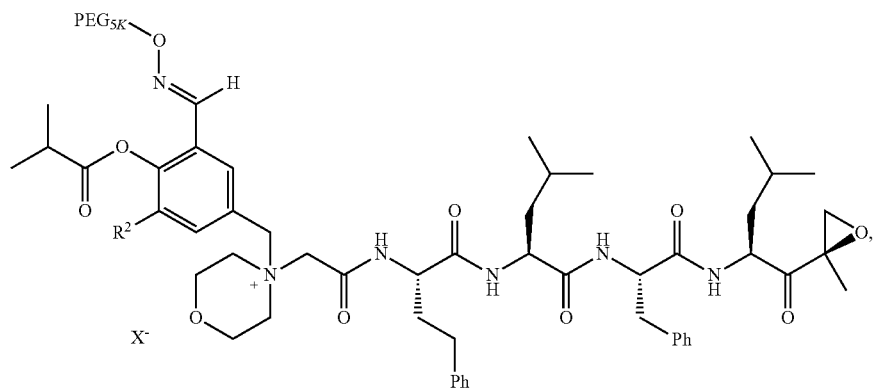

wherein X is a halide, a sulfonate or an alkyl-sulfonate counterion salt.

In aspect 14 of the invention, the invention provides the compound of any one of aspects 1-11 wherein the compound is

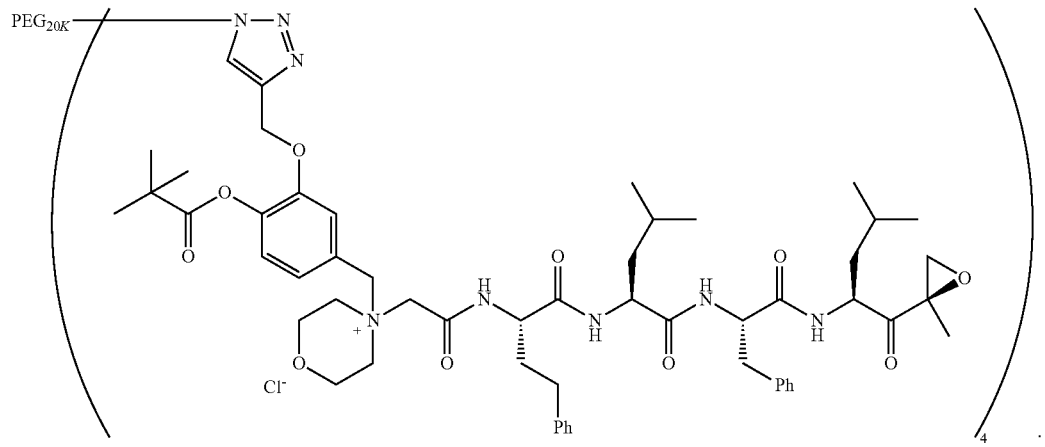

In aspect 15 of the invention, the invention provides the compound of any one of aspects 1 and 2 wherein $R^1$ is methyl, ethyl, propyl, isopropyl, butyl, t-butyl, pentyl, hexyl or heptyl;

each $R^2$, independently, is $CH_3$ or halogen:

linker is a moiety having the structure of

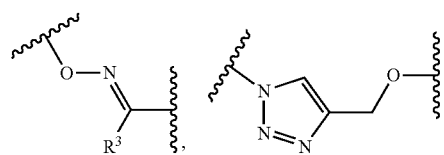

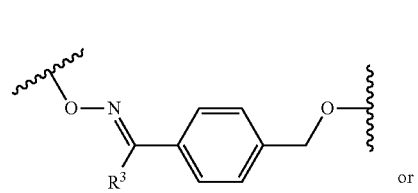

or

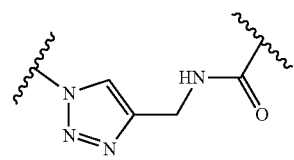

wherein $R^1$ is H or $CH_3$; and

PEG is a polyethylene glycol polymeric moiety having a molecular weight of 2000, 3000, 5000 or 20,000.

In aspect 16 of the invention, the invention provides the compound of aspect 15 wherein $R^1$ is methyl, ethyl, propyl, isopropyl, butyl, t-butyl, pentyl, hexyl or heptyl;

each $R^2$, independently, is $CH_3$:

linker is a moiety having the structure of

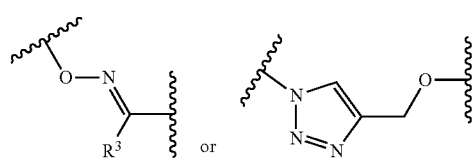

wherein $R^3$ is H; and

PEG is a polyethylene glycol polymeric moiety having a molecular weight of 3000, 5000 or 20,000.

In aspect 17 of the invention, the invention provides the compound of any one of aspects 1-16 wherein the compound is an individual compound as represented in examples 1-34 described hereinbelow in Table 2, or a pharmaceutically acceptable salt thereof.

In aspect 18 of the invention, the invention provides the compound of any one of aspects 1-17 wherein the compound is

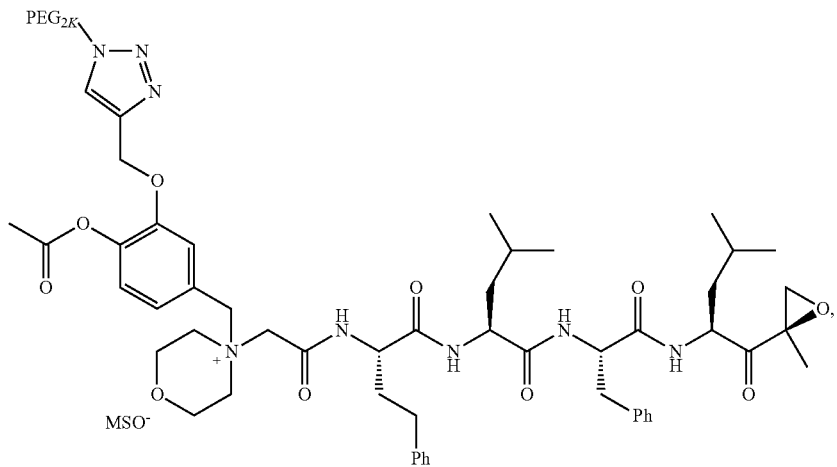
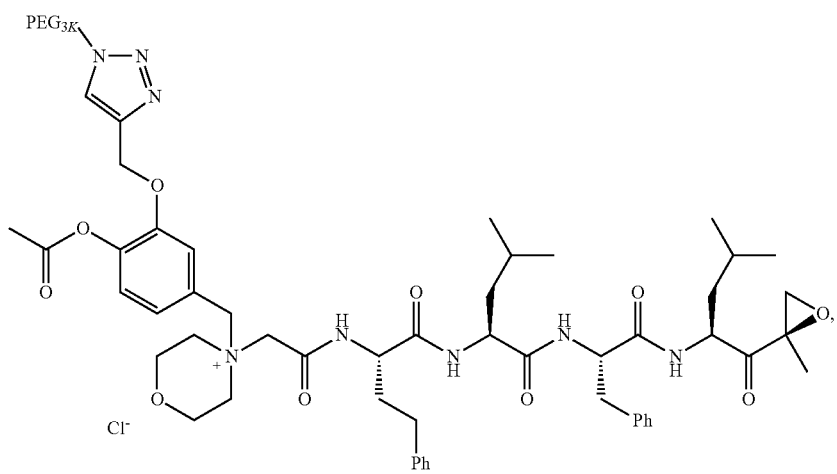
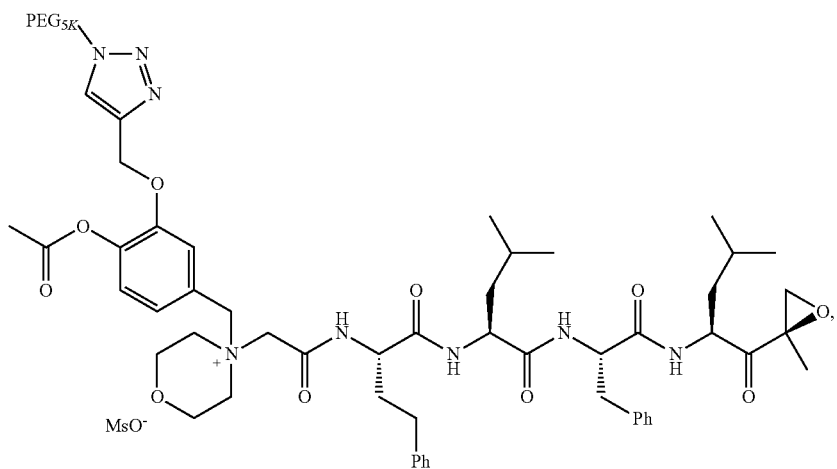

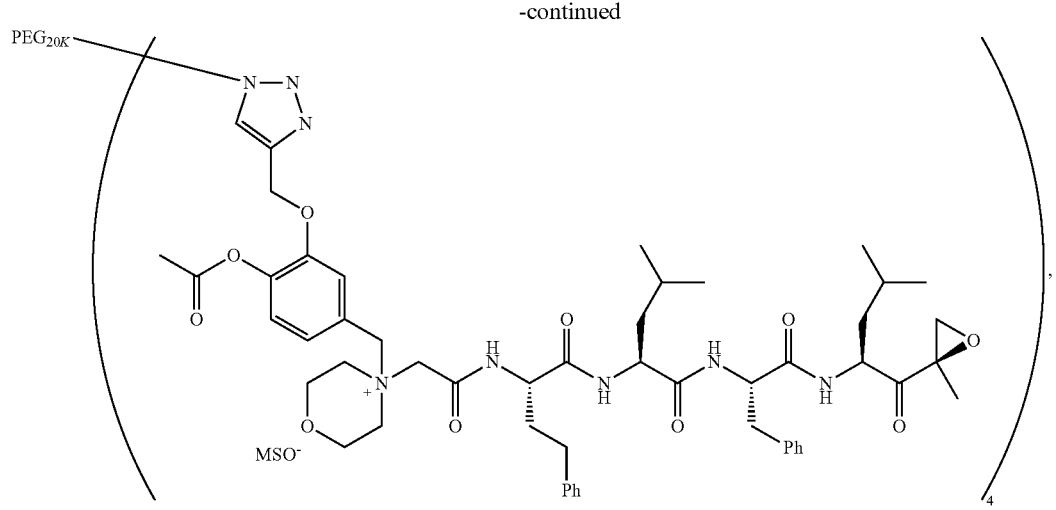
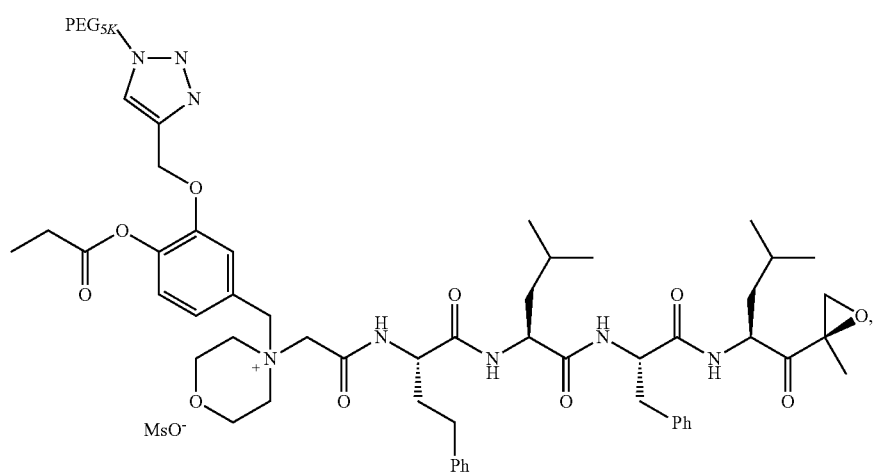
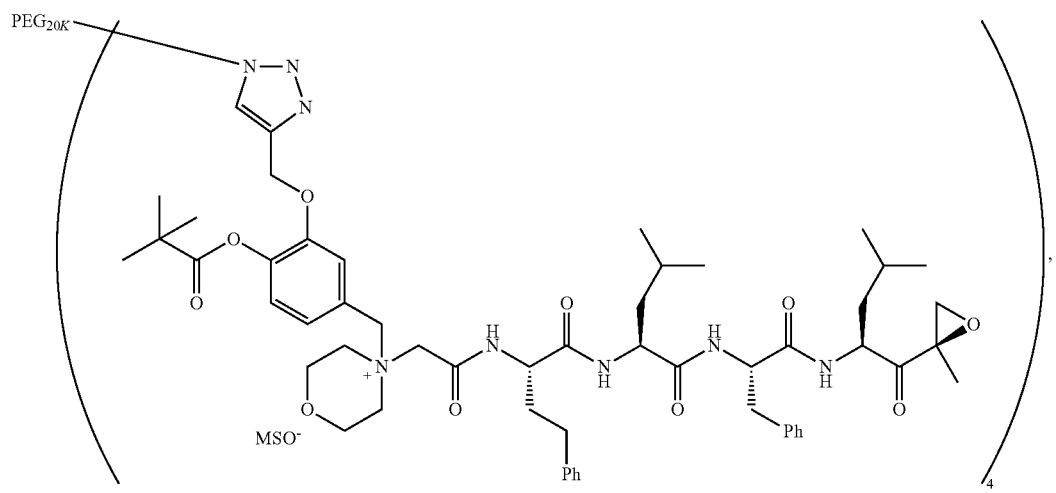

-continued
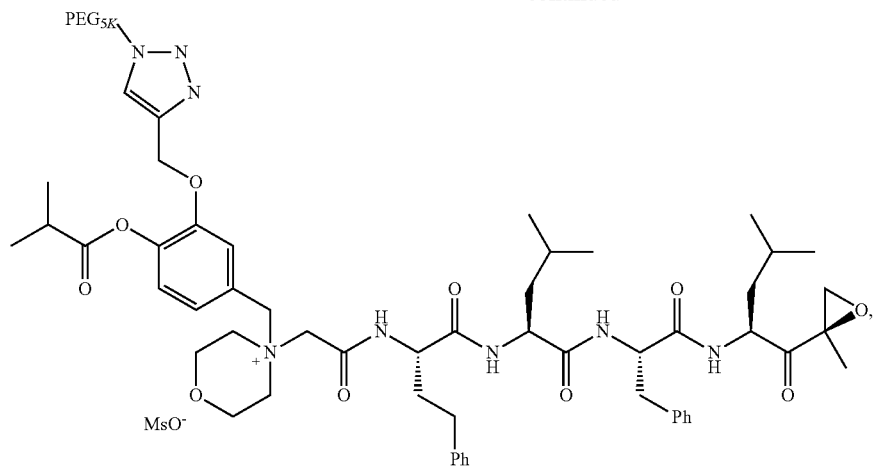
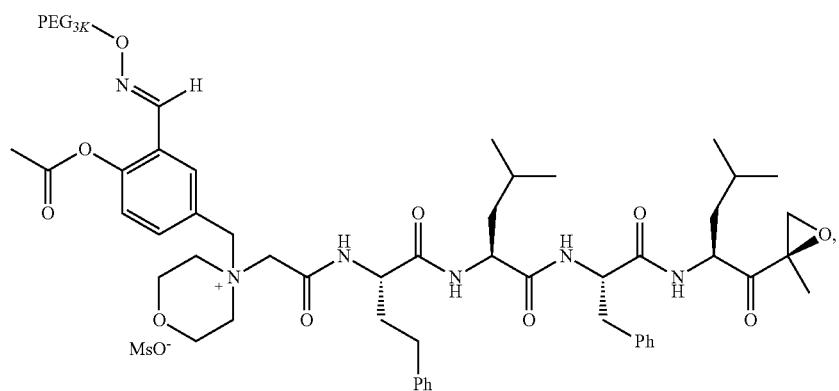
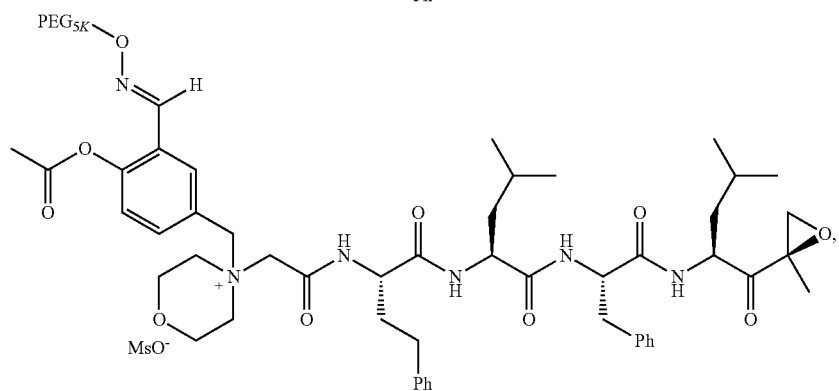
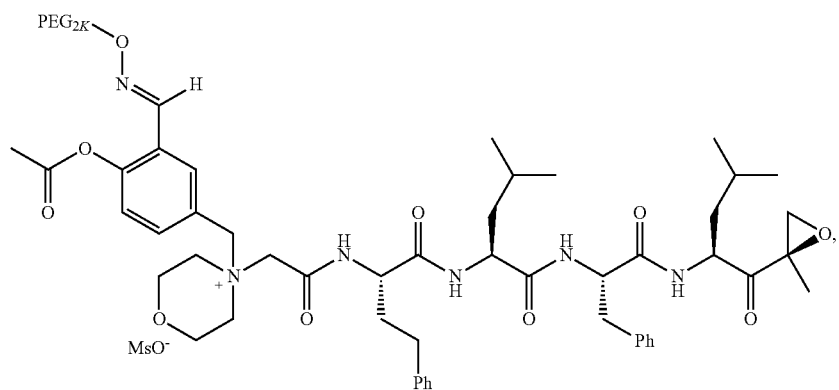

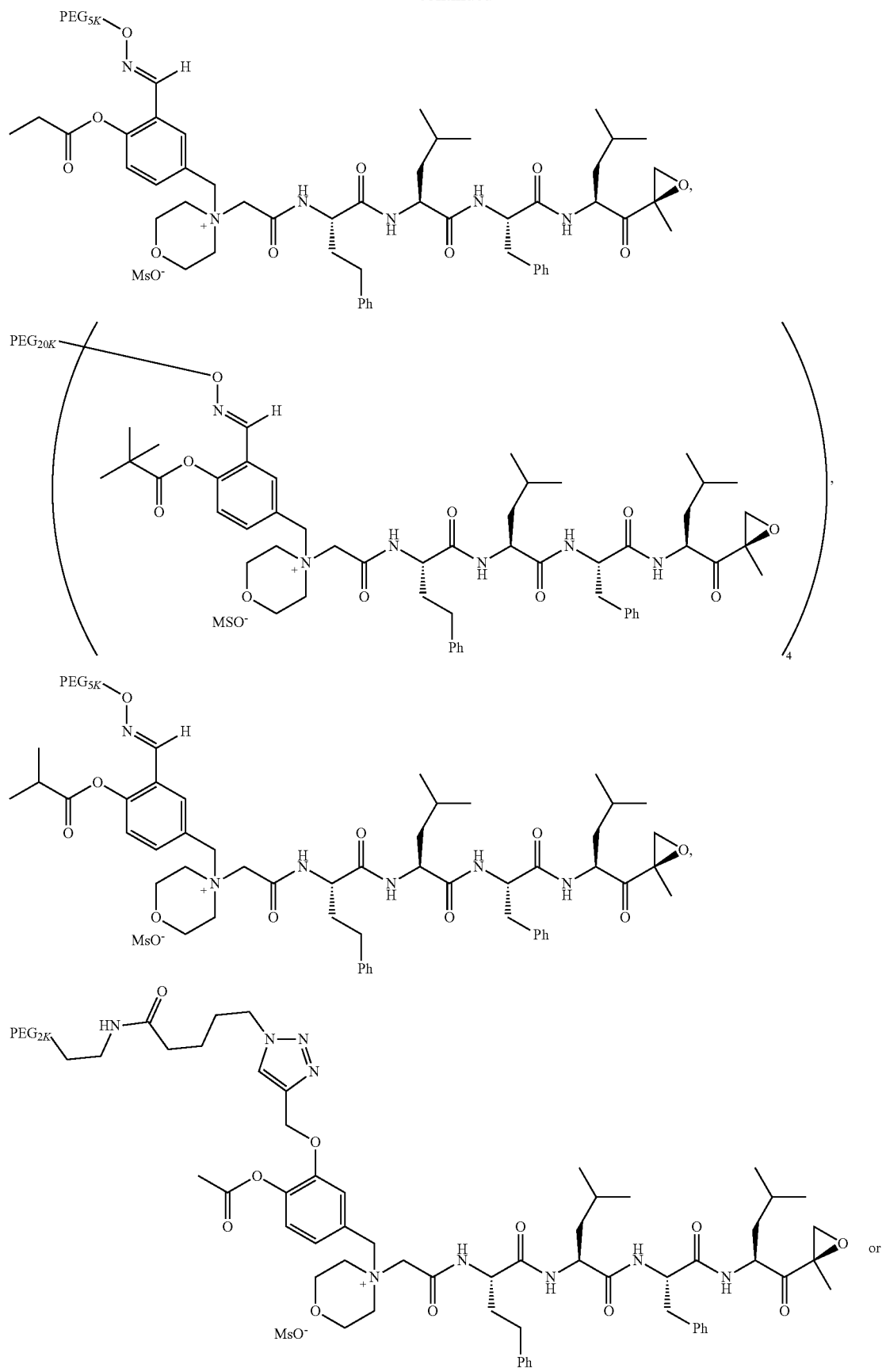

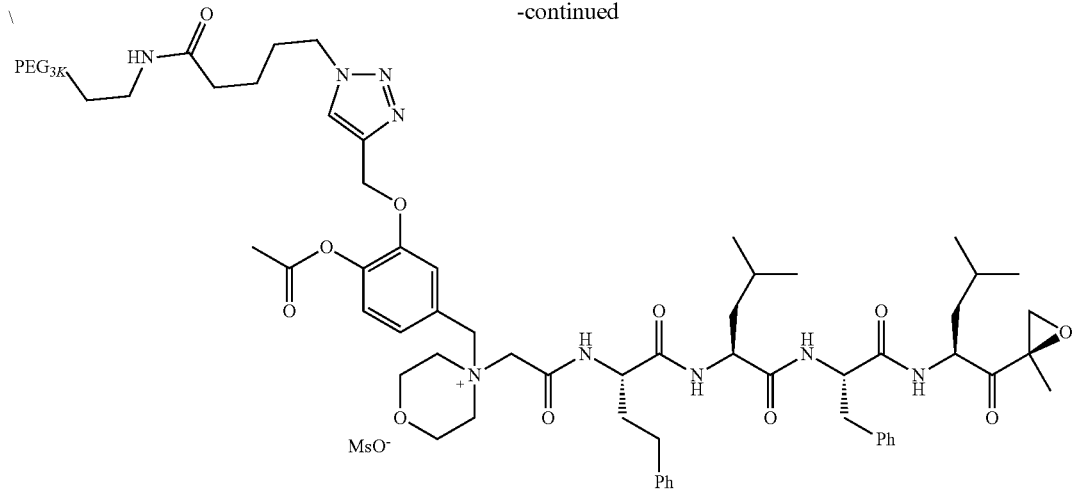
20
or a pharmaceutically acceptable salt thereof.
In aspect 19 of the invention, the invention provides the compound of any one of aspects 1-18 wherein the compound is
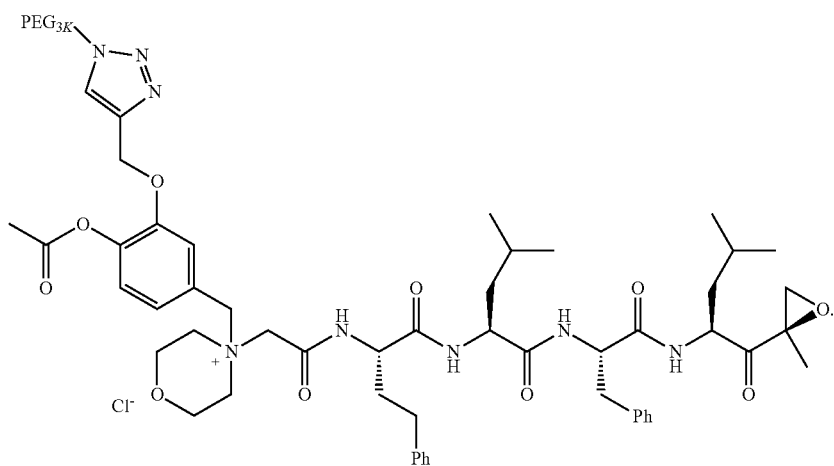
45
In aspect 19a of the invention, the invention provides the compound of any one of aspects 1-18 wherein the compound is
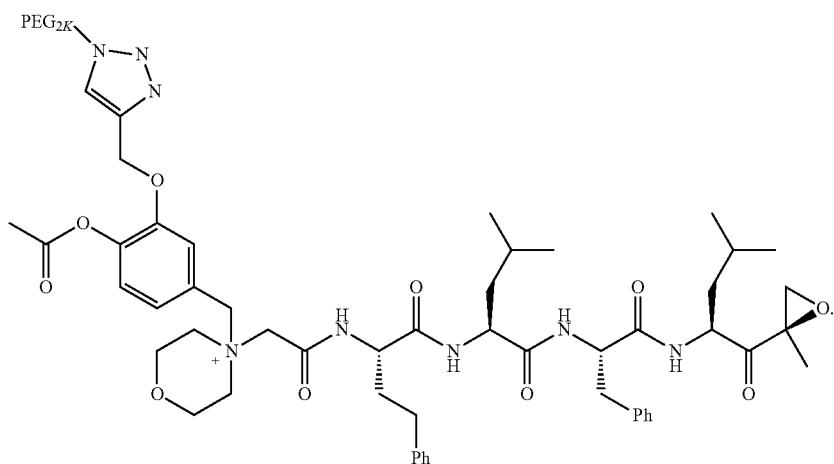

In aspect 20 of the invention, the invention provides the compound of any one of aspects 1-18 wherein the compound is
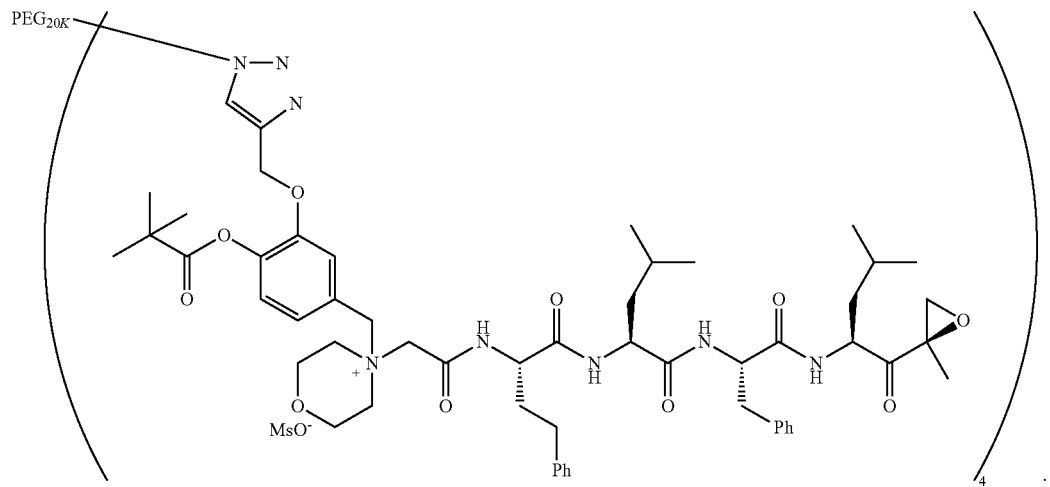
In aspect 21 of the invention, the invention provides the compound of any one of aspects 1-18 wherein the compound is
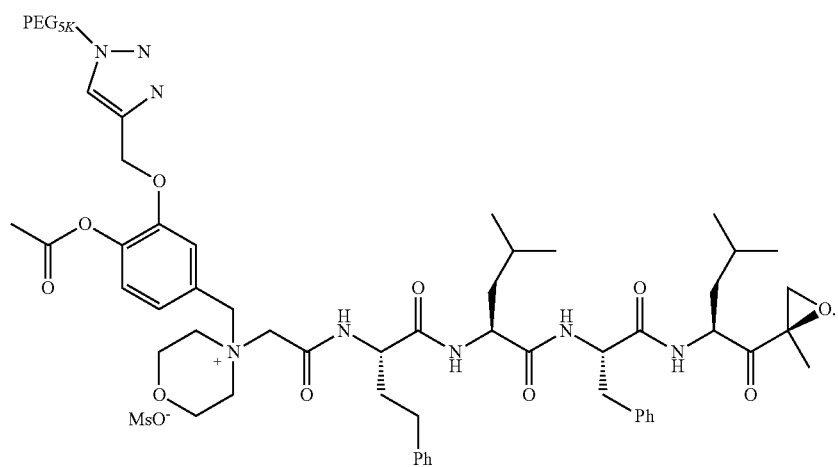

In aspect 22 of the invention, the invention provides the compound of any one of aspects 1-18 wherein the compound is
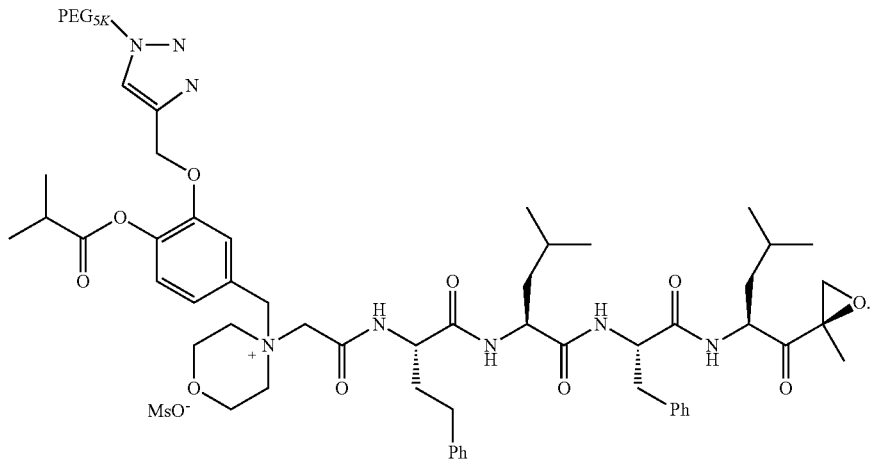
In aspect 23 of the invention, the invention provides the compound of any one of aspects 1-18 wherein the compound is
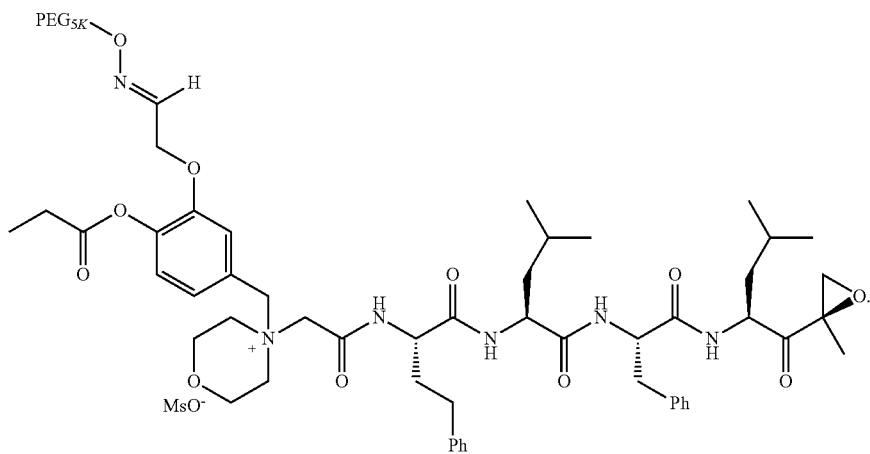
in aspect 24 of the invention, the invention provides the compound of any one of aspects 1-18 wherein the compound is
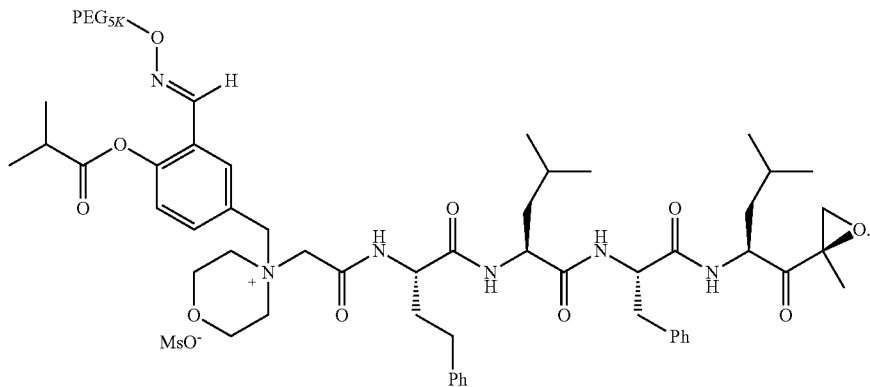

In aspect 25 of the invention, the invention provides the compound of any one of aspects 1-18 wherein the compound is

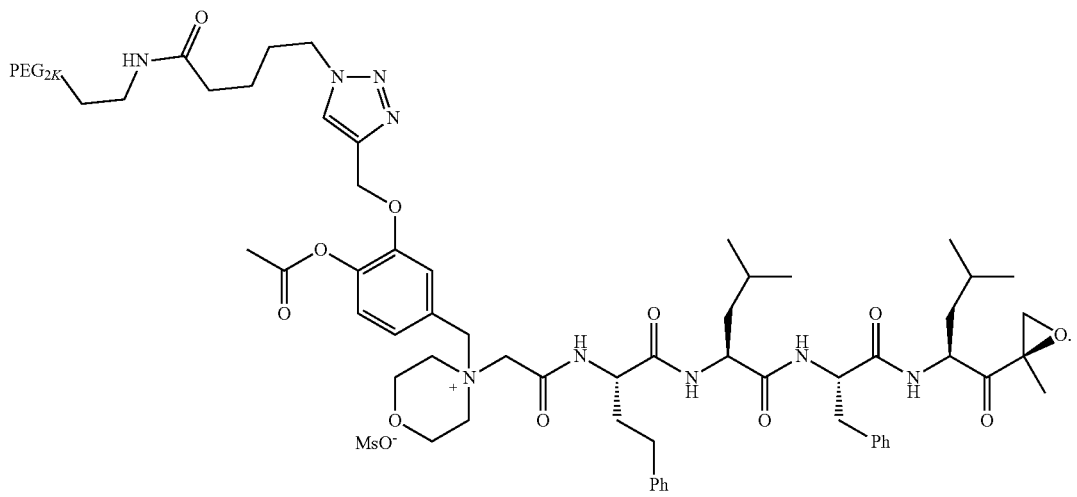

25

In aspect 26 of the invention, the invention provides the compound of any one of aspects 1-18 wherein the compound

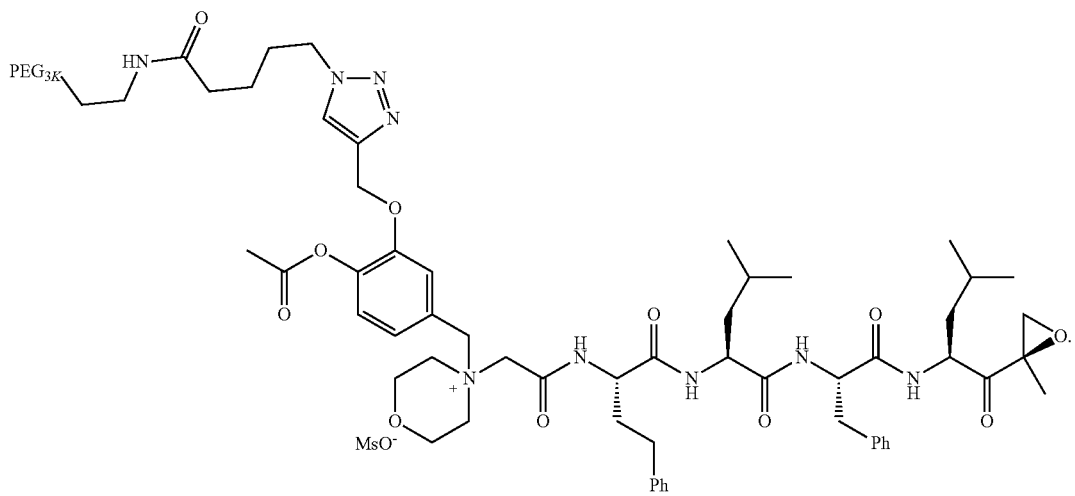

In aspect 27 of the invention, the invention provides the compound of any one of aspects 1-16 wherein the PEG has a weight ranging from about 2K to about 20K.

In aspect 28 of the invention, the invention provides the compound of any one of aspects 1-16 wherein the PEG has a weight of 3K, 5K or 20K.

In aspect 29 of the invention, the invention provides the compound of any one of aspects 1-16 that is a pharmaceutically acceptable salt comprising a counter anion selected from a chloride anion, a bisulfate anion, a sulfate anion, a nitrate anion, a phosphate anion, an alky-sulfonate anion or an aryl-sulfonate anion.

In aspect 30 of the invention, the invention provides the compound of aspect 29 wherein the counter anion is a chloride anion or an alky-sulfonate anion.

In aspect 31 of the invention, the invention provides the compound of aspect 29 wherein the counter anion is a chloride anion or methane-sulfonate anion.

In aspect 32 of the invention, the invention provides a pharmaceutical composition comprising the compound according to any one of aspects 1-26 and a pharmaceutically acceptable excipient, carrier or diluent.

In aspect 33 of the invention, the invention provides pharmaceutical composition of aspect 32 that is administered orally or parenterally administrable by infusion or injection.

In aspect 34 of the invention, the invention provides the pharmaceutical composition according to any one of aspects 32-33 that comprises one or more of the compounds according to any one of aspects 1-26 in conjunction with a pharmaceutically acceptable excipient, carrier or diluent.

In aspect 35 of the invention, the invention provides the pharmaceutical composition according to any one of aspects 32-34 that comprises at least two compounds according to any one of aspects 1-28 in conjunction with a pharmaceutically acceptable excipient, carrier or diluent.

In aspect 36 of the invention, the invention provides a method of treating multiple myeloma comprising administering to a patient in need thereof, a therapeutically effective amount of the compound of any one of aspects 1-31 or the pharmaceutical composition of any one of aspects 32-35.

In aspect 37 of the invention, the invention provides the method of aspect 34 wherein the multiple myeloma is relapsed, refractory or relapsed and refractory multiple myeloma.

In aspect 38 of the invention, the invention provides the method of aspect 36 wherein the multiple myeloma is newly diagnosed multiple myeloma.

In aspect 39 of the invention, the invention provides the a process of making the compound according to any one of aspects 1-16, the process comprising the step of

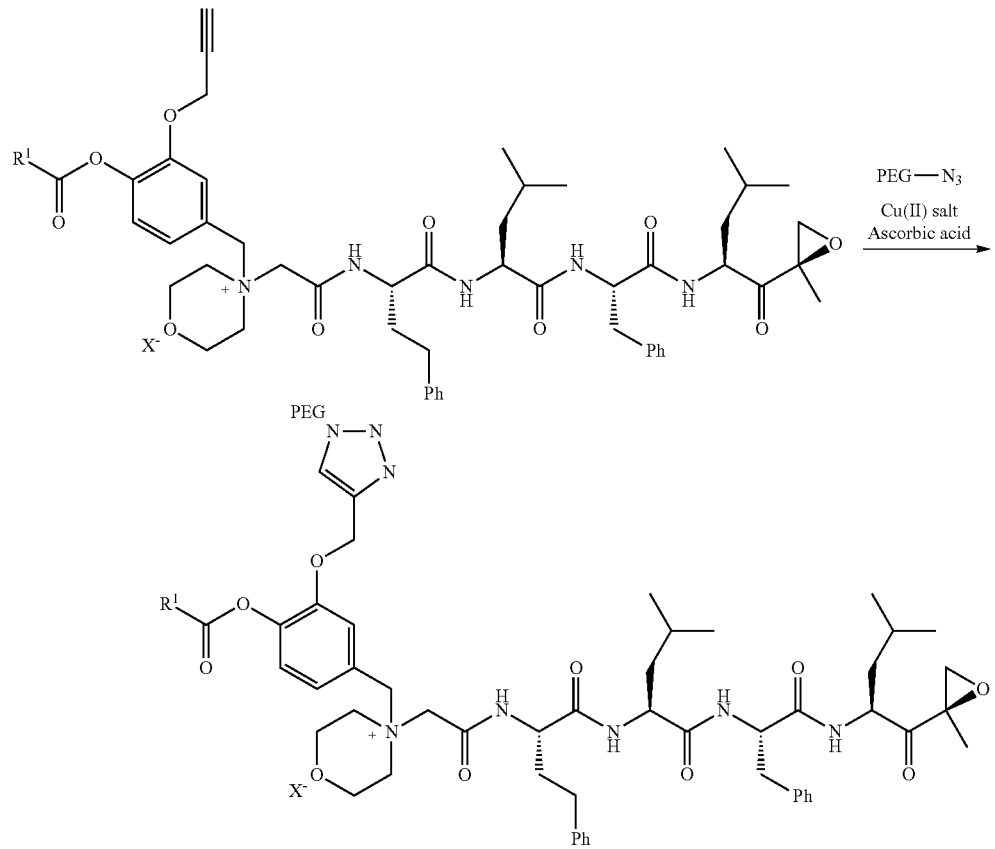

wherein X— is a counter ion salt selected from the group consisting of a chloride anion, a bisulfate anion, a sulfate anion, a nitrate anion, a phosphate anion, an alky-sulfonate anion or an aryl-sulfonate anion, and PEG has a weight ranging from about 2K to about 20K, to prepare a compound of Formula I In aspect 40 of the invention, the invention provides the a process of making the compound of Formula I according to aspect 1, the process comprising the step of

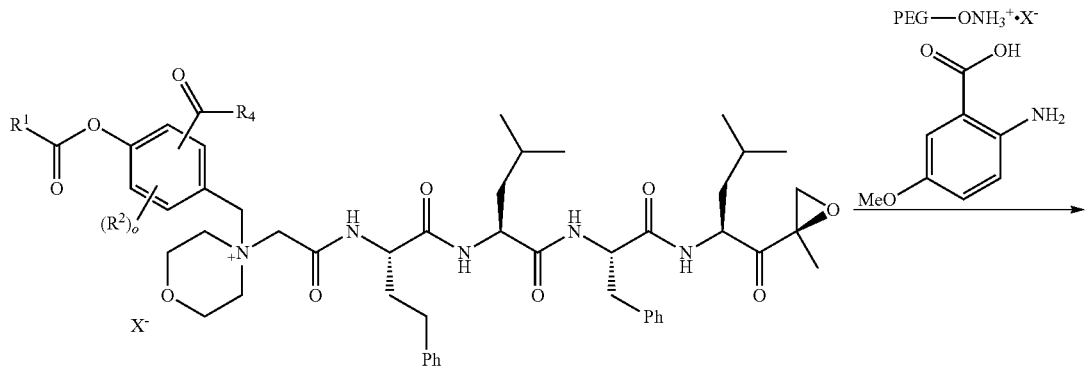

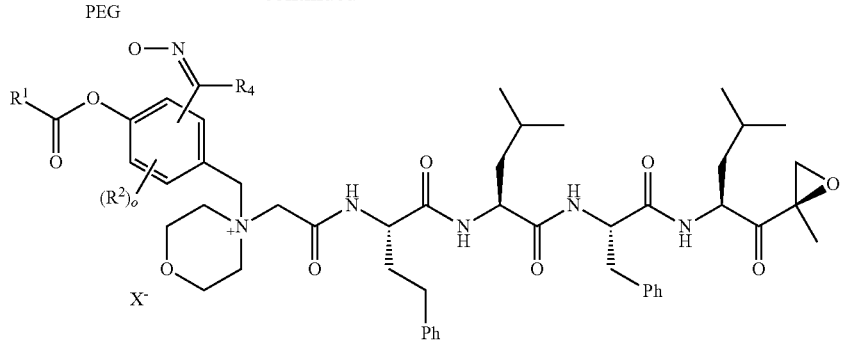

wherein

X— is a counterion salt of a chloride anion, a bisulfate anion, a sulfate anion, a nitrate anion, a phosphate anion, an alky-sulfonate anion or an aryl-sulfonate anion;

PEG has a weight ranging from about 2K to about 20K; and $R^1$, $R^2$, $R^4$ and o are as defined in aspect 1, to prepare a compound of Formula I.

In other aspects, the invention provides compounds having the formula $(SM)_m$-PEG, or a pharmaceutically acceptable salt thereof, in which each SM is an independently selected compound of formula I or of formula II as defined in above and anywhere herein and is attached to PEG of defined weight at n number of locations, wherein n is 2-10 (e.g., n=4 in the compound of aspect 14; See also Table 1 hereinbelow).

In some embodiments, the nitrogen atom of the carfilzomib morpholine ring is substituted with the benzylic ester moiety as shown in formulas I and II, thereby forming a quaternary nitrogen atom and wherein the positive charge associated with the quaternary nitrogen atom is balanced by a pharmaceutically acceptable anion, as defined herein by $X^-$.

In some aspects of the invention, the compounds described herein themselves exhibit lower therapeutic activity when compared with said corresponding epoxy ketone protease inhibitors and exhibit enhanced solubility, permeability, pharmacokinetics and/or pharmacodynamics properties in vivo when compared with said corresponding epoxy ketone protease inhibitors.

In some aspects of the invention, the polymeric moiety or peg moiety is cleaved from the carfilzomib active ingredient by pH change and/or enzymes such as, but not limited to, esterases, cytochrome P450, phosphodiesterase, phosphoamidase, phosphatase, and DT-diaphorase, or any combination thereof.

In some aspects of the invention, the PEG is a linear PEG. In some aspects of the invention, the PEG is a bifunctional PEG that can conjugate 1-2 compounds per PEG. In some aspects of the invention, the PEG is a four-arm PEG that can conjugate 1-4 compounds per PEG. In some aspects of the invention, the PEG is an eight-arm PEG with a hexaglycerin core that can conjugate 1-8 compounds per PEG. In some aspects of the invention, the PEG is an eight-arm PEG with a tripentaerythritol core that can conjugate 1-8 compounds per PEG. In some aspects of the invention, the PEG is a branched two-arm PEG. In some aspects of the invention, the PEG is a branched four-arm PEG. In addition, the compounds can further include solubilizers, permeability enhancers, masking agents, macromolecular carriers, targeting moieties, and biologics to improve half-life and disease specificity that are attached directly to the compound or indirectly attached via a spacer moiety.

While not wishing to be bound by theory, it is possible that the compounds of the invention may mask or partially mask the protease inhibitory activity temporarily until the pegylated linked moieties have been cleaved releasing free carfilzaomib, a tested and regulatory approved active pharmaceutical moiety, into the systemic circulation can reduce undesired side effects, which may otherwise be associated with various routes of administration. To this end, the pegylated carfilzomib compounds of the present invention may act as pro-drugs of carfilzomib. Alternatively, as the pegylated moiety is positioned near the morpholine end of the carilzomib tetrapeptide backbone structure, the compounds of the present invention, prior to peg cleavage, may very well possess active proteasome inhibitory activity.

The beneficial properties of the compounds of the present invention may also facilitate subcutaneous administration and extend half-life of carfilzomib, e.g. to beyond four hours. In aspect 41 of the invention, the human plasma half-life of the compounds of the invention is longer than 0.5 hr. In aspect 42 0f the invention, the human plasma half-life of the compounds is between 0.5 and 5 hr. In aspect 43 of the invention, the human plasma half-life of the compound is longer than 5 hr. In aspect 44 of the invention, the human plasma half-life of the compound is between 5 and 100 hr. In aspect 45 of the invention, the human plasma half-life of the compound is longer than 100 hr. In aspect 46 of the invention, the human plasma half-life of the compound is between 100 and 836 hr. In aspect 47 of the invention, the human plasma half-life of the compound is between 200 and 300 hr. In aspect 48 of the invention, the human plasma half-life of the compound is about 267 hr. In aspect 49 of the invention, the human plasma half-life of the compound is up to 836 hr. By virtue of extending the half-life of carfilzomib, the invention potentially improves dosing as well as patient convenience and compliance in treatment with carfilzomib.

In aspect 50 of the invention, the invention provides a pharmaceutical composition, which includes a PEG carfilzomib compound as described anywhere herein and a pharmaceutically acceptable excipient, carrier or diluent.

In other aspects or embodiments of the invention, which are later described herein, methods are featured for treating a disease or condition selected from the group consisting of cancer, autoimmune disease, graft or transplant-related condition, neurodegenerative disease, fibrotic-associated condition, ischemic-related conditions, infection (viral, parasitic or prokaryotic) and diseases associated with bone loss, the method includes administering to a patient a therapeutically effective amount of a compound as described anywhere herein. In still further aspects, methods for treating cancer (e.g., multiple myeloma, e.g., multiple myeloma that is relapsed and/or refractory) in a patient are provided by the invention, which include administering to a patient a therapeutically effective amount of a compound as described herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety, as if here written. In case of conflict, the present specification, including definitions, will control. Other features and advantages of the disclosure will be apparent from the following detailed description and from the claims.

As used herein, the term "aspect" is used synonymously with the term "embodiment."

Definitions

The following definitions should further assist in understanding the terms as used herein and the scope of the invention described herein.

The term "$C_{x-y}$alkyl" refers to substituted or unsubstituted saturated hydrocarbon groups, including straight-chain alkyl and branched-chain alkyl groups that contain from x to y carbons in the chain. The term "haloalkyl" refers to alkyl groups in which at least one hydrogen atom is replace by a halo (e.g., fluoro, chloro, bromo, iodo). e.g., $CH_2F$, $CHF_2$, trifluoromethyl and 2,2,2-trifluoroethyl.

The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond, respectively. In some embodiments, divalent groups alkenylene and alkynylene include from 2 to 12 carbon atoms. In certain embodiments, alkylene and alkynylene include from 2 to 10 carbon atoms. In certain embodiments, alkylene and alkynylene include from 2 to 6 carbon atoms (e.g., 2, 3, 4, 5, or 6 carbon atoms).

The term "alkoxyl" refers to an alkyl group having an oxygen attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{3-y}$cycloalkyl", as used herein, refers to a fully saturated, substituted or unsubstituted, ring in which each atom of the ring is carbon, and the ring contains from 3 to γ carbon atoms in size. For instance, the term $C_{3-7}$cycloalkyl is intended to mean a carbocyclic ring containing anywhere from 3 to 7 carbon atoms in size. Such rings include, for example, cyclopropyl, cyclobutyl, cyclopentyl, cyclohexyl and cycloheptyl rings. These rings may further be substituted as specified.

The terms "cancer" and "cancerous" when used herein refer to or describe the physiological condition in subjects that is typically characterized by unregulated cell growth. Examples of cancer include, without limitation, hematologic malignancies or blood borne cancers such as multiple myeloma and leukemia, and other cancers such as carcinoma, lymphoma, sarcoma, and blastoma. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers, in a subject, which have become resistant in some degree to treatment with anti-cancer agents, including without limitation chemotherapeutic agents, antimitotic agents, anthracyclines and the like, and for cancers which have relapsed post treatment with such anti-cancer agents.

The term "comprising" is meant to be open ended, including the indicated component(s) but not excluding other elements.

The term or abbreviation "cg" or "eg." as used herein is intended to mean "example."

The term "inhibitor" is meant to describe a compound that blocks or reduces an activity of an enzyme or system of enzymes, receptors, or other pharmacological target (for example, inhibition of proteolytic cleavage of standard fluorogenic peptide substrates such as suc-LLVY-AMC. Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

The terms "drug resistant" and "multidrug resistant" when used herein refers to cancer cells that have developed and/or are resistant to drug. These include cancer cells exhibiting little to no efficacy or decreased efficacy from that exhibited at the initial dose of the drug. The cancer cells may be resistant to one drug or to multiple drugs of different chemical structures that are directed to act at different biological targets within the cancer cell.

The term "pharmaceutically-acceptable salt" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compound may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of the compound include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, histidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound.

The term "proteasome" as used herein is meant to include immuno- and constitutive proteasomes.

The term "refractory" when used here is intended to refer to not-yielding to, resistant or non-responsive to treatment, stimuli (therapy) or cure, including resistance to multiple therapeutic curative agents, "Refractory" when used herein in the context of characterizing a cancer or tumor is intended to refer to the cancer or tumor being non-responsive or having a resistant or diminished response to treatment with one or more anticancer agents. The treatment typically is continual, prolonged and/or repetitive over a period of time resulting in the cancer or tumor relapsing or developing resistance or becoming refractory to that very same treatment.

The term "subject" as used herein refers to any mammal, including humans, and animals such as cows, horses, dogs and cats. Thus, the invention may be used in human patients as well as in veterinary subjects and patients. In one embodiment of the invention, the compounds of the invention may be administered to a human subject.

The phrase "therapeutically-effective" or "therapeutically effective amount" is intended to quantify the amount of the compound of the invention, which when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. Thus, it is the amount of the compound of the invention that can treat cancer, whether it is multiple myeloma or other hematologic malignancy or a solid tumor.

The terms "treat", "treating" and "treatment" as used herein refer to therapy, including without limitation, curative therapy, prophylactic therapy, and preventative therapy and generally include reversing, reducing, or arresting the symptoms, clinical signs, and underlying pathology of a condition in manner to improve or stabilize a patient's condition. Prophylactic treatment generally constitutes either preventing the onset of disorders altogether or delaying the onset of a pre-clinically evident stage of disorders in individuals. The term "prophylactic or therapeutic" treatment is art-recognized and includes administration to the host of one or more of the subject compositions. If it is administered prior to clinical manifestation of the unwanted condition (e.g., disease or other unwanted state of the host animal), or after the condition has subsided, then the treatment is prophylactic. (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term PEG as used herein, is intended to have its commonly understood and traditional meaning. Particularly. PEG is a moiety made up of repeating poly(ethylene glycol) polymeric units, the precise number of which determines its molecule weight. For instance, the PEG moiety used in the present invention can have any one of the architectures as described herein as well as, e.g., depicted in formulas A-I as shown in Table 1. The unit of this molecular weight is daltons. Thus, it is intended that reference to a molecular weight of PEG as used herein (the specification, claims and abstract), for example, reference of "2K", "3K", "5K" and "20K" or "2000", "3000", "5000" or "20000" with respect to a given PEG means a 2000 dalton (or 2 kilodalton), 3000 dalton (or 3 kilodalton), 5000 dalton (or 5 kilodalton), and 20000 dalton (or 20 kilodalton), respectively, PEG weight. Further, as used herein "KDa" means kilodalton. It will be understood that the carfilzomib compounds shown in Formulas A, B, C, D, E, F, G H and I in Table 1 illustrate different PEG moieties covalently attached through linkers as described and defined by the invention herein. To assist with understanding each Formula in Table 1.

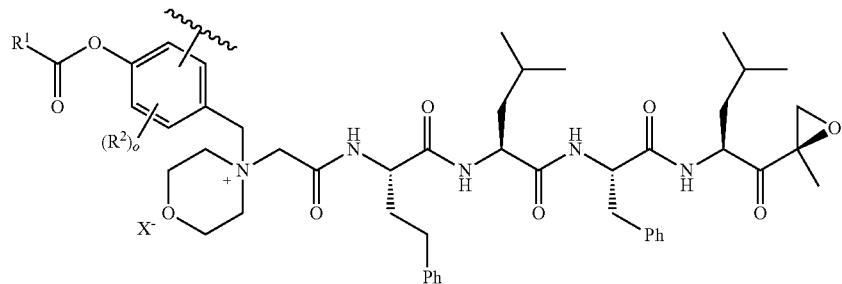

wherein $R^1$ and $R^2$ are as defined herein in Formulas I and II. Counter anion $X^-$ is as defined in Formulas I and II herein. For instance, counter anion $X^-$ can be $Cl^-$, $HSO_4^-$, $SO_4^{-2}$, $NO_3^-$, $H_2PO_4^-$, alkyl/aryl-$SO_3^-$ such as a tosylate (tolylsulfonic acid), mesylate (methanesulfonic acid) or benzylate (benzylsulfonic acid) anion. The PEG portion of the carfilzomib compound typically has a molecular weight in the rage from about 400 daltons to about 50.000 daltons. The linker portion of the compounds illustrated in Formulas A-I below are also as defined herein in Formulas I and II. For example, the linker may be

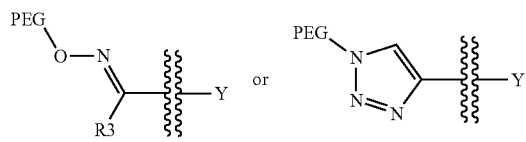

wherein $R^3$ is H or Me.

TABLE 1

| Entry | Structure | PEG Type | Carfilzomib molecules |
|---|---|---|---|
| A | 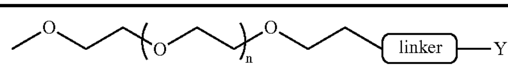 | linear | 1 |
| B | 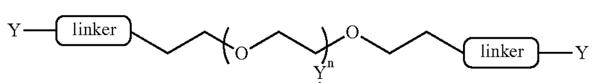 | bi-functional | 2 |
| C | 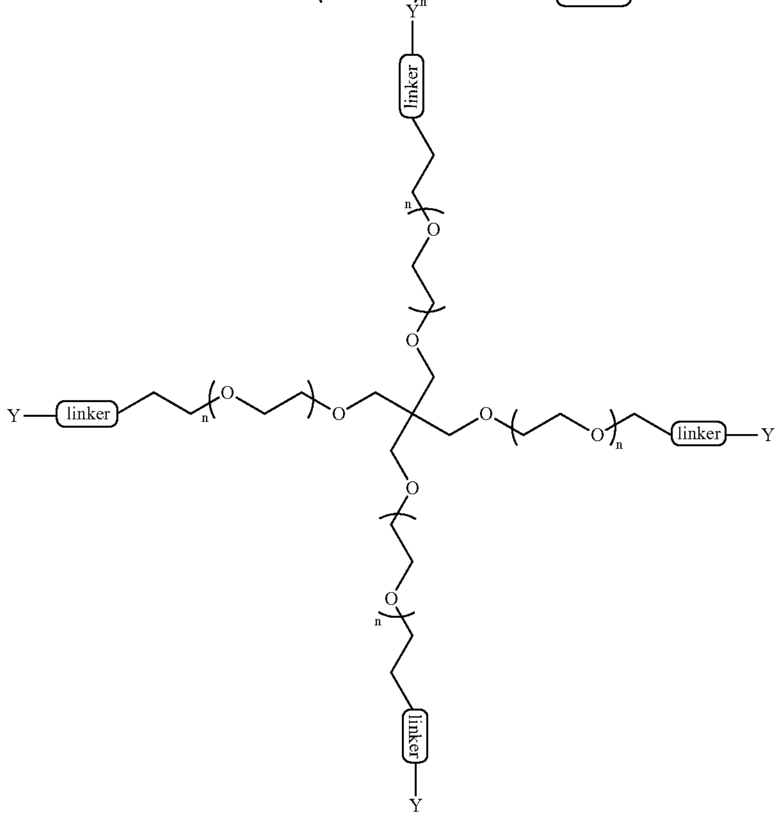 | 4-Arm | 4 |

TABLE 1-continued

| Entry | Structure | PEG Type | Carfilzomib molecules |
|---|---|---|---|
| D | 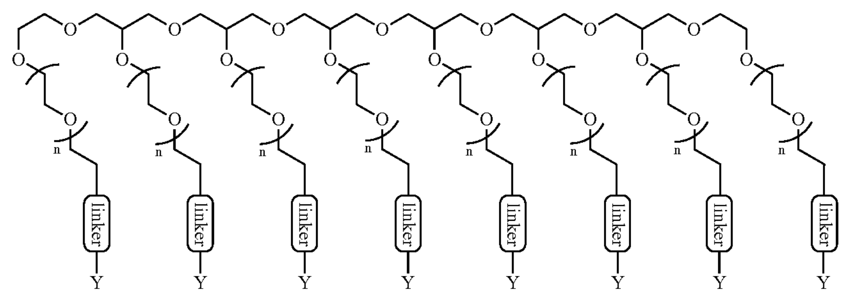 | 8-Arm Hexaglycerine Core | 8 |
| E | 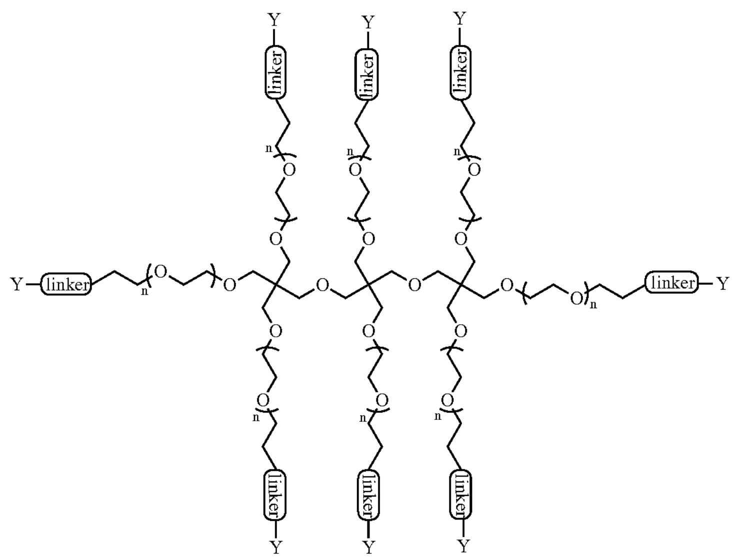 | 8-Arm Tripentaerythritol Core | 8 |
| F | 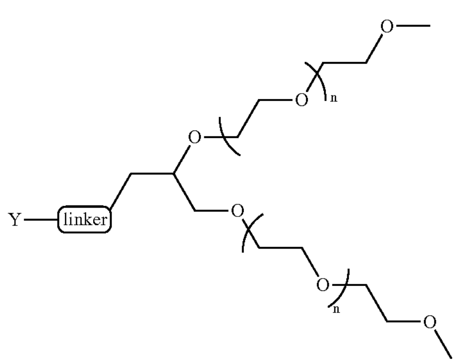 | Branched 2-Arm | 1 |

TABLE 1-continued
| Entry | Structure | PEG Type | Carfilzomib molecules |
|---|---|---|---|
| G | 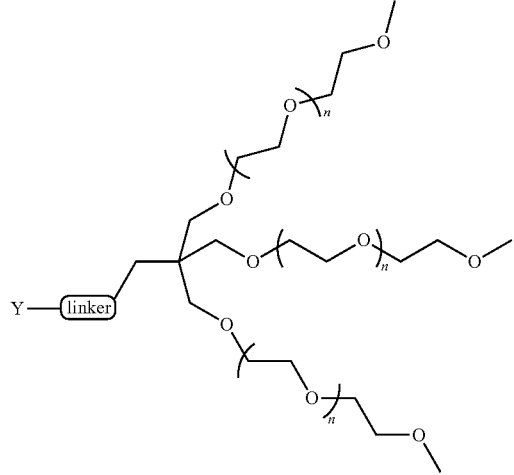 | Branched 3-Arm | 1 |
| H | 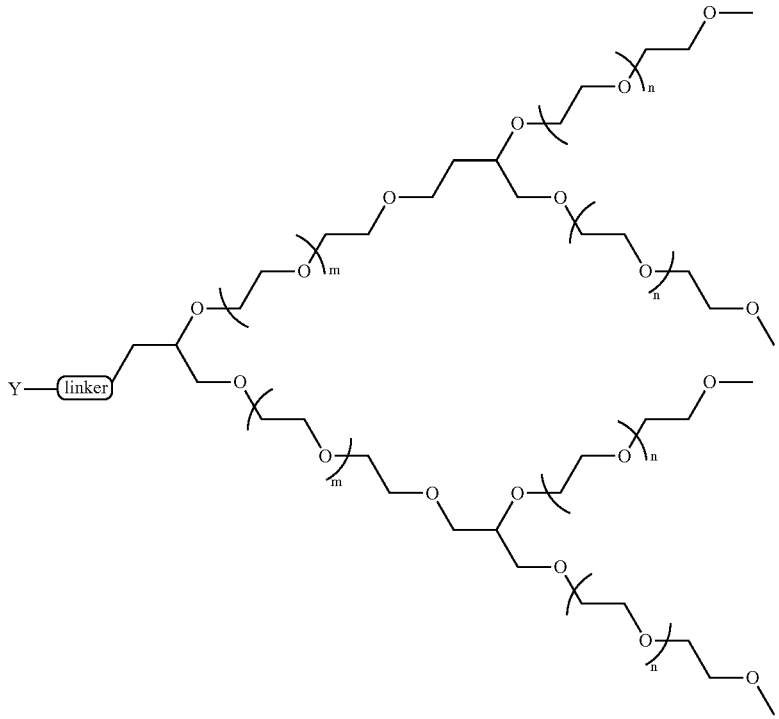 | Branched 4-Arm | 1 |

TABLE 1-continued

| Entry | Structure | PEG Type | Carfilzomib molecules |
|---|---|---|---|
| I | 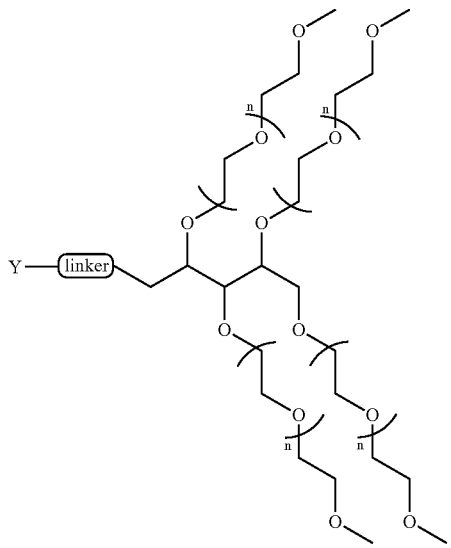 | Branched 4-Arm | 1 |

In embodiment 51. PEG has a molecular weight of greater than 1 kDa.

In embodiment 52. PEG has a molecular weight of about 1 kDa.

In embodiment 53. PEG has a molecular weight of greater than 2 kDa.

In embodiment 54, PEG has a molecular weight of about 2 kDa.

In embodiment 55, PEG has a molecular weight of greater than 5 kDa.

In embodiment 56, PEG has a molecular weight of about 5 kDa.

In embodiment 57, PEG has a molecular weight of greater than 10 kDa.

In embodiment 58, PEG has a molecular weight of about 10 kDa.

In embodiment 59, PEG has a molecular weight of greater than 20 kDa.

In embodiment 60, PEG has a molecular weight of about 20 kDa.

In embodiment 61, PEG has a molecular weight of greater than 30 kDa.

In embodiment 62, PEG has a molecular weight of about 30 kDa.

In embodiment 63, PEG has a molecular weight of greater than 40 kDa.

In embodiment 64, PEG has a molecular weight of about 40 kDa.

In embodiment 65, PEG has a molecular weight of greater than 50 kDa.

In embodiment 66, prior to conjugation to epoxy ketone protease inhibitors, PEG has a plurality of reactive functional groups (e.g. azide groups).

In some embodiments, prior to conjugation to epoxy ketone protease inhibitors. PEG has 1, 2, 3, 4, 5, 6, 7, 8, 9, or 10 reactive functional groups (e.g., azide groups).

The PEG carfilzomib compounds of the invention possess a polyethylene glycol (PEG) polymer chain conjugated to the carfilzomib active pharmaceutical ingredient (API). To this end, the invention provides in aspect 67, a carfilzomib PEG compound of formula I or formula II wherein n is 1, 2, 3, 4, 5, 6, 7, 8, 9, or 10, e.g., 2, 3, 4, 5, 6, 7, 8, 9, or 10. In embodiment 68, n is 8. In embodiment 69, n is 4. In embodiment 70, n is 2. In embodiment 71, n is 1

General Synthesis and Representative Examples of the Invention

As described, the pegylated carfilzomib compounds in formulas I and II are cleavable polymer PEG carriers of the active pharmaceutical ingredient, carfilzomib (Formulas I and II) and release free carfilzomib in vivo. The solubilizing polymer carrier, polyethylene glycol (PEG) of desired size and/or weight are commercially available and may be, for example, purchased from ThermoFisher Scientific. Sigma-Aldrich and similar commercial suppliers of polymeric materials. The PEG group may be appended to carfilzomib as a quaternary salt on the morpholine ring in a variety of linkers, including via a self-immolative para-alkanoyloxy substituted benzyl linker, as described herein. The linker contains a latent nucleophilic phenol group which becomes electron-donating after a biological or chemical triggering mechanism and then initiates an electronic cascade leading ultimately to the release of carfilzomib. The unique combination of solubilizing polymer carrier and quaternary salt formation results in conjugates with extraordinarily high aqueous solubility. Carfilzomib is released from the conjugate enzymatically via an esterase enzyme or chemically by a hydroxide catalyzed hydrolysis. It should be noted that this PEG conjugate alone/itself is active as a proteasome inhibitor, and quickly releases the more active pharmaceutical ingredient carfilzomib when the conjugate is exposed to an appropriate esterase enzyme or to a slightly basic environment. The rate of displacement may be varied over a time range by the introduction of sterically bulky group(s) which limit enzyme access, and/or electron density modulating group(s) at position $R^2$ in formulas I and II.

Abbreviations: The following abbreviations used throughout both the general schemes and the examples, are intended to mean the following:

DCM dichloromethane; methylene dichloride
DMF dimethylformamide
DMSO dimethyl sulfoxide
EtOAc ethyl acetate
MeOH methanol
mpk milligram per kilogram; mg/kg
RT, rt room temperature
NaCl sodium chloride
tBuOH t-butanol; t-butyl alcohol The starting material carfilzomib, used to prepare the compounds of the invention, are described in PCT publications WO2006017842, WO2009045497. WO2014169897, WO2013169282. WO2014011695. WO2006063154, WO2014015016. WO02010048298 and U.S. Pat. Nos. 7,714,042 and 7,737,112, each specification of which is hereby incorporated herein by reference in its entirety.

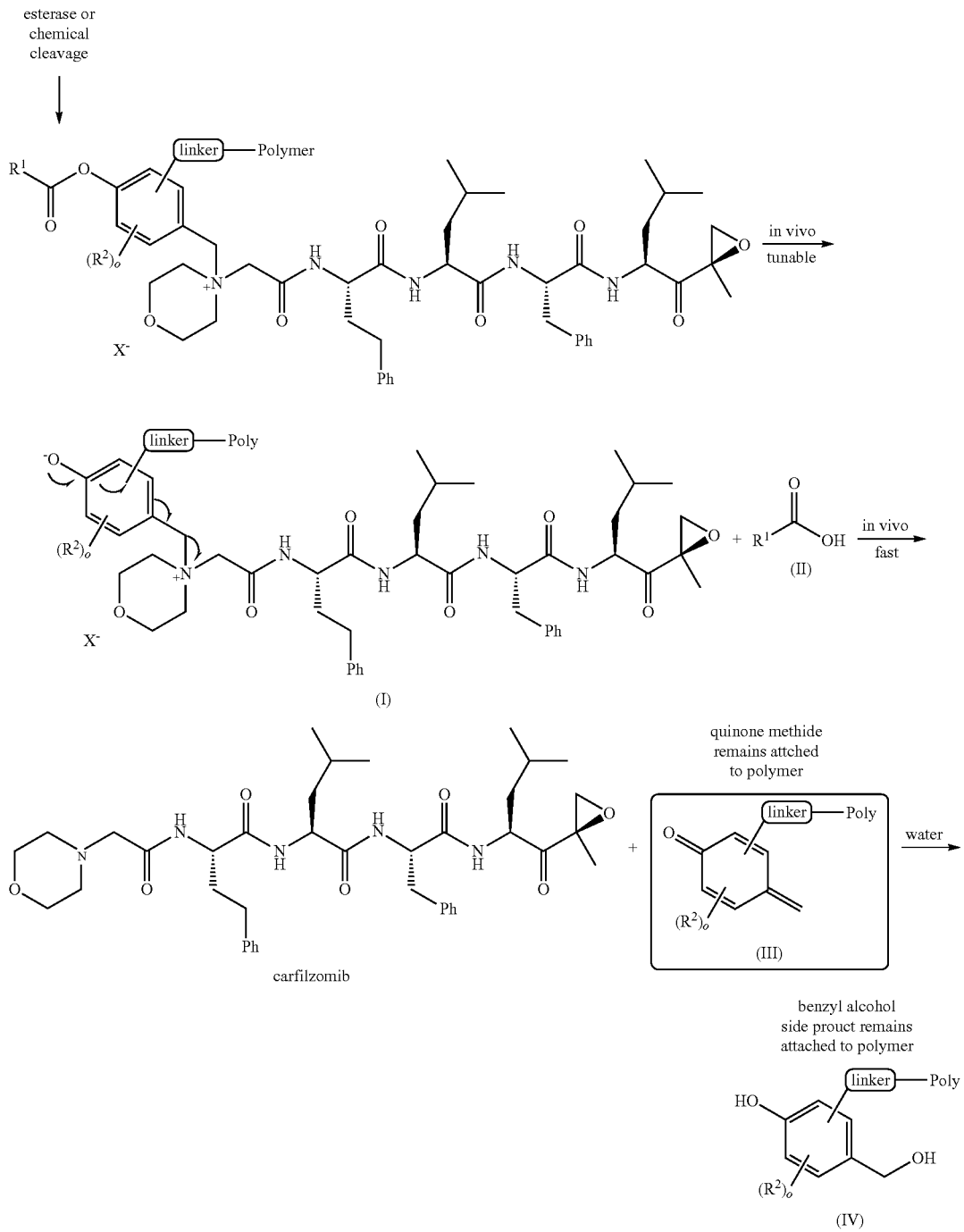

Scheme 1: Cleavage of benzyl elimination quaternary salt

Enzymatic and/or chemical hydrolysis of the phenyl ester provides a carboxylic acid (II) and a phenolate intermediate (I) which undergoes rapid 1, 6 elimination to provide free carfilzomib and a quinone methide which remains covalently attached to the solubilizing PEG polymer. Quinone methides are known to be reactive Michael acceptors and are believed to present risks related to potential genotoxicity. In this invention, permanent attachment of the quinone methide linker byproduct to the polymer may attenuate toxicity by preventing cellular access and lowering reactivity to serum nucleophiles. The most likely fate of intermediate III in vivo is reaction with water to form a benzyl alcohol-polymer adduct that is quickly removed from the body by excretion.

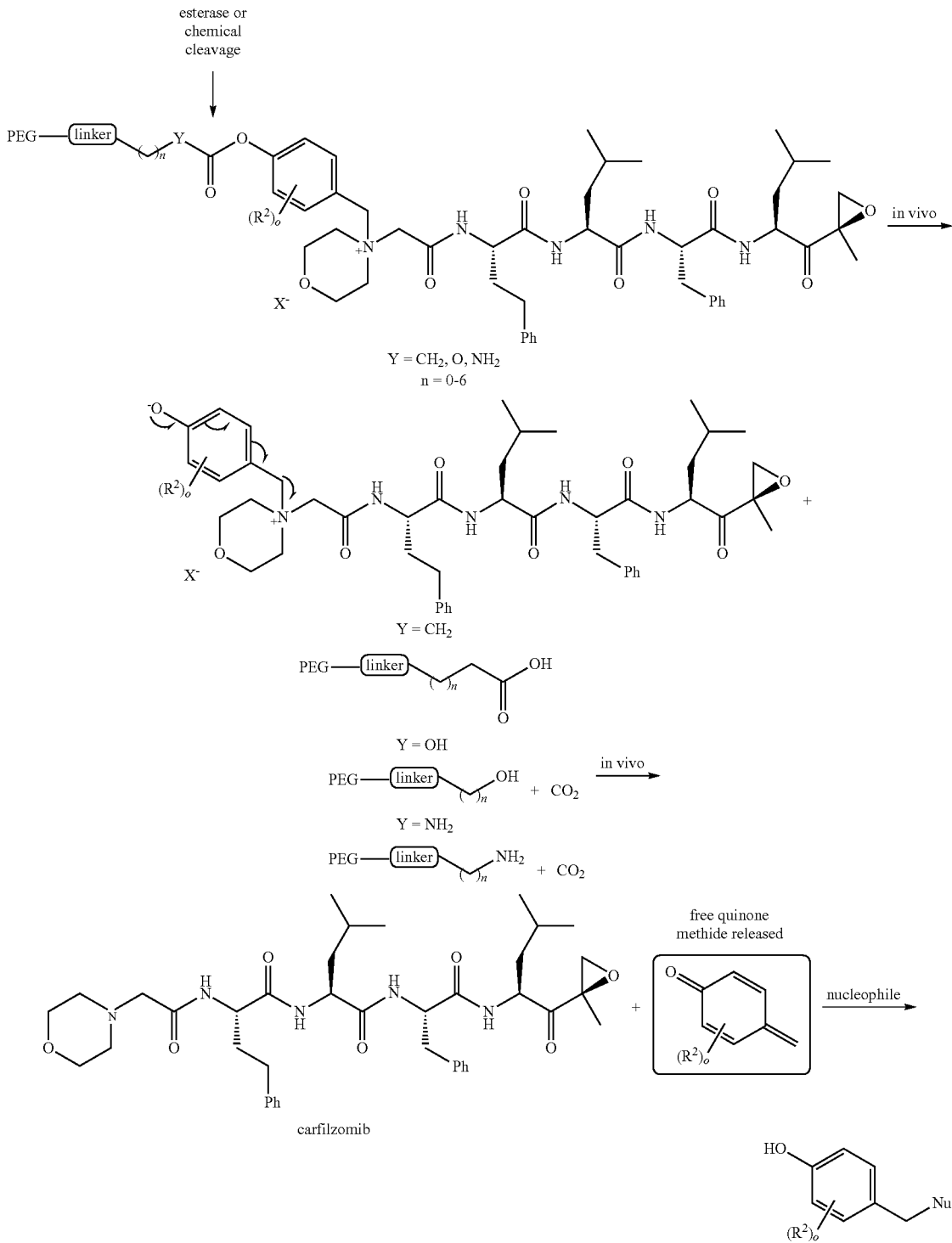

Scheme 2: Cleavage of previously described carfilzomib-polymer conjugates

Scheme 2 illustrates one metabolic pathway for the carfilzomib polymer compounds described in WO2014011695. Here, as illustrated above, the carfilzomib-polymer conjugates interact with an esterase enzyme or are subject to chemical attack as shown by the arrow. This attack results in the release of a free quinone methide (encapsulated above) upon ester hydrolysis. This methide intermediate is free to react further with cellular nucleophiles, which may possibly result in toxicity. The pegylated carfilzomib compounds of the present invention avoid this potentially toxic byproduct, as described in scheme 1.

Scheme 3: Two-step PEG polymer conjugation procedure

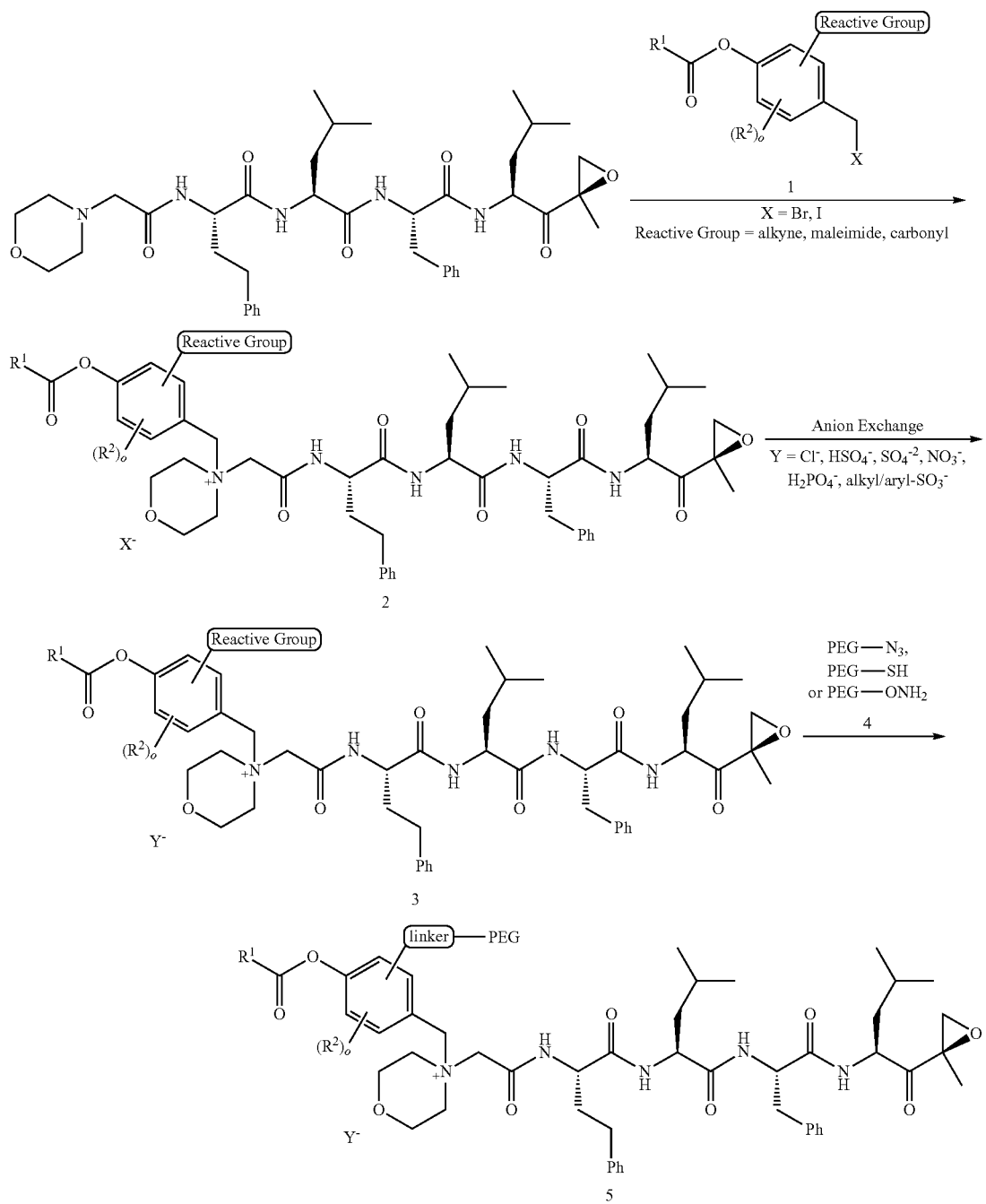

The carfilzomib-PEG compounds provided by the present invention are prepared in a two-step procedure, as shown in Scheme 3. Carfilzomib is first reacted with an appropriately substituted para-alkanoyloxy substituted benzyl halide (1) to give a quaternary salt intermediate (2). The quaternary salt bromide or iodide anion may be exchanged to a pharmaceutically acceptable anion such as bisulfate, sulfate, nitrate, dihydrogen phosphate or alkyl/aryl sulfonate via ion exchange resin to give intermediate (3). This intermediate is conveniently appended with a reactive group suitable for reaction with a complimentarily functionalized polymer reagent (4) to afford desired product 5. A large number of PEG reagents are commercially available in a range of molecular weights, architectures, end group chemistries, and number of reactive end groups (arms) (see Table 1). They may be directly compatible with the linker chemistries described in this disclosure or may require some further chemical manipulation by known methods. Branched chain and multi-arm PEGs may offer advantages over linear PEGs such as the potential for higher drug loading, improved stability, and/or lower formulation viscosities.

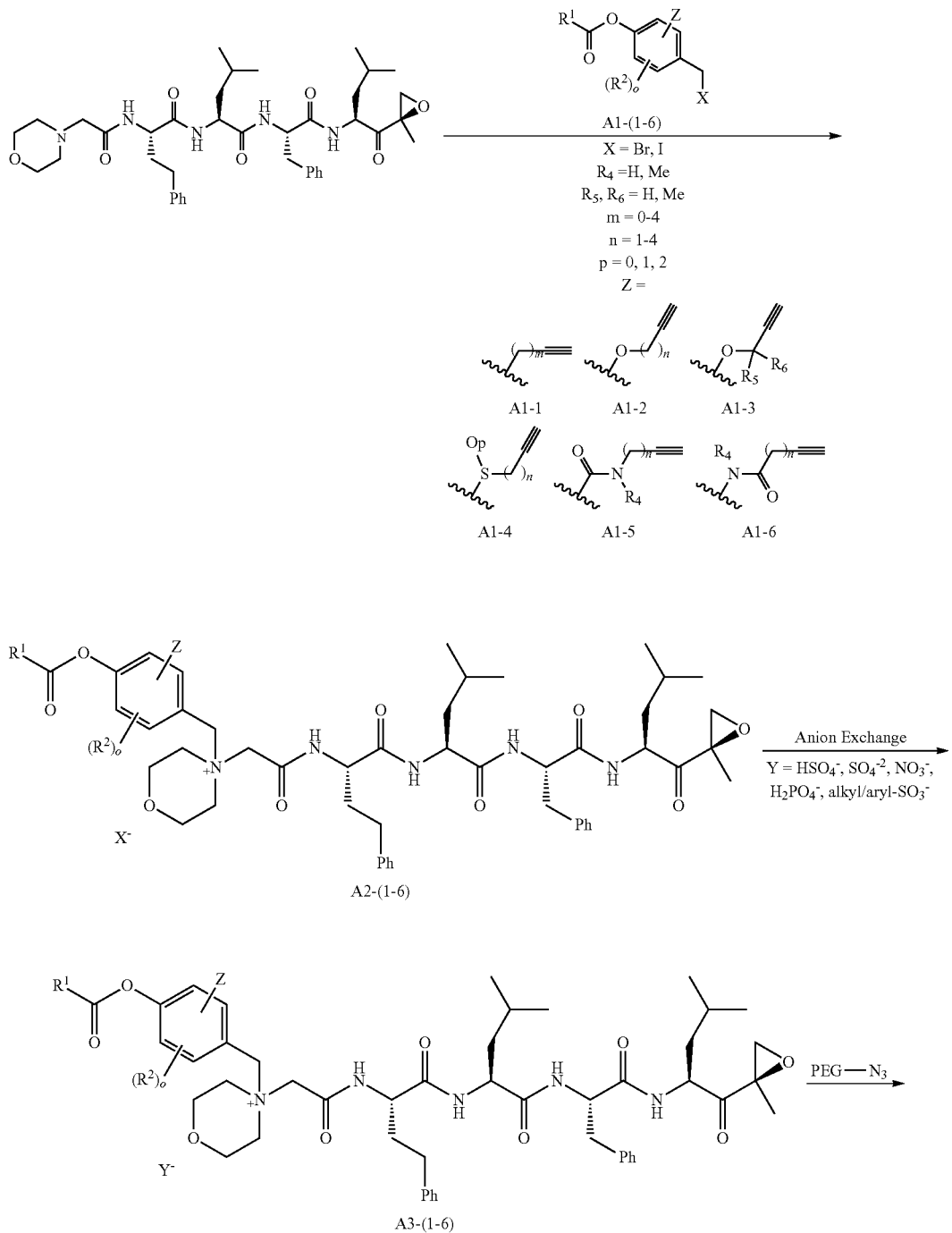

Scheme 4: Two-step polymer conjugation via azide/alkyne Click chemistry

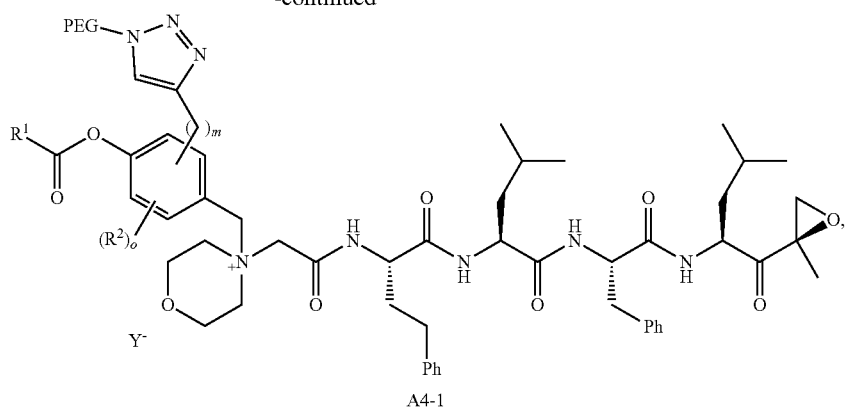
A4-1
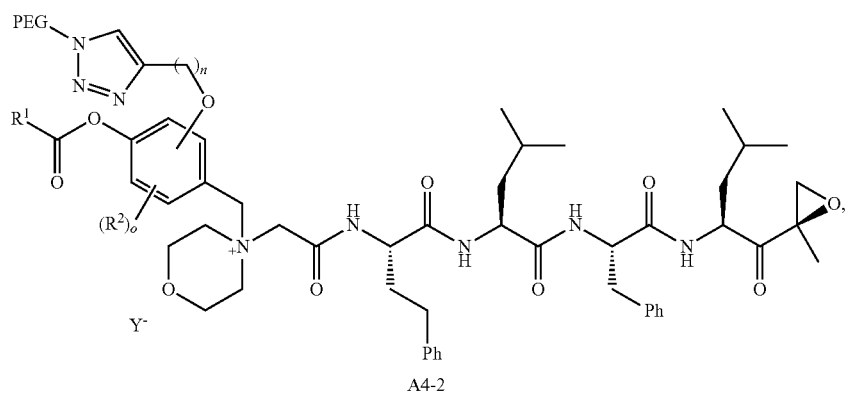
A4-2
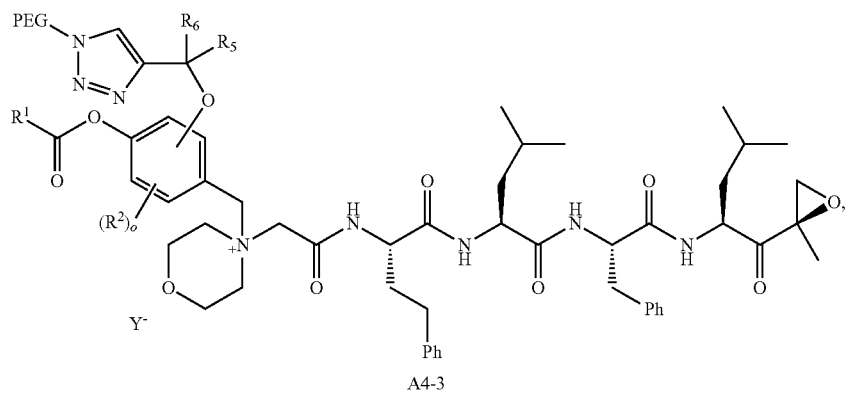
A4-3
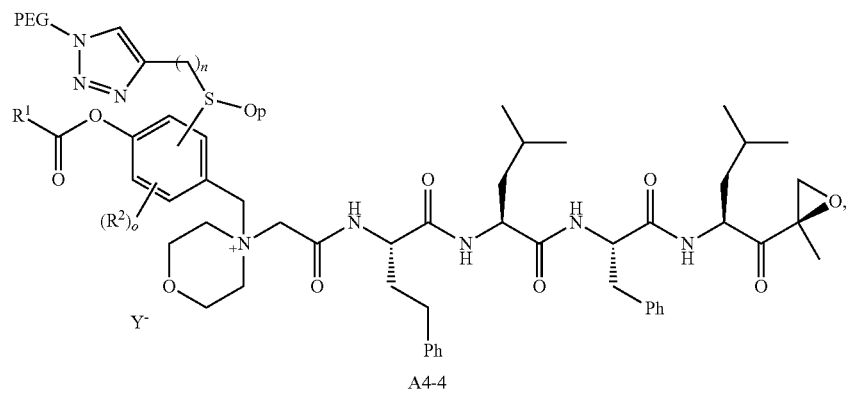
A4-4

-continued

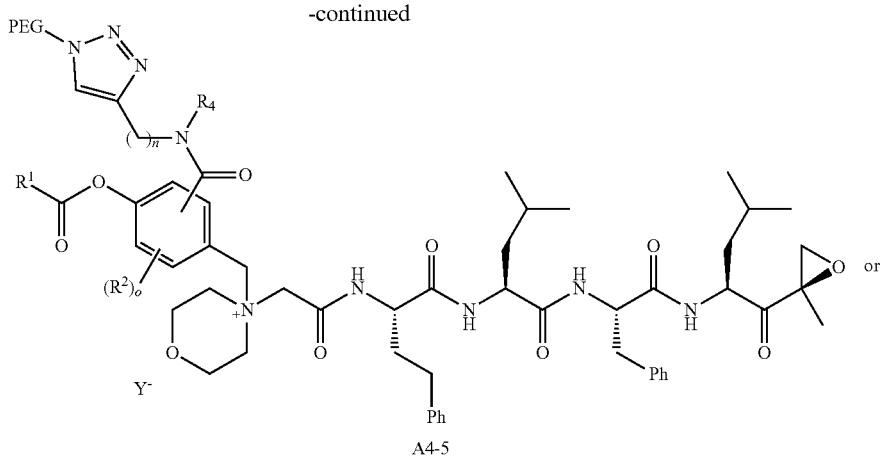

A4-5

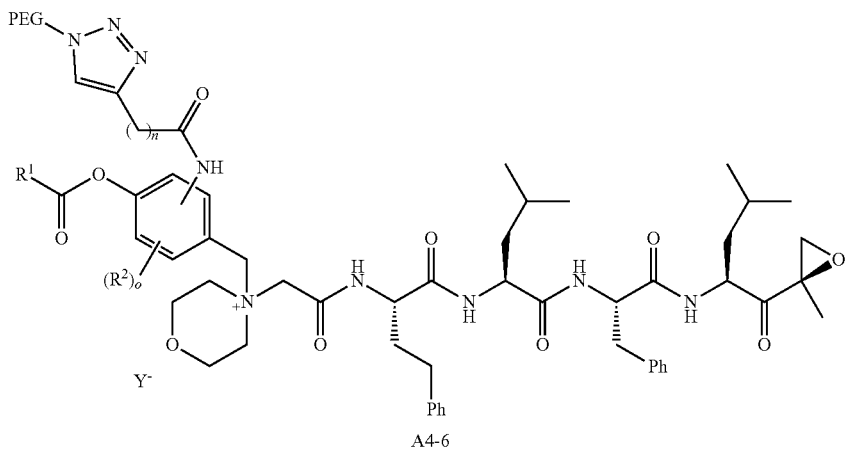

A4-6

Scheme 4 illustrates "Click" chemistries, such as Huisgen 1,3-dipolar azide/alkyne cycloaddition and aminooxy/aldehyde oximation that are particularly well suited for polymer and polymeric PEG attachments due to high chemical yields, inoffensive byproducts, large thermodynamic driving forces, and starting material availability.

Huisgen 1,3-dipolar azide/alkyne cycloaddition requires that the benzyl group be substituted with an alkyne group (A1-(1-6)) capable of reacting with an azide functionalized polymeric carrier such as PEG-Azide (—N$_3$) to give a 1,2,3-triazole linked conjugate (A4-(1-6)). The alkyne moiety may be directly linked or linked via an alkyl spacer (A1-1), linked via an ether (A1-2,3), thioether, sulfoxide or sulfone (A1-4) bond, or linked via an amide bond (A1-5,6). Many azido substituted PEG reagents are now commercially available in a wide variety of sizes and architectures, but also may be readily prepared from any available PEG-alcohol via activation by mesylation or tosylation followed by reaction with an azide salt. The cycloaddition reaction can be performed using commercially available cuprous salt catalysts, but works more efficiently using a mixture of copper (II) (e.g. copper (II) sulfate, copper (II) methanesulfonate) and a reducing agent (e.g. sodium ascorbate) to produce Cu (I) in situ. Since copper (I) is unstable in aqueous solution and in the presence of oxygen, stabilizing ligands such as tris-(benzyltriazolylmethyl)amine (TBTA), tris(3-hydroxypropyltriazolylmethyl)amine (THPTA), 2-[4-({bis[(1-tert-butyl-1H-1,2,3-triazol-4-yl)methyl]amino}methyl)-1H-1,2,3-triazol-1-yl]ethyl hydrogen sulfate (BTTES) or 2-[4-({bis[(1-tert-butyl-1H-1,2,3-triazol-4-yl)methyl]amino}methyl)-1H-1,2,3-triazol-1-yl]acetic acid (BTTAA) may be optionally added. The reaction can be run at RT or at an elevated temperature in a variety of solvents, and mixtures of water and a variety of miscible organic solvents including alcohols, DMSO. DMF, tBuOH and acetone. The final PEG-carfilzomib product (A4-(1-6)) may be conveniently worked up by dilution of the reaction mixture with water or brine, extraction with an organic solvent such as DCM, and reprecipitation from isopropanol or ether/isopropanol mixtures until product of desired purity is obtained. The exposure of intermediates or products to anions during workup procedures, such as chloride anions in brine, typically result in a mixture of anions in the final product, and a final anion exchange resin treatment may be necessary to ensure product salt homogeneity.

The intermediate quaternary halide salt (bromide or iodide. (A2-(1-6)) can be converted to an anion which does not precipitate with the copper (I) catalyst such as methanesulfonate, bisulfate or sulfate (A3-(1-6)) to achieve high reaction yields. In addition it may be desirable to exchange the halide anion to prevent opening of the epoxide and possible formation of bromohydrin or iodohydrin sideproducts.

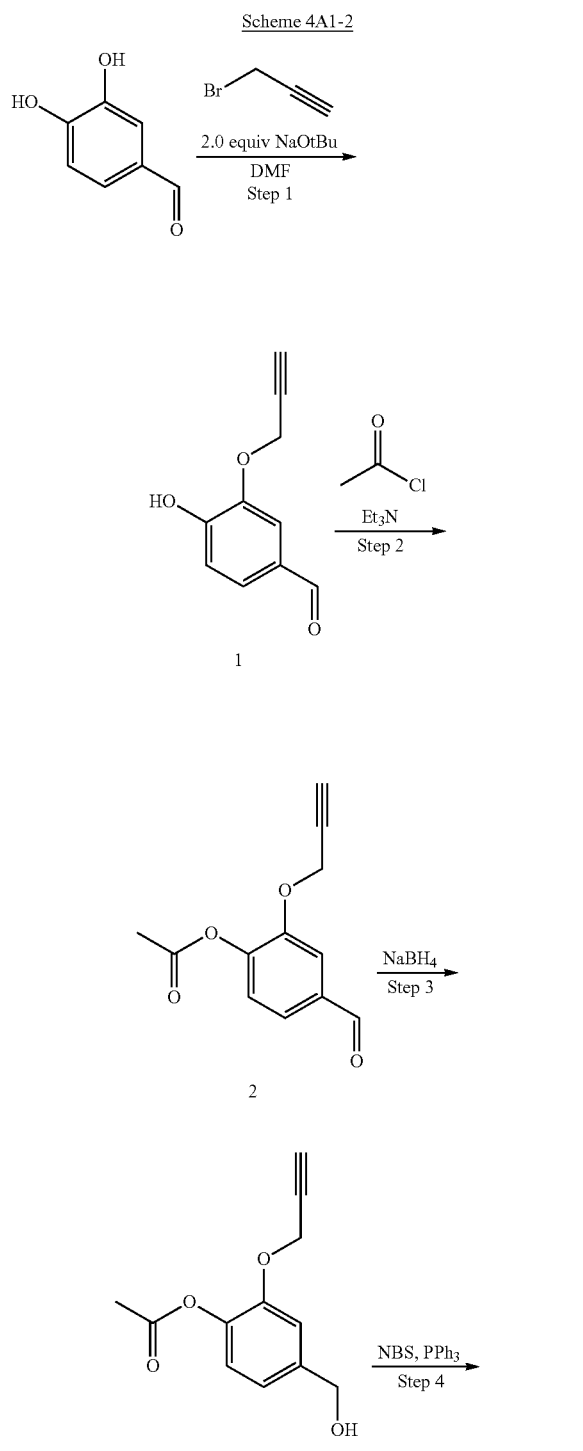

Synthesis of 4-(Bromomethyl)-2-(prop-2-ynyloxy) phenyl acetate(intermediate A1-2 in Scheme 4)

Step 1: 4-Hydroxy-3-(prop-2-ynyloxy)benzaldehyde (1)

To a mixture of NaOtBu in DMF (150 mL) was added 3,4-dihydroxybenzaldehyde (10 g, 72.5 mmol) in DMF (50 mL) at 20° C. The mixture was cooled with an ice bath and stirred while 3-bromoprop-1-yne (8.62 g, 72.5 mmol) was added portionwise, attempting to keep internal temperature between 15-20° C. The reaction mixture was stirred at RT for 2 hours. The mixture was diluted with water (300 mL) and extracted with EtOAc (200 mL×3). The combined organic layers were washed with water to remove DMF, dried over anhydrous $Na_2SO_4$, and concentrated to a brown solid. The residue was crystallized repeatedly from DCM/Petroleum Ether (30 mL/500 mL) to afford compound 1. 1H NMR (CDCl3, 300 MHz,): δ 9.87 (s, 1H), 7.54 (d, J=1.2 Hz, 1H), 7.49 (dd, J1=1.5 Hz, J2=8.1 Hz, 1H), 7.09 (d, J=8.1 Hz, 1H), 4.82 (m, 2H), 2.62 (m, 1H).

Step 2: 4-Formyl-2-(prop-2-ynyloxy)phenyl acetate (2)

To a solution of compound 1 (10.00 g, 56.82 mmol) in DCM (150 mL) was added $Et_3N$ (11.48 g, 113.64 mmol) followed by acetyl chloride (5.35 g, 68.18 mmol) at 0° C. The reaction mixture was stirred at RT for 2 hours. The mixture was washed with saturated 2N aqueous HCl (100 mL) and water (50 mL), dried over anhydrous $MgSO_4$, and concentrated to afford compound 2, which was used in the next step without further purification. $^1$H NMR ($CDCl_3$, 400 MHz): δ 9.96 (s, 1H), 7.63 (d, J=1.6 Hz, 1H), 7.54 (dd, $J_1$=1.6 Hz, $J_2$=8.0 Hz, 1H), 7.25 (d, J=8.0 Hz, 1H), 4.79 (d, J=2.4 Hz, 2H), 2.57 (t, J=2.4 Hz, 1H), 2.35 (s, 3H).

Step 3: 4-(Hydroxymethyl)-2-(prop-2-ynyloxy)phenyl acetate (3)

To a solution of compound 2 (12.00 g, 55.05 mmol) in DCM/MeOH (150 mL/15 mL) was added $NaBH_4$ (3.06 g, 82.57 mmol) in small portions at 0° C. The reaction mixture was stirred at RT for 30 min. The mixture was quenched by acetone (5 mL), and concentrated. The residue was purified by flash column chromatography on silica gel (Petroleum Ether/EtOAc=2:1) to afford compound 3. $^1$H NMR ($CDCl_3$, 400 MHz): δ 7.16 (d, J=1.6 Hz, 1H), 7.04 (d, J=8.0 Hz, 1H), 6.98 (dd, $J_1$=1.6 Hz, $J_2$=8.0 Hz, 1H), 4.72 (d, J=2.4 Hz, 2H), 4.69 (s, 2H), 2.53 (t, J=2.4 Hz, 1H), 2.32 (s, 3H).

Step 4: 4-(Bromomethyl)-2-(prop-2-ynyloxy)phenyl acetate (4)

To a solution of compound 3 (11.50 g, 52.27 mmol) in DCM (150 mL) were added $PPh_3$ (20.50 g, 78.41 mmol) and NBS (11.04 g, 62.73 mmol) at 0° C. The reaction mixture was stirred at room temperature for 0.5 hour. An excess of solvent was concentrated and the residue was purified by flash column chromatography on silica gel (Petroleum Ether/EtOAc=20:1) to afford compound 4 (7.82 g, 53% yield). $^1$H NMR ($CDCl_3$, 400 MHz): δ 7.14 (m, 1H), 7.02 (m, 2H), 4.73 (d, J=2.4 Hz, 2H), 4.48 (s, 2H), 2.55 (t, J=2.4 Hz, 1H), 2.32 (s, 3H).

Scheme 5: Quaternary salt anion exchange

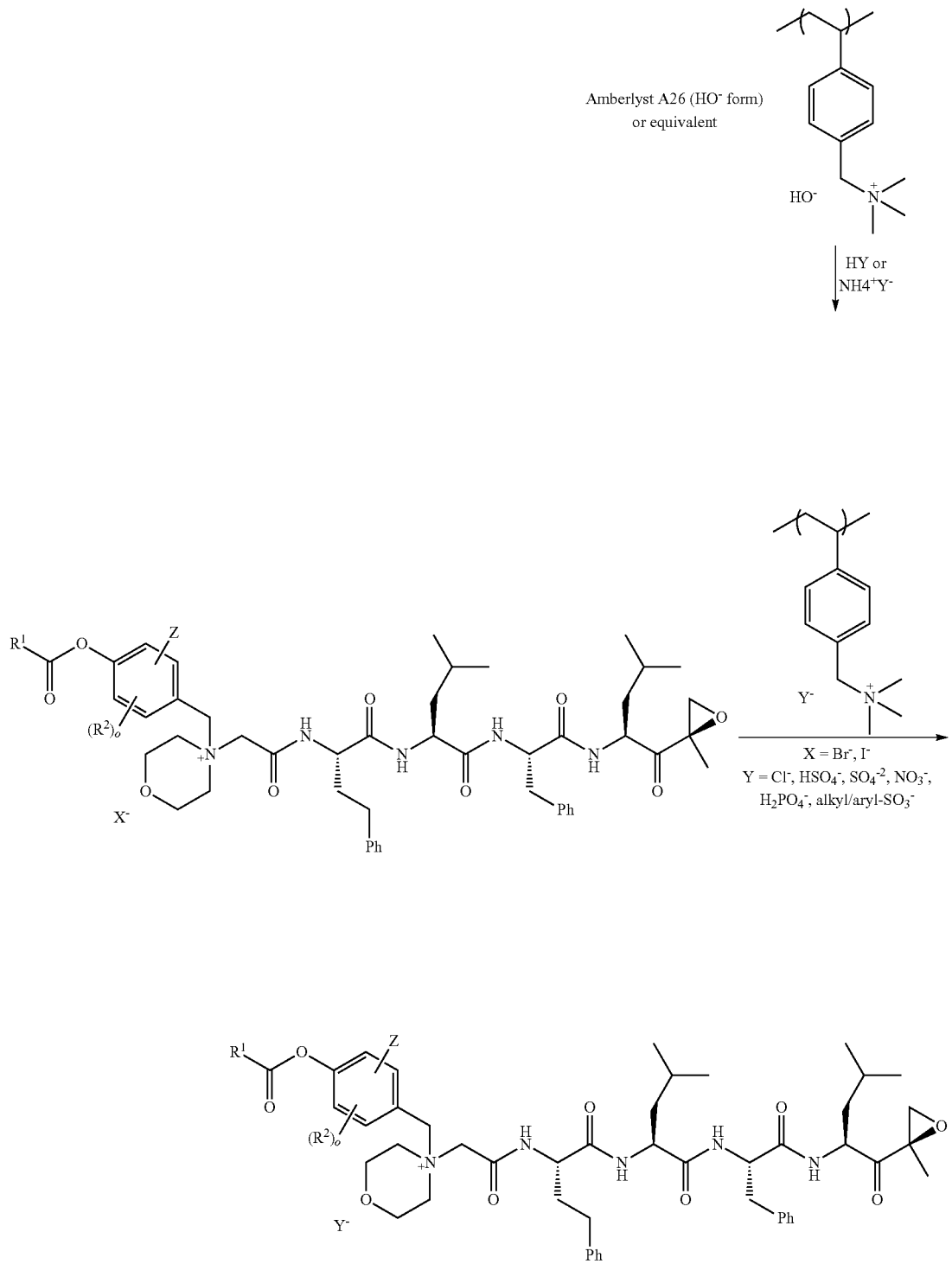

Ion exchange may be accomplished by reaction of the intermediate quaternary halide with a silver salt or more practically, passage through an ion exchange resin, as shown in Scheme 5. The carfilzomib quaternary salt anion present in intermediates or final products may be efficiently converted to a different strong acid anion such as bisulfate, sulfate, dihydrogen phosphate, nitrate or alkyl/aryl sulfonate via anion exchange resin. An anion exchange resin such as Amberlyst A26 (OH⁻ form) is pretreated with the desired acid or ammonium salt, and then the quaternary halide salt is passed through. Conjugates prepared from weak acid anions such as acetate, formate or lactate are unstable due to the increased basicity of the quaternary salt and incompatibility with the ester trigger group.

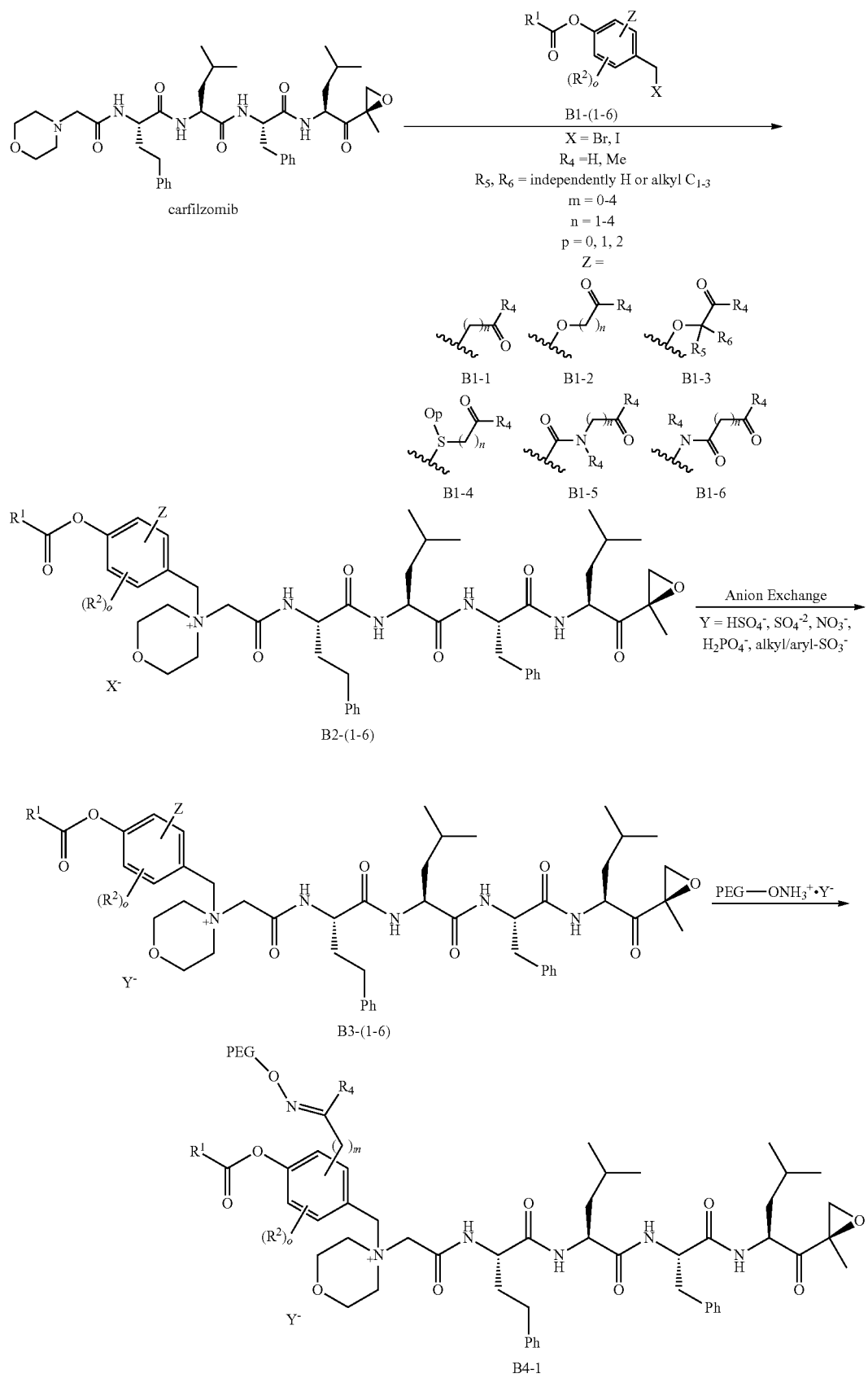

-continued
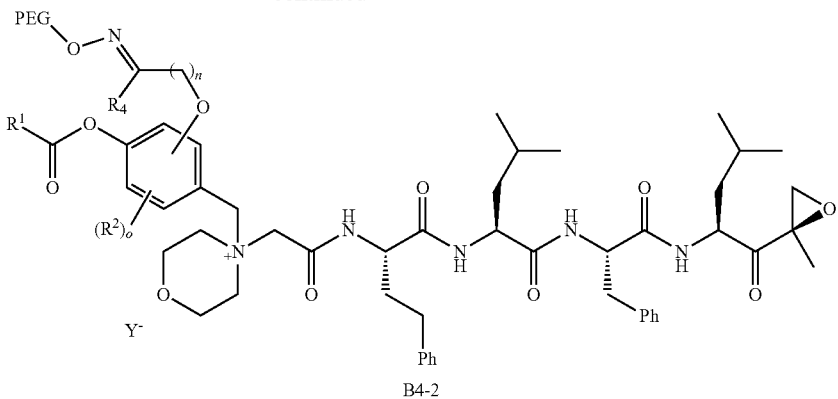
B4-2
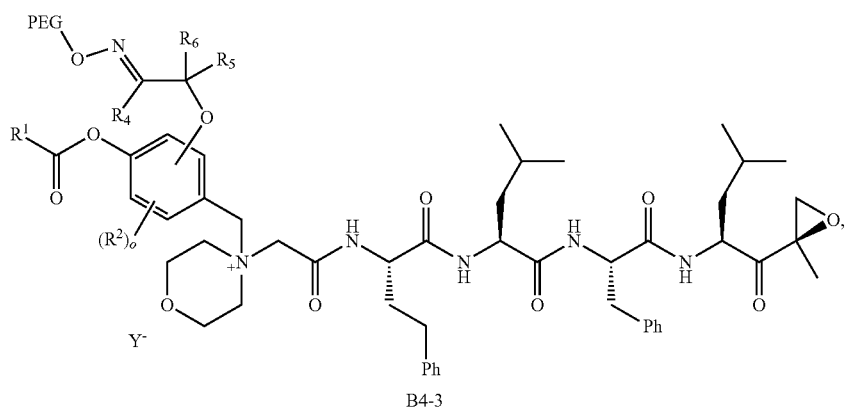
B4-3
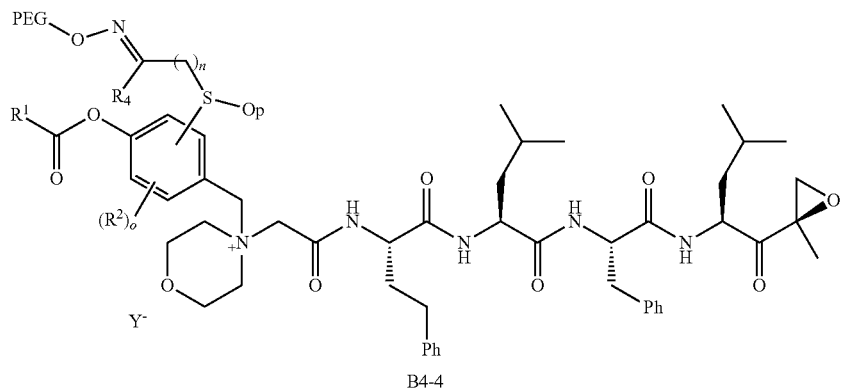
B4-4
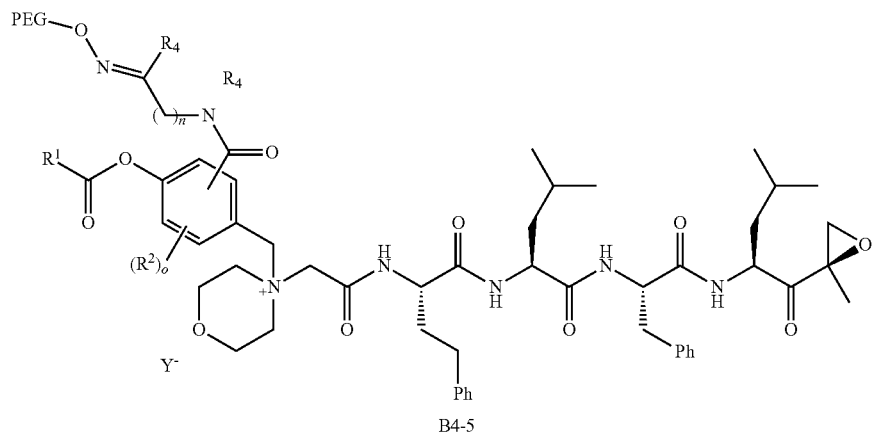
B4-5

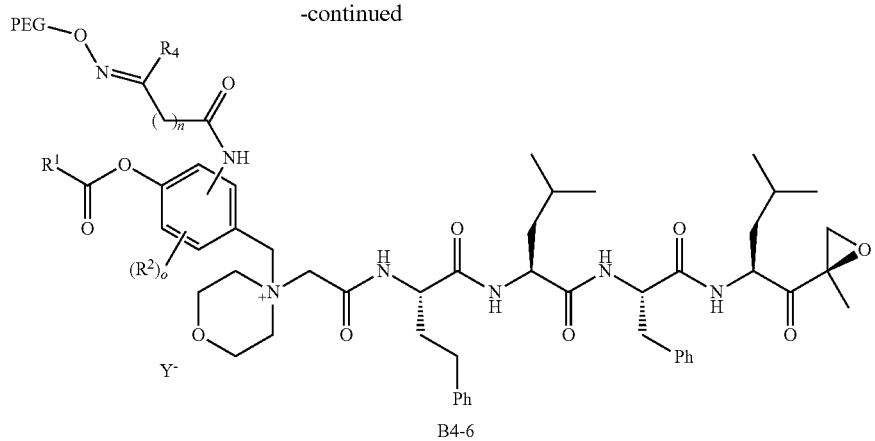

B4-6

Alternatively, the benzyl group (B1-(1-6)) may be substituted with a carbonyl (aldehyde or ketone) group which is capable of reacting with an aminooxy functionalized polymeric carrier such as PEG-aminooxy (—ONH$_2$) to provide a stable oxime linked conjugate (B4-(1-6)). The carbonyl moiety may be directly linked or linked via an alkyl spacer (B1-1), linked via an ether (B1-2,3), thioether, sulfoxide or sulfone (B1-4) bond, or linked via an amide bond (B1-5,6). Carfilzomib and benzyl halide (B1-(1-6)) are allowed to react at RT or at an elevated temperature in a suitable organic solvent such as acetonitrile to provide quaternary intermediate (B2-(1-6)) as a bromide or iodide salt. It is desirable to exchange this halide anion to prevent opening of the epoxide and possible formation of bromohydrin or iodohydrin side-products. Anion exchange may be accomplished by reaction of the intermediate quaternary halide with a silver salt or more practically, passage through an ion exchange resin as described previously (Scheme 5). The carfilzomib quaternary salt intermediate (B3-(1-6)) and the PEG-ONH$_3^+$Y$^-$ polymer reagent are then allowed to react at RT or at an elevated temperature in a suitable organic such as DCM or a mixed aqueous organic solvent. Oximation catalysts such as aniline, p-phenylenediamine, or 5-methoxyanthranilic acid may be optionally added but are not usually necessary. Note that the carfilzomib quaternary salt intermediate (B3-(1-6)) and PEG-aminooxy reagent anion salts are identical to obviate the formation of a mixed anion salt final product and the need for any further anion manipulation. The final PEG-carfilzomib product may be conveniently worked up by evaporation of the reaction solvent and re-precipitation of the residue from isopropanol or ether/isopropanol mixtures until product of desired purity is obtained.

Scheme 7: Synthesis of PEG-Aminooxy reagents

A.

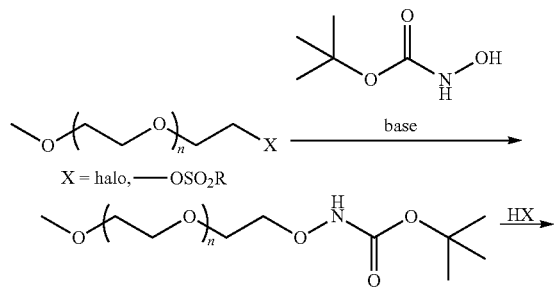

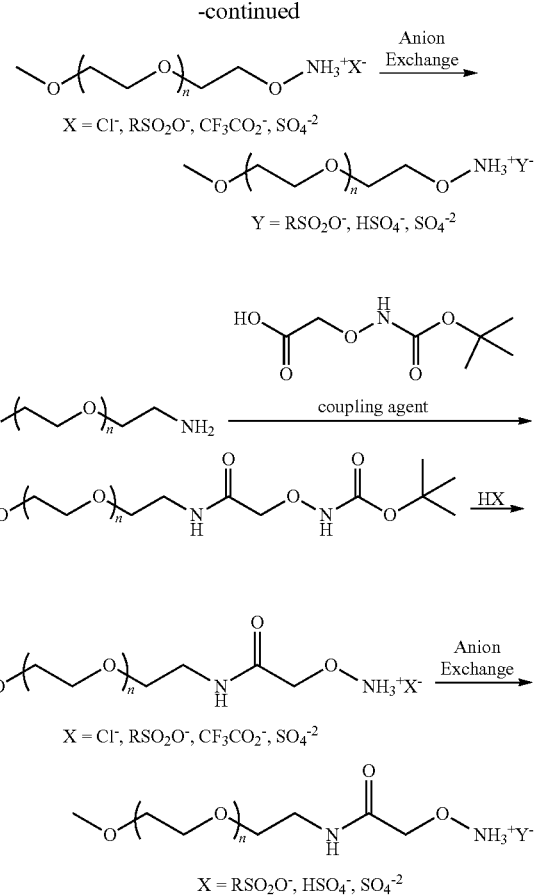

PEG-Aminooxy reagents may be commercially available or readily prepared from mesyl or tosyl activated PEG-Alcohols, PEG-Halides (A) or PEG-Amine (B) starting materials, as depicted in Scheme 7. The tert-butyloxycarbonyl protected intermediate may be deprotected with a strong acid such as hydrogen chloride, methanesulfonic acid, trifluoroacetic acid, or sulfuric acid to give the PEG-Aminooxy reagent as a chloride, trifluoroacetate or sulfate salt. The PEG-Aminooxy reagent anion may be optionally exchanged for a different anion via anion exchange resin.

Scheme 8: Oxime isomers

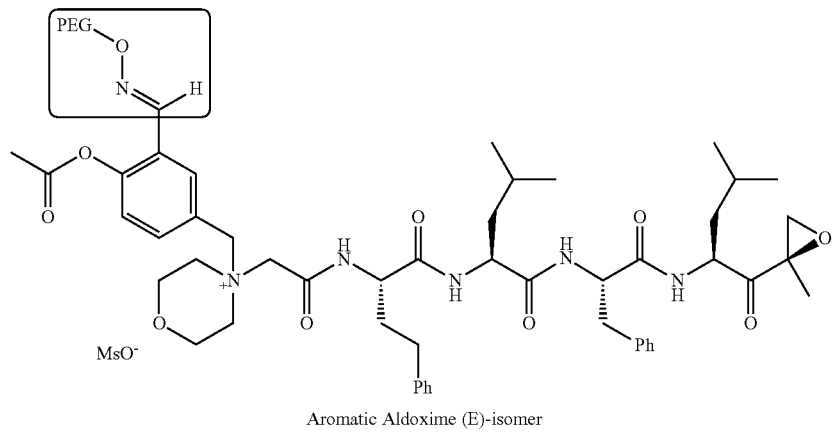

Aromatic Aldoxime (E)-isomer

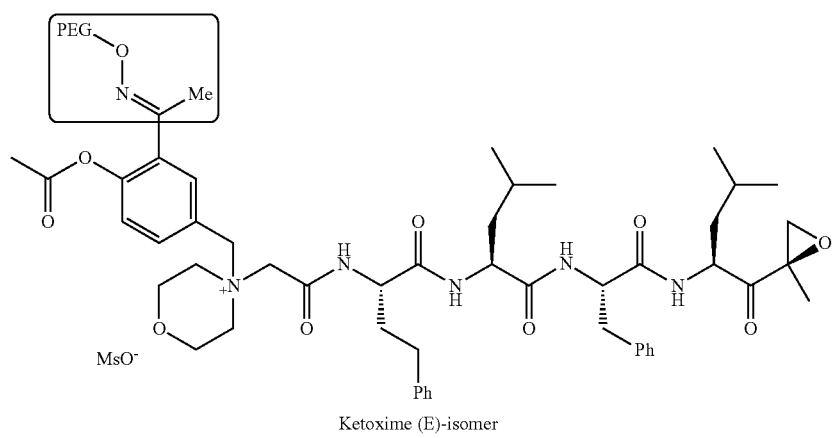

Ketoxime (E)-isomer

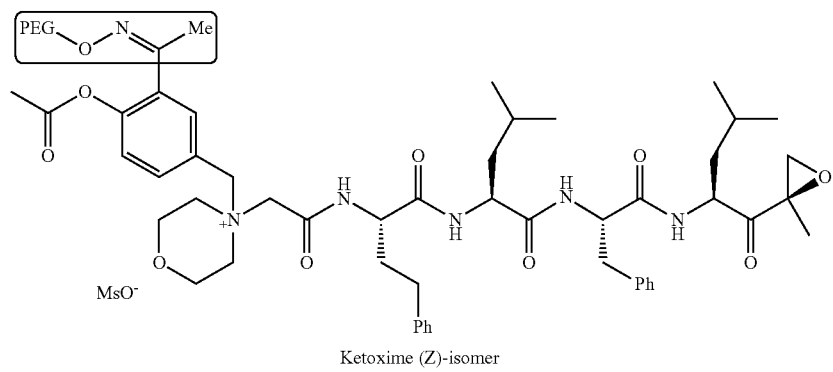

Ketoxime (Z)-isomer

It is readily understood by persons of ordinary skill in the art that oximes may exist as two geometric isomers: a syn (Z)-isomer and an anti (E)-isomer, as depicted in Scheme 8. Many of the examples in this disclosure are aromatic aldoximes and exist only as (E)-isomers. Non-aromatic aldoximes and ketoximes can usually be completely separated and obtained as a (Z)-isomer and an (E)-isomer. The pegylated non-aromatic aldoximes and ketoximes described in this invention may exist as separate (Z) and (E)-isomers or as a mixture of (Z) and (E)-isomers.

Scheme 9: Direct polymer conjugation to form quaternary salt

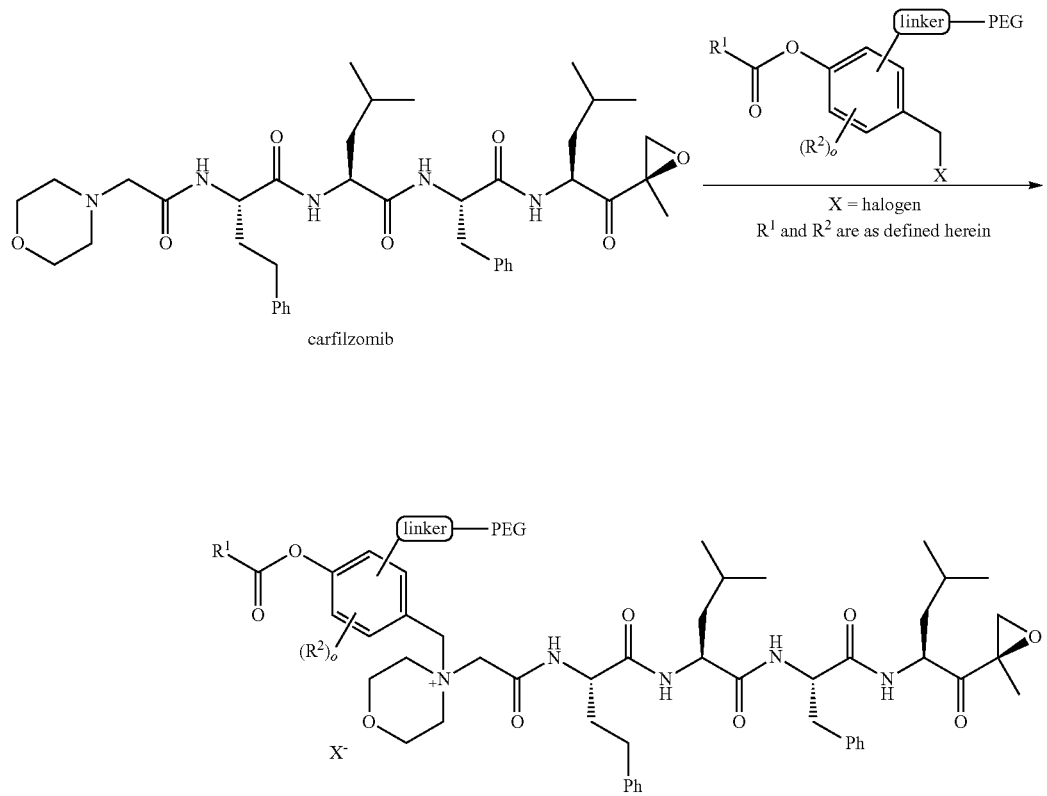

Alternatively, the carfilzomib-polymer conjugates described in this invention may be prepared in a one-step reaction of carfilzomib and a para-alkanoyloxy substituted benzyl halide pre-appended with the desired polymer chain, as shown in Scheme 9. The polymer chain may be appended via a wide variety of known chemistries or the alkyne/azide or carbonyl/aminooxy chemistries described previously. This route may be less desirable due to the difficulty in separating PEG containing products from unreacted pegylated starting materials.

Representative Examples of the Invention

The following pegylated carfilzomib compounds are representative examples of the invention and are not intended to be construed as limiting the scope of the present invention. The pegylated carfilzomib compounds were prepared using the following two general PEG linking methods (A and B).

PEG Triazole-Linker Method A

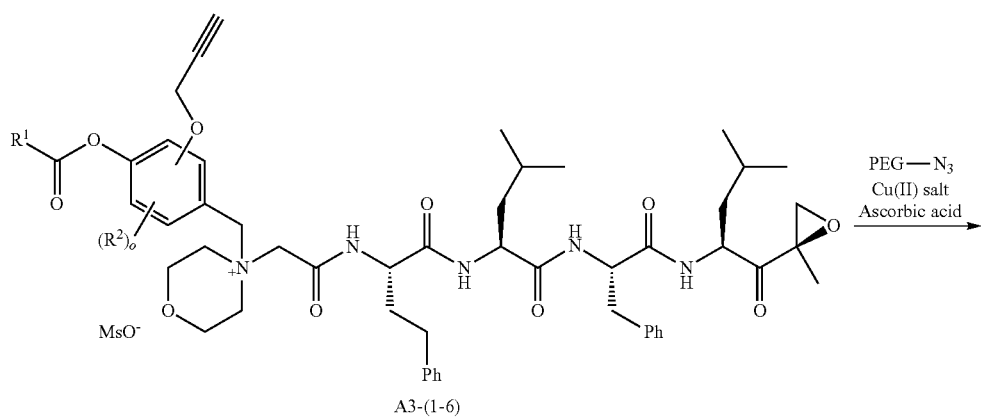

A3-(1-6)

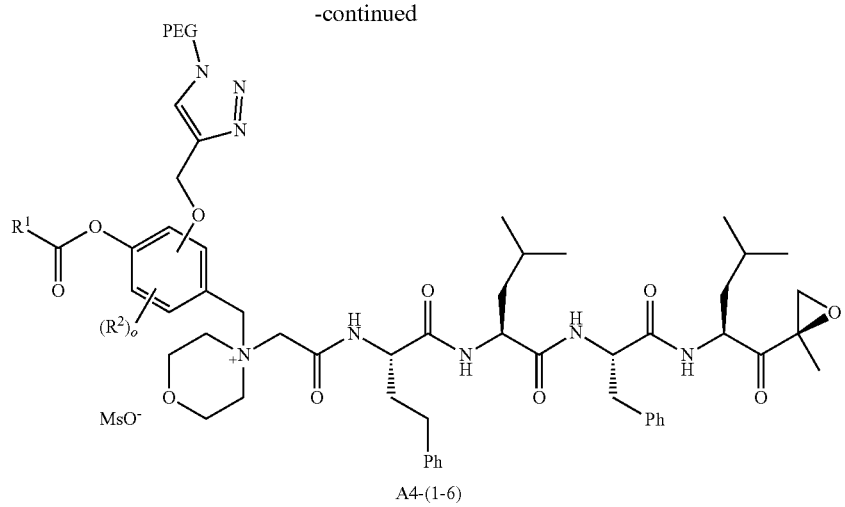

A4-(1-6)

Carfilzomib quaternary salt intermediate A3-(1-6) (1.5 eq). PEG-Azide (1 eq) and (L)-ascorbic acid (0.75 eq) were mixed in DMF (50 mL/mmol PEG-Azide) to give a cream-colored suspension. The mixture was stirred vigorously for 5 minutes and a solution of copper (II) sulfate pentahydrate (0.3 eq) in water (10 mL/mmol PEG-Azide) added rapidly dropwise. The reaction darkened immediately to a yellowish-brown color and the suspension turned clear within 5 min. After 1 hour, a second portion of ascorbic acid (0.75 eq) was added and the reaction mixture stirred for 60 minutes. A third portion of ascorbic acid (0.38 eq) was added and the reaction mixture stirred overnight at RT. Water (100 mL/mmol PEG-Azide) and NaCl (15 g/mmol PEG-Azide) were added and the mixture stirred until the NaCl dissolved. The product was extracted with DCM (3×35 mL/mmol PEG-Azide). The extract was dried over anhydrous sodium sulfate, filtered, and concentrated under vacuum at 40° C. The residue was dissolved in isopropanol (125 mL/mmol PEG-Azide) at 40° C. Once the solids dissolved completely, diethyl ether (90 mL/mmol PEG-Azide) was added and the solution cooled in an ice bath. The resulting solid was filtered and the filter cake washed with 2-propanol and diethyl ether each twice. The filter cake was dissolved in DCM and concentrated under vacuum. The residue was dissolved in warm (40° C.) isopropanol (200 mL/mmol PEG-Azide) and then allowed to cool in an ice bath. The resulting solid was filtered and the filter cake washed with 2-propanol and diethyl ether each twice and then dried under vacuum.

PEG Oxime-Linker Method B

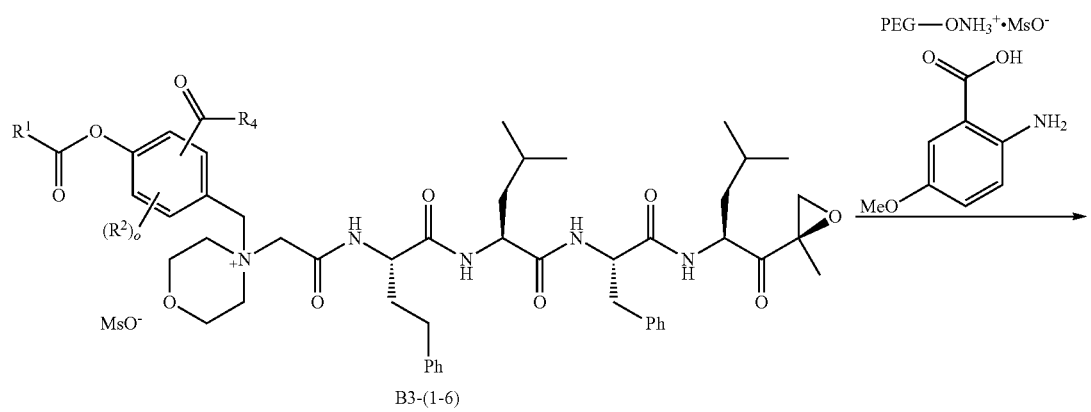

B3-(1-6)

-continued

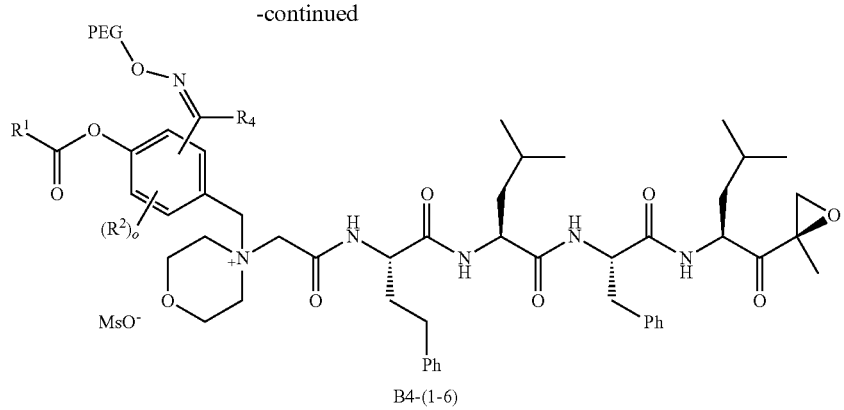
B4-(1-6)

Carfilzomib quaternary salt intermediate B3-(1-6) (1 eq). PEG-ONH$_3^+$MsO$^-$ (0.8 eq) and 5-methoxyanthranilic acid (oximation catalyst, 0.3 eq) in DCM (15 mL/mmol B3-(1-6)) were stirred at RT until complete consumption of the PEG reagent was observed by HPLC (ELS detector). The reaction mixture was evaporated to dryness and the residue dissolved in isopropanol (15 mL/mmol B3-(1-6)) at 40° C. The clear solution was cooled to RT and ether (5 mL/mmol B3-(1-6)) added to induce crystallization. The mixture was cooled in an ice bath for 5-10 minutes and the formed solid collected by filtration. Recrystallization from isopropanol/ether was repeated one or two more times until all the unreacted carfilzomib quaternary salt intermediate B3-(1-6) was removed as detected by HPLC. The final solid was dried under vacuum at 30° C. Typical yields: 60-80%; Typical reaction times: 10-30 min for intermediates containing an aldehyde function, 24 h for intermediates with a ketone function.

Examples of PEG-Carfilzomib compounds prepared, PEG architecture and PEG linker methodology are listed in Table 2. Table 2 further includes the size and weight (Daltons) of the PEG adduct and method used to append the PEG moiety to the carfilzomib backbone.

TABLE 2

| Example | Structure | PEG Size/Arms | PEG Linker Method |
|---|---|---|---|
| 1 | (structure with PEG$_{20K}$) | 20K/4 | A |
| 2 | (structure with PEG$_{5K}$) | 5K/1 | A |

TABLE 2-continued
| Example | Structure | PEG Size/ Arms | PEG Linker Method |
|---|---|---|---|
| 3 | 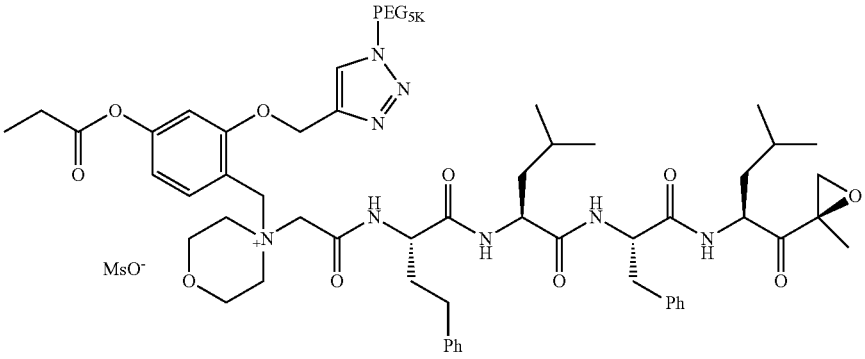 | 5K/1 | A |
| 4 | 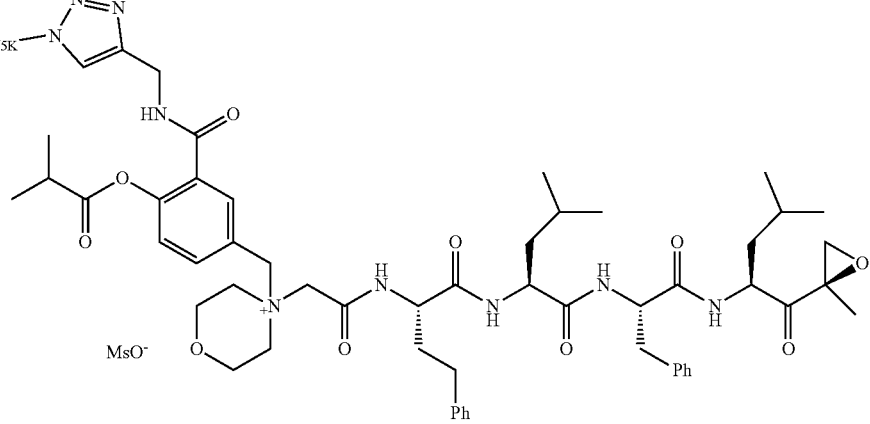 | 5K/1 | A |
| 5 | 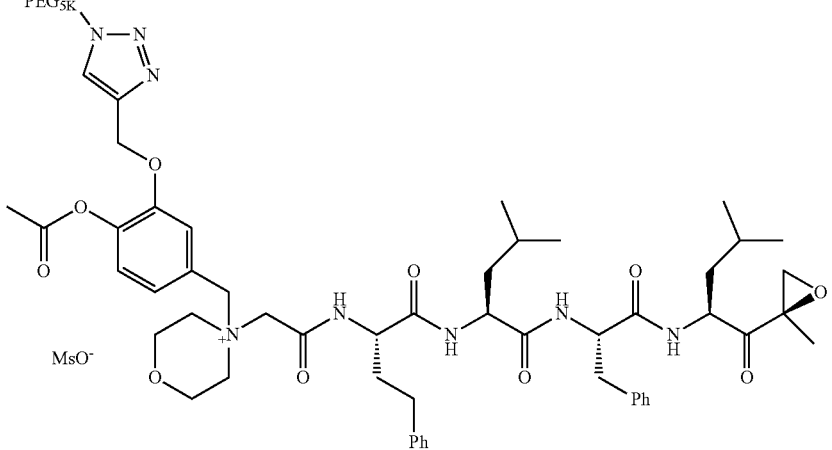 | 5K/1 | A |

TABLE 2-continued

| Example | Structure | PEG Size/Arms | PEG Linker Method |
|---|---|---|---|
| 6 | 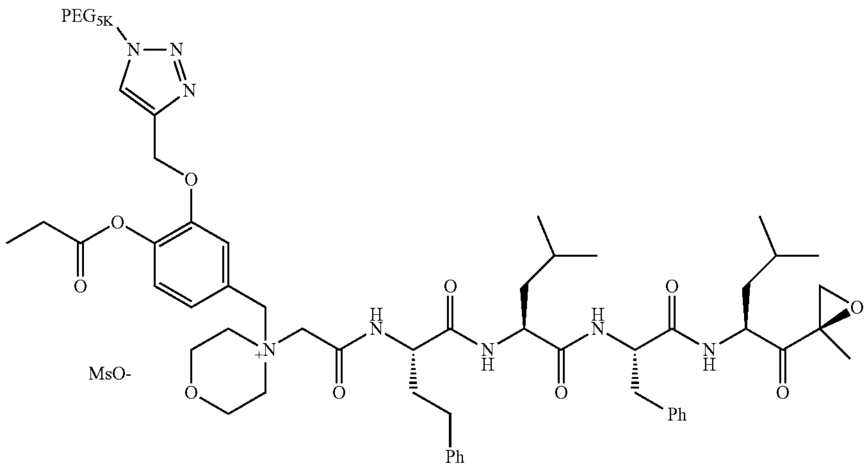 | 5K/1 | A |
| 7 | 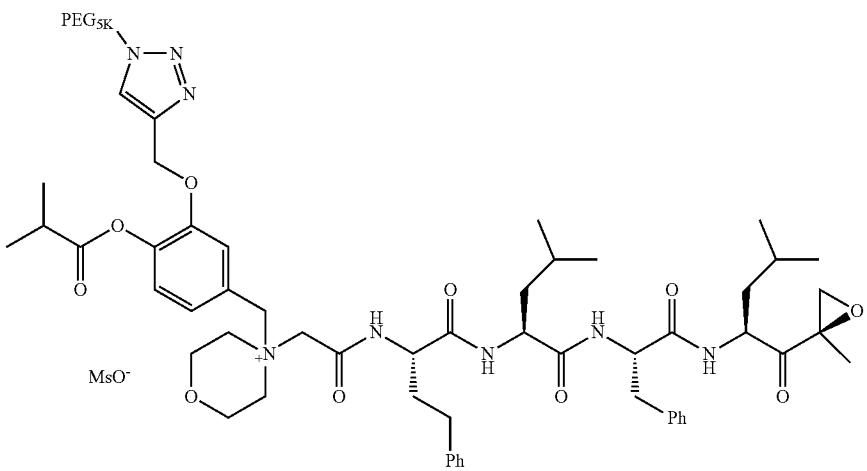 | 5K/1 | A |
| 8 | 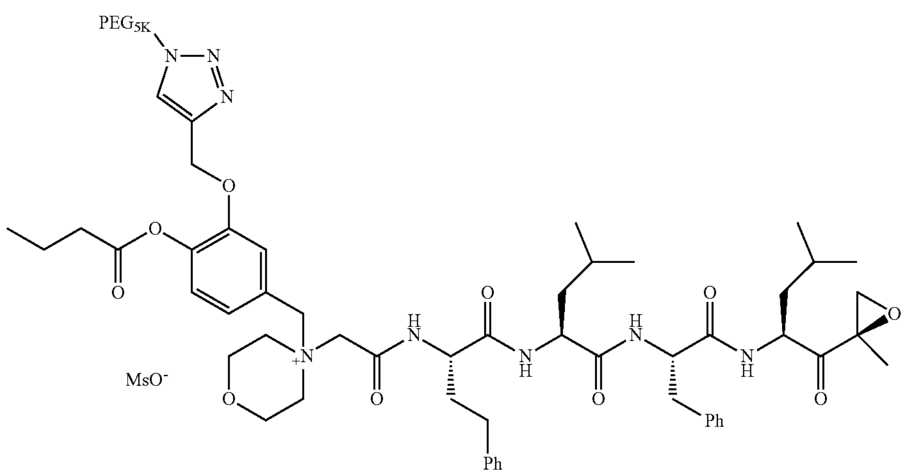 | 5K/1 | A |

TABLE 2-continued
| Example | Structure | PEG Size/ Arms | PEG Linker Method |
|---|---|---|---|
| 9 | 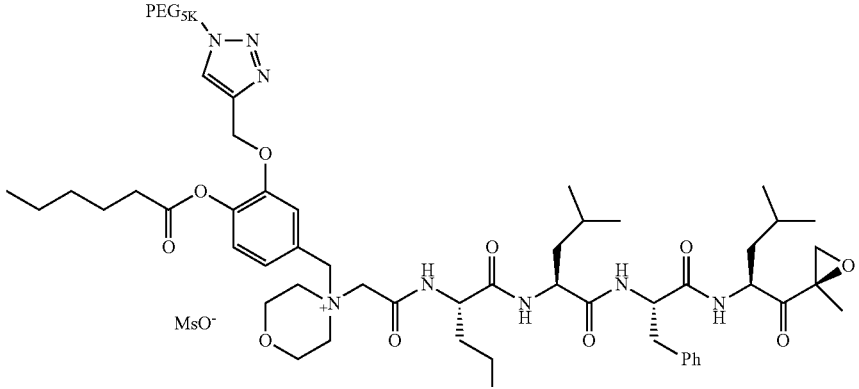 | 5K/1 | A |
| 10 | 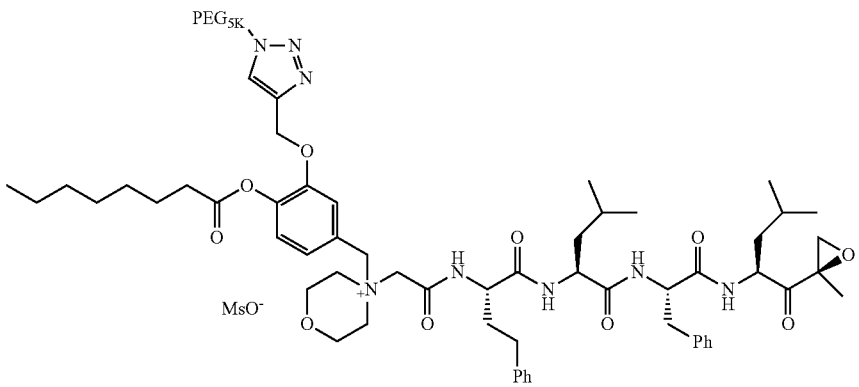 | 5K/1 | A |
| 11 | 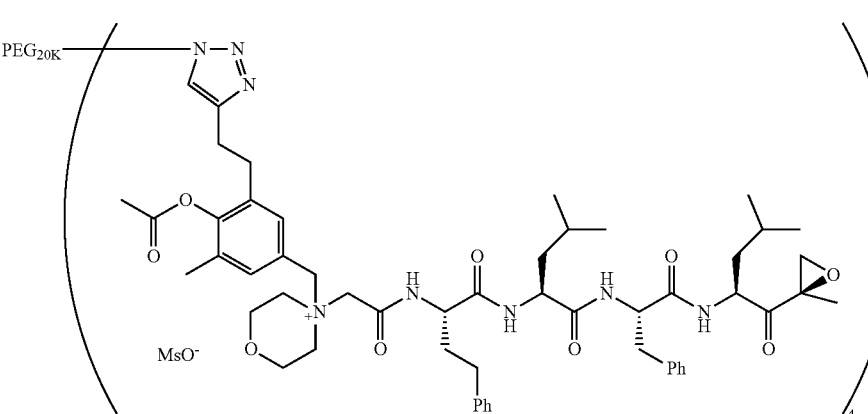 | 20K/4 | A |

TABLE 2-continued
| Example | Structure | PEG Size/Arms | PEG Linker Method |
|---|---|---|---|
| 12 | 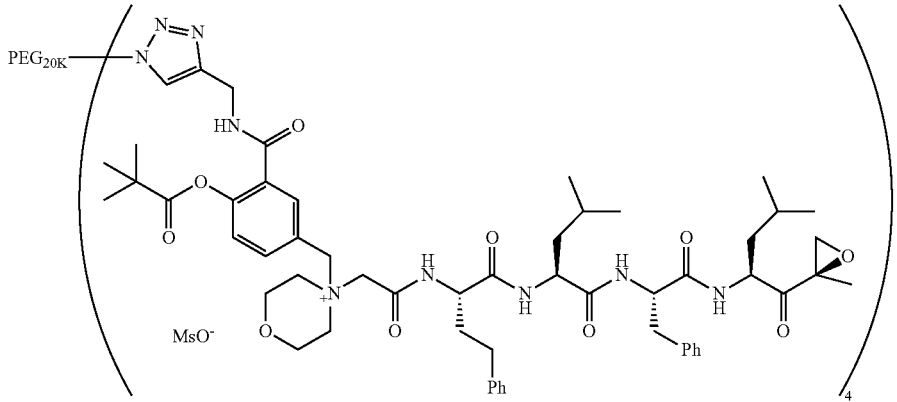 | 20K/4 | A |
| 13 | 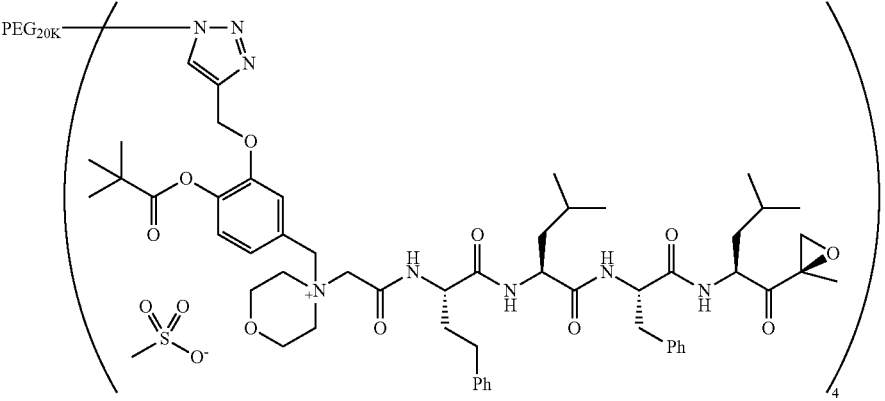 | 20K/4 | A |
| 14 | 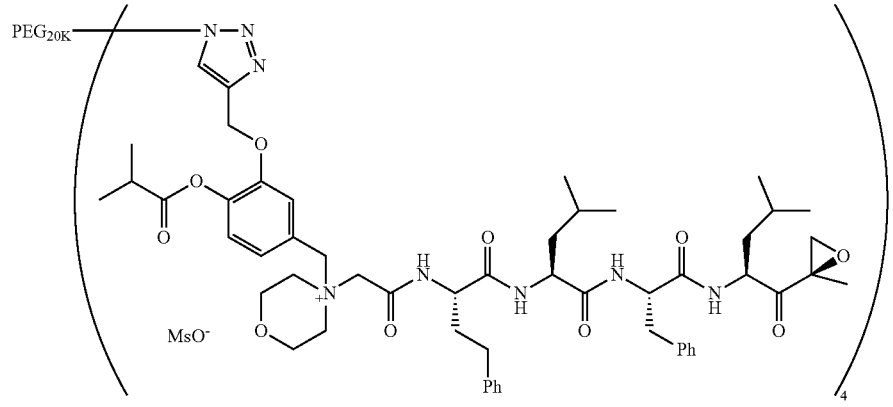 | 20K/4 | A |
| 15 | 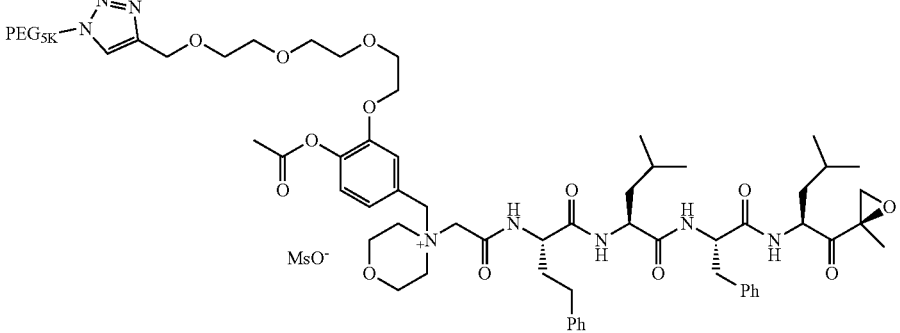 | 5K/1 | A |

TABLE 2-continued
| Example | Structure | PEG Size/Arms | PEG Linker Method |
|---|---|---|---|
| 16 | 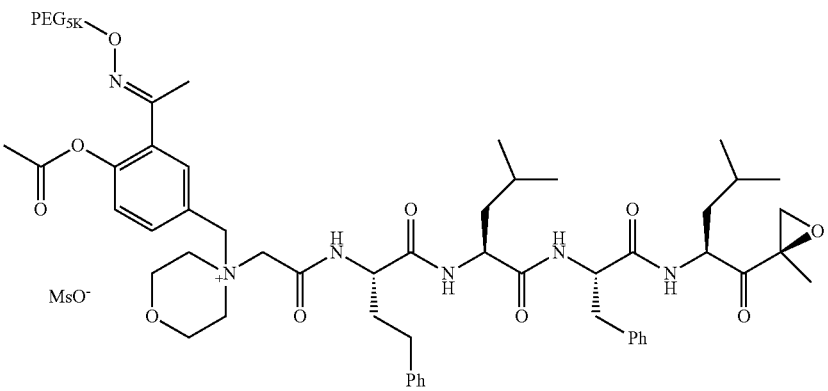 | 5K/1 | B |
| 17 | 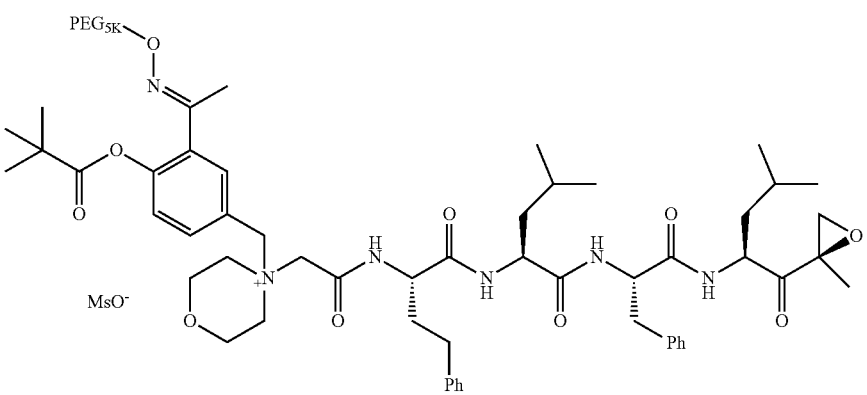 | 5K/1 | B |
| 18 | 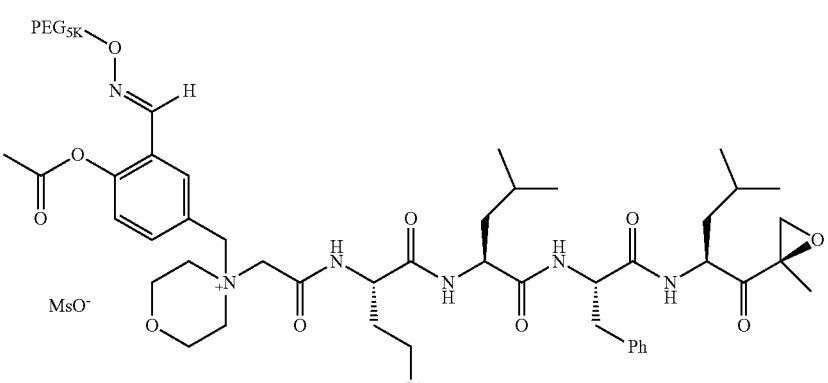 | 5K/1 | B |

TABLE 2-continued
| Example | Structure | PEG Size/Arms | PEG Linker Method |
|---|---|---|---|
| 19 | 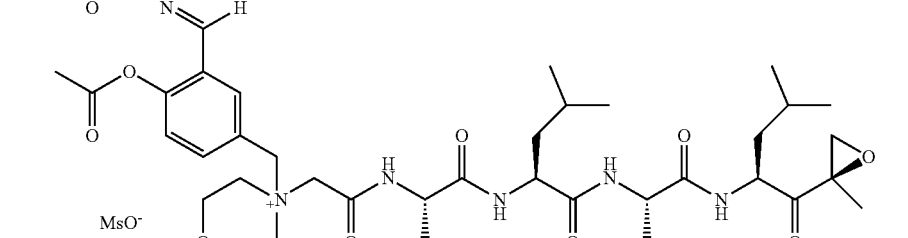 | 5K/1 | B |
| 20 | 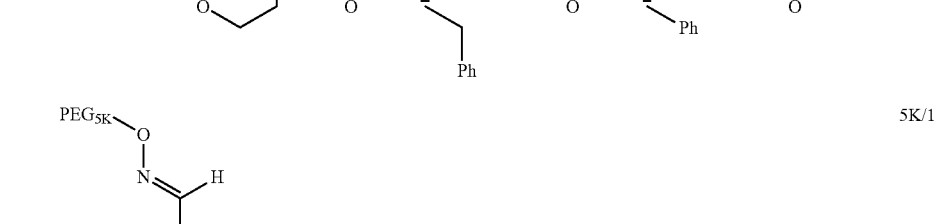 | 5K/1 | B |
| 21 | 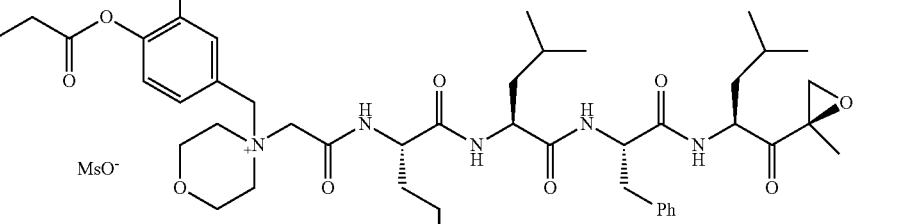 | 2K/1 | B |
| 22 | 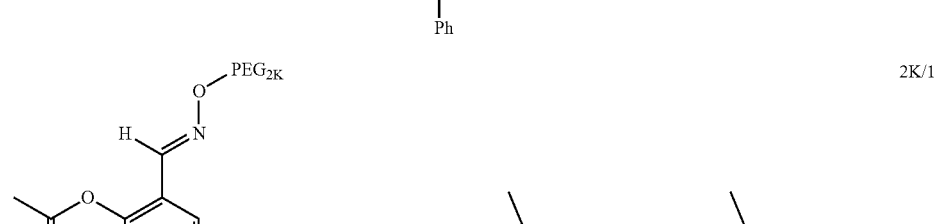 | 2K/1 | B |

TABLE 2-continued

| Example | Structure | PEG Size/Arms | PEG Linker Method |
|---|---|---|---|
| 23 | 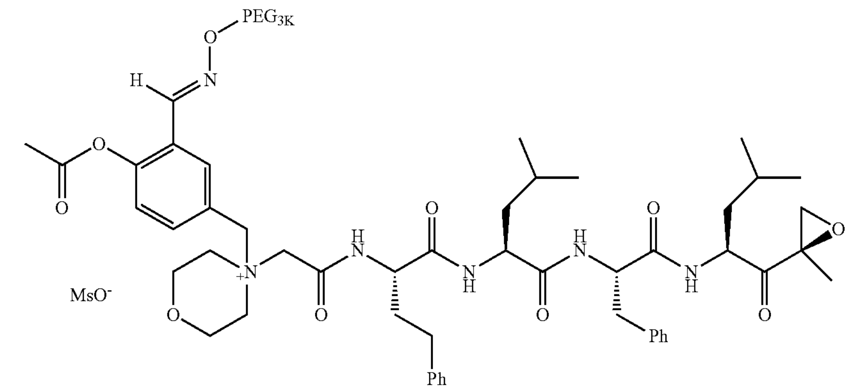 | 3K/1 | B |
| 24 | 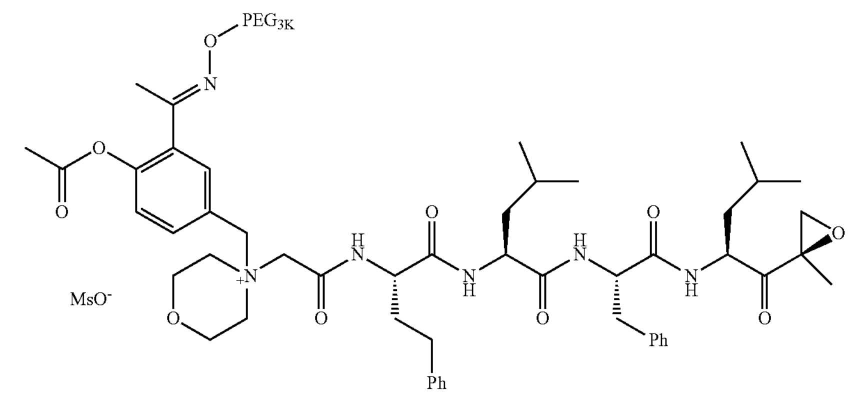 | 3K/1 | B |
| 25 | 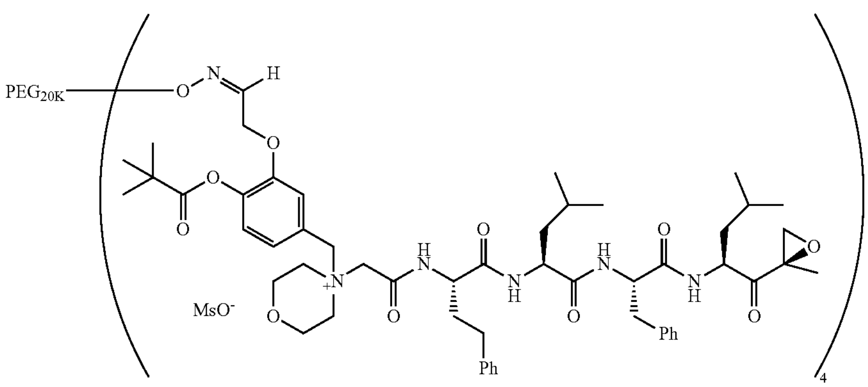 | 20K/4 | B |
| 26 | 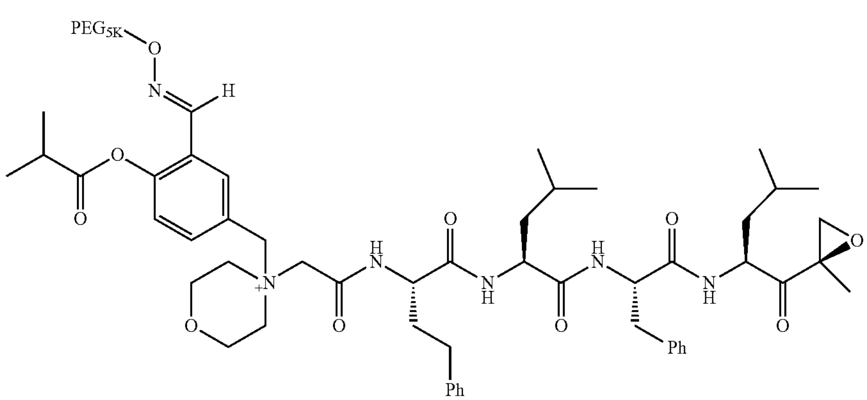 | 5K/1 | B |

TABLE 2-continued

| Example | Structure | PEG Size/Arms | PEG Linker Method |
|---|---|---|---|
| 27 | 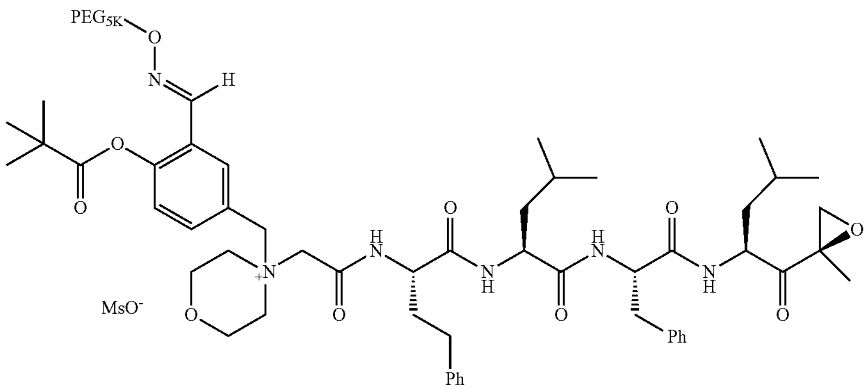 | 5K/1 | B |
| 28 | 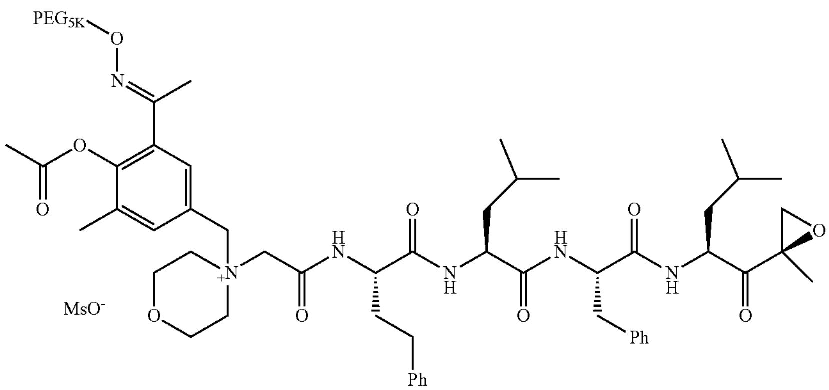 | 5K/1 | B |
| 29 | 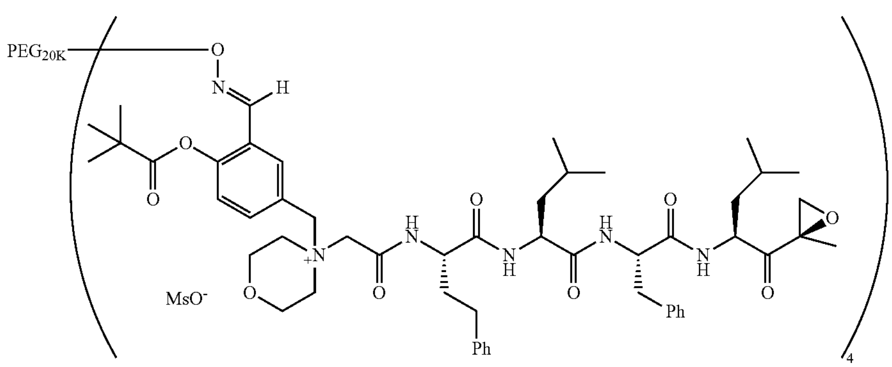 | 20K/4 | B |
| 30 | 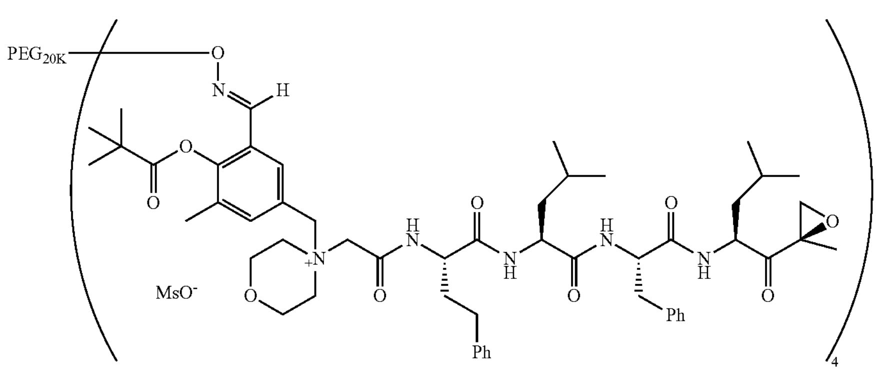 | 20K/4 | B |

TABLE 2-continued
| Example | Structure | PEG Size/Arms | PEG Linker Method |
|---|---|---|---|
| 31 | 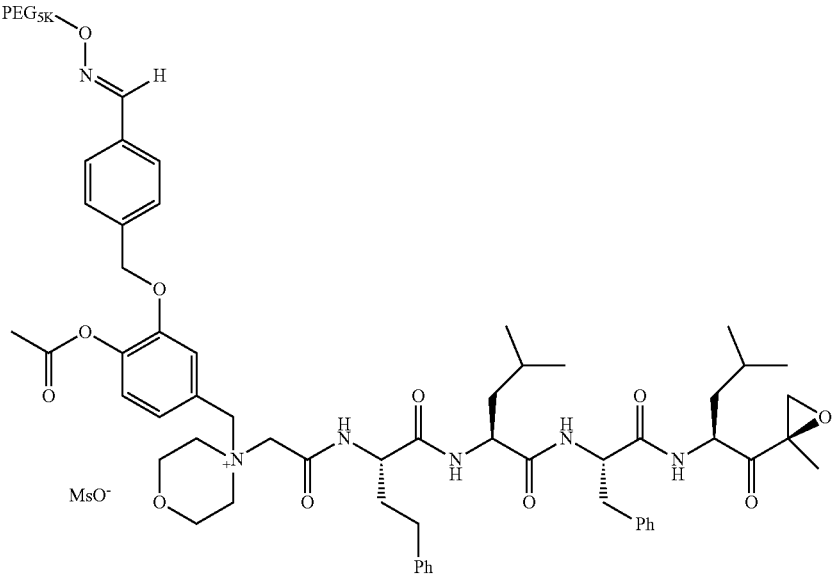 | 5K/1 | B |
| 32 | 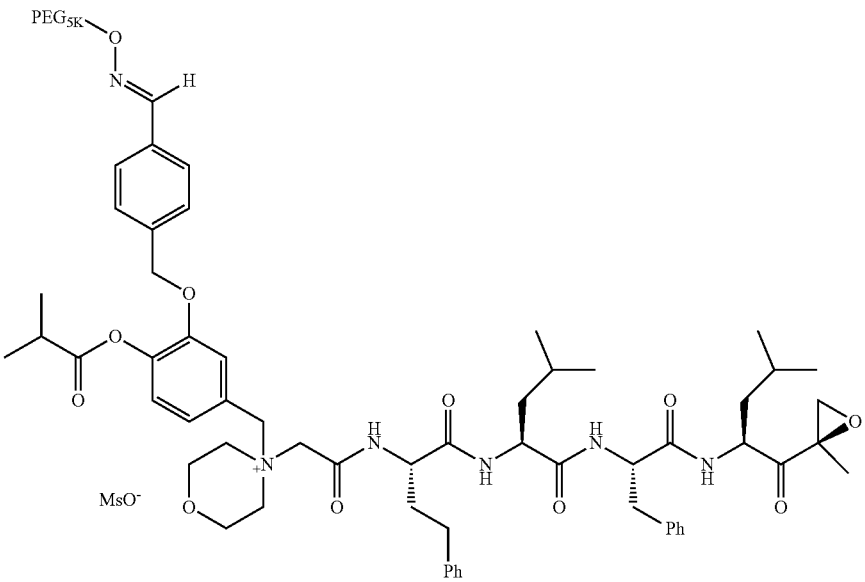 | 5K/1 | B |

TABLE 2-continued
| Example | Structure | PEG Size/ Arms | PEG Linker Method |
|---|---|---|---|
| 33 | 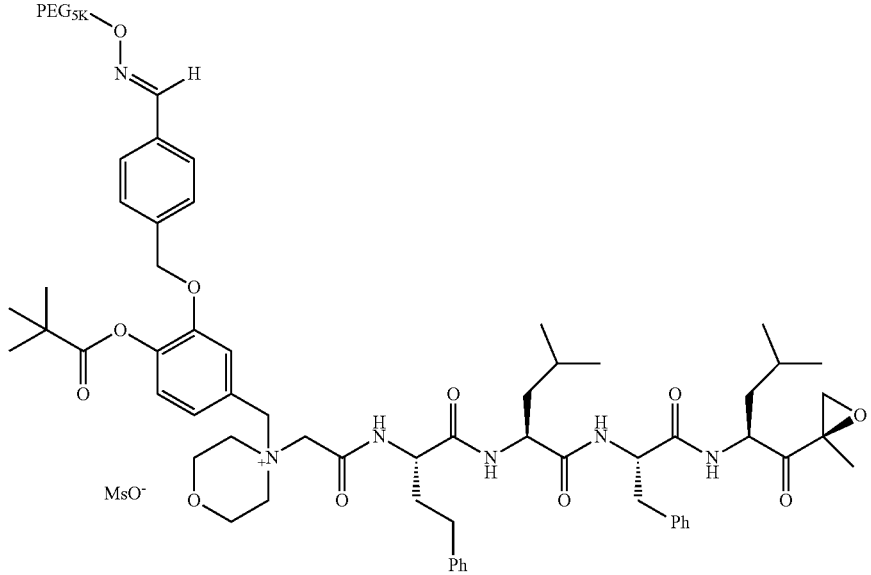 | 5K/1 | B |
| 34 | 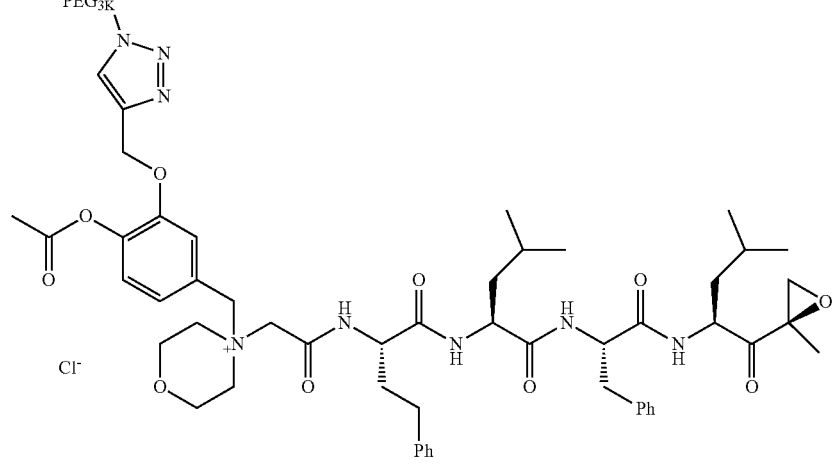 | 3K/1 | A |
| 35 | 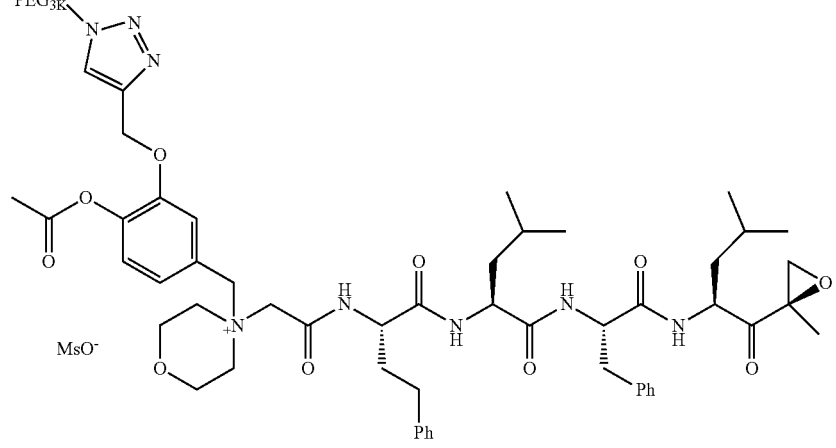 | 3K/1 | A |

TABLE 2-continued

| Example | Structure | PEG Size/Arms | PEG Linker Method |
|---|---|---|---|
| 36 | 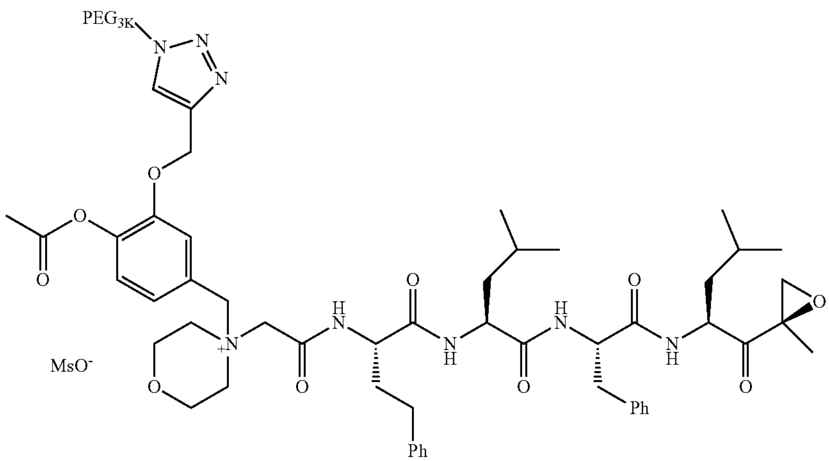 | 2K/1 | A |
| 37 | 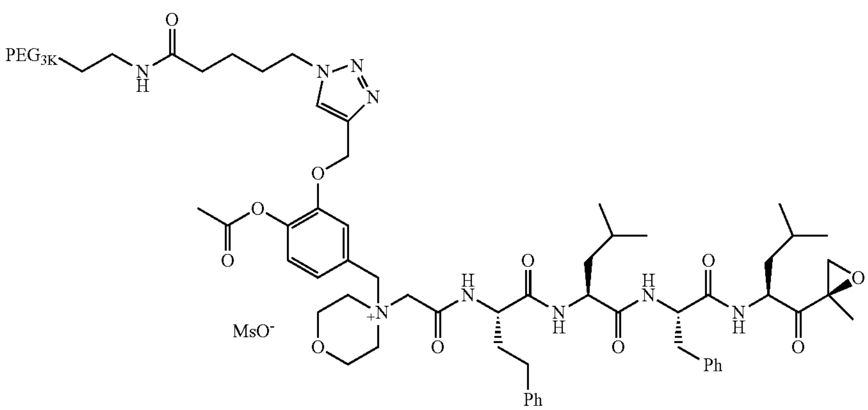 | 3K/1 | A |
| 38 | 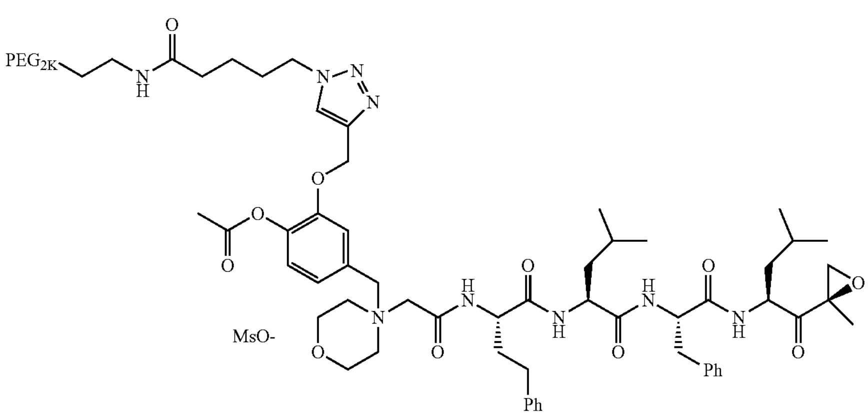 | 2K/1 | A |

Example 1: 4-(4-Acetoxy-3-((1-(PEG$_{20K}$-4-Arm)-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)
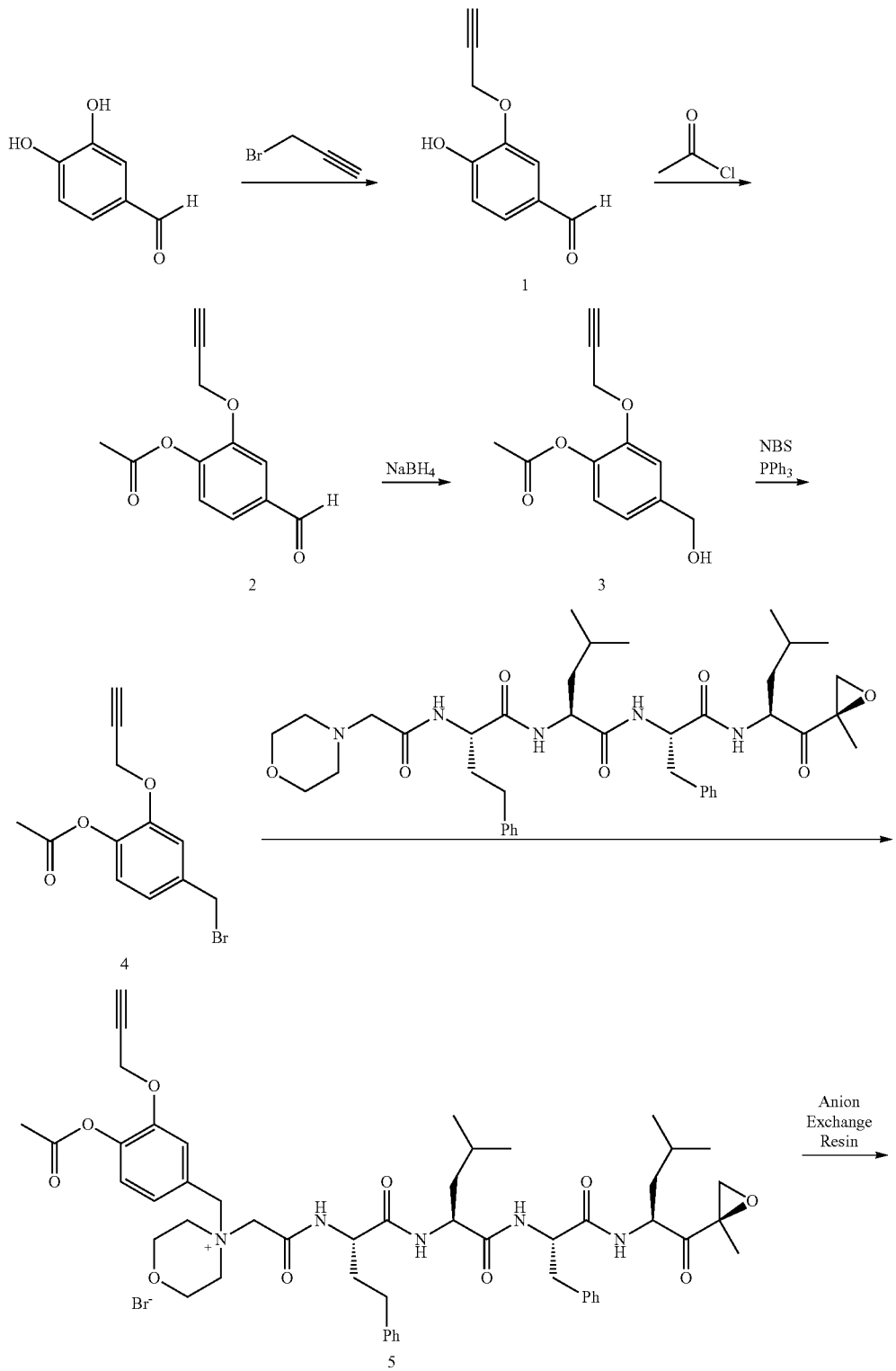

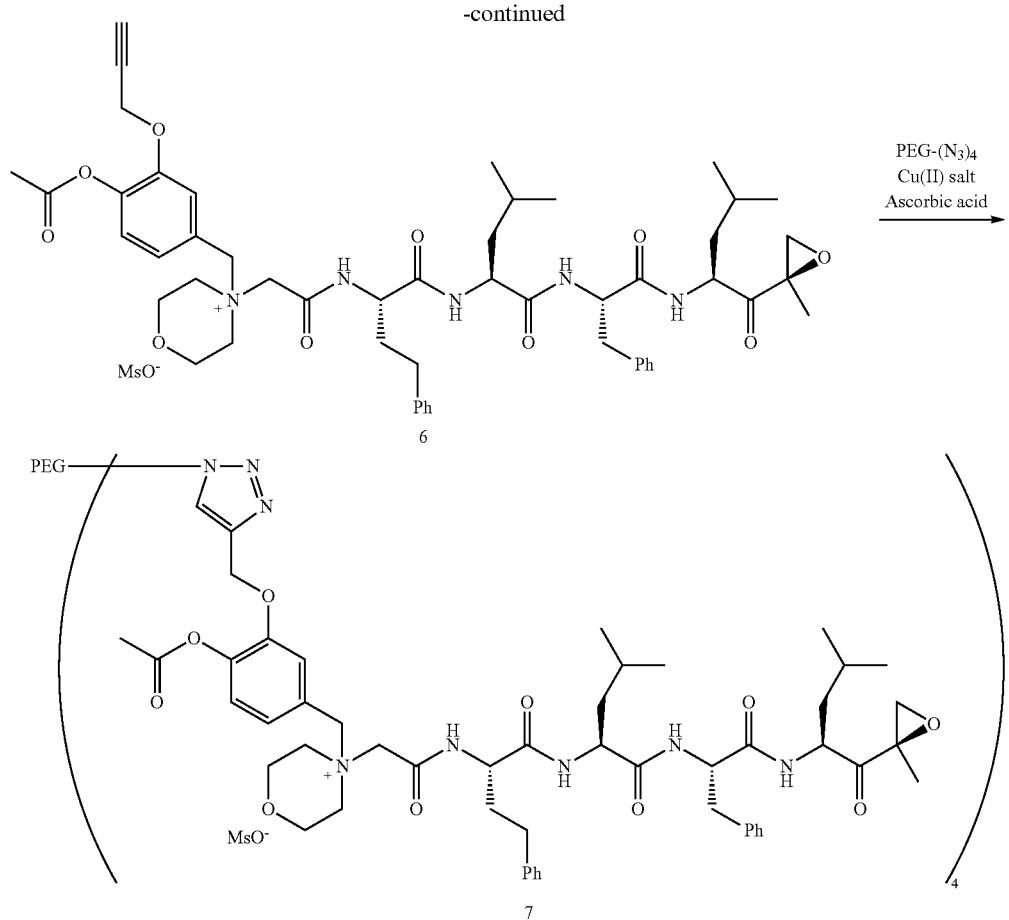

4-Hydroxy-3-(prop-2-ynyloxy)benzaldehyde (1)

To a mixture of NaH in DMSO (300 mL) was added 3,4-dihydroxybenzaldehyde (30 g, 217.39 mmol) in DMSO (50 mL) at 20° C. The mixture was stirred for 30 min and 3-bromoprop-1-yne (25.87 g, 217.39 mmol) was added. The reaction mixture was stirred at RT for one hour. The mixture was poured into ice water (800 mL) and the resulting solution was adjusted to pH=2. The mixture was extracted with EtOAc (500 mL×3), dried over anhydrous MgSO$_4$, and concentrated. The residue was crystallized repeatedly from DCM/Petroleum Ether (30 mL/500 mL) to afford compound 1 (30 g, 78% yield); $^1$H NMR (CDCl$_3$, 300 MHz,): δ 9.87 (s, 1H), 7.54 (d, J=1.2 Hz, 1H), 7.49 (dd, J$_1$=1.5 Hz, J$_2$=8.1 Hz, 1H), 7.09 (d, J=8.1 Hz, 1H), 4.82 (m, 2H), 2.62 (m, 1H).

4-Formyl-2-(prop-2-ynyloxy)phenyl acetate (2)

To a solution of compound 1 (10.00 g, 56.82 mmol) in DCM (150 mL) was added Et$_3$N (11.48 g, 113.64 mmol) followed by acetyl chloride (5.35 g, 68.18 mmol) at 0° C. The reaction mixture was stirred at RT for 2 hours. The mixture was washed with saturated 2 N aqueous HCl (100 mL) and water (50 mL), dried over anhydrous MgSO$_4$, and concentrated to afford compound 2 (12 g, 97% yield), which was used in the next step without further purification; $^1$H NMR (CDCl$_3$, 400 MHz): δ 9.96 (s, 1H), 7.63 (d, J=1.6 Hz, 1H), 7.54 (dd, J$_1$=1.6 Hz, J$_2$=8.0 Hz, 1H), 7.25 (d, J=8.0 Hz, 1H), 4.79 (d, J=2.4 Hz, 2H), 2.57 (t, J=2.4 Hz, 1H), 2.35 (s, 3H)

4-(Hydroxymethyl)-2-(prop-2-ynyloxy)phenyl acetate (3)

To a solution of compound 2 (12.00 g, 55.05 mmol) in DCM/MeOH (150 mL/15 mL) was added NaBH$_4$ (3.06 g, 82.57 mmol) in small portions at 0° C. The reaction mixture was stirred at RT for 30 min. The mixture was quenched by acetone (5 mL), and concentrated. The residue was purified by flash column chromatography on silica gel (Petroleum Ether/EtOAc=2:1) to afford compound 3 (10.32 g, 85% yield); $^1$H NMR (CDCl$_3$, 400 MHz): δ 7.16 (d, J=1.6 Hz, 1H), 7.04 (d, J=8.0 Hz, 1H), 6.98 (dd, J$_1$=1.6 Hz, J$_2$=8.0 Hz, 1H), 4.72 (d, J=2.4 Hz, 2H), 4.69 (s, 2H), 2.53 (L 0.1=2.4 Hz, 1H), 2.32 (s, 3H).

4-(Bromomethyl)-2-(prop-2-ynyloxy)phenyl acetate (4)

To a solution of compound 3 (11.50 g, 52.27 mmol) in DCM (150 mL) were added PPh$_3$ (20.50 g, 78.41 mmol) and NBS (11.04 g, 62.73 mmol) at 0° C. The reaction mixture was stirred at RT for 0.5 hour. An excess of solvent was concentrated and the residue was purified by flash column chromatography on silica gel (Petroleum Ether/EtOAc=20:1) to afford compound 4 (7.82 g, 53% yield); $^1$H NMR (CDCl$_3$, 400 MHz): δ 7.14 (m, 1H), 7.02 (m, 2H), 4.73 (d, J=2.4 Hz, 2H), 4.48 (s, 2H), 2.55 (t, J=2.4 Hz, 1H), 2.32 (s, 3H).

4-(4-Acetoxy-3-(prop-2-yn-1-yloxy)benzyl)-4-((4S,7S,10S,13S)-10-benzyl-7-isobutyl-15-methyl-13-((R)-2-methyloxirane-2-carbonyl)-25,8,11 I-tetraoxo-4-phenethyl-3,6,9,12-tetraazahexadecyl) morpholin-4-ium methanesulfonate (6)

To a solution of compound 4 (5.85 g, 20.67 mmol) in MeCN (50 mL) was added (S)-4-methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)pentanamide (4.96 g, 6.89 mmol). The reaction mixture was stirred at 45° C. for 2 days. An excess of solvent was concentrated and the residue was purified by flash column chromatography on silica gel (EtOAc/MeOH=100:6) to afford desired compound 5, which was transformed into the corresponding mesylate (3.2 g, 50% yield) by treatment with ion exchange resin; $^1$H NMR (CDCl$_3$, 400 MHz): δ 9.66 (m, 1H), 7.83 (m, 1H), 7.36 (m, 1H), 7.26-7.14 (m, 13H), 6.72 (m, 1H), 5.18 (m, 1H), 4.90 (m, 2H), 4.77 (m, 2H), 4.53-4.36 (m, 4H), 4.26 (m, 3H), 4.08 (m, 1H), 3.92 (m, 2H), 3.74 (m, 1H), 3.46 (m, 1H), 3.35 (m, 1H), 3.13 (m, 1H), 3.04 (m, 2H), 2.81 (s, 3H), 2.75 (m, 2H), 2.62 (m, 1H), 2.33 (m, 3H), 2.20 (m, 1H), 2.12 (m, 1H), 1.70-1.53 (m, 3H), 1.50-1.33 (m, 5H), 1.25 (m, 2H), 0.90-0.81 (m, 12H).

Example 1 was prepared from compound 6 and PEG$_{20K}$(N$_3$)$_4$ following general pegylation procedure A; $^1$H NMR (500 MHz, relaxation time=10 sec) DMSO-d$_6$ NMR: δ 9.50 (s, 4H), 8.50 (s, 4H), 8.39 (d, J=8 Hz, 4H), 8.27 (d, J=8 Hz, 4H), 8.11 (s, 4H), 8.05 (d, J=8 Hz, 4H), 7.58 (s, 4H), 7.26-7.29 (m, 12H), 7.12-7.23 (m, 32H), 7.03-7.06 (m, 4H), 5.26 (m, 8H), 4.89-5.00 (m, 8H), 4.52-4.56 (m, 12H), 4.28-4.38 (m, 16H), 4.17-4.20 (m, 4H), 4.05 (m, 16H), 3.81 (t, J=5.5 Hz, 8H), 3.63-3.66 (m, 8H), 3.50 (s, 2098H), 3.10 (d, J=5 Hz, 4H), 2.94-2.98 (m, 12H), 2.72-2.78 (m, 4H), 2.50-2.65 (m, 8H), 2.24 (s, 12H), 1.90-1.98 (m, 4H), 1.78-1.88 (m, 4H), 1.58-1.66 (m, 8H), 1.39 (s, 12H), 1.25-1.38 (m, 12H), 0.836-0.882 (m, 24H), 0.786-0.817 (m, 24H); Loading: 87%.

Example 2: 4-(4-Acetoxy-2-((1-PEG$_{5K}$-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (9)

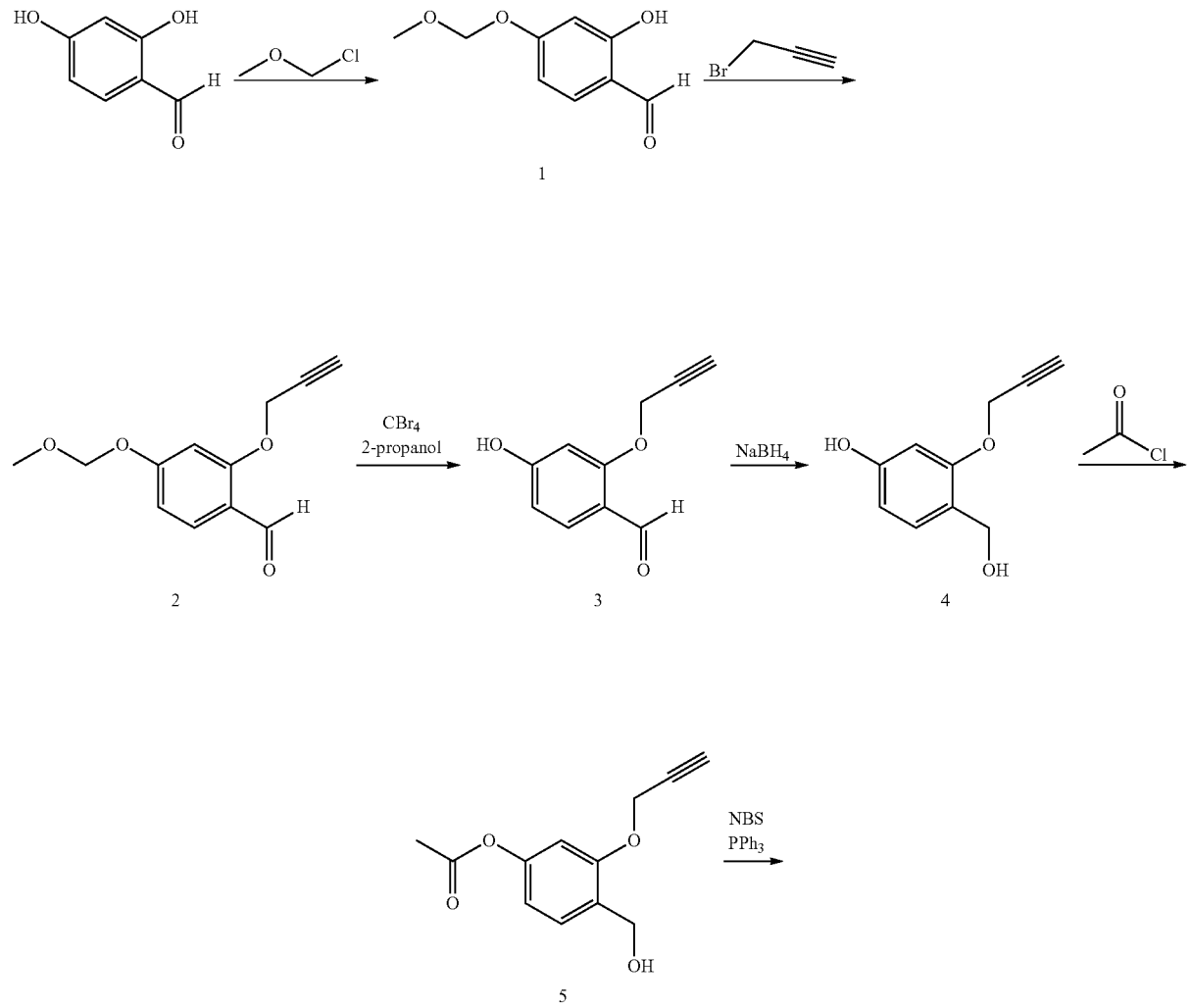

-continued
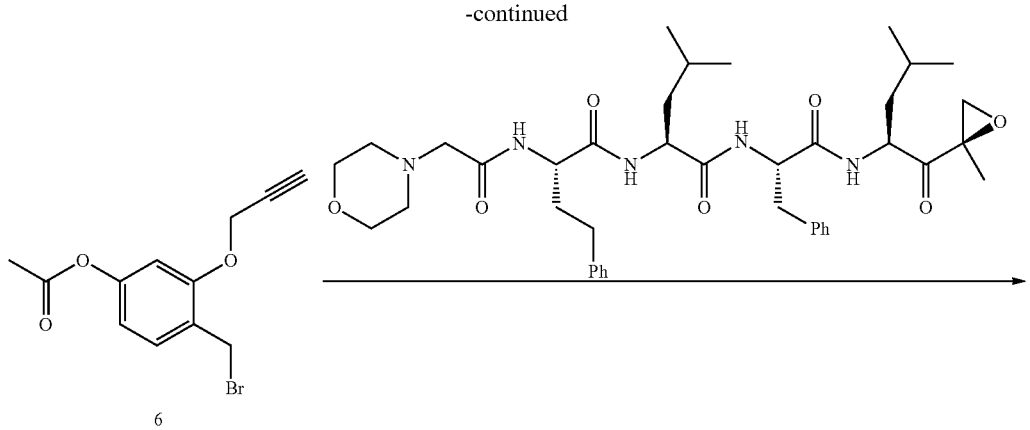
6
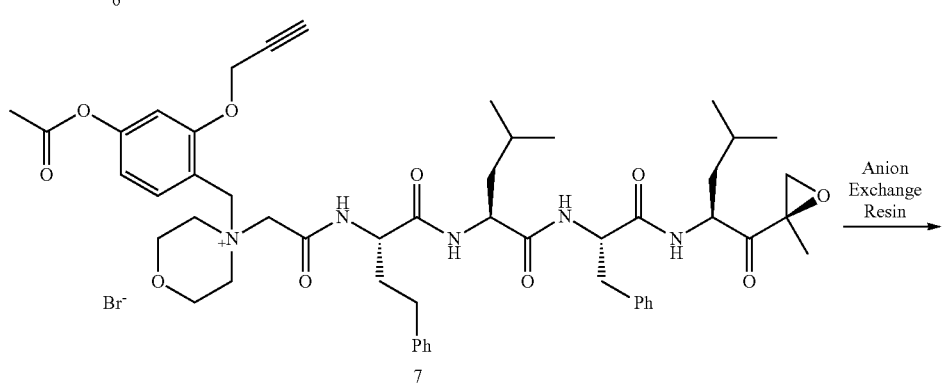
7
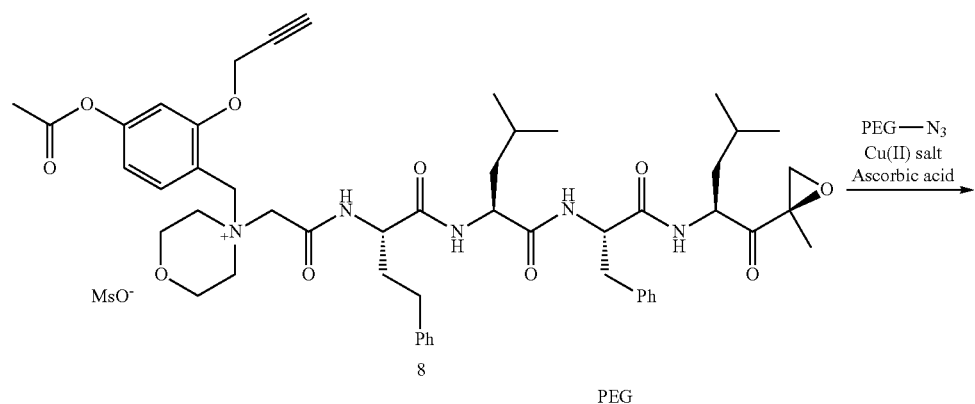
8
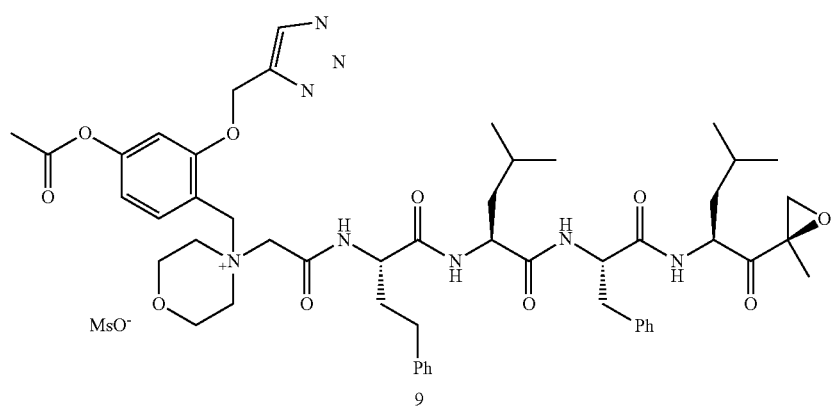
9

2-Hydroxy-4-(methoxyl)methoxy)benzaldehyde (1)

To a solution of compound 2,4-dihydroxybenzaldehyde (5.04 g, 36.24 mmol) in THF (100 mL) were added DIPEA (6.52 g, 54.35 mmol) and chloro(methoxy)methane (3.21 g, 39.86 mmol). The reaction mixture was stirred at RT overnight. An excess of solvent was concentrated and the residue was purified by flash column chromatography on silica gel (Petroleum Ether/EtOAc=15:1) to afford compound 1 (3.96 g, 60% yield); $^1$H NMR (300 MHz, CDCl$_3$): δ 11.41 (s, 1H), 9.76 (s, 1H), 7.48 (dd, J$_1$=2.7 Hz, J$_2$=8.4 Hz, 1H), 6.67 (dd, J$_1$=2.4 Hz, J$_2$=8.7 Hz, 1H), 6.62 (d, J=2.1 Hz, 1H), 5.25 (d, J=2.7 Hz, 2H), 3.51 (d, J=3.0 Hz, 3H).

4-(Methoxyl)methoxy)-2-(prop-2-ynyloxy)benzaldehyde (2)

To a mixture of NaH (900 mg, 21.252 mmol) in DMSO (100 mL) was added compound 1 (2.0 g, 10.63 mmol) in DMSO (50 mL) at 20° C. The mixture was stirred at the same temperature for 30 min and then 3-bromoprop-1-yne (1.90 g, 15.94 mmol) was added dropwise. The reaction mixture was stirred at the same temperature for 4 hours and then was poured into ice water (100 mL). The resulting solution was adjusted to pH=2-3 and EtOAc (100 mL) was added. The two phases were separated and the water phase was extracted with EtOAc (100 mL×3). The organic combined organic phases were dried and concentrated. The residue was purified by flash column chromatography on silica gel (Petroleum Ether/EtOAc=3:1) to afford compound 2 (1.89 g, 80% yield): $^1$H NMR (300 MHz, CDCl$_3$): δ 10.34 (s, 1H), 7.85 (d, J=9.3 Hz, 1H), 6.76 (m, 2H), 5.26 (s, 2H), 4.83 (d, J=2.4 Hz, 2H), 3.52 (s, 3H), 2.60 (q, J=2.4 Hz, 1H).

4-Hydroxy-2-(prop-2-ynyloxy)benzaldehyde (3)

To a solution of compound 2 (5.1 g, 23.18 mmol) in propan-2-ol (100 mL) was added CBr$_4$ (760 mg, 2.32 mmol). The reaction mixture was refluxed overnight. An excess of solvent was concentrated and the residue was purified by flash column chromatography on silica gel (Petroleum Ether/EtOAc=3:1) to afford compound 3 (2.44 g, 60% yield); $^1$H NMR (400 MHz, DMSO-d6): δ 10.76 (s, 1H), 10.11 (s, 1H), 7.60 (d, J=8.8 Hz, 1H), 6.59 (d, J=2.0 Hz, 1H), 6.52 (dd, J1=2.0 Hz, J2=8.8 Hz, 1H), 4.92 (d, J=2.4 Hz, 2H), 3.70 (q, J=2.4 Hz, 1H).

4-(Hydroxymethyl)-3-(prop-2-ynyloxy)phenol (4)

To a solution of compound 3 (2.45 g, 13.92 mmol) in MeOH (40 mL) was added NaBH$_4$ (618 mg, 16.698 mmol) in small portions at 0° C. The reaction mixture was stirred at the same temperature for 1 hour and then quenched with water (1.5 mL). An excess of solvent was concentrated and the residue was re-dissolved in EtOAc (100 mL). The resulting solution was dried and concentrated to afford compound 4 (1.80 g, 74% yield), which was used in the next step without further purification: $^1$H NMR (400 MHz, DMSO-d6): δ 6.98 (d, J=8.0 Hz, 1H), 6.32 (s, 1H), 6.26 (d, J=8.0 Hz, 1H), 4.65 (d, J=2.0 Hz, 2H), 4.32 (s, 2H), 3.54 (m, 1H).

4-(Hydroxymethyl)-3-(prop-2-ynyloxy)phenyl acetate (5)

To a solution of compound 4 (1.20 g, 6.74 mmol) in DCM (30 mL) was added TEA (1.70 g, 16.85 mmol) followed by acetyl chloride (634 mg, 8 mmol) dropwise at 0° C. The reaction mixture was stirred at RT for 30 min. An excess of solvent was concentrated and the residue was purified by flash column chromatography on silica gel (Petroleum Ether/EtOAc=5:1) to afford compound 5 (360 mg, 30% yield); $^1$H NMR (400 MHz, DMSO-d6): δ 7.38 (d, J=8.0 Hz, 1H), 6.79 (d, J=2.0 Hz, 1H), 6.75 (dd, J1=2.0 Hz, J2=8.0 Hz, 1H), 5.09 (m, J=5.6 Hz, 1H), 4.82 (d, J=2.4 Hz, 1H), 4.46 (d, J=5.6 HZ, 2H), 3.60 (q, J=2.4 Hz, 1H), 2.26 (s, 3H).

4-(Bromomethyl)-3-(prop-2-ynyloxy)phenyl acetate (6)

To a solution of compound 5 (360 mg, 1.64 mmol) in DCM (15 mL) was added PPh$_3$ (515 mg, 1.96 mmol) followed by NBS (318 mg, 1.80 mmol) in small portions at 0° C. The reaction mixture was stirred at the same temperature for 30 min. An excess of solvent was concentrated and the residue was purified by flash column chromatography on silica gel (Petroleum Ether/EtOAc=50:1) to afford compound 6 (190 mg, 41% yield); $^1$H NMR (400 MHz, CDCl$_3$): δ 7.36 (d, J=8.4 Hz, 1H), 6.78 (d, J=2.0 Hz, 1H), 6.73 (dd, J1=2.0 Hz, J2=8.4 Hz, 1H), 4.77 (d, J=2.4 Hz, 2H), 4.54 (s, 2H), 2.56 (q, J=2.4 Hz, 1H), 2.31 (s, 3H).

4-(4-Acetoxy-2-(prop-2-yn-1-yloxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

To a solution of compound 6 (190 mg, 0.67 mmol) in MeCN (10 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (480 mg, 0.67 mmol). The reaction mixture was stirred at 45° C. overnight. An excess of solvent was concentrated and the residue was purified by flash column chromatography on silica gel (MeOH/EtOAc=1:50) to afford desired compound 7, which was transformed into the corresponding mesylate (340 mg, 74% yield) by treatment with ion exchange resin; $^1$H NMR (400 MHz, CDCl$_3$): δ 9.68 (m, 1H), 7.88 (m, 1H), 7.63 (m, 1H), 7.33~7.16 (m, 10H), 6.89 (m, 3H), 6.50 (m, 1H), 5.16 (m, 1H), 5.05 (m, 1H), 4.87 (m, 1H), 4.75 (m, 2H), 4.47 (m, 2H), 4.45~4.12 (m, 8H), 4.02 (m, 3H), 3.72 (m, 1H), 3.54 (m, 1H), 3.38 (m, 1H), 3.20 (m, 1H), 3.06 (m, 2H), 2.80 (s, 3H), 2.74 (m, 2H), 2.63 (m, 2H), 2.40~2.08 (m, 5H), 1.64 (m, 2H), 1.47 (s, 3H), 0.85 (m, 12H).

The compound of Example 2 was prepared from compound 8 and PEG$_{5K}$N$_3$ following general pegylation procedure A Example 3: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9-tetraoxo-4-phenetraazahexadecyl)-4-(2-((1-PEG$_{5K}$-1H-1,2,3-triazol-4-yl)methoxy)-4-(propionyloxy)benzyl)morpholin-4-ium methanesulfonate (9)
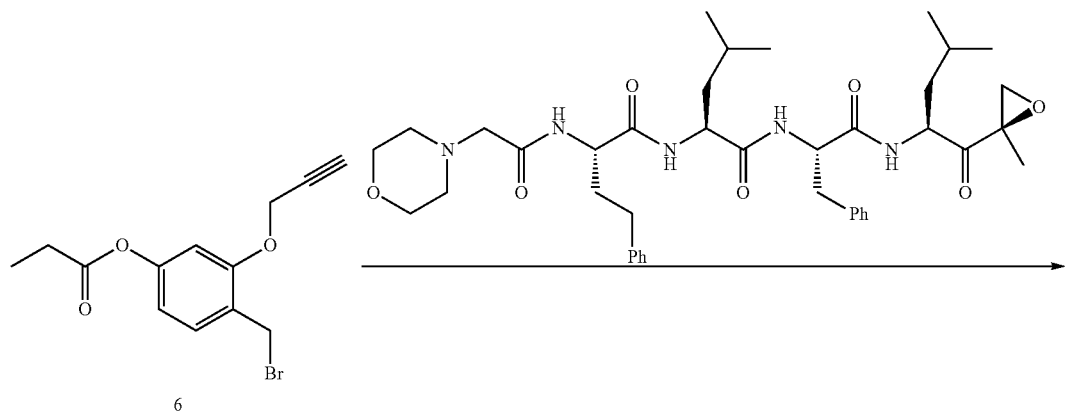
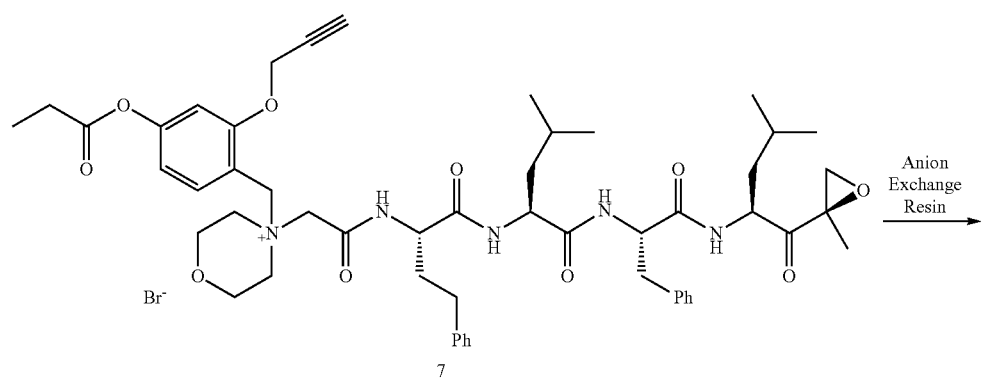
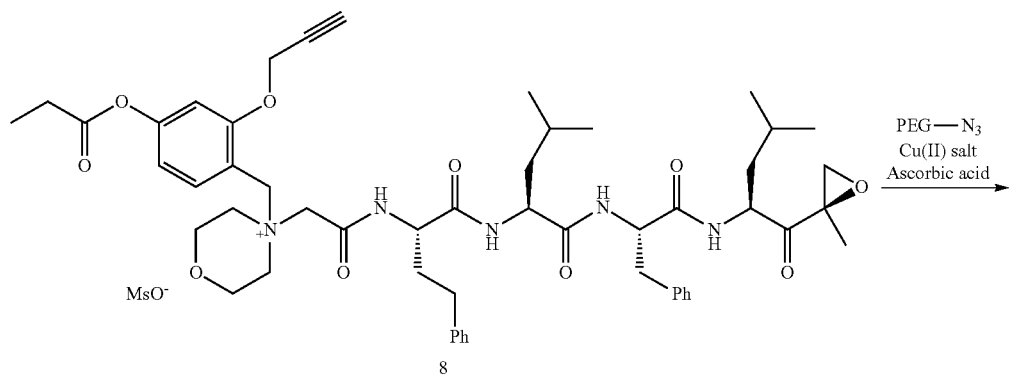

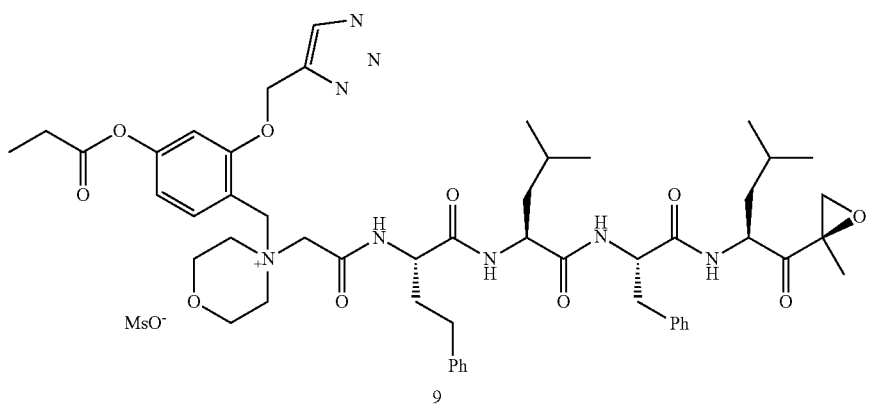

9

2-Hydroxy-4-(methoxyl)methoxy)benzaldehyde (1)

To a solution of 2,4-dihydroxybenzaldehyde (5.0 g, 36.23 mmol) in THF were added DIPEA (6.52 g, 54.35 mmol) and chloro(methoxy)methane (3.21 g, 39.86 mmol). The reaction mixture was stirred overnight. An excess of solvent was concentrated and the residue was purified by flash column chromatography on silica gel (Petroleum Ether/EtOAc=15:1) to afford compound 1 (3.96 g, 60% yield); $^1$H NMR (300 MHz, CDCl$_3$): δ 11.41 (s, 1H), 9.76 (s, 1H), 7.48 (dd, J1=2.7 Hz, J2=8.4 Hz, 1H), 6.67 (dd, J1=2.4 Hz, J2=8.7 Hz, 1H), 6.62 (d, J=2.1 Hz, 1H), 5.25 (d, J=2.7 Hz, 2H), 3.51 (d, J=3.0 Hz, 3H).

4-(Methoxyl)methoxy)-2-(prop-2-ynyloxy)benzaldehyde (2)

To a mixture of NaH (900 mg, 21.252 mmol) in DMSO (100 mL) was added compound 1 (2.0 g, 10.626 mmol) in DMSO (50 mL) at 20° C. The mixture was stirred at the same temperature for 30 min and then 3-bromoprop-1-yne (1.90 g, 15.94 mmol) was added dropwise. The reaction mixture was stirred at the same temperature for 4 hours and then was poured into ice water (100 mL). The resulting solution was adjusted to pH=2-3 and EtOAc (100 mL) was added. The two phases were separated and the water phase was extracted with EtOAc (100 mL×3). The combined organic phases were dried and concentrated. The residue was purified by flash column chromatography on silica gel (Petroleum Ether/EtOAc=3:1) to afford compound 2 (1.89 g, 800/% yield); $^1$H NMR (300 MHz, CDCl$_3$): δ 10.34 (s, 1H), 7.85 (d, J=9.3 Hz, 1H), 6.76 (m, 2H), 5.26 (s, 2H), 4.83 (d, J=2.4 Hz, 2H), 3.52 (s, 3H), 2.60 (q, J=2.4 Hz, 1H).

4-Hydroxy-2-(prop-2-ynyloxy)benzaldehyde (3)

To a solution of compound 2 (5.1 g, 23.18 mmol) in propan-2-ol (100 mL) was added CBr$_4$ (760 mg, 2.318 mmol). The reaction mixture was refluxed overnight. An excess of solvent was concentrated and the residue was purified by flash column chromatography on silica gel (Petroleum Ether/EtOAc=3:1) to afford compound 3 (2.44 g, 60% yield); $^1$H NMR (400 MHz, DMSO-d6): δ 10.76 (s, 1H), 10.11 (s, 1H), 7.60 (d, J=8.8 Hz, 1H), 6.59 (d, J=2.0 Hz, 1H), 6.52 (dd, J1=2.0 Hz, J2=8.8 Hz, 1H), 4.92 (d, J=2.4 Hz, 2H), 3.70 (q, J=2.4 Hz, 1H).

4-(Hydroxymethyl)-3-(prop-2-ynyloxy)phenol (4)

To a solution of compound 3 (2.45 g, 13.92 mmol) in MeOH (40 mL) was added NaBH$_4$ (618 mg, 16.698 mmol) in small portions at 0° C. The reaction mixture was stirred at the same temperature for 1 hour and then was quenched by water (1.5 mL). An excess of solvent was concentrated and the residue was re-dissolved in EtOAc (100 mL). The resulting solution was dried and concentrated to afford compound 4 (1.80 g, 74% yield), which was used in the next step without further purification; $^1$H NMR (400 MHz, DMSO-d6): δ 6.98 (d, J=8.0 Hz, 1H), 6.32 (s, 1H), 6.26 (d, J=8.0 Hz, 1H), 4.65 (d, J=2.0 Hz, 2H), 4.32 (s, 2H), 3.54 (m, 1H).

4-(Hydroxymethyl)-3-(prop-2-ynyloxy)phenyl propionate (5)

To a solution of compound 4 (2.4 g, 13.5 mmol) in DCM/THF (30 mL/5 mL) were added Et$_3$N (3.41 g, 33.75 mmol) and propionic anhydride (1.93 g, 14.8 mmol) at 0° C. The reaction mixture was stirred at RT overnight. An excess of solvent was concentrated and the residue was purified by flash column chromatography on silica gel (Petroleum Ether/EtOAc=3:1) to afford compound 5 (850 mg, 30% yield): $^1$H NMR (400 MHz, DMSO-d6): δ 7.38 (d, J=8.0 Hz, 1H), 6.81 (d, J=2.4 Hz, 1H), 6.74 (dd, J1=2.4 Hz, J2=8.4 Hz, 1H), 5.08 (br, s, 1H), 4.80 (d, J=2.4 Hz, 1H), 4.46 (s, 2H), 3.60 (m, 1H), 2.20 (m, 2H), 1.16 (m, 3H).

4-(Bromomethyl)-3-(prop-2-ynyloxy)phenyl propionate (6)

To a solution of compound 5S (850 ng, 3.63 mmol) in DCM (40 mL) were added PPh$_3$ (1.24 g, 4.72 mmol) and NBS (767.4 mg, 4.36 mmol) at RT. The reaction mixture was stirred for 30 min. An excess of solvent was concentrated and the residue was purified by flash column chromatography on silica gel (Petroleum Ether/EtOAc=3:1) to afford compound 6 (780 mg, 73% yield); $^1$H NMR (400 MHz, CDCl$_3$): δ 7.34 (d, J=8.0 Hz, 1H), 6.78 (d, J=2.0 Hz, 1H), 6.73 (dd, J1=2.4 Hz, J2=8.4 Hz, 1H), 4.77 (d, J=2.4 Hz, 1H), 4.54 (m, 1H), 2.60 (m, 2H), 2.56 (m, 1H), 1.27 (q, J=7.6 Hz, 3H).

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(2-(prop-2-yn-1-yloxy)-4-(propionyloxy)benzyl)morpholin-4-ium methanesulfonate (8)

To a solution of compound 6 (780 mg, 2.626 mmol) in MeCN (10 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (945 mg, 1.313 mmol). The reaction mixture was stirred at RT overnight. An excess of solvent was concentrated and the residue was purified by flash column chromatography on silica gel (EtOAc/MeOH=100:3) to afford the desired compound 7 (760 mg, 57% yield), which was transformed into the corresponding mesylate (740 mg, 97% yield) by treatment with ion exchange resin; $^1$H NMR (400 MHz, CDCl$_3$): δ 9.64 (m, 1H), 7.88 (m, 1H), 7.63 (m, 1H), 7.26 (m, 10H), 6.92 (m, 1H), 6.89 (m, 2H), 6.50 (m, 1H), 5.16 (m, 1H), 5.05 (m, 1H), 4.87 (m, 1H), 4.78 (m, 2H), 4.47 (m, 2H), 4.45~4.12 (m, 8H), 3.72 (m, 1H), 3.54 (m, 1H), 3.38 (m, 1H), 3.20 (m, 1H), 3.06 (m, 2H), 2.84 (m, 1H), 2.80 (s, 3H), 2.74 (m, 2H), 2.63 (m, 3H), 2.40~2.08 (m, 5H), 1.64 (m, 2H), 1.47 (s, 3H), 1.24 (m, 3H), 0.85 (m, 12H).

The pegylated carfilzomib compound Example 3 was prepared from compound 8 and PEG$_{5K}$N$_3$ following general pegylation procedure A.

Example 4: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-(((1-PEG$_{5K}$-1H-1,2,3-triazol-4-yl)methyl)carbamoyl)benzyl)morpholin-4-ium methanesulfonate (9)

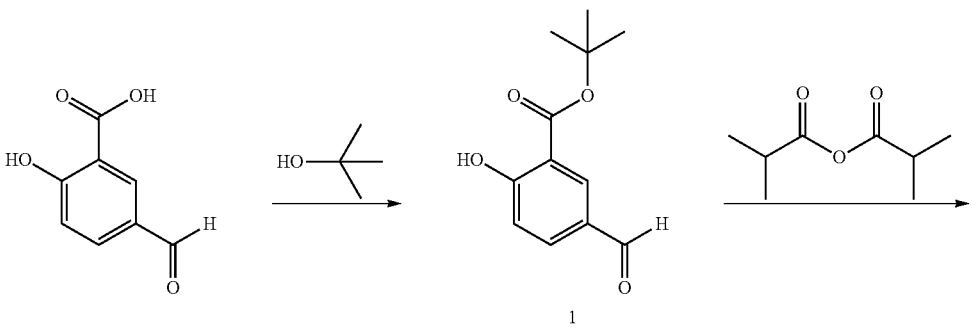

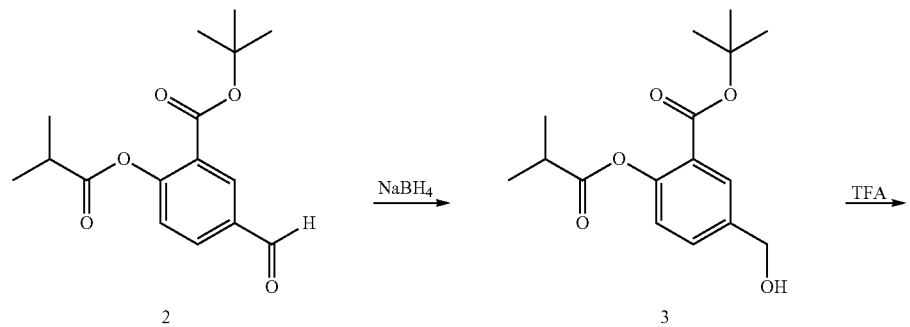

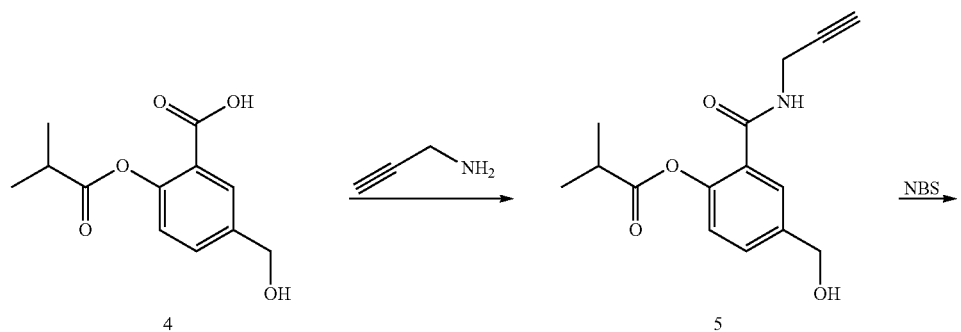

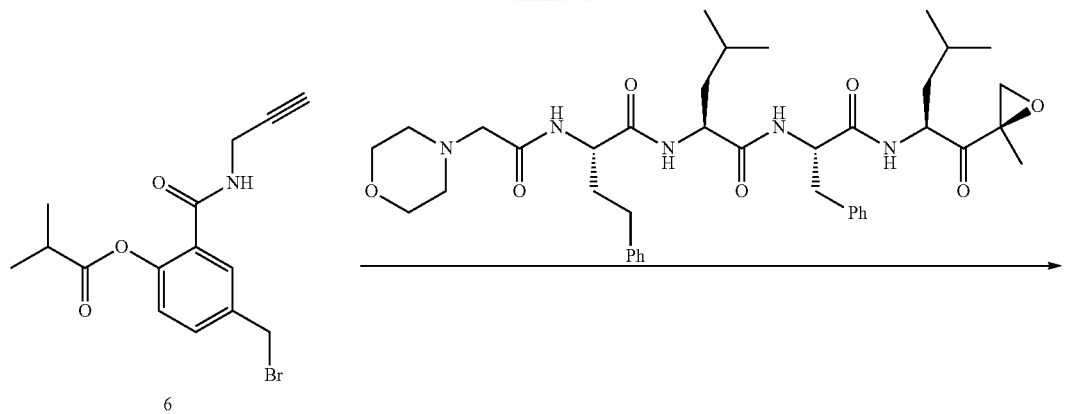
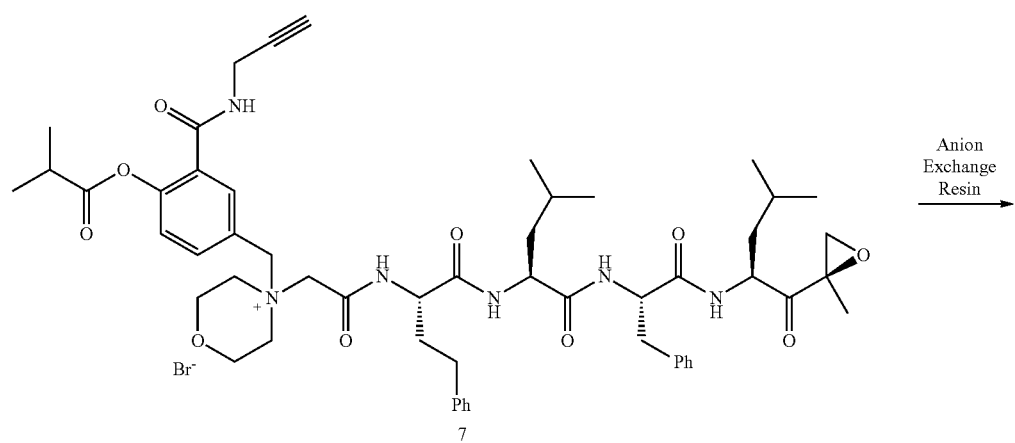
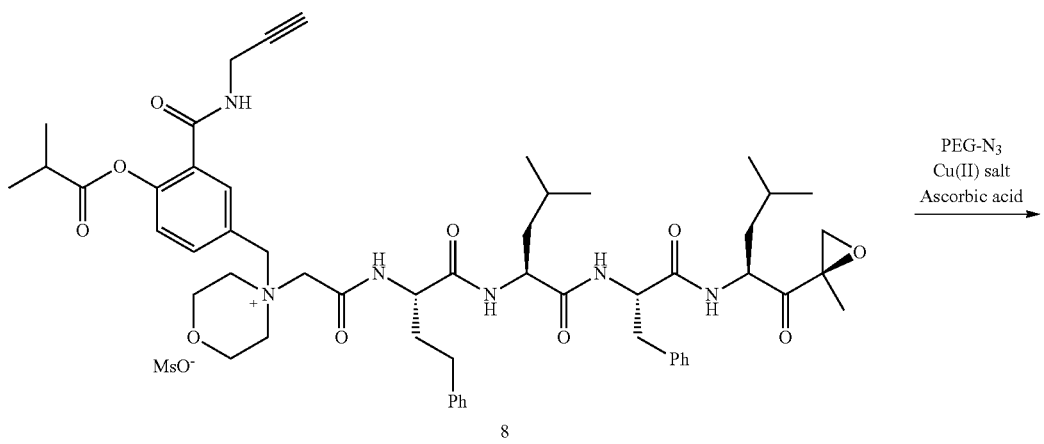

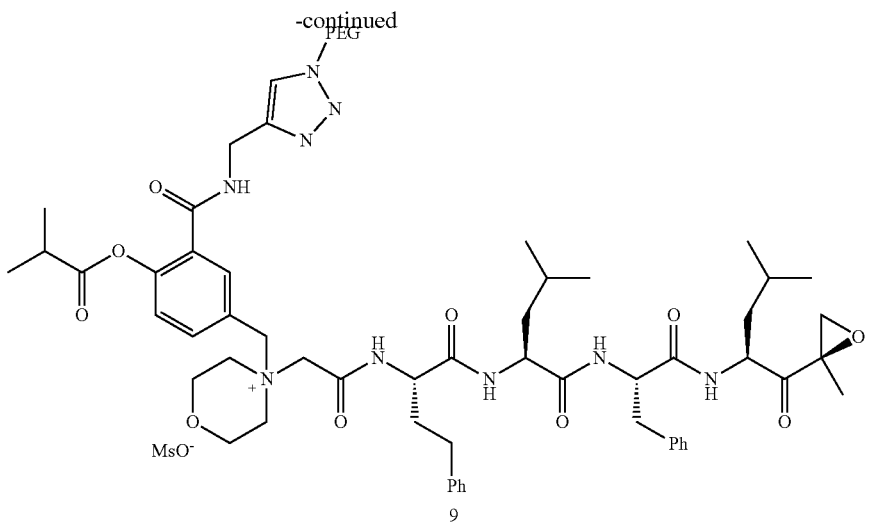

9 tert-Butyl 5-formyl-2-hydroxybenzoate (1)

To a solution of compound 5-formyl-2-hydroxybenzoic acid (2.01 g, 12 mmol) in 2-methylpropan-2-ol (70 mL) was added DCC (2.3 g, 12 mmol) at RT. The reaction mixture was stirred under reflux for 3 hours. The solvent was concentrated and the residue was purified by flash column chromatography on silica gel (Petroleum Ether/EtOAc=5:1) to afford compound 1 (1.8 g, 75% yield). $^1$H NMR (300 MHz, CDCl$_3$): δ 11.76 (s, 1H), 9.91 (s, 1H), 8.33 (d, J=2.1 Hz, 1H), 8.00 (dd, J$_1$=1.8 Hz, J$_2$=8.7 Hz, 1H), 7.11 (d, J=8.4 Hz, 1H), 1.68 (s, 9H).

tert-Butyl 5-formyl-2-(isobutyryloxy)benzoate (2)

To a solution of compound 1 (1.01 g, 4.5 mmol) in THF (20 mL) were added pyridine (1.07 g, 13.5 mmol) and isobutyric anhydride (1.423 g, 9 mmol) at RT. The reaction mixture was stirred for 3 hours. An excess of solvent was concentrated and the residue was purified by flash column chromatography on silica gel (Petroleum Ether/EtOAc=10:1) to afford compound 2 (420 mg, 36% yield). $^1$H NMR (300 MHz, CDCl$_3$): δ 10.04 (s, 1H), 8.36 (d, J=1.8 Hz, 1H), 8.04 (dd, J$_1$=2.1 Hz, J$_2$=8.4 Hz, 1H), 7.25 (m, 1H), 2.91 (m, 1H), 1.59 (s, 9H), 1.36 (d, J=6.9 Hz, 6H)

tert-Butyl 5-(hydroxymethyl)-2-(isobutyryloxy)benzoate (3)

To a solution of compound 2 (400 mg, 1.37 mmol) in THF (20 mL) was added NaBH$_4$ (57.3 mg, 1.5 mol) at RT. The reaction mixture was stirred for 1 hour and then was quenched by acetone (1 mL). An excess of solvent was concentrated and the residue was purified by flash column chromatography on silica gel (Petroleum Ether/EtOAc=8:1) to afford compound 3 (300 mg, 75% yield). $^1$H NMR (300 MHz, CDCl$_3$): δ7.85 (m, 1H), 7.52 (d, J=8.1 Hz, 1H), 7.06 (d, J=8.1 Hz, 1H), 4.73 (s, 2H), 2.88 (m, 1H), 1.57 (s, 9H), 1.30 (m, 6H).

5-(Hydroxymethyl)-2-(isobutyryloxy)benzoic acid (4)

A solution of compound 3 (400 mg, 1.38 mmol) in TFA/DCM (v/v, 3 mL/12 mL) was stirred at RT overnight. The mixture was poured into water and the aqueous solution was adjusted to pH=3-4. The two phases were separated and the organic phase was dried over anhydrous MgSO$_4$ and concentrated to afford compound 4 (202 mg, 62% yield), which was used in the next step without further purification.

4-(Hydroxymethyl)-2-(prop-2-ynylcarbamoyl)phenyl isobutyrate (5)

To a solution of compound 4 (202 mg, 0.85 mmol) in DCM (20 mL) were added DIPEA (219.3 mg, 1.7 mmol), HATU (969 mg, 2.55 mmol) and prop-2-yn-1-amine (93.5 mg, 1.7 mmol) at 0° C. The reaction mixture was stirred for 30 min. An excess of solvent was concentrated and the residue was purified by flash column chromatography on silica gel (Petroleum Ether/EtOAc=5:1) to afford compound 5 (130 mg, 60% yield); $^1$H NMR (300 MHz, CDCl$_3$): δ 7.83 (m, 1H), 7.52 (m, 1H), 7.10 (m, 1H), 4.65 (s, 2H), 4.24 (m, 2H), 2.87 (m, 1H), 2.30 (m, 1H), 1.26 (m, 6H).

4-(Bromomethyl)-2-(prop-2-ynylcarbamoyl)phenyl isobutyrate (6)

To a solution of compound 5S (130 mg, 0.5 mmol) in DCM (15 mL) were added PPh3 (170.3 mg, 0.65 mmol) and NBS (105.6 mg, 0.6 mmol) at 0° C. The reaction mixture was stirred for 30 min and the solvent was concentrated. The residue was purified by flash column chromatography on silica gel (Petroleum Ether/EtOAc=10:1) to afford compound 6 (50 mg, 32% yield). $^1$H NMR (300 MHz, CDCl$_3$): δ 7.88 (m, 1H), 7.37 (m, 1H), 7.11 (m, 1H), 4.51 (s, 2H), 4.23 (m, 2H), 2.87 (m, 1H), 2.31 (m, 1H), 1.37 (m, 6H).

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(4-(isobutyryloxy)-3-(prop-2-yn-1-ylcarbamoyl)benzyl)morpholin-4-ium bromide (8)

To a solution of compound 6 (360 mg, 1.1 mmol) in MeCN (4 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (720 mg, 1.0 mmol). The reaction mixture was stirred at 45° C. overnight. The solvent was concentrated and the residue was purified by flash column chromatography on silica gel (EtOAc/MeOH=50:1) to afford desired product 7, which was then transformed into the corresponding mesylate (150 mg, 15% yield) by treatment with ion exchange resin: $^1$H NMR (400 MHz, CDCl$_3$): δ 9.61 (m, 1H), 7.90 (m, 1H), 7.64 (m, 2H), 7.34-7.10 (m, 12H), 6.92 (m, 1H), 6.68 (m, 1H), 5.03 (m, 2H), 4.86 (m, 1H), 4.58-4.32 (m, 4H), 4.28-4.10 (m, 5H), 3.96 (m, 4H), 3.47-3.31 (m, 2H), 3.18 (m, 1H), 3.06-2.87 (m, 2H), 2.83 (s, 3H), 2.76 (m, 2H), 2.26 (m, 1H), 2.23-2.04 (m, 3H), 1.66-1.58 (m, 2H), 1.42 (m, 4H), 1.38-1.30 (m, 6H), 1.27 (m, 4H), 0.90-0.84 (m, 12H).

The pegylated carfilzomib compound Example 4 was prepared from compound 8 and PEG$_{5K}$N$_3$ following general pegylation procedure A.

Example 5: 4-(4-Acetoxy-3-((1-PEG$_{5K}$-1H-1,2,3-triazol-4-yl)methoxy)benzyl)-4-((4S,7S,10S,13S)-10-benzyl-7-isobutyl-15-methyl-13-((R)-2-methyl-oxirane-2-carbonyl)-2,5,8,11-tetraoxo-4-phenethyl-3,6,9,12-tetraazahexadecyl)morpholin-4-ium methanesulfonate (7)

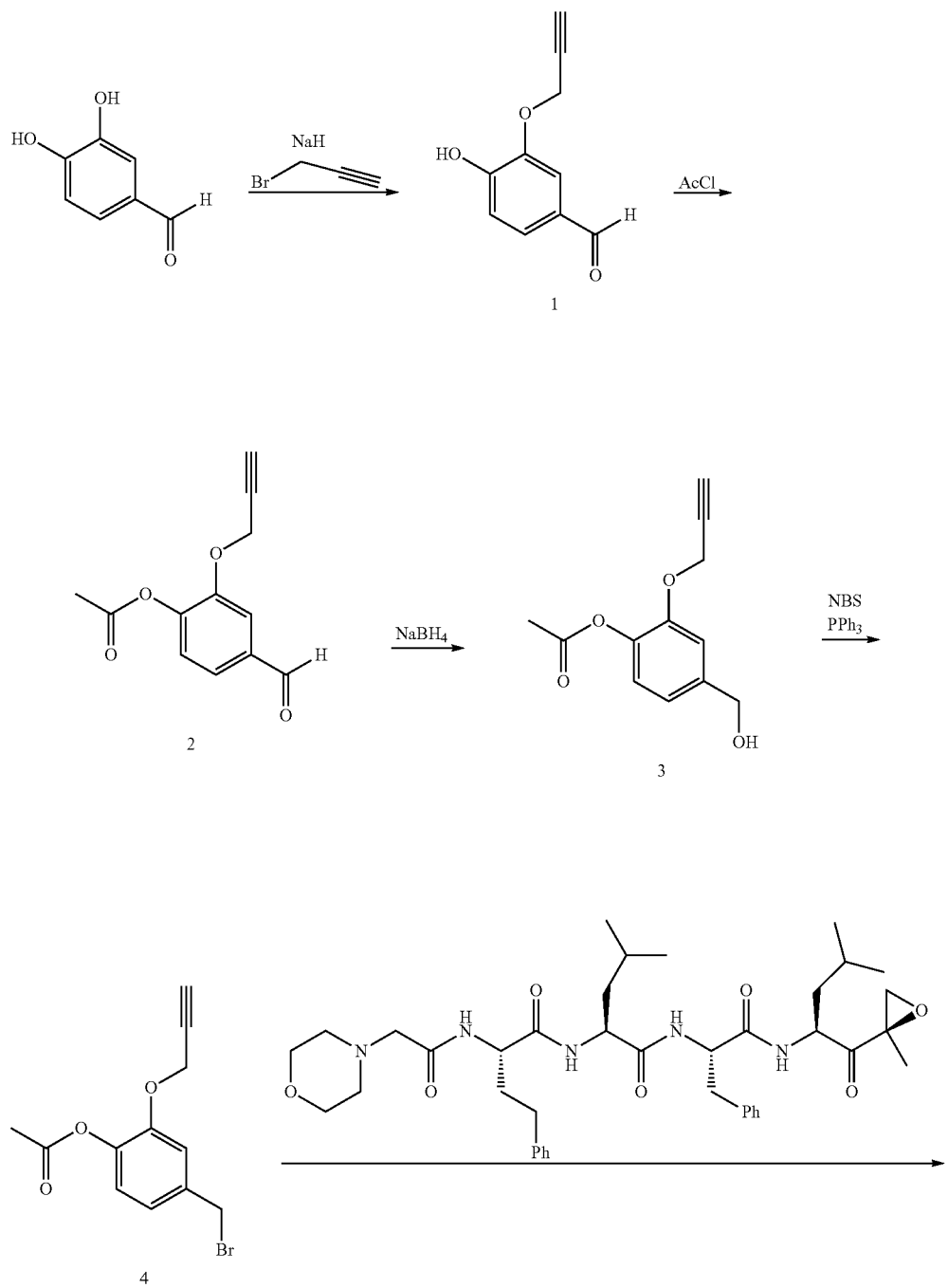

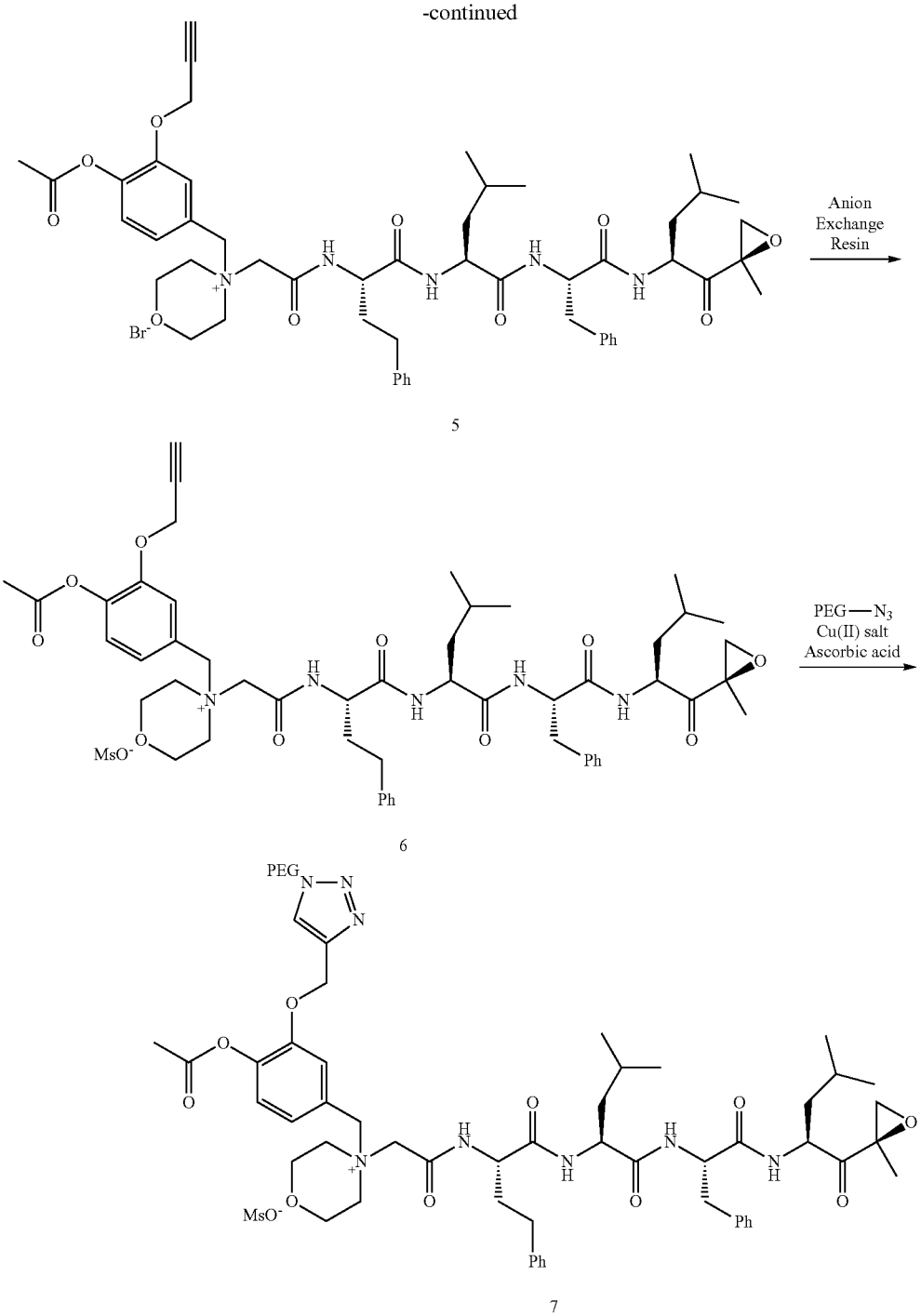

4-Hydroxy-3-(prop-2-ynyloxy)benzaldehyde (1)

To a mixture of NaH in DMSO (300 mL) was added 3,4-dihydroxybenzaldehyde (30 g, 217.39 mmol) in DMSO (50 mL) at 20° C. The mixture was stirred for 30 min and 3-bromoprop-1-yne (25.87 g, 217.39 mmol) was added. The reaction mixture was stirred at RT for one hour. The mixture was poured into ice water (800 mL) and the resulting solution was adjusted to pH=2. The mixture was extracted with EtOAc (500 mL×3), dried over anhydrous MgSO$_4$, and concentrated. The residue was crystallized repeatedly from DCM/Petroleum Ether (30 mL/500 mL) to afford compound 1 (30 g, 78% yield); $^1$H NMR (CDCl$_3$, 300 MHz,): δ 9.87 (s, 1H), 7.54 (d, J=1.2 Hz, 1H), 7.49 (dd, J$_1$=1.5 Hz, J$_2$=8.1 Hz, 1H), 7.09 (d, J=8.1 Hz, 1H), 4.82 (m, 2H), 2.62 (m, 1H).

4-Formyl-2-(prop-2-ynyloxy)phenyl acetate (2)

To a solution of compound 1 (10.00 g, 56.82 mmol) in DCM (150 mL) was added Et$_3$N (11.48 g, 113.64 mmol) followed by acetyl chloride (5.35 g, 68.18 mmol) at 0° C. The reaction mixture was stirred at RT for 2 hours. The mixture was washed with saturated 2 N aqueous HCl (100 mL) and water (50 mL), dried over anhydrous MgSO$_4$, and concentrated to afford compound 2 (12 g, 97% yield), which was used in the next step without further purification; $^1$H NMR (CDCl$_3$, 400 MHz): δ 9.96 (s, 1H), 7.63 (d, J=1.6 Hz, 1H), 7.54 (dd, J$_1$=1.6 Hz, J$_2$=8.0 Hz, 1H), 7.25 (d, J=8.0 Hz, 1H), 4.79 (d, J=2.4 Hz, 2H), 2.57 (t, J=2.4 Hz, 1H), 2.35 (s, 3H).

4-(Hydroxymethyl)-2-(prop-2-ynyloxy)phenyl acetate (3)

To a solution of compound 2 (12.00 g, 55.05 mmol) in DCM/MeOH (150 mL/15 mL) was added NaBH$_4$ (3.06 g, 82.57 mmol) in small portions at 0° C. The reaction mixture was stirred at RT for 30 min. The mixture was quenched by acetone (5 mL), and concentrated. The residue was purified by flash column chromatography on silica gel (Petroleum Ether/EtOAc=2:1) to afford compound 3 (10.32 g, 85% yield); $^1$H NMR (CDCl$_3$, 400 MHz): δ 7.16 (d, J=1.6 Hz, 1H), 7.04 (d, J=8.0 Hz, 1H), 6.98 (dd, J$_1$=1.6 Hz, J$_2$=8.0 Hz, 1H), 4.72 (d, J=2.4 Hz, 2H), 4.69 (s, 2H), 2.53 (t, J=2.4 Hz, 1H), 2.32 (s, 3H).

4-(Bromomethyl)-2-(prop-2-ynyloxy)phenyl acetate (4)

To a solution of compound 3 (11.50 g, 52.27 mmol) in DCM (150 mL) were added PPh$_3$ (20.50 g, 78.41 mmol) and NBS (11.04 g, 62.73 mmol) at 0° C. The reaction mixture was stirred at RT for 0.5 hour. An excess of solvent was concentrated and the residue was purified by flash column chromatography on silica gel (Petroleum Ether/EtOAc=20:1) to afford compound 4 (7.82 g, 53% yield); $^1$H NMR (CDCl$_3$, 400 MHz): δ 7.14 (m, 1H), 7.02 (m, 2H), 4.73 (d, J=2.4 Hz, 2H), 4.48 (s, 2H), 2.55 (t, J=2.4 Hz, 1H), 2.32 (s, 3H).

4-(4-Acetoxy-3-(prop-2-yn-1-yloxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (6)

To a solution of compound 4 (5.85 g, 20.67 mmol) in MeCN (50 mL) was added (S)-4-methyl-N—((S)-1-(((S)-4-methyl-1-(R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (4.96 g, 6.89 mmol). The reaction mixture was stirred at 45° C. for 2 days. An excess of solvent was concentrated and the residue was purified by flash column chromatography on silica gel (EtOAc/MeOH=100:6) to afford desired compound 5, which was transformed into the corresponding mesylate (3.2 g, 50% yield) by treatment with ion exchange resin; $^1$H NMR (CDCl$_3$, 400 MHz): δ 9.66 (m, 1H), 7.83 (m, 1H), 7.36 (m, 1H), 7.26-7.14 (n, 13H), 6.72 (m, 1H), 5.18 (m, 1H), 4.90 (m, 2H), 4.77 (m, 2H), 4.53-4.36 (m, 4H), 4.26 (m, 3H), 4.08 (m, 1H), 3.92 (m, 2H), 3.74 (m, 1H), 3.46 (m, 1H), 3.35 (m, 1H), 3.13 (m, 1H), 3.04 (m, 2H), 2.81 (s, 3H), 2.75 (m, 2H), 2.62 (m, 1H), 2.33 (m, 3H), 2.20 (m, 1H), 2.12 (m, 1H), 1.70-1.53 (m, 3H), 1.50-1.33 (m, 5H), 1.25 (m, 2H), 0.90-0.81 (m, 12H).

The pegylated carfilzomib compound Example 5 was prepared from compound 6 and PEG$_{5K}$N$_3$ following general pegylation procedure A.

Example 6: 4-((4S,7S,10S,13S)-1-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-((1-PEG$_{5K}$-1H-1,2,3-triazol-4-yl)methoxy)-4-(propionyloxy)benzyl)morpholin-4-ium methanesulfonate (6)

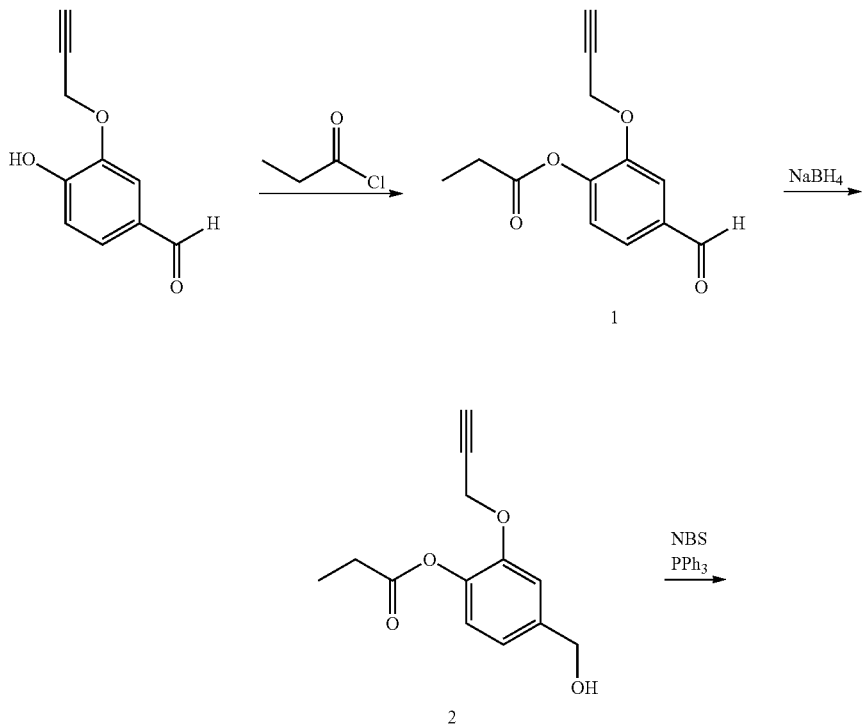

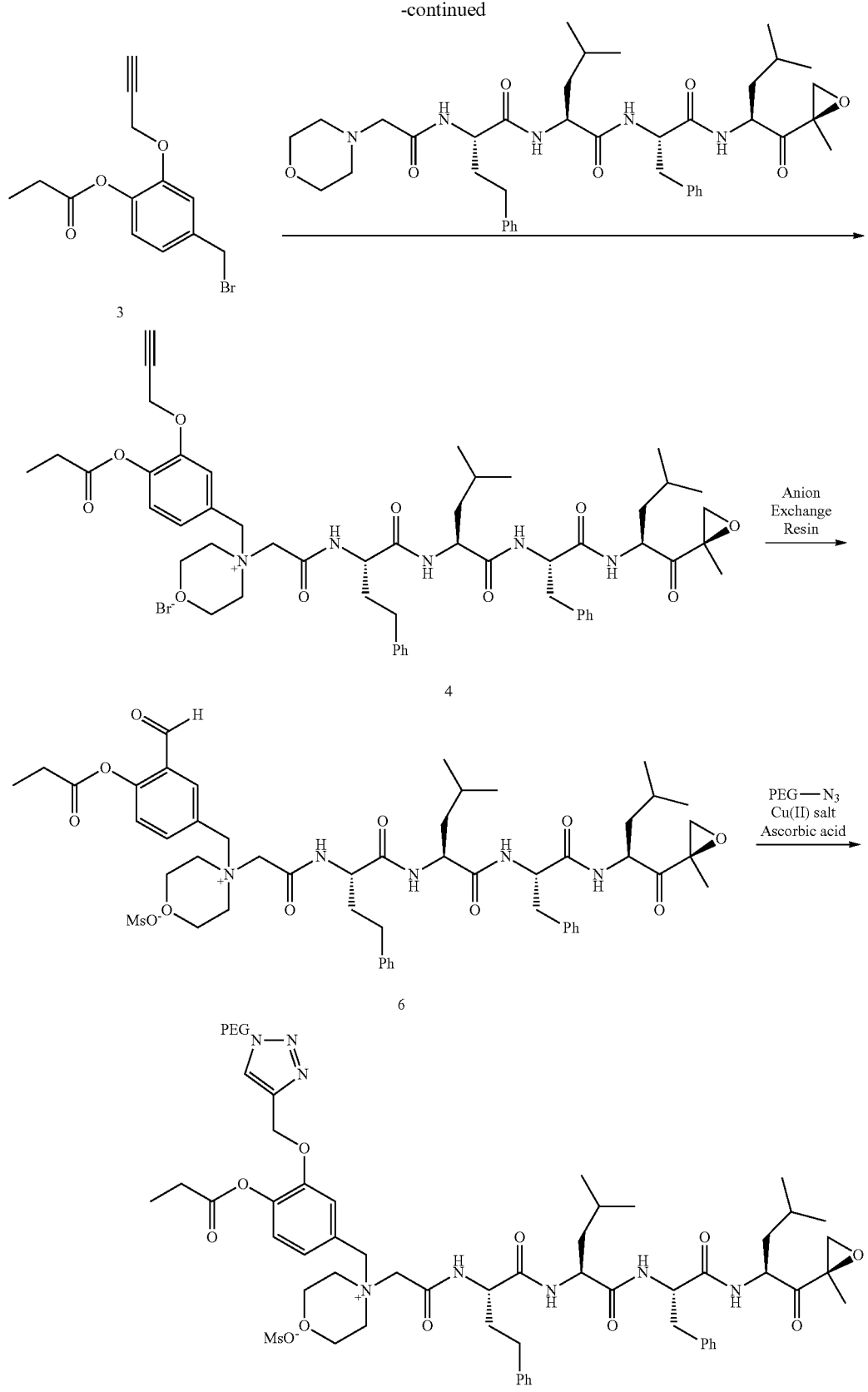

4-Formyl-2-(prop-2-yn-1 yloxy)phenyl propionate (1)

To a solution of 4-hydroxy-3-(prop-2-ynyloxy)benzaldehyde (2.4 g, 15 mmol) in DCM (30 mL) were added TEA (3 g, 30 mmol) and propionyl chloride (1.67 g, 18 mmol) at 0° C. The reaction mixture was stirred at RT for one hour. This mixture was quenched with water (50 mL) and the DCM phase was collected, dried over anhydrous MgSO$_4$ and concentrated. The residue was purified by flash column chromatography on silica gel (Petroleum Ether/EtOAc=10:1) to afford compound 1 (2.4 g, 85% yield); $^1$H NMR (300 MHz, CDCl$_3$): δ 9.97 (s, 1H), 7.64 (d, J=1.5 Hz, 1H), 7.55 (d, J1=1.5 Hz, J$_2$=7.8 Hz, 1H) 7.26 (d, J=8.1 Hz, 1H), 4.79 (d, J=2.1 Hz, 1H), 2.68 (q, J=7.5 Hz, 2H), 2.58 (t, J=2.4 Hz, 1H), 1.31 (t, J=7.5 Hz, 1H).

4-(Hydroxymethyl)-2-(prop-2-ynyloxy)phenyl propionate (2)

To a solution of compound 1 (2.32 g, 0.01 mol) in THF (30 mL) was added NaBH$_4$ (570 mg, 0.015 mol) at 0° C. in small portions. The reaction mixture was stirred at room temperature for 2 hours and then was quenched by saturated NH$_4$Cl (15 mL). The organic phase was collected and the aqueous phase was extracted by DCM (20 mL×3). The organic phases were combined, dried over anhydrous MgSO$_4$, and concentrated. The residue was purified by flash column chromatography on silica gel (Petroleum Ether/EtOAc=2:1) to afford compound 2 (1.7 g, 73% yield); $^1$H NMR (400 MHz, CDCl$_3$): δ 7.12~6.95 (m, 3H), 4.68 (m, 2H), 4.62 (m, 2H), 2.63 (m, 2H), 2.53 (m, 1H), 1.27 (m, 3H).

4-(Bromomethyl)-2-(prop-2-ynyloxy)phenyl propionate (3)

To a solution of compound 2 (1.7 g, 7.26 mmol) in DCM (30 mL) were added PPh$_3$ (2.28 g, 8.7 mmol) and DIPEA (1.12 g, 8.7 mmol) sequentially. The mixture was cooled to 0° C., and NBS (1.4 g, 7.78 mmol) was added in small portions. The reaction mixture was stirred at the same temperature for 20 min. An excess of solvent was concentrated and the residue was purified by flash column chromatography on silica gel (Petroleum Ether/EtOAc=10:1) to afford compound 3 (400 mg, 19% yield).

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(prop-2-yn-1-yloxy)-4-(propionyloxy) benzyl)morpholin-4-ium methanesulfonate (5)

To a solution of compound 3 (400 mg, 1.34 mmol) in MeCN (5 mL) was added compound (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (484.8 mg, 0.67 mmol). The reaction mixture was heated at 45° C. overnight. An excess of solvent was concentrated and the residue was purified by flash column chromatography on silica gel to afford the desired compound 4 (380 mg, 48% yield), which was transformed into the corresponding mesylate (370 mg, quantitative) by treatment with ion exchange resin; $^1$H NMR (400 MHz, CDCl$_3$): δ 9.63 (m, 1H), 7.82 (m, 1H), 7.35~7.09 (m, 13H), 6.91 (m, 1H), 6.52 (m, 1H), 5.13 (m, 1H), 5.02~4.82 (m, 5H), 4.72 (m, 2H), 4.50~3.83 (m, 11H), 3.52~3.31 (m, 2H), 3.18~2.58 (m, 11H), 1.68~1.18 (m, 9H), 0.88 (m, 12H).

The pegylayted carfilzomib compound Example 6 was prepared from compound 5 and PEG$_{5K}$N$_3$ following general pegylation procedure A.

Example 7: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((1-PEG$_{5K}$-1H-1,2,3-triazol-4-yl)methoxy)benzyl)morpholin-4-ium methanesulfonate (6)

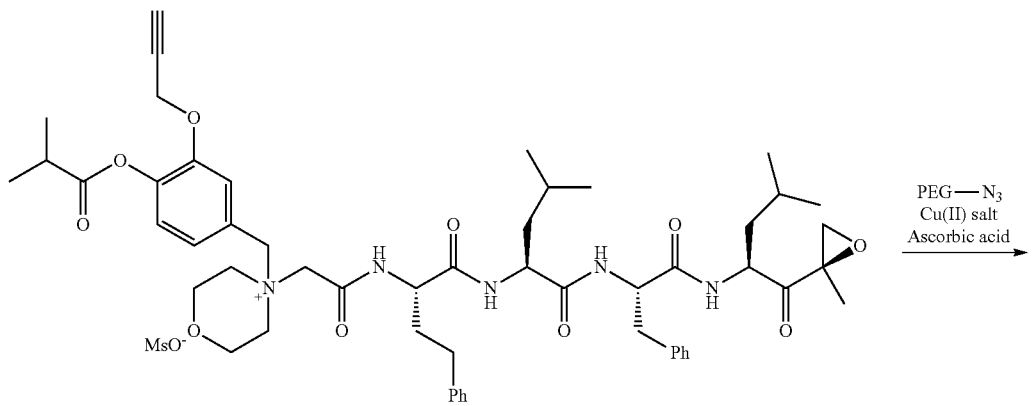

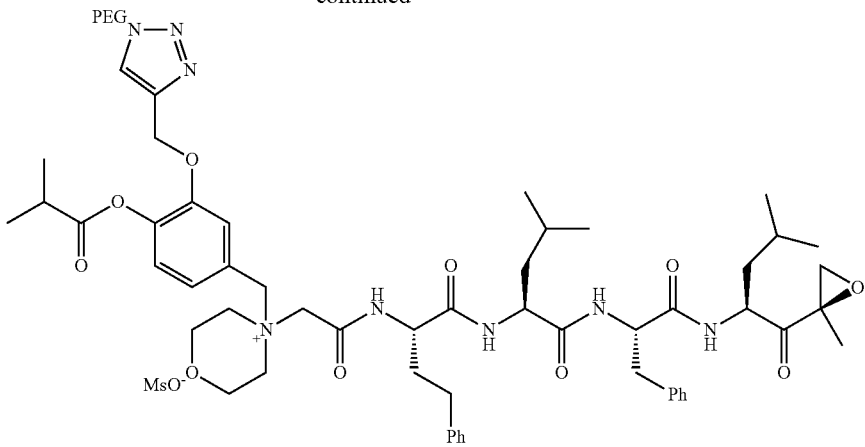

6

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-(prop-2-yn-1-yloxy)benzyl)morpholin-4-ium methanesulfonate (5)

To a solution of compound 3 (0.5 g, 1.6 mmol) in MeCN (9 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (864 mg, 1.2 mmol). The reaction mixture was stirred at 45° C. for 20 hours. The solvent was concentrated and the residue was purified by flash column chromatography on silica gel (EtOAc/MeOH=100:6) to afford desired compound 4, which was then transformed into the corresponding mesylate (500 mg, 44% yield) by treatment with ion exchange resin; $^1$H NMR (400 MHz, CDCl$_1$): δ 9.67 (m, 1H), 7.82 (m, 1H), 7.27 (m, 16H), 6.85 (m, 1H), 6.47 (m, 1H), 5.13 (m, 1H), 5.02 (m, 1H), 4.85 (m, 1H), 4.70 (m, 2H), 4.45 (m, 2H), 4.37 (m, 2H), 4.23 (m, 4H), 3.92 (m, 2H), 3.84 (m, 1H), 3.46 (m, 1H), 3.35 (m, 1H), 3.15 (m, 1H), 3.03 (m, 1H), 2.92 (m, 1H), 2.80 (s, 3H), 2.73 (m, 2H), 2.58 (m, 1H), 2.20 (m, 1H), 2.12 (m, 1H), 1.70 (m, 1H), 1.62 (m, 3H), 1.43 (m, 4H), 1.28 (m, 6H), 1.21 (m, 3H), 0.85 (m, 12H).

Example 7 was prepared by methods analogous to those described in Examples 3 and 5, wherein the intermediates were made in similar fashion, and compound 5 and PEG$_{5K}$N; were reacted following general pegylation procedure A.

Example 8: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(butyryloxy)-3-((1-PEG$_{5K}$-1H-1,2,3-triazol-4-yl)methoxy)benzyl)morpholin-4-ium methanesulfonate (6)

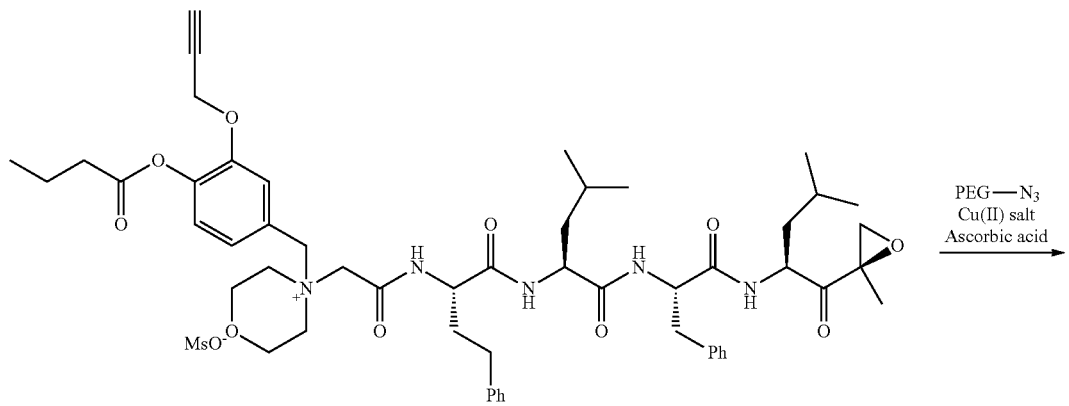

5

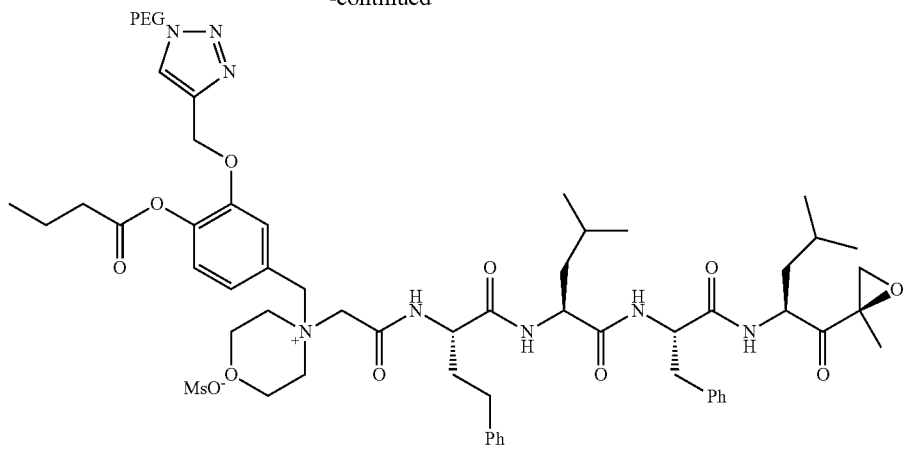

6

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(4-(butyryloxy)-3-(prop-2-yn-1-yloxy)benzyl)morpholin-4-ium methanesulfonate (5)

To a solution of compound 3 (0.7 g, 2.25 mmol) in MeCN (8 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (0.8 g, 1.125 mmol). The reaction mixture was stirred at 45° C. overnight. An excess of solvent was concentrated and the residue was purified by flash column chromatography on silica gel (EtOAc/MeOH=100/3) to afford the desired compound 4 (500 mg, 23.3% yield), which was transformed into the corresponding mesylate (460 mg, 92% yield) by treatment with ion exchange resin: $^1$H NMR (400 MHz, CDCl$_3$): δ 9.73 (m, 1H), 7.76 (m, 1H), 7.33~7.10 (m, 13H), 6.91 (m, 1H), 6.52 (m, 1H), 5.18 (m, 1H), 5.08~4.85 (m, 2H), 4.72 (m, 2H), 4.50~3.78 (m, 11H), 3.52~3.31 (m, 2H), 3.18~2.58 (m, 11H), 2.18 (m, 2H), 1.68~1.24 (m, 12H), 0.84 (m, 12H).

Example 8 was prepared by methods analogous to those described in Example 3, wherein the intermediates were made in similar fashion (using propanoyl chloride to generate the correlary to intermediate 1 shown in eg 3), and compound 5 and PEG$_{5K}$N$_3$ were reacted following general pegylation procedure A.

Example 9: 4-((4S,7S,10S,13S)-10-Benzyl-7-isobutyl-15-methyl-13-((R)-2-methyloxirane-2-carbonyl)-2,5,8,1-tetraoxo-4-phenethyl-3,6,9,12-tetraazahexadecyl)-4-(4-(hexanoyloxy)-3-((1-PEG$_{5K}$-1H-1,2,3-triazol-4-yl)methoxy)benzyl)morpholin-4-ium methanesulfonate (6)

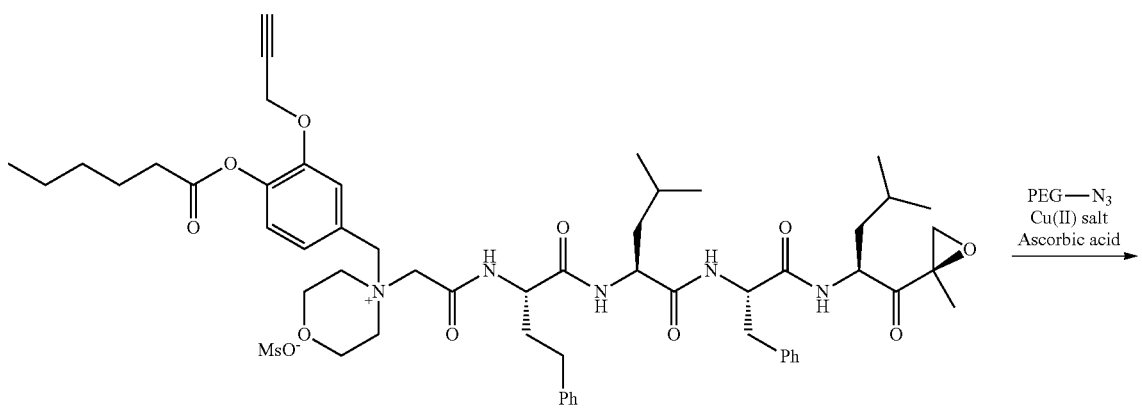

5

-continued

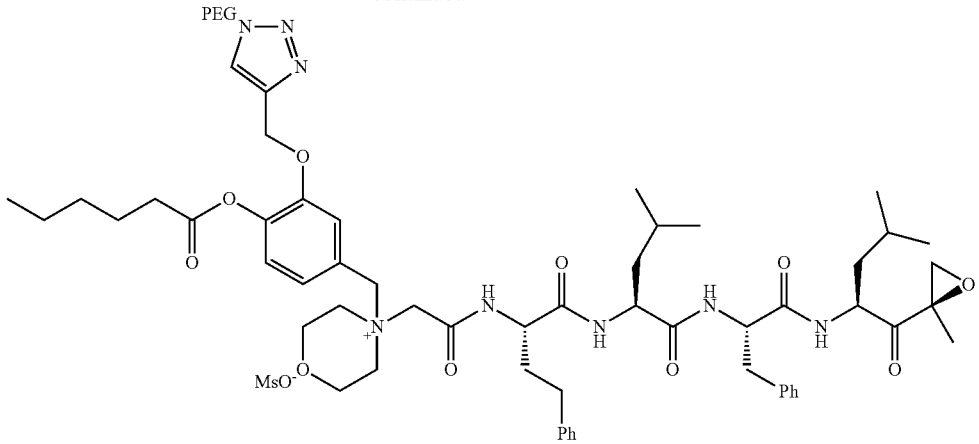

6

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(hexanoyloxy)-3-(prop-2-yn-1-yloxy)benzyl)morpholin-4-ium methanesulfonate (5)

To a solution of compound 3 (1.41 g, 4.16 mmol) in MeCN (25 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (1.0 g, 1.39 mmol). The reaction mixture was heated at 40~45° C. overnight. An excess of solvent was concentrated and the residue was purified by flash column chromatography on silica gel (EtOAc/MeOH=20:1) to afford the desired compound 4, which was transformed into the mesylate salt (570 mg, 41% yield) by treatment with ion exchange resin; $^1$H NMR (400 MHz, CDCl$_3$): δ 9.72 (m, 1H), 7.82 (m, 1H), 7.34~7.15 (m, 12H), 7.10 (m, 1H), 6.82 (m, 1H), 6.43 (m, 1H), 5.15 (m, 1H), 4.98 (m, 1H), 4.76 (m, 2H), 4.46 (m, 2H), 4.38 (m, 2H), 4.25 (m, 3H), 4.12 (m, 1H), 4.01 (m, 2H), 3.85 (m, 2H), 3.47 (m, 1H), 3.36 (m, 1H), 3.15 (m, 1H), 3.01 (m, 2H), 2.80 (s, 3H), 2.72 (m, 2H), 2.60 (m, 2H), 2.51 (m, 1H), 2.35~2.14 (m, 4H), 1.76 (m, 2H), 1.55 (m, 2H), 1.48 (m, 4H), 1.37 (m, 6H), 1.23 (m, 3H), 0.86 (m, 12H).

Example 9 was prepared by methods analogous to those described in Example 3, wherein the intermediates were made in similar fashion (using pentanoyl chloride to generate the correlary to intermediate 1 shown in eg 3), and compound 5 and PEG$_{5K}$N$_3$ were reacted following general pegylation procedure A.

Example 10: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-((1-PEG$_{5K}$-1H-1,2,3-triazol-4-yl)methoxy)-4-(octanoyloxy)benzyl)morpholin-4-ium methanesulfonate (6)

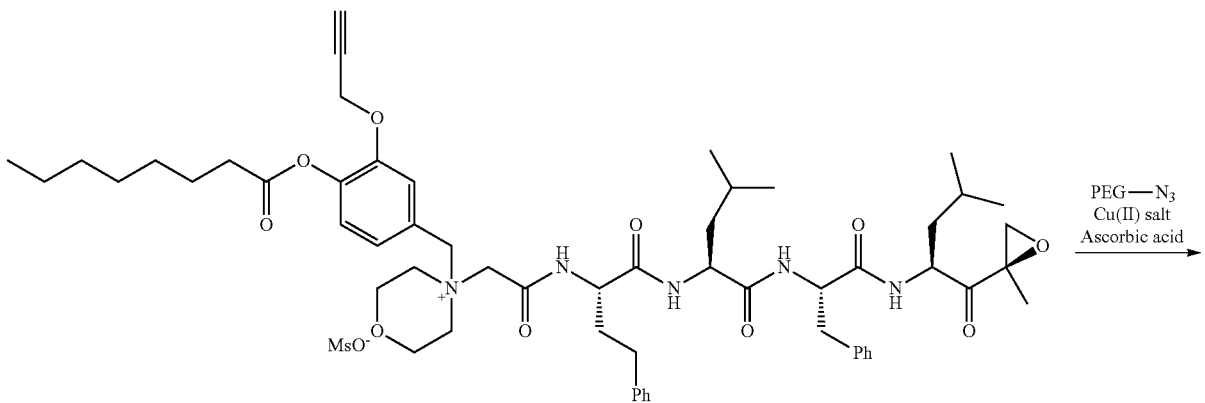

5

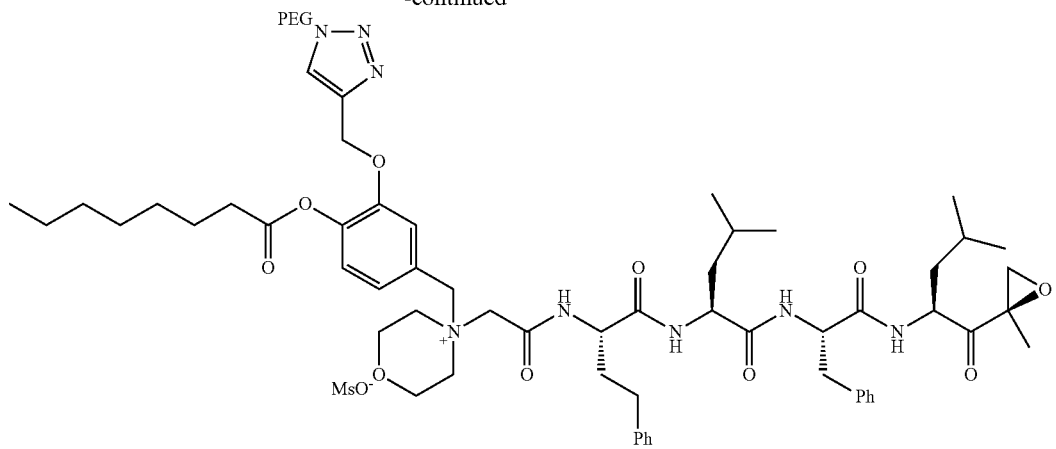

6

Example 10 was prepared by methods analogous to those described in Example 3, wherein the intermediates were made in similar fashion (using heptanoyl chloride and trimethylamine to generate the correlary to intermediate 1 aldehyde shown in eg, 3), and compound 5 and PEG$_{5K}$N$_3$ were reacted following general pegylation procedure A.

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(octanoyloxy)-3-(prop-2-yn-1-yloxy)benzyl)morpholin-4-ium methanesulfonate (5)

To a solution of compound 3 (1.53 g, 4.17 mmol) in MeCN (25 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (1.00 g, 1.39 mmol). The reaction mixture was stirred at 40~45° C. overnight. The solvent was concentrated and the residue was purified by flash column chromatography on silica gel (EtOAc/MeOH=100:5) to afford the desired compound 4, which was then transformed into corresponding mesylate (620 mg, 44% yield) by treatment with ion exchange resin; $^1$H NMR (400 MHz, CDCl$_3$): δ 9.69 (m, 1H), 7.82 (m, 1H), 7.34~7.15 (m, 12H), 7.10 (m, 1H), 6.88 (m, 1H), 6.51 (m, 1H), 5.15 (m, 1H), 4.98 (m, 1H), 4.88 (m, 1H), 4.74 (m, 2H), 4.46 (m, 2H), 4.38 (m, 2H), 4.25 (m, 4H), 4.02 (m, 2H), 3.85 (m, 1H), 3.47 (m, 1H), 3.36 (m, 1H), 3.15 (m, 1H), 3.01 (m, 2H), 2.83 (s, 3H), 2.72 (m, 2H), 2.60 (m, 3H), 2.35~2.14 (m, 3H), 1.76 (m, 2H), 1.55 (m, 2H), 1.48~1.23 (15H), 0.92~0.78 (12H).

Example 11: 4-(4-Acetoxy-3-methyl-5-((1-PEG$_{5K}$-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,1-tetraoxo-4-phenethyl-3,6,9,12-tetraazahexadecyl)morpholin-4-ium methanesulfonate (8)

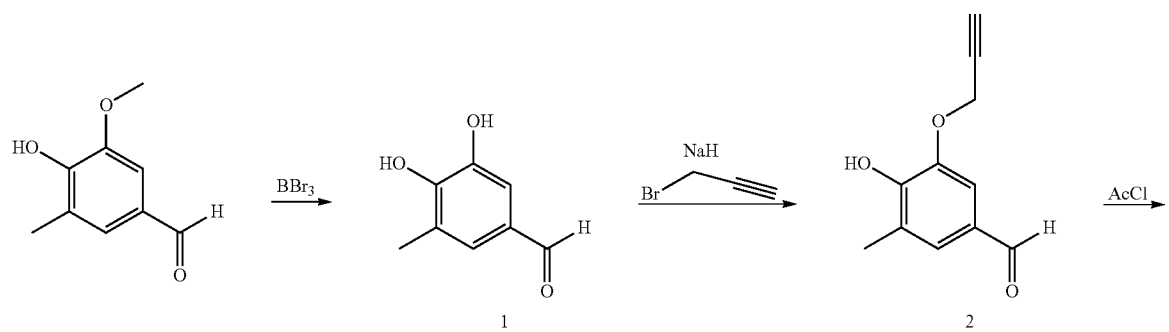

-continued
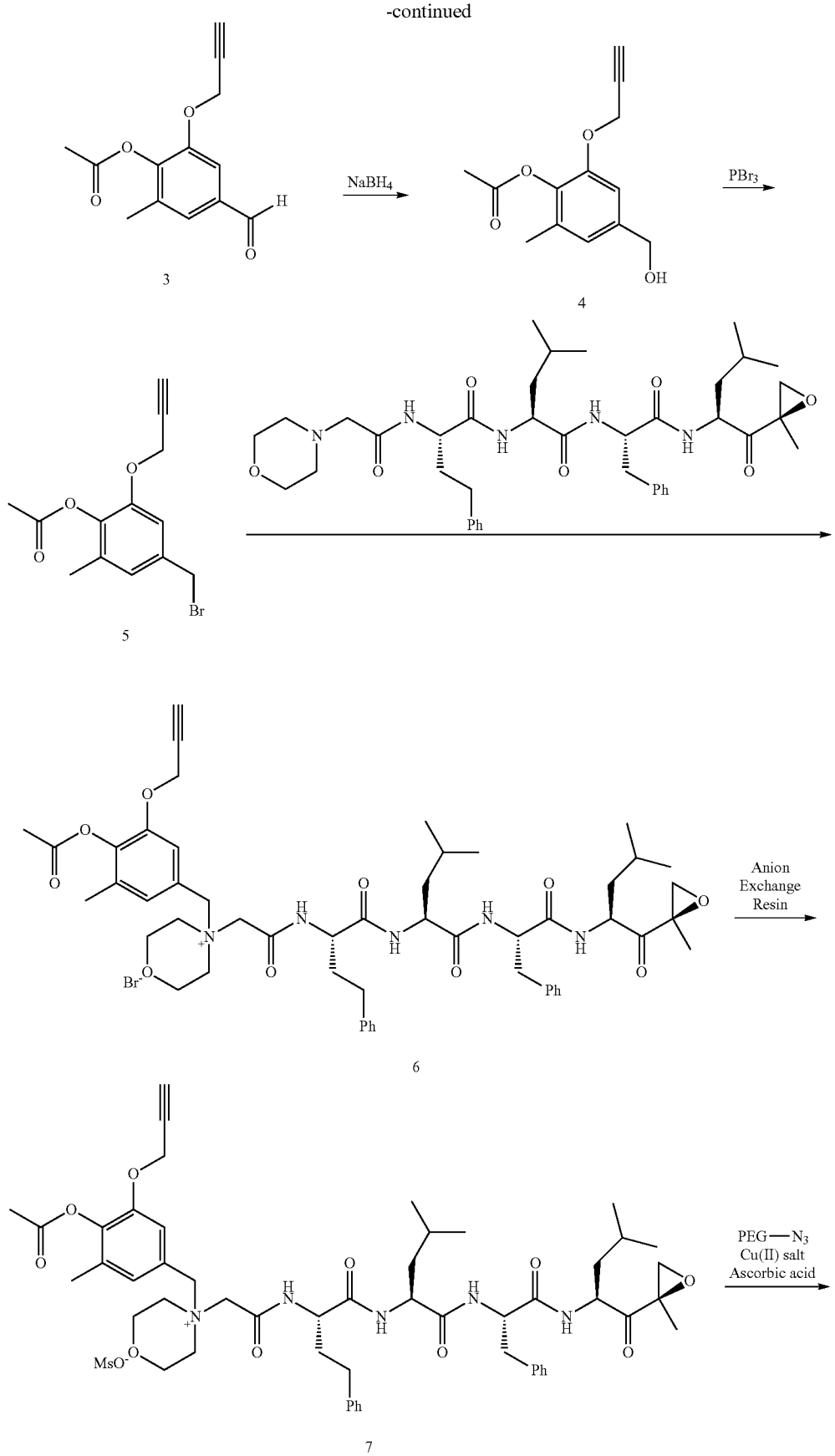

-continued

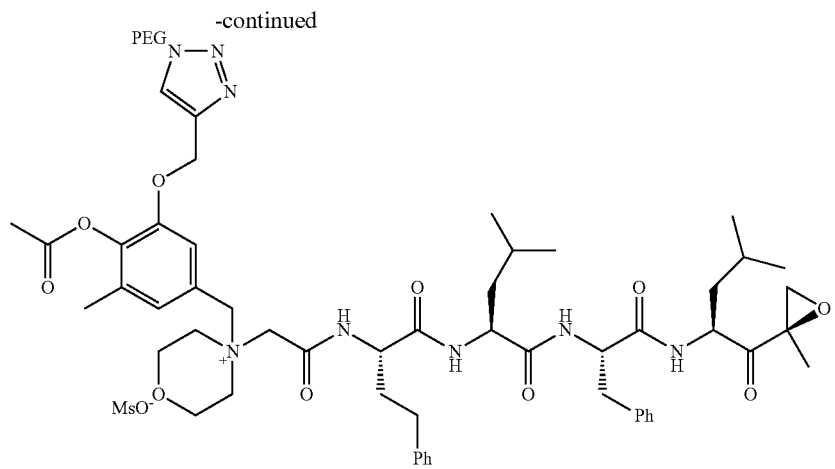

8

3,4-Dihydroxy-5-methylbenzaldehyde (1)

To a solution of compound 4-hydroxy-3-methoxy-5-methyl-benzaldehyde (2.00 g, 12.04 mmol) in DCM (100 mL) was added $BBr_3$ (3.02 g, 12.04 mmol) at −78° C. The reaction mixture was stirred at room temperature overnight. The mixture was quenched with saturated $NH_4Cl$ (100 mL) at −20° C. The two phases were separated and the aqueous solution was extracted with EtOAc (50 mL). The combined organic phases were dried over anhydrous $MgSO_4$ and concentrated. The residue was purified by flash column chromatography on silica gel (Petroleum Ether/EtOAc=10:1) to afford compound 1 (1.56 g, 85% yield); $^1$H NMR (300 MHz, DMSO-d6): δ 9.94 (s, 1H), 9.69 (s, 1H), 9.47 (s, 1H), 7.21 (s, 1H), 7.15 (s, 1H), 2.02 (s, 3H).

4-Hydroxy-3-methyl-5-(prop-2-ynyloxy)benzaldehyde (2)

To a mixture of NaH (489.12 mg, 20.38 mmol) in DMSO (30 mL) was added compound 1 (1.55 g, 10.19 mmol) in DMSO (10 mL) at 0° C. The mixture was stirred for 30 min and then 3-bromoprop-1-yne (1.21 g, 10.19 mmol) was added at the same temperature. The reaction mixture was stirred for 30 min and quenched with water (100 mL). The resulting solution was adjusted to pH=4-5 and extracted with EtOAc (400 mL×3). The combined EtOAc phases were washed with brine (50 mL), dried over anhydrous $MgSO_4$ and concentrated. The residue was purified by flash column chromatography on silica gel (Petroleum Ether/EtOAc=10:1) to afford compound 2 (1.7 g, 88% yield); $^1$H NMR (300 MHz, DMSO-d6): δ 9.84 (s, 1H), 9.77 (s, 1H), 7.42 (m, 2H), 4.94 (d, J=2.1 Hz, 2H), 3.65 (m, 1H), 2.22 (s, 3H).

4-Formyl-2-methyl-6-(prop-2-ynyloxy)phenyl acetate (3)

To a solution of compound 2 (1.60 g, 8.41 mmol) in DCM was added pyridine (2.00 g, 25.23 mmol) followed by acetyl chloride (1.32 g, 16.82 mmol) in droplet at 0° C. The reaction mixture was stirred at RT for 1 hour and then water (100 mL) was added. The two phases were separated and the organic phase was washed with diluted HCl (1 N, 50 mL), dried over anhydrous $MgSO_4$ and concentrated to afford compound 3 (2.0 g, quantitative), which was used in the next step without further purification; $^1$H NMR (300 MHz, DMSO-d6): δ 9.95 (s, 1H), 7.56 (m, 2H), 4.96 (m, 2H), 3.67 (m, 1H), 2.36 (m, 3H), 2.23 (s, 3H).

4-(Hydroxymethyl)-2-methyl-6-(prop-2-ynyloxy)phenyl acetate (4)

To a solution of compound 3 (2.00 g, 8.61 mmol) in THF (50 mL) was added $NaBH_4$ (325.80 mg, 8.61 mmol) in small portions at 0° C. The reaction mixture was stirred at the same temperature for 1 hour and then quenched with water (1 mL). The mixture was diluted with DCM (100 mL), dried directly over anhydrous $MgSO_4$ and concentrated. The residue was purified by flash column chromatography on silica gel (Petroleum Ether/EtOAc=5:1) to afford compound 4 (1.5 g, 74% yield); $^1$H NMR (300 MHz, DMSO-d6): δ 7.00 (s, 1H), 6.86 (s, 1H), 5.26 (m, 1H), 4.78 (d, J=2.4 Hz, 2H), 4.47 (m, 2H), 3.61 (m, 1H), 2.31 (s, 3H), 2.11 (s, 3H).

4-(Bromomethyl)-2-methyl-6-(prop-2-ynyloxy)phenyl acetate (5)

To a solution of compound 4 (1.50 g, 6.46 mmol) in DCM (50 mL) was added $PBr_3$ (1.75 g, 6.46 mmol) at 0° C. The reaction mixture was stirred for 30 min and then quenched with water (50 mL). The two phases were separated and the organic phase was dried over anhydrous $MgSO_4$ and concentrated. The residue was purified by flash column chromatography on silica gel (Petroleum Ether/EtOAc=30:1) to afford compound 5 (750 mg, 39% yield). $^1$H NMR (300 MHz, $CDCl_3$): δ 7.00 (s, 1H), 6.94 (s, 1H), 4.73 (d, J=2.4 Hz, 2H), 4.47 (s, 2H), 2.57 (m, 1H), 2.37 (s, 3H), 2.19 (s, 3H).

4-(4-Acetoxy-3-methyl-5-(prop-2-yn-1-yloxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl) morpholin-4-ium methanesulfonate (7)

To a solution of compound 5 (351.25 mg, 1.19 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (428.35 mg, 595.00 umol). The reaction mixture was stirred at 40-45° C. overnight. An excess of solvent was concentrated and the residue was purified by flash column chromatography on silica gel (EtOAc/MeOH=100:1) to afford desired compound 6, which was transformed into the corresponding mesylate (280 mg, 50% yield) by treatment with ion exchange resin; $^1$H NMR (300 MHz, CDCl$_1$): δ 9.68 (m, 1H), 7.82 (m, 1H), 7.26 (m, 11H), 7.00 (m, 2H), 6.60 (m, 1H), 5.17 (m, 1H), 5.08 (m, 1H), 4.78 (m, 3H), 4.46 (m, 4H), 4.22 (m, 4H), 4.01 (m, 2H), 3.80 (m, 2H), 3.45 (m, 2H), 3.18 (m, 1H), 3.05 (m, 2H), 2.80 (s, 3H), 2.73 (m, 2H), 2.60 (m, 1H), 2.43 (m, 3H), 2.20 (min, 3H), 1.58 (m, 2H), 1.46 (m, 6H), 1.32 (m, 3H), 0.88 (m, 12H).

Example 11 was prepared from compound 7 and PEG$_{5K}$N$_3$ were reacted following general pegylation procedure A.

Example 12: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(((1-PEG$_{5K}$-1H-1,2,3-triazol-4-yl)methyl)carbamoyl)-4-(pivaloyloxy)benzyl)morpholin-4-ium methanesulfonate (9)

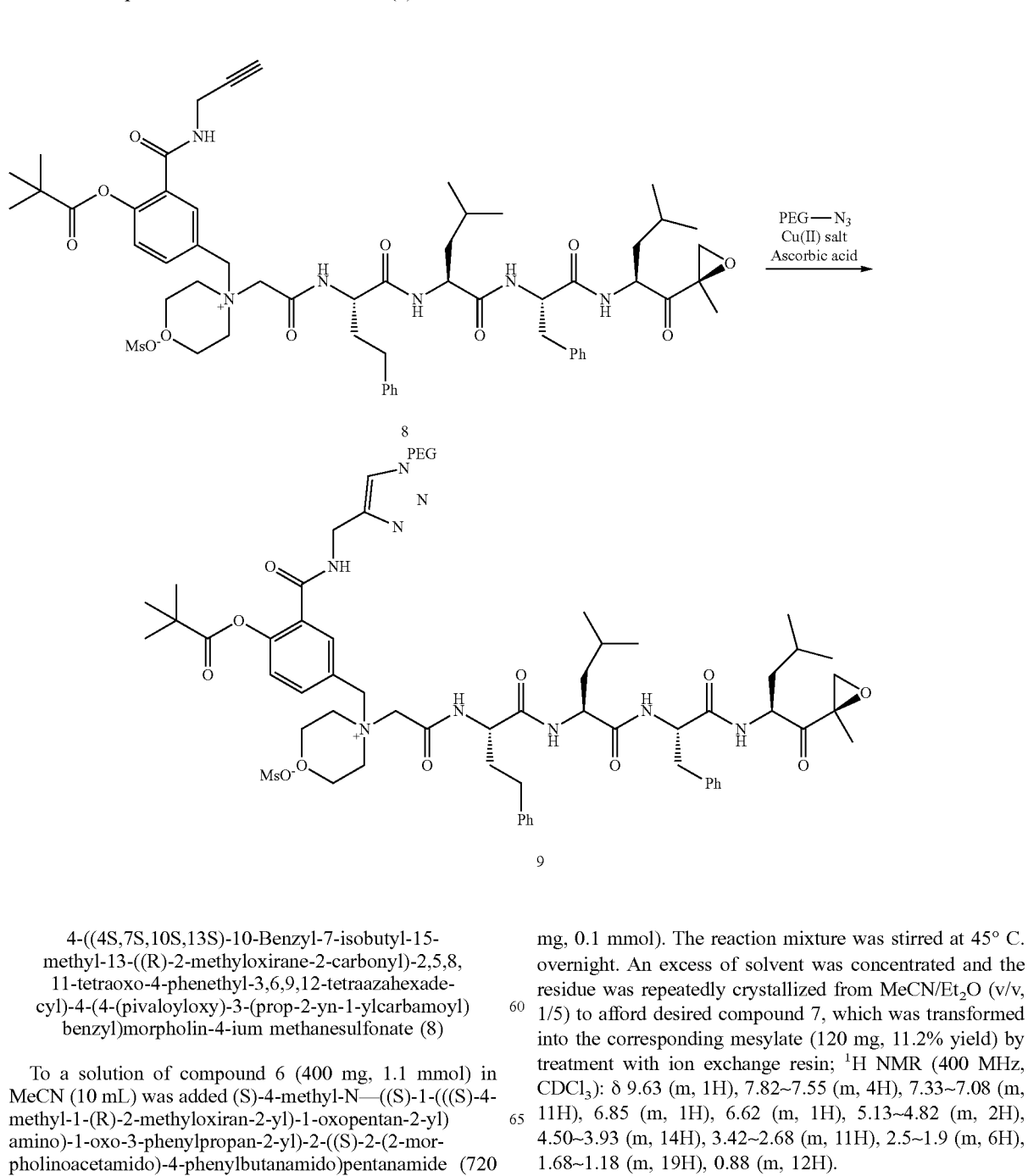

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(pivaloyloxy)-3-(prop-2-yn-1-ylcarbamoyl)benzyl)morpholin-4-ium methanesulfonate (8)

To a solution of compound 6 (400 mg, 1.1 mmol) in MeCN (10 mL) was added (S)-4-methyl-N—((S)-1-(((S)-4-methyl-1-(R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (720 mg, 0.1 mmol). The reaction mixture was stirred at 45° C. overnight. An excess of solvent was concentrated and the residue was repeatedly crystallized from MeCN/Et$_2$O (v/v, 1/5) to afford desired compound 7, which was transformed into the corresponding mesylate (120 mg, 11.2% yield) by treatment with ion exchange resin; $^1$H NMR (400 MHz, CDCl$_3$): δ 9.63 (m, 1H), 7.82~7.55 (m, 4H), 7.33~7.08 (m, 11H), 6.85 (m, 1H), 6.62 (m, 1H), 5.13~4.82 (m, 2H), 4.50~3.93 (m, 14H), 3.42~2.68 (m, 11H), 2.5~1.9 (m, 6H), 1.68~1.18 (m, 19H), 0.88 (m, 12H).

Example 12 was prepared by methods analogous to those described in Example 4, wherein the intermediates were made in similar fashion (using t-butanoyl chloride to generate the correlary to intermediate 1 shown in eg 4), and compound 8 and $PEG_{5K}N_3$ were reacted following general pegylation procedure A.

Example 13: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-((1-($PEG_{5K}$-4-Arm)-1H-1,2,3-triazol-4-yl)methoxy)-4-(pivaloyloxy)benzyl)morpholin-4-ium formate (7)

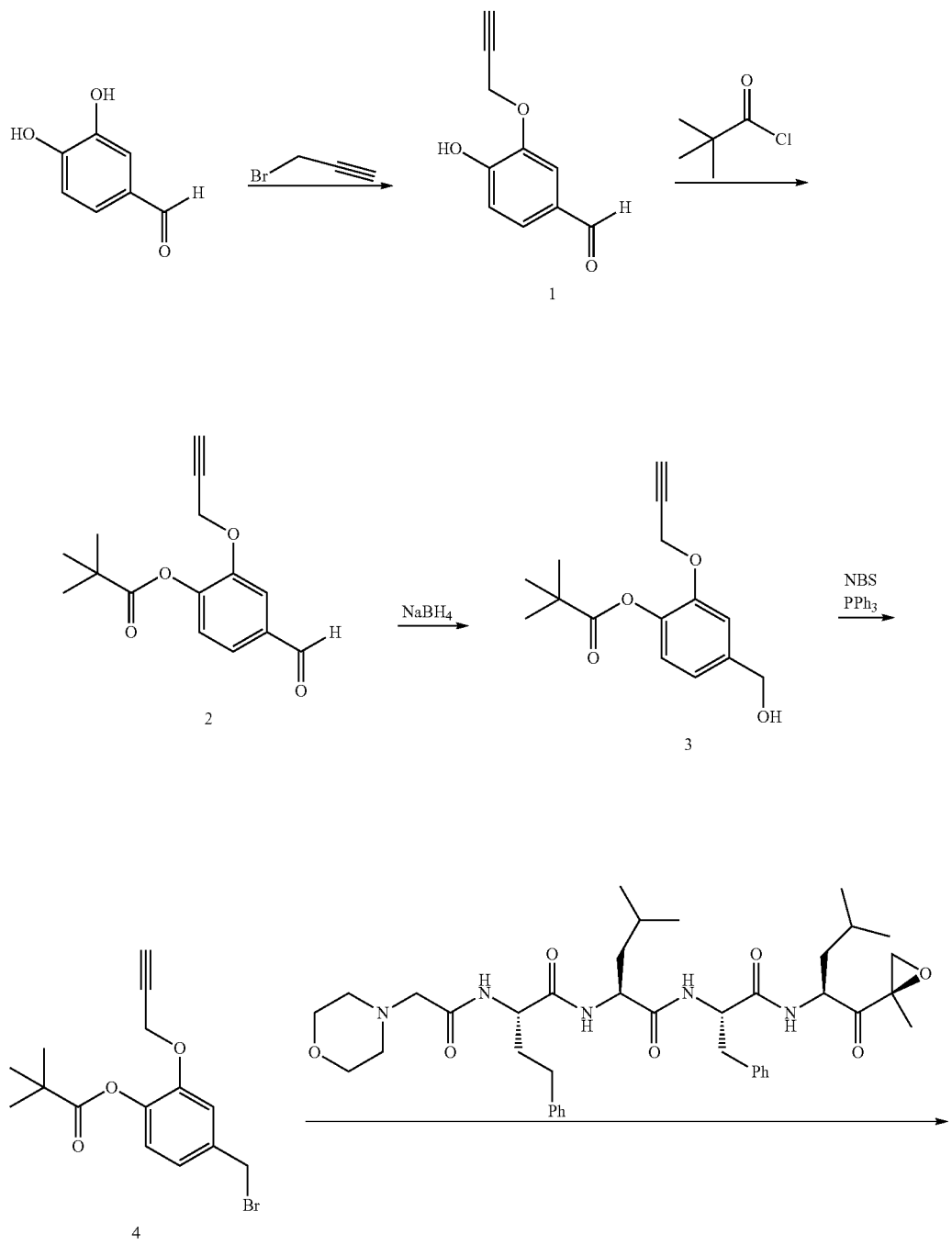

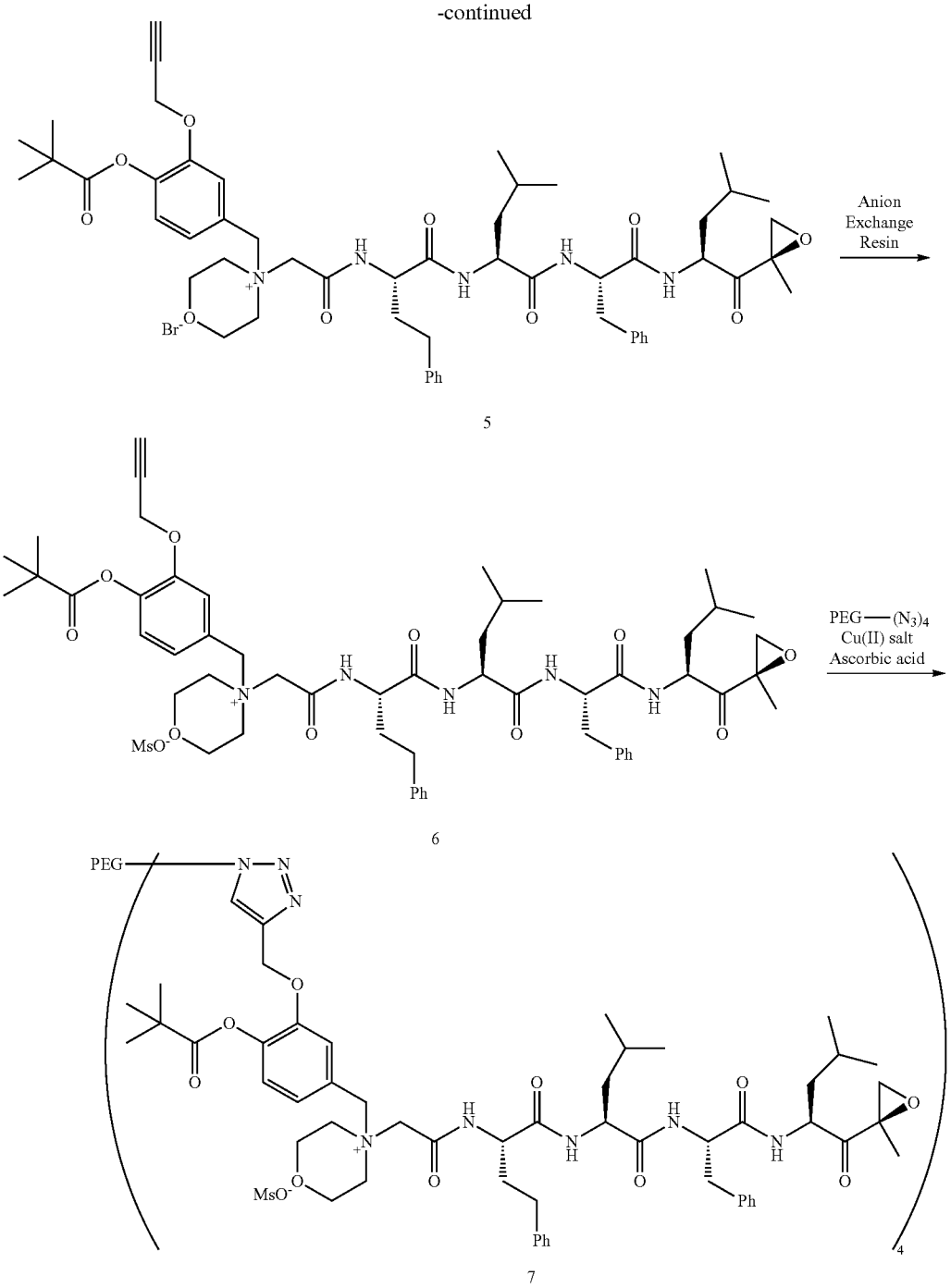

4-Hydroxy-3-(prop-2-ynyloxy)benzaldehyde (1)

To a mixture of NaH in DMSO (300 mL) was added 3,4-dihydroxybenzaldehyde (30 g, 217.39 mmol) in DMSO (50 mL) at 20° C. The mixture was stirred for 30 min and 3-bromoprop-1-yne (25.87 g, 217.39 mmol) was added. The reaction mixture was stirred at RT for one hour and then poured into ice water. The resulting solution was adjusted to pH=2 and then extracted with EtOAc (500 mL×3). The combined organic phases were dried over anhydrous MgSO$_4$ and concentrated. The residue was repeatedly crystallized from DCM/Petroleum Ether (30 mL/500 mL) to afford compound 1 (30 g, 78% yield); $^1$H NMR (CDCl$_3$, 300 MHz,): δ 9.89 (s, 1H), 7.54 (d, J=1.2 Hz, 1H), 7.49 (dd, J$_1$=1.5 Hz, J$_2$=8.1 Hz, 1H), 7.09 (d, J=8.1 Hz, 1H), 4.82 (m, 2H), 2.62 (m, 1H).

4-Formyl-2-(prop-2-ynyloxy)phenylpivalate (2)

To a solution of compound 1 (3.0 g, 17 mmol) in DCM (120 mL) was added Et$_3$N (3.45 g, 34 mmol) followed by pivaloyl chloride (2.34 g, 20.4 mmol) at 0° C. The reaction mixture was stirred at RT for 2 hours. The mixture was washed with saturated NaHCO$_3$ (20 mL) and water (20 mL), dried over anhydrous MgSO$_4$, and concentrated. The residue was purified by flash column chromatography on silica gel (Petroleum Ether/EtOAc=50:1) to afford compound 2 (2.10 g, 47% yield) as a white solid; $^1$H NMR (CDCl$_3$, 300 MHz): δ 9.99 (s, 1H), 7.61 (d, J=1.8 Hz, 1H), 7.55 (dd, J=1.8 Hz, J$_2$=8.1 Hz, 1H), 7.26 (d, J=8.1 Hz, 1H), 4.77 (d, J=2.4 Hz, 2H), 2.58 (t, J=2.4 Hz, 1H), 1.42 (s, 9H).

4-(Hydroxymethyl)-2-(prop-2-ynyloxy)phenylpivalate (3)

To a solution of compound 2 (1.8 g, 6.9 mmol) in DCM/MeOH (100 mL/10 mL) was added NaBH$_4$ (0.37 g, 10.4 mmol) at 0° C. The reaction mixture was stirred at RT for 30 min. The mixture was quenched by acetone (3 mL) and the solvent was concentrated. The residue was purified by flash column chromatography on silica gel (Petroleum Ether/EtOAc=3:1) to afford compound 3 (1.50 g, 83% yield); $^1$H NMR (CDCl$_3$, 300 MHz): δ 7.11 (m, 1H), 7.00 (m, 2H), 4.68 (m, 4H), 2.53 (m, 1H), 1.41 (s, 9H).

4-(Bromomethyl)-2-(prop-2-ynyloxy)phenylpivalate (4)

To a solution of compound 3 (1.50 g, 5.7 mmol) in DCM (60 mL) were added PPh$_3$ (1.80 g, 6.8 mmo) and NBS (1.11 g, 6.3 mmol) at 0° C. The reaction mixture was stirred at RT for 0.5 hour. An excess of solvent was concentrated and the residue was purified by flash column chromatography on silica gel (Petroleum Ether/EtOAc=50:1) to afford compound 4 (1.34 g, 81% yield); $^1$H NMR (CDCl$_3$, 300 MHz): δ 7.12 (d, J=1.5 Hz, 1H), 7.03 (m, 2H), 4.70 (d, J=2.4 Hz, 2H), 4.51 (d, J=3.9 Hz, 2H), 2.56 (t, J=2.4 Hz, 1H), 1.40 (s, 9H).

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(4-(pivaloyloxy)-3-(prop-2-yn-1-yloxy)benzyl)morpholin-4-ium methanesulfonate (6)

To a solution of compound 4 (2.38 g, 7.3 mmol) in MeCN (30 ml) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (2.64 g, 3.7 mmol). The reaction mixture was stirred at 45° C. overnight. An excess of solvent was concentrated and the residue was purified by flash column chromatography on silica gel (EtOAc/MeOH=100:6) to afford desired compound 5, which was transformed into the corresponding mesylate (1.23 g, 25% yield) by treatment with ion exchange resin; $^1$H NMR (CDCl$_1$, 300 MHz): δ 9.83 (m, 1H), 7.92 (m, 1H), 7.50-7.11 (m, 13H), 7.03 (m, 1H), 6.62 (m, 1H), 5.25 (m, 1H), 5.15-4.90 (m, 2H), 4.88-4.75 (m, 2H), 4.70-4.20 (m, 7H), 4.20-3.90 (m, 3H), 3.70-3.40 (m, 4H), 3.26 (m, 1H), 3.15 (m, 2H), 2.90 (s, 3H), 2.85 (m, 2H), 2.40-2.10 (m, 2H), 1.87-1.63 (m, 5H), 1.55 (m, 3H), 1.41 (s, 9H), 1.38 (m, 2H), 0.89-1.05 (m, 12H).

Compound Example 13 was prepared from compound 6 and PEG$_{20K}$(N$_3$)$_4$ following general pegylation procedure A. Compound Example 13 is also designated as OP-59381 in various of the figures illustrated herein. $^1$H NMR (500 MHz, relaxation time=10 sec. DMSO-d$_6$) δ 8.47 (s, 4H), 8.42 (d, J=8.5 Hz, 4H), 8.29 (d, J=7.5 Hz, 4H), 8.11 (s, 4H), 8.07 (d, J=8 Hz, 4H), 7.53 (s, 4H), 7.26-7.29 (m, 4H), 7.11-7.19 (m, 32H), 7.05-7.06 (m, 4H), 5.21 (s, 8H), 4.95 (dd, J=12.5 Hz and 39.0 Hz, 8H), 4.52-4.54 (m, 12H), 4.28-4.38 (m, 16H), 4.17-4.20 (m, 4H), 4.06 (m, 20H), 3.78 (t, J=5.5 Hz, 8H), 3.61-3.65 (m, 8H), 3.50 (s, 2133H), 3.35-3.37 (m, 8H), 3.10 (d, J=5 Hz, 4H), 2.94-2.98 (m, 12H), 2.73-2.78 (m, 4H), 2.50-2.65 (m, 8H), 1.90-1.98 (m, 4H), 1.78-1.88 (m, 4H), 1.51-1.68 (m, 8H), 1.39 (s, 12H), 1.25-1.38 (m, 16H), 1.18 (s, 36H), 0.833-0.881 (m, 24H), 0.782-0.815 (m, 24H); Loading: 86%.

Example 14: 4-((4S,7S,10S,13S)-10-Benzyl-7-isobutyl-5-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((1-PEG$_{20K}$-4-Arm-1H-1,2,3-triazol-4-yl)methoxy)benzyl)morpholin-4-ium methanesulfonate (14)

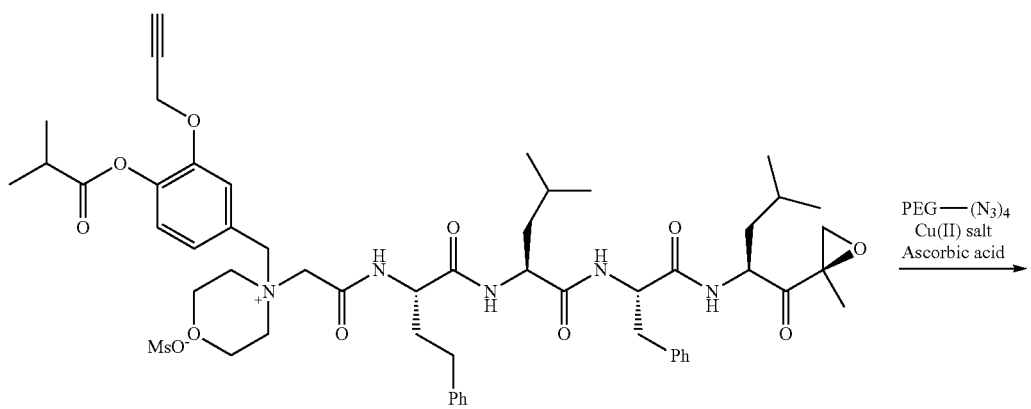

-continued

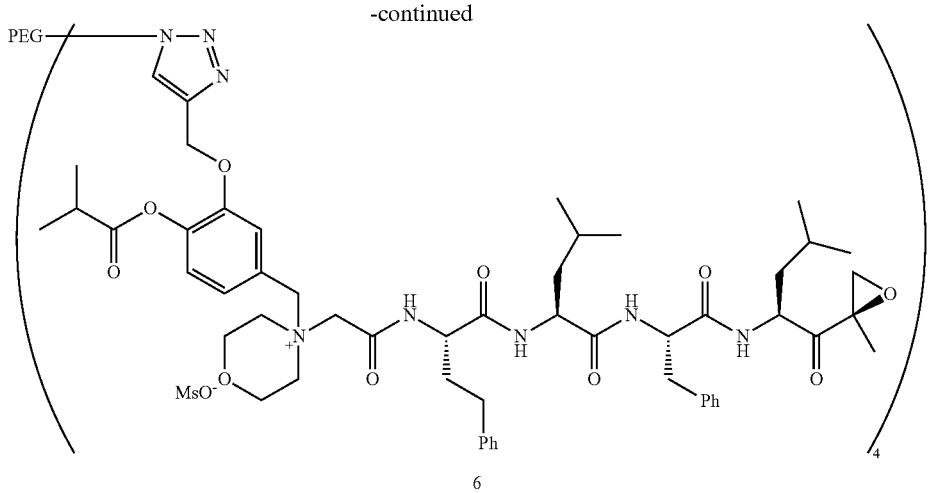

6

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(4-(isobutyloxy)-3-(prop-2-yn-1-yloxy)benzyl)morpholin-4-ium methanesulfonate (5)

To a solution of compound 3 (0.5 g, 1.6 mmol) in MeCN (9 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (864 mg, 1.2 mmol). The reaction mixture was stirred at 45° C. for 20 hours. The solvent was concentrated and the residue was purified by flash column chromatography on silica gel (EtOAc/MeOH=100:6) to afford desired compound 4, which was then transformed into the corresponding mesylate (500 mg, 44% yield) by treatment with ion exchange resin; $^1$H NMR (400 MHz, CDCl$_3$): δ 9.67 (m, 1H), 7.82 (m, 1H), 7.27 (m, 16H), 6.85 (m, 1H), 6.47 (m, 1H), 5.13 (m, 1H), 5.02 (m, 1H), 4.85 (m, 1H), 4.70 (m, 2H), 4.45 (m, 2H), 4.37 (m, 2H), 4.23 (m, 4H), 3.92 (m, 2H), 3.84 (m, 1H), 3.46 (m, 1H), 3.35 (m, 1H), 3.15 (m, 1H), 3.03 (m, 1H), 2.92 (m, 1H), 2.80 (s, 3H), 2.73 (m, 2H), 2.58 (m, 1H), 2.20 (m, 1H), 2.12 (m, 1H), 1.70 (m, 1H), 1.62 (m, 3H), 1.43 (m, 4H), 1.28 (m, 6H), 1.21 (m, 3H), 0.85 (m, 12H).

Example 14 was prepared by methods analogous to those described in Example 3, 5 and 7 wherein the intermediates were made in similar fashion (using isopropanoyl chloride to generate the correlary to intermediate 1 shown in eg 3), and compound 5 and PEG$_{20K}$N$_3$ were reacted following general pegylation procedure A.

Example 15: 4-(4-Acetoxy-3-(2-(2-(2-((1-PEG$_{5K}$-1H-1,2,3-triazol-4-yl)methoxy)ethoxy)ethoxy)ethoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (9)

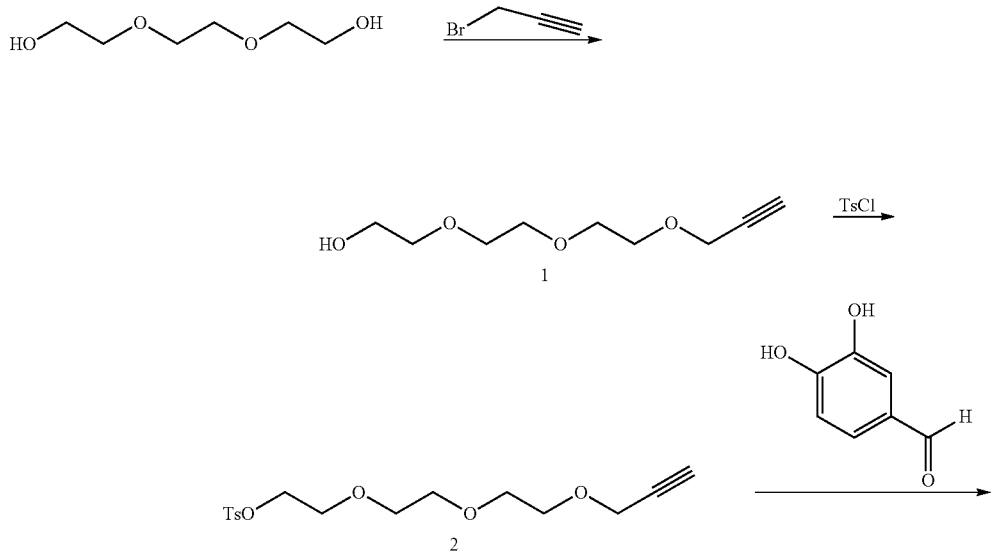

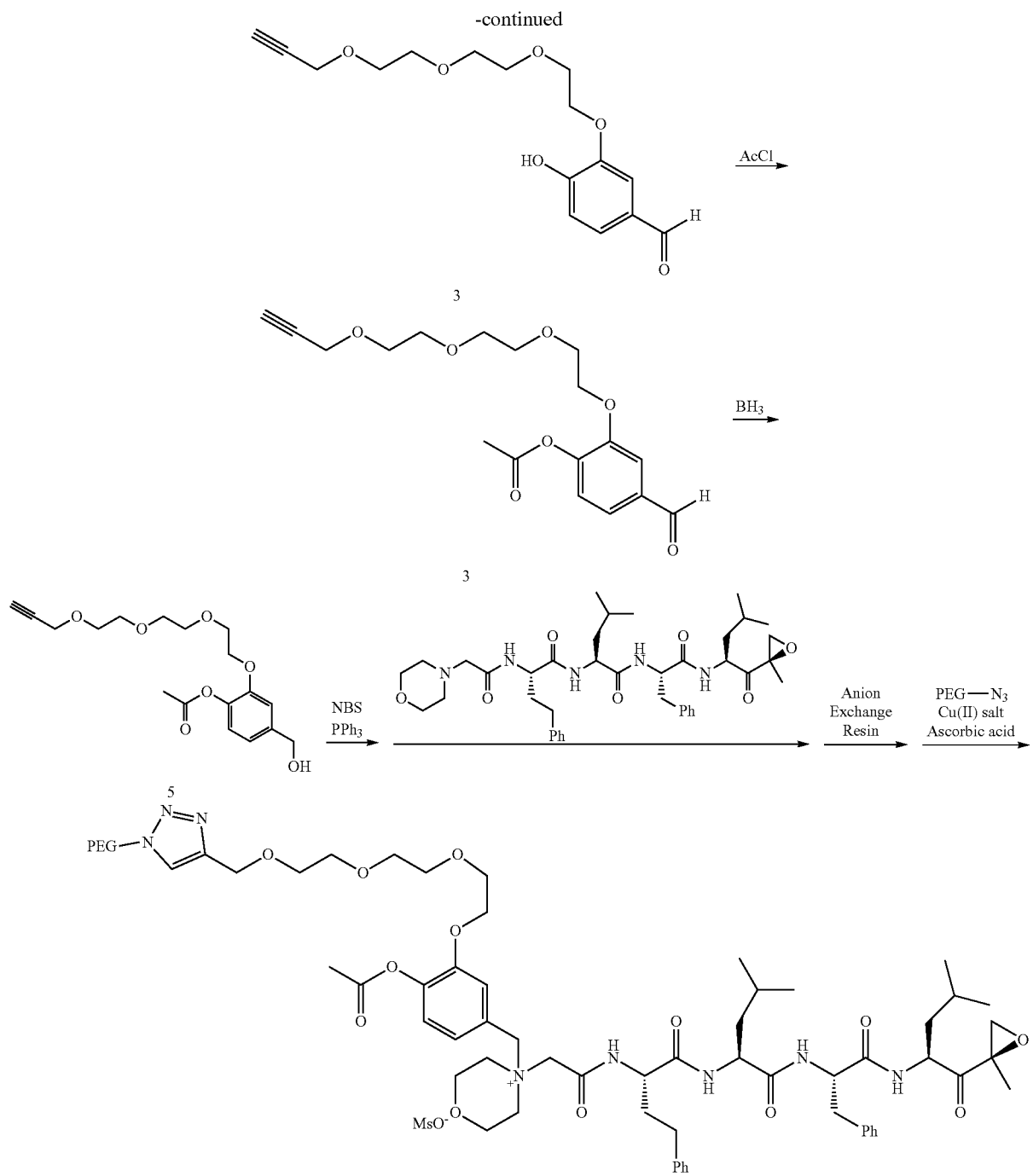

2-(2-(2-(Prop-2-yn-1-yloxy)ethoxy)ethoxy)ethan-1-ol (1)

To a mixture of NaH (3.47 g, 0.086 mol) in THF (320 mL) was added 2,2'-(ethane-1,2-diylbis(oxy))diethanol (20 g, 0.133 mol) at 0° C. The mixture was stirred at the same temperature for 30 min and then 3-bromoprop-1-yne (7.93 g, 0.066 mol) was added. The reaction mixture was kept at the 0° C. for 2 hours and then left to RT overnight. The mixture was quenched with water (4 mL) and the resulting solution was dried over anhydrous MgSO₄ directly and concentrated. The residue was purified by flash column chromatography on silica gel (Petroleum Ether/EtOAc=1:1) to afford compound 1 (10.12 g, 80% yield); $^1$H NMR (400 MHz, CDCl$_3$): δ 4.21 (d, J=2.0 Hz, 2H), 3.75-3.68 (m, 10H), 3.62 (m, 2H), 2.44 (m, 1H), 2.23 (s, 1H).

2-(2-(2-(Prop-2-yn-11-yloxy)ethoxy)ethoxy)ethyl 4-methylbenzenesulfonate (2)

To a solution of compound 1 (5 g, 26.6 mol) in DCM (80 mL) was added TsCl (7.6 g, 39.89 mmol) at 0° C. followed by pyridine (25 mL). The reaction mixture was stirred at RT overnight. The DCM solution was washed with HCl (3 N, 50 mL×4), dried and concentrated to afford compound 2 (7.89 g, 87% yield), which was used in the next step without further purification; $^1$H NMR (400 MHz, CDCl$_3$): δ 7.80 (d, J=8.4 Hz, 2H), 7.34 (d, J=8.0 Hz, 2H), 4.20 (m, 4H), 3.68 (m, 6H), 3.61 (m, 4H), 2.45 (m, 1H), 2.40 (m, 3H).

4-Hydroxy-3-(2-(2-(2-(prop-2-ynyloxy)ethoxy)ethoxy)ethoxy)benzaldehyde (3)

To a mixture of NaH (0.82 g, 20.47 mmol) in DMSO (50 mL) were added a solution of 3,4-dihydroxybenzaldehyde (1.41 g, 10.23 mmol) in DMSO (5 mL) and a solution of compound 2 (3.5 g, 10.23 mmol) in DMSO (5 mL) at 20° C. sequentially. The reaction mixture was stirred at RT overnight. The mixture was poured into ice water (500 mL) and this aqueous solution was adjusted to pH=2 by 2 N HCl. The resulting mixture was extracted with EtOAc (50 mL×3) and the combined EtOAc phases were dried over anhydrous MgSO$_4$ and concentrated. The residue was purified by flash column chromatography on silica gel (Petroleum Ether/EtOAc=1:1) to afford compound 3 (579 mg, 18% yield); $^1$H NMR (400 MHz, CDCl$_3$): δ9.80 (s, 1H), 7.46 (m, 2H), 7.03 (d, J=7.6 Hz, 1H), 4.25 (m, 4H), 3.88 (m, 2H), 3.70 (m, 8H), 2.45 (m, 1H).

4-Formyl-2-(2-(2-(2-(prop-2-ynyloxy)ethoxy)ethoxy)ethoxy)phenyl acetate (4)

To a solution of compound 3 (479 mg, 1.56 mmol) in THF (20 nL) were added TEA (471 mg, 4.67 mmol) and Ac$_2$O (238 mg, 2.33 mmol) at 0° C. The reaction mixture was stirred at room temperature for 3 hours. An excess of solvent was concentrated and the residue was dissolved in EtOAc (40 mL). The resulting solution was washed with water (50 mL), dried over anhydrous MgSO$_4$ and concentrated. The residue was purified by flash column chromatography on silica gel (Petroleum Ether/EtOAc=2:1) to afford compound 4 (400 mg, 74% yield): $^1$H NMR (400 MHz, CDCl$_3$): δ 9.94 (s, 1H), 7.52 (d, J=1.6 Hz, 1H), 7.49 (dd, J$_1$=1.6 Hz, J$_2$=8.0 Hz, 1H), 7.22 (d, J=8.0 Hz, 1H), 4.23 (m, 2H), 4.20 (m, 2H), 3.86 (m, 2H), 3.72 (m, 8H), 2.43 (m, 1H), 2.34 (s, 3H).

4-(Hydroxymethyl)-2-(2-(2-(2-(prop-2-ynyloxy)ethoxy)ethoxy)ethoxy)phenyl acetate (5)

To a solution of compound 4 (1.18 g, 3.38 mmol) in THF (50 mL) was added BH$_3$/THF solution (3.4 mL, 3.38 mmol) dropwise at 0° C. The reaction mixture was stirred for 30 min and then quenched with MeOH (5 mL). The reaction solution was concentrated and the residue was purified by flash column chromatography on silica gel (Petroleum Ether/EtOAc=1:1) to afford compound 5 (700 mg, 59% yield): $^1$H NMR (300 MHz, CDCl$_3$): δ 7.09 (d, J=1.8 Hz, 1H), 7.03 (d, J=8.1 Hz, 1H), 6.94 (dd, J$_1$=1.8 Hz, J$_2$=8.1 Hz, 1H), 4.68 (s, 2H), 4.22 (m, 4H), 3.85 (m, 2H), 3.74 (m, 8H), 2.46 (m, 1H), 2.33 (s, 3H).

4-(Bromomethyl)-2-(2-(2-(2-(prop-2-ynyloxy)ethoxy)ethoxy)ethoxy)phenyl acetate) (6)

To a solution of compound 5 (680 mg, 1.93 mmol) in DCM (40 mL) was added PPh$_3$ (607 mg, 2.32 mmol) followed by NBS (374 mg, 2.13 mmol) in small portions at 0° C. An excess of solvent was concentrated and the residue was purified by flash column chromatography on silica gel (Petroleum Ether/EtOAc=3:1) to afford compound 6 (430 mg, 54% yield); $^1$H NMR (400 MHz, CDCl$_3$): δ 7.03 (s, 1H), 6.99 (m, 2H), 4.46 (s, 2H), 4.20-4.16 (m, 4H), 3.83 (m, 2H), 3.68 (m, 8H), 2.43 (m, 1H), 2.29 (s, 3H). Compound 6 was converted to compound 8 using analogous methods as described herein.

4-(4-Acetoxy-3-(2-(2-(2-(prop-2-yn-1-yloxy)ethoxy)ethoxy)ethoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

To a solution of compound 6 (430 mg, 1.04 mmol) in MeCN (5 mL) was added compound (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (743 mg, 1.04 mmol). The reaction mixture was stirred at RT overnight. An excess of solvent was concentrated and the residue was purified by flash column chromatography on silica gel (EtOAc/MeOH=10:1) to afford desired product 7 (160 mg, 14% yield), which was then transformed to the corresponding mesylate salt (135 mg, 85% yield) by treatment with ion exchange resin; $^1$H NMR (400 MHz, CDCl$_3$): δ 9.68 (m, 1H), 7.73 (m, 1H), 7.29-7.05 (m, 13H), 6.82 (m, 1H), 6.40 (m, 1H), 5.15 (m, 1H), 5.08 (m, 1H), 5.02 (m, 1H), 4.82 (m, 2H), 4.51 (m, 2H), 4.38 (m, 3H), 4.20 (m, 4H), 4.15 (m, 2H), 4.03 (m, 2H), 3.84 (m, 1H), 3.76 (m, 2H), 3.65 (m, 9H), 3.50 (m, 1H), 3.38 (m, 1H), 3.18 (m, 1H), 3.02 (m, 2H), 2.86 (m, 1H), 2.80 (s, 3H), 2.64 (m, 2H), 2.46 (m, 1H), 2.32 (m, 3H), 2.30-2.05 (m, 3H), 1.60 (m, 2H), 1.52 (m, 6H), 1.24 (m, 2H), 0.84 (12H).

Example 15 was prepared from compound 8 and PEG$_{5K}$N$_3$ following general pegylation procedure A.

Example 16: 4-(4-Acetoxy-3-(1-(PEG$_{5K}$-imino)ethyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (5)

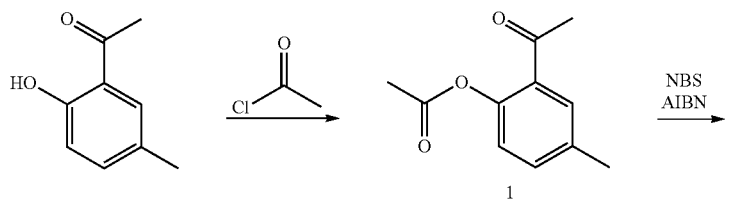

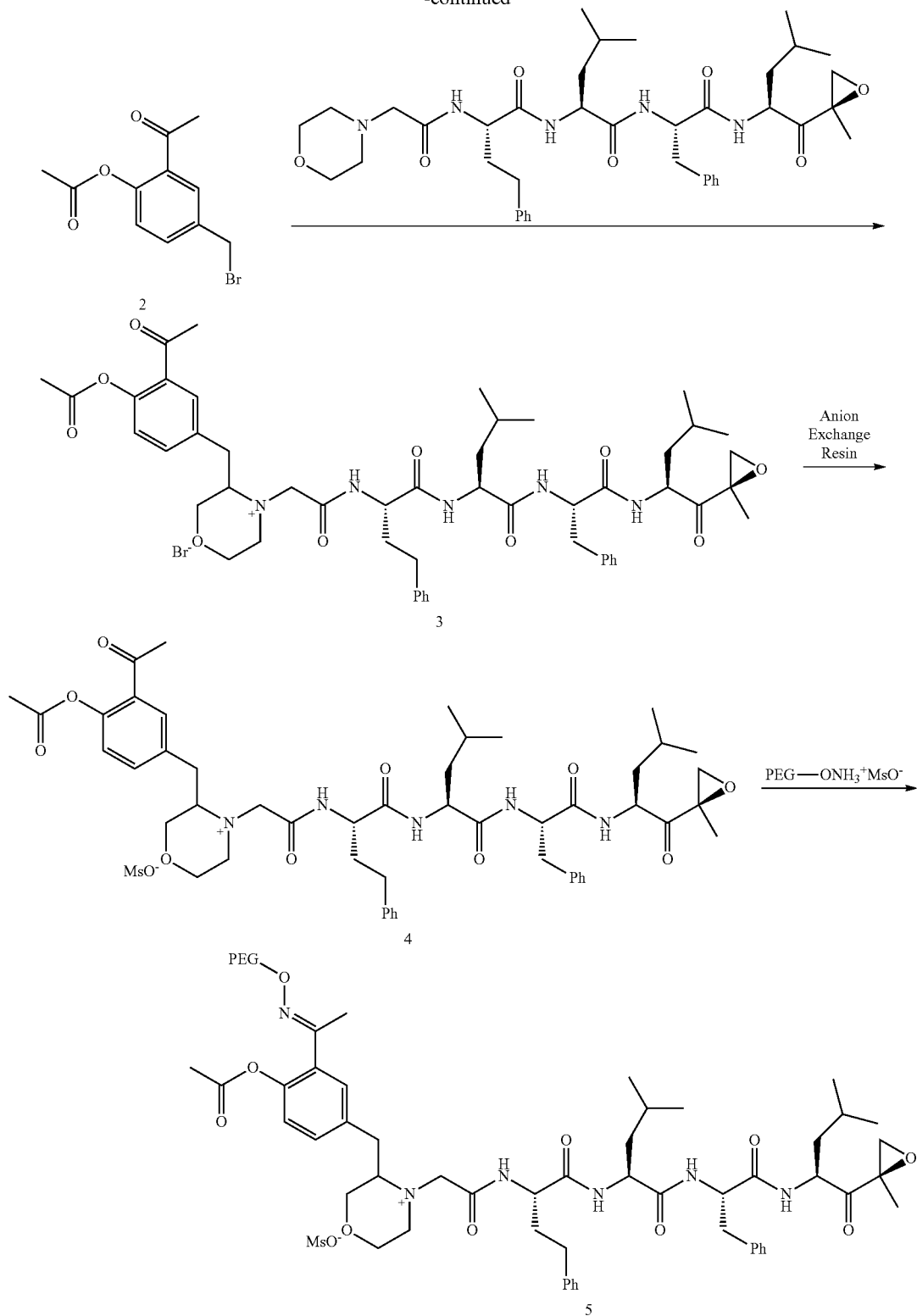

2-Acetyl-4-methylphenyl acetate (1)

To a solution of 1-(2-hydroxy-5-methylphenyl)ethanone (1.5 g, 0.01 mol) in DCM (15 mL) were added TEA (1.5 g, 0.015 mol) and acetyl chloride (0.94 g, 0.012 mol) at 0° C. The reaction mixture was stirred at room temperature overnight. This mixture was quenched with water (20 mL). The DCM phase was collected, washed with brine (20 mL), dried over anhydrous $MgSO_4$, and concentrated. The residue was purified by flash column chromatography on silica gel (Petroleum Ether/EtOAc=3:1) to afford compound 1 (0.9 g, 47% yield); $^1$H NMR (300 MHz, CDCl$_3$): δ 7.64 (m, 1H), 7.37 (m, 1H), 7.02 (d, J=8.1 Hz, 1H), 2.57 (s, 3H), 2.42 (s, 3H), 2.37 (s, 3H).

2-Acetyl-4-(bromomethyl)phenyl acetate (2)

To a solution of compound 1 (0.5 g, 2.6 mmol) in CCl$_4$ (20 mL) were added NBS (573 mg, 3.25 mmol) and AIBN (42.6 mg, 0.26 mmol). The reaction mixture was heated under reflux overnight. The mixture was cooled to RT and filtered. The filtrate was concentrated and the residue was purified by flash column chromatography on silica gel (Petroleum Ether/EtOAc=10:1) to afford compound 2 (160 mg, 23% yield); $^1$H NMR (300 MHz, DMSO-d6): δ 8.02 (m, 1H), 7.73 (d, J=8.1 Hz, 1H), 7.25 (d, J=8.4 Hz, 1H), 4.81 (s, 2H), 2.53 (s, 3H), 2.32 (s, 3H).

4-(4-Acetoxy-3-acetylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (4)

To a solution of compound 2 (1.03 g, 3.7 mmol) in MeCN (10 mL) was added compound (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (884.7 mg, 1.23 mmol). The reaction mixture was heated at 45° C. overnight. An excess of solvent was concentrated and the residue was purified by flash column chromatography on silica gel (EtOAc/MeOH=100:3) to afford the desired compound 3, which was transformed into the corresponding mesylate (260 mg, 21% yield) by treatment with ion exchange resin; $^1$H NMR (300 MHz, CDCl$_3$): δ 9.62 (m, 1H), 8.06 (m, 1H), 7.88~7.71 (m, 2H), 7.33~7.11 (m, 11H), 6.95 (m, 1H), 6.66 (m, 1H), 5.33~4.91 (m, 2H), 4.55~3.90 (m, 11H), 3.58~2.91 (m, 4H), 2.85 (s, 3H), 2.74 (m, 2H), 2.61 (s, 3H), 2.40 (s, 3H), 2.31~1.94 (m, 7H), 1.72~1.18 (m, 8H), 0.88 (m, 12H).

Example 16 was prepared from compound 4 and PEG$_{5K}$ONH$_3^+$.MsO$^-$ following general pegylation procedure B.

Example 17: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(1-(PEG$_{5K}$-imino)ethyl)-4-(pivaloyloxy)benzyl)morpholin-4-ium methanesulfonate (5)

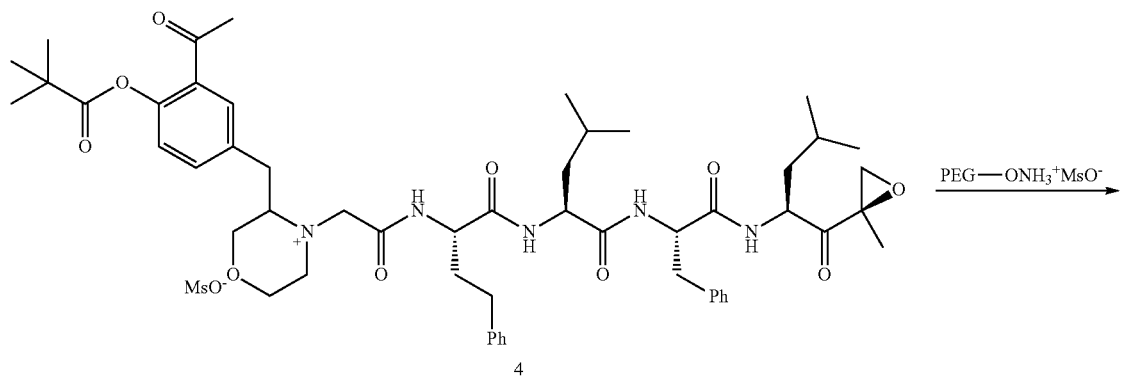

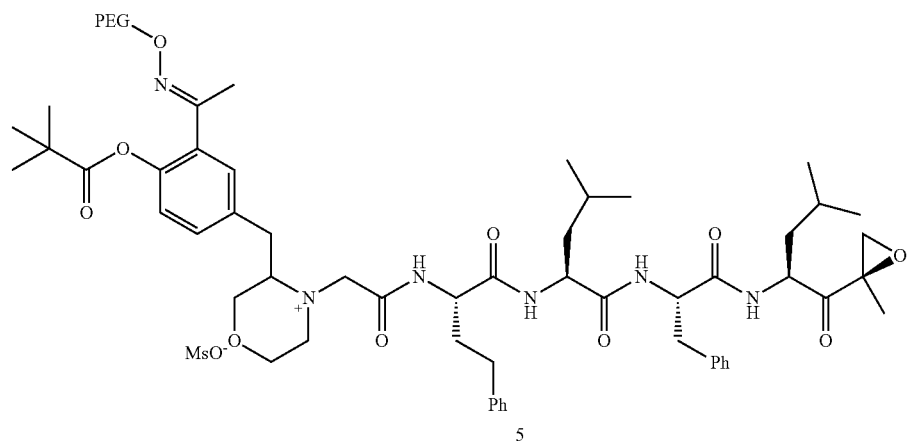

4-(3-Acetyl-4-(pivaloyloxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (4)

To a solution of compound 2 (1.03 g, 3.2 mmol) in MeCN (10 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (766 mg, 1.06 mmol). The reaction mixture was stirred at 45° C. overnight. An excess of solvent was concentrated and the residue was repeatedly crystallized from EtOAc/Et$_2$O (5/1, v/v) to afford desired compound 3, which was transformed into the corresponding mesylate (300 mg, 32% yield) by treatment with ion exchange resin; $^1$H NMR (300 MHz, CDCl$_3$): δ 9.68 (m, 1H), 8.06 (m, 1H), 7.75 (m, 1H), 7.40-7.15 (m, 12H), 6.92 (m, 1H), 6.65 (m, 1H), 5.28-4.96 (m, 2H), 4.55-4.42 (m, 4H), 4.38-4.18 (m, 4H), 4.07-3.90 (m, 3H), 3.60-3.30 (m, 2H), 3.17 (m, 2H), 3.04 (m, 2H), 2.85 (s, 3H), 2.80 (m, 2H), 2.63 (s, 3H), 2.44 (s, 3H), 2.28-2.12 (m, 2H), 2.04 (m, 3H), 1.76 (m, 3H), 1.50-1.40 (m, 6H), 1.30-1.18 (m, 4H), 0.92-0.84 (m, 12H).

Example 17 was prepared by methods analogous to those described in Example 16, wherein the intermediates were made in similar fashion (using t-butanoyl chloride to generate the correlary to intermediate 1 shown in eg 16), and compound 4 and PEG$_{5K}$ONH$_3^+$.MsO$^-$ following general pegylation procedure B.

Example 18: 4-(3-Acetoxy-4-((PEG$_{5K}$-imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

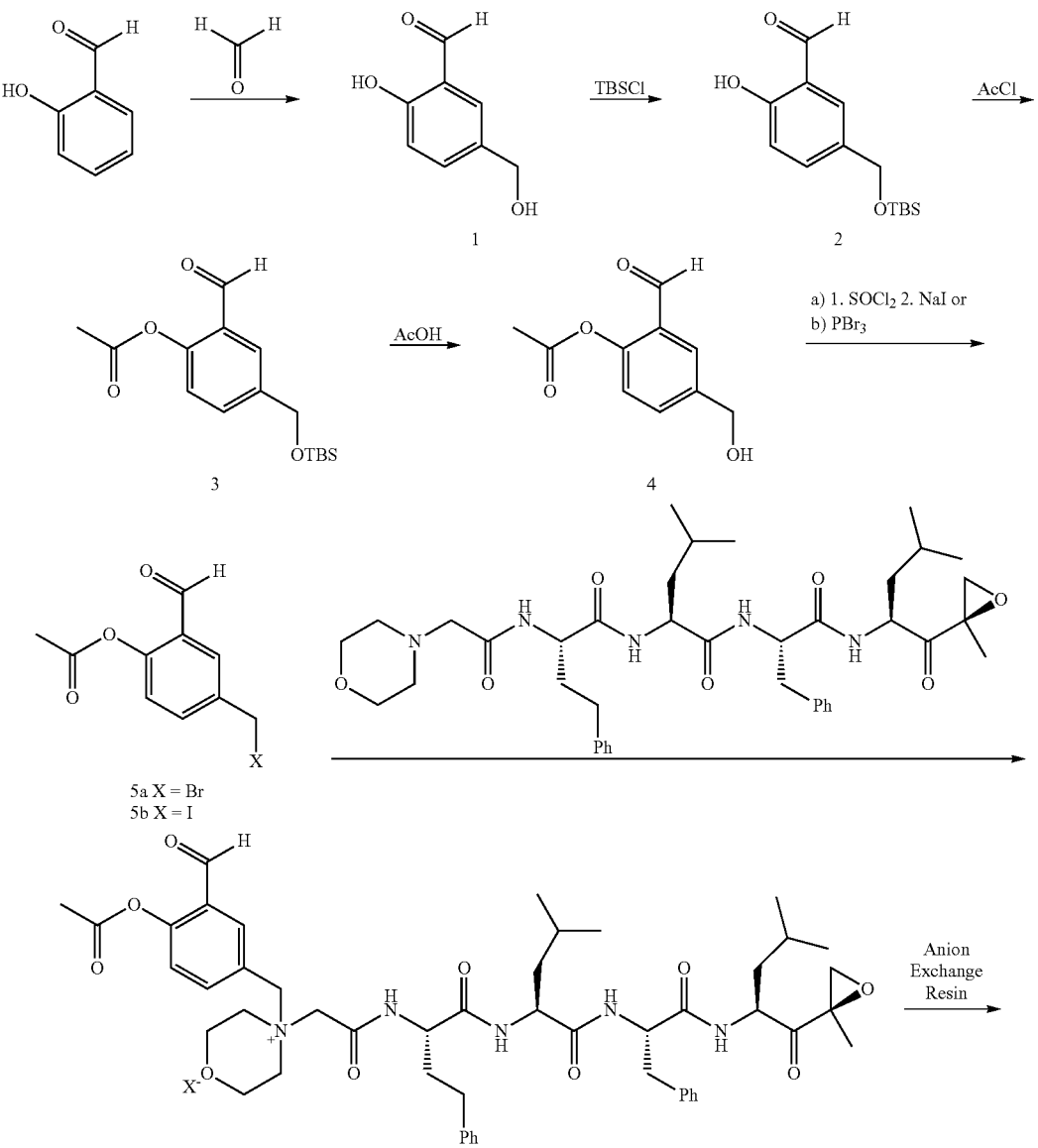

-continued

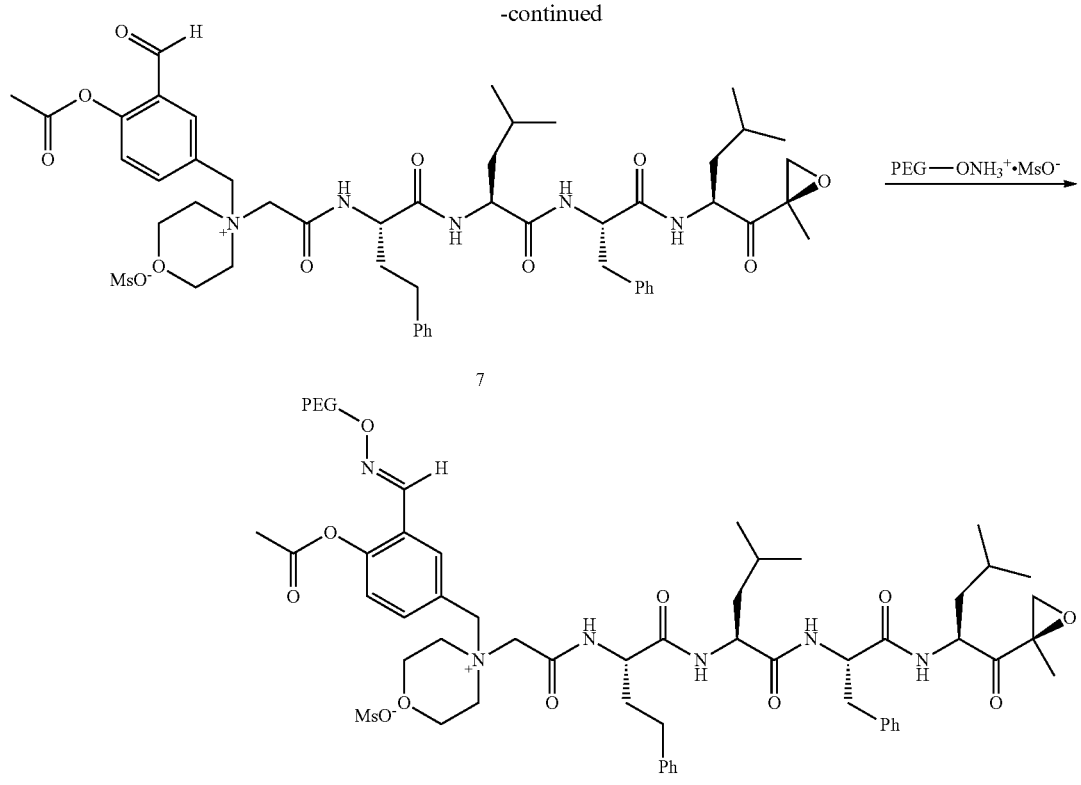

2-Hydroxy-5-(hydroxymethyl)benzaldehyde (1)

To an aqueous solution of formaldehyde (37%, 17 mL) were added 2-hydroxybenzaldehyde (10.3 g, 84.4 mmol) and concentrated HCl (42 mL). The reaction mixture was heated under reflux overnight. The mixture was cooled to RT and then extracted with EtOAc (200 mL). The organic phase was dried over anhydrous sodium sulfate and concentrated. The residue was purified by flash column chromatography on silica gel (Petroleum Ether/EtOAc=3:1) to afford compound 1 (1.97 g, 15% yield); $^1$H NMR (DMSO-$d_6$, 300 MHz): δ 10.61 (s, 1H), 10.26 (s, 1H), 7.60 (d, J=2.1 Hz, 1H), 7.46 (dd, J=2.4, 8.7 Hz, 1H), 6.96 (d, J=8.4 Hz, 1H), 5.18 (m, 1H), 4.42 (d, J=3.3 Hz, 2H).

5-(((tert-Butyldimethylsilyl)oxy)methyl)-2-hydroxybenzaldehyde (2)

To a solution of compound 1 (2.01 g, 13.2 mmol) in DCM (60 mL) was added imidazole (1.43 g, 21 mmol). The solution was cooled to 0° C., and tert-butylchloro dimethylsilane (2.57 g, 17.1 mmol) was added. The reaction mixture was stirred at RT for 3 h and then poured into water (50 mL).

The two phases were separated and the organic phase was dried over anhydrous sodium sulfate and concentrated. The residue was purified by flash column chromatography on silica gel (Petroleum Ether/EtOAc=50:1) to afford compound 2 (3.2 g, 91% yield); $^1$H NMR (CDCl$_3$, 400 MHz): δ 10.85 (br, s, 1H), 9.78 (s, 1H), 7.41 (d, J=2.0 Hz, 1H), 7.35 (dd, J=2.0, 8.4 Hz, 1H), 6.85 (d, J=8.4 Hz, 1H), 4.59 (s, 2H), 0.82 (s, 9H), 0.00 (s, 6H).

4-((tert-Butyldimethylsilyloxy)methyl)-2-formylphenyl acetate (3)

To a solution of compound 2 (25 g, 94 mmol) in DCM (500 mL) was added TEA (19.0 g, 188 mmol). The mixture was cooled to 0° C., and acetyl chloride (11.1 g, 141 mmol) was added. The reaction mixture was stirred at room temperature for 2 h. The mixture was washed with water (500 mL). The organic phase was dried over anhydrous sodium sulfate and concentrated. The residue was purified by flash column chromatography on silica gel (Petroleum Ether/EtOAc=100:1) to afford compound 3 (19.7 g, 68% yield); $^1$H NMR (CDCl$_3$, 400 MHz): δ 9.98 (s, 1H), 7.70 (d, J=2.0 Hz, 1H), 7.49 (dd, J=2.4, 8.4 Hz, 1H), 7.03 (d, J=2.4 Hz, 1H), 4.66 (s, 2H), 2.28 (s, 3H), 0.83 (s, 9H), 0.00 (s, 6H).

2-Formyl-4-(hydroxymethyl)phenyl acetate (4)

Compound 3 (3.6 g, 11.7 mmol) was dissolved in AcOH/THF/H$_2$O (50 mL/25 mL/25 mL). The reaction mixture was stirred at 30° C. for 3 h. An excess of THF was removed and the resulting solution was adjusted to pH=7-8 and then extracted with EtOAc (50 mL×3). The combined organic phases were dried over anhydrous sodium sulfate and concentrated. The residue was purified by flash column chromatography on silica gel (Petroleum Ether/EtOAc=3:1) to afford compound 4 (2.04 g, 90% yield); $^1$H NMR (DMSO-$d_6$, 400 MHz): δ 10.08 (s, 1H), 7.85 (d, J=2.0 Hz, 1H), 7.67 (dd, J=2.4, 8.4 Hz, 1H), 7.26 (d, J=8.4 Hz, 1H), 4.57 (s, 2H), 2.35 (s, 3H).

4-(Bromomethyl)-2-formylphenyl acetate (5a)

To a solution of compound 4 (2.03 g, 10.3 mmol) in DCM (80 mL) was added PBr$_3$ (2.79 g, 10.3 mmol) at 0° C. The reaction mixture was stirred at RT for 4 h. The reaction was quenched by addition of water (20 mL) and the resulting mixture was adjusted to pH=7 with saturated aqueous NaHCO$_3$. The organic phase was separated, dried over anhydrous sodium sulfate and concentrated. The residue was purified by flash column chromatography on silica gel (Petroleum Ether/EtOAc=3:1) to afford compound 5a (300 mg, 11% yield); $^1$H NMR (CDCl$_3$, 300 MHz): δ 10.12 (s, 1H), 792 (d, J=2.1 Hz, 1H), 7.68 (dd, J=2.4, 8.4 Hz, 1H), 7.22 (d, J=8.1 Hz, 1H), 4.54 (s, 2H), 2.42 (s, 3H).

4-(Iodomethyl)-2-formylphenyl acetate (5b)

To a solution of compound 4 (5.0 g, 27.55 mmol) in DCM (300 mL) was added SOCl$_2$ (6.13 g, 51.55 mmol) at 0° C. The reaction mixture was heated under reflux overnight. The mixture was concentrated and the residue was purified by flash column chromatography on silica gel (Petroleum Ether/EtOAc=10:1) to afford the corresponding benzyl chloride (2.4 g, 44% yield). $^1$H NMR (CDCl$_3$, 300 MHz): δ 10.12 (s, 1H), 7.92 (d, J=2.4 Hz, 1H), 7.68 (dd, J=2.4, 8.4 Hz, 1H), 7.22 (d, J=2.4 Hz, 1H), 4.64 (s, 2H), 2.42 (s, 3H).

To a solution of benzyl chloride (2.4 g, 11.29 mmol) in acetone (160 mL) was added NaI (16.94 g, 112.94 mmol). The reaction mixture was stirred at 30° C. overnight. The mixture was concentrated and the residue was dissolved in DCM (100 mL). The resulting solution was washed with saturated aqueous Na$_2$S$_2$O$_3$ (50 mL×3) and water (50 mL), dried over anhydrous sodium sulfate and concentrated to afford compound 5b (2.1 g, 61% yield), which was used in the next step without further purification. $^1$H NMR (CDCl$_3$, 300 MHz): δ 10.10 (s, 1H), 7.90 (d, J=2.4 Hz, 1H), 7.66 (dd. J=2.1, 8.4 Hz, 1H), 7.16 (d, J=2.4 Hz, 1H), 4.49 (s, 2H), 2.41 (s, 3H).

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^1$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 11H), 0.89-0.83 (m, 12H).

Compound 5a could also be used for this reaction.

Example 18 was prepared from compound 7 and PEG$_{5K}$ONH$_3^+$.MsO$^-$ following general pegylation procedure A.

Example 19: 4-(4-Acetoxy-3-((E)-((2-(PEG$_{5K}$-amino)-2-oxoethoxy)imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

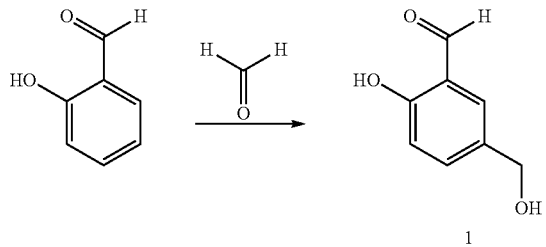
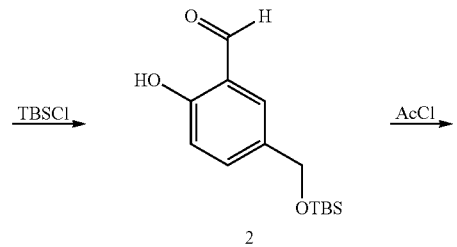

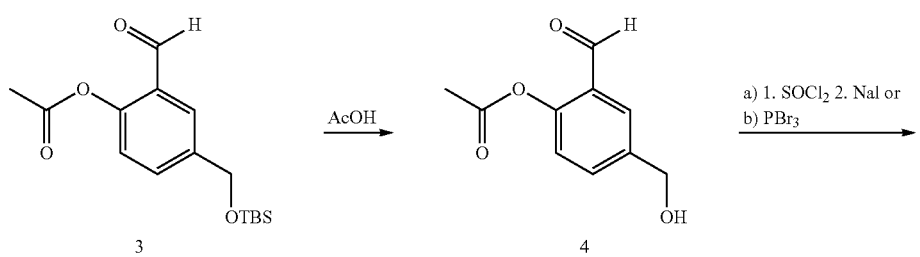

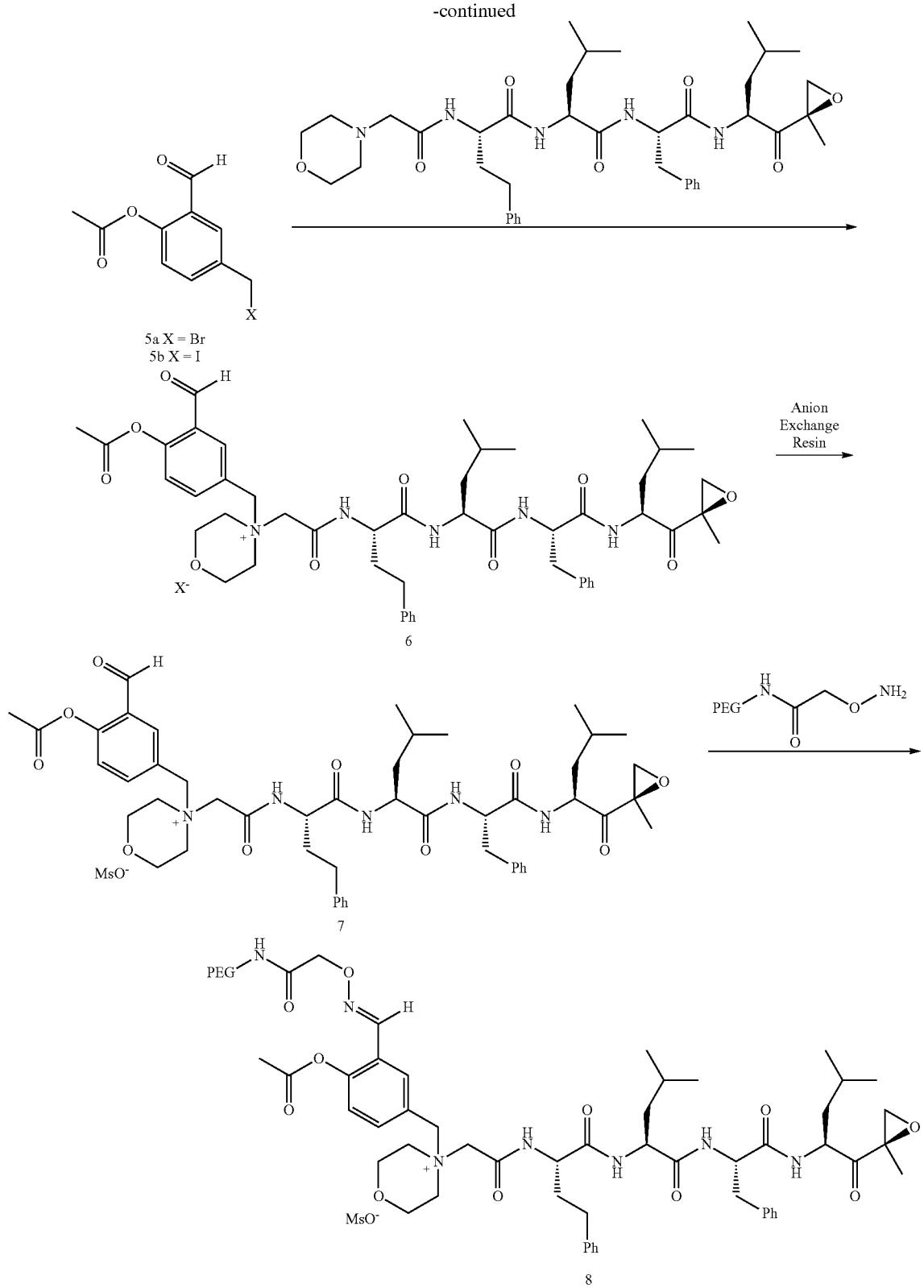
2-Hydroxy-5-(hydroxymethyl)benzaldehyde (1)
To an aqueous solution of formaldehyde (37%, 17 mL) were added 2-hydroxybenzaldehyde (10.3 g, 84.4 mmol) and concentrated HCl (42 mL). The reaction mixture was heated under reflux overnight. The mixture was cooled to RT and then extracted with EtOAc (200 mL). The organic phase was dried over anhydrous sodium sulfate and concentrated.

The residue was purified by flash column chromatography on silica gel (Petroleum Ether/EtOAc=3:1) to afford compound 1 (1.97 g, 15% yield); $^1$H NMR (DMSO-d$_6$, 300 MHz): δ 10.61 (s, 1H), 10.26 (s, 1H), 7.60 (d, J=2.1 Hz, 1H), 7.46 (dd, J=2.4.8.7 Hz, 1H), 6.96 (d, J=8.4 Hz, 1H), 5.18 (m, 1H), 4.42 (d, J=3.3 Hz, 2H).

5-(((tert-Butyldimethylsilyl)oxy)methyl)-2-hydroxybenzaldehyde (2)

To a solution of compound 1 (2.01 g, 13.2 mmol) in DCM (60 mL) was added imidazole (1.43 g, 21 mmol). The solution was cooled to 0° C., and tert-butylchloro dimethylsilane (2.57 g, 17.1 mmol) was added. The reaction mixture was stirred at RT for 3 h and then poured into water (50 mL). The two phases were separated and the organic phase was dried over anhydrous sodium sulfate and concentrated. The residue was purified by flash column chromatography on silica gel (Petroleum Ether/EtOAc=50:1) to afford compound 2 (3.2 g, 91% yield); $^1$H NMR (CDCl$_3$, 400 MHz): δ 10.85 (br, s, 1H), 9.78 (s, 1H), 7.41 (d, J=2.0 Hz, 1H), 7.35 (dd, J=2.0, 8.4 Hz, 1H), 6.85 (d, J=8.4 Hz, 1H), 4.59 (s, 2H), 0.82 (s, 9H), 0.00 (s, 6H).

4-((tert-Butyldimethylsilyloxy)methyl)-2-formylphenyl acetate (3)

To a solution of compound 2 (25 g, 94 mmol) in DCM (500 mL) was added TEA (19.0 g, 188 mmol). The mixture was cooled to 0° C., and acetyl chloride (11.1 g, 141 mmol) was added. The reaction mixture was stirred at RT for 2 h. The mixture was washed with water (500 mL). The organic phase was dried over anhydrous sodium sulfate and concentrated. The residue was purified by flash column chromatography on silica gel (Petroleum Ether/EtOAc=100:1) to afford compound 3 (19.7 g, 68% yield); $^1$H NMR (CDCl$_3$, 400 MHz): δ 9.98 (s, 1H), 7.70 (d, J=2.0 Hz, 1H), 7.49 (dd, J=2.4, 8.4 Hz, 1H), 7.03 (d, J=2.4 Hz, 1H), 4.66 (s, 2H), 2.28 (s, 3H), 0.83 (s, 9H), 0.00 (s, 6H).

2-Formyl-4-(hydroxymethyl)phenyl acetate (4)

Compound 3 (3.6 g, 11.7 mmol) was dissolved in AcOH/THF/H$_2$O (50 mL/25 mL/25 mL). The reaction mixture was stirred at 30° C. for 3 h. An excess of THF was removed and the resulting solution was adjusted to pH=7-8 and then extracted with EtOAc (50 mL×3). The combined organic phases were dried over anhydrous sodium sulfate and concentrated. The residue was purified by flash column chromatography on silica gel (Petroleum Ether/EtOAc=3:1) to afford compound 4 (2.04 g, 90% yield); $^1$H NMR (DMSO-d$_6$, 400 MHz): δ 10.08 (s, 1H), 7.85 (d, J=2.0 Hz, 1H), 7.67 (dd, J=2.4, 8.4 Hz, 1H), 7.26 (d, J=8.4 Hz, 1H), 4.57 (s, 2H), 2.35 (s, 3H).

4-(Bromomethyl)-2-formylphenyl acetate (5a)

To a solution of compound 4 (2.03 g, 10.3 mmol) in DCM (80 mL) was added PBr$_3$ (2.79 g, 10.3 mmol) at 0° C. The reaction mixture was stirred at RT for 4 h. The reaction was quenched by addition of water (20 mL) and the resulting mixture was adjusted to pH=7 with saturated aqueous NaHCO$_3$. The organic phase was separated, dried over anhydrous sodium sulfate and concentrated. The residue was purified by flash column chromatography on silica gel (Petroleum Ether/EtOAc=3:1) to afford compound 5a (300 mg, 11% yield): $^1$H NMR (CDCl$_3$, 300 MHz): δ 10.12 (s, 1H), 7.92 (d, J=2.1 Hz, 1H), 7.68 (dd, J=2.4, 8.4 Hz, 1H), 7.22 (d, J=8.1 Hz, 1H), 4.54 (s, 2H), 2.42 (s, 3H).

4-(Iodomethyl)-2-formylphenyl acetate (5b)

To a solution of compound 4 (5.0 g, 27.55 mmol) in DCM (300 mL) was added SOCl$_2$ (6.13 g, 51.55 mmol) at 0° C. The reaction mixture was heated under reflux overnight. The mixture was concentrated and the residue was purified by flash column chromatography on silica gel (Petroleum Ether/EtOAc=10:1) to afford the corresponding benzyl chloride (2.4 g, 44% yield); $^1$H NMR (CDCl$_3$, 300 MHz): δ 10.12 (s, 1H), 7.92 (d, J=2.4 Hz, 1H), 7.68 (dd, J=2.4, 8.4 Hz, 1H), 7.22 (d, J=2.4 Hz, 1H), 4.64 (s, 2H), 2.42 (s, 3H).

To a solution of benzyl chloride (2.4 g, 11.29 mmol) in acetone (160 mL) was added NaI (16.94 g, 112.94 mmol). The reaction mixture was stirred at 30° C. overnight. The mixture was concentrated and the residue was dissolved in DCM (100 mL). The resulting solution was washed with saturated aqueous Na$_2$S$_2$O$_3$ (50 mL×3) and water (50 mL), dried over anhydrous sodium sulfate and concentrated to afford compound 5b (2.1 g, 61% yield), which was used in the next step without further purification. $^1$H NMR (CDCl$_3$, 300 MHz): δ 10.10 (s, 1H), 7.90 (d, J=2.4 Hz, 1H), 7.66 (dd, J=2.1, 8.4 Hz, 1H), 7.16 (d, J=2.4 Hz, 1H), 4.49 (s, 2H), 2.41 (s, 3H).

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^1$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 11H), 0.89-0.83 (m, 12H).

Compound 5a could also be used for this reaction.

Example 19 was prepared from compound 7 and PEG$_{5K}$NHC(O)CH$_2$ONH$_2$ (Creative PEGWorks, Chapel Hill. N.C. US) following general pegylation procedure A.

Example 20: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(((PEG$_{5K}$-imino)methyl)-4-(propionyloxy)benzyl)morpholin-4-ium methanesulfonate (7)

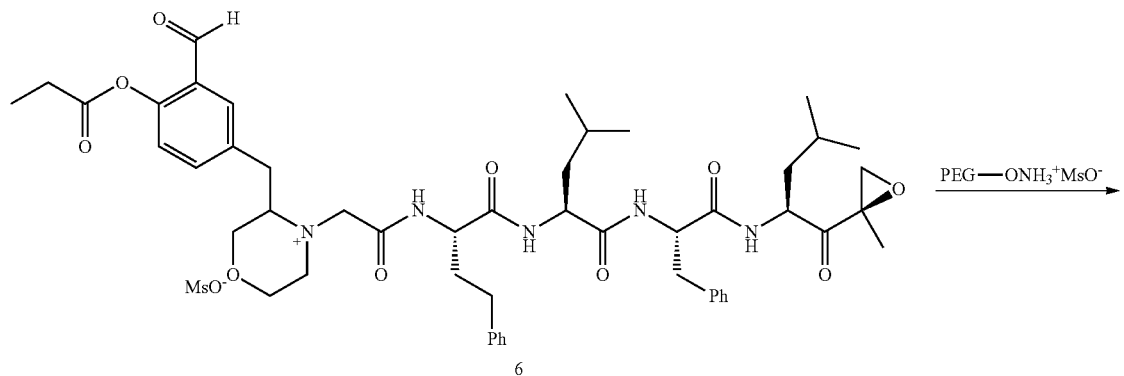

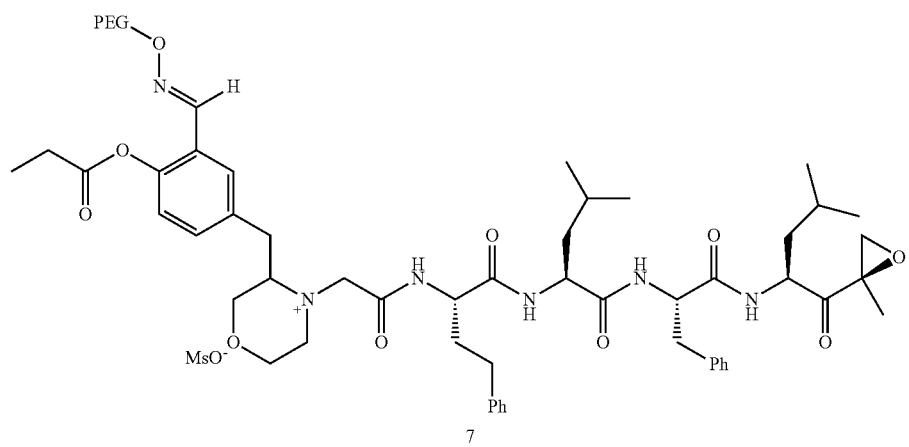

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(3-formyl-4-(propionyloxy)benzyl)morpholin-4-ium methanesulfonate (6)

To a solution of compound 4 (400 mg, 1.476 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (318.8 mg, 0.442 mmol). The reaction mixture was stirred at 45° C. overnight. An excess of solvent was concentrated and the residue was crystallized repeatedly from MeCN/Et$_2$O (1/5, v/v) to afford the desired compound 5, which was transformed into the corresponding mesylate (200 mg, 15% yield) by treatment with ion exchange resin; $^1$H NMR (300 MHz, CDCl$_3$): δ 10.18 (s, 1H), 7.68 (br, s, 1H), 8.03 (s, 1H), 7.88 (m, 1H), 7.72 (br, 1H), 7.38 (m, 1H), 7.30~7.15 (m, 10H), 6.74 (m, 1H), 6.37 (br, 1H), 5.25~5.01 (m, 3H), 4.50~3.90 (m, 12H), 3.47~3.12 (m, 3H), 2.97 (m, 2H), 2.97~2.71 (m, 7H), 2.15 (m, 2H), 2.71~1.10 (m, 9H), 0.87 (m, 12H).

Example 20 was prepared by methods analogous to those described in Example 16, wherein the intermediates were made in similar fashion (using ethanoyl chloride to generate the correlary to intermediate 1 shown in eg 16), and compound 6 and PEG$_{5K}$ONH$_3^+$.MsO$^-$ following general pegylation procedure B.

Example 21: 4-(3-Acetoxy-4-((PEG$_{2K}$-imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

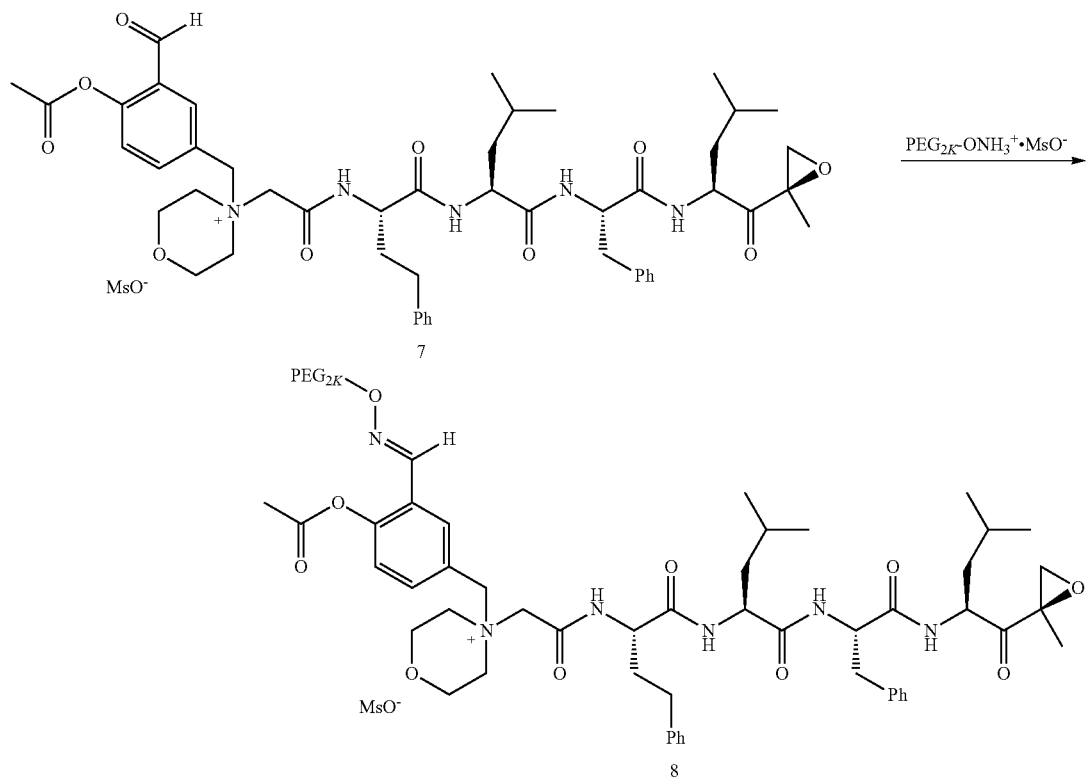

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^{1}$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 11H), 0.89-0.83 (m, 12H).

Example 21 was prepared from compound 7 and PEG$_{2K}$ONH$_3$$^{+}$.MsO$^{-}$ following general pegylation procedure A.

Example 22: 4-(4-Acetoxy-3-(1-PEG$_2$-imino)ethyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (5)

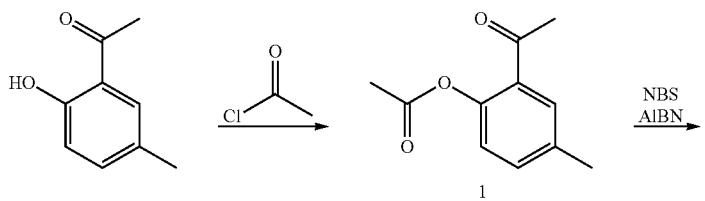

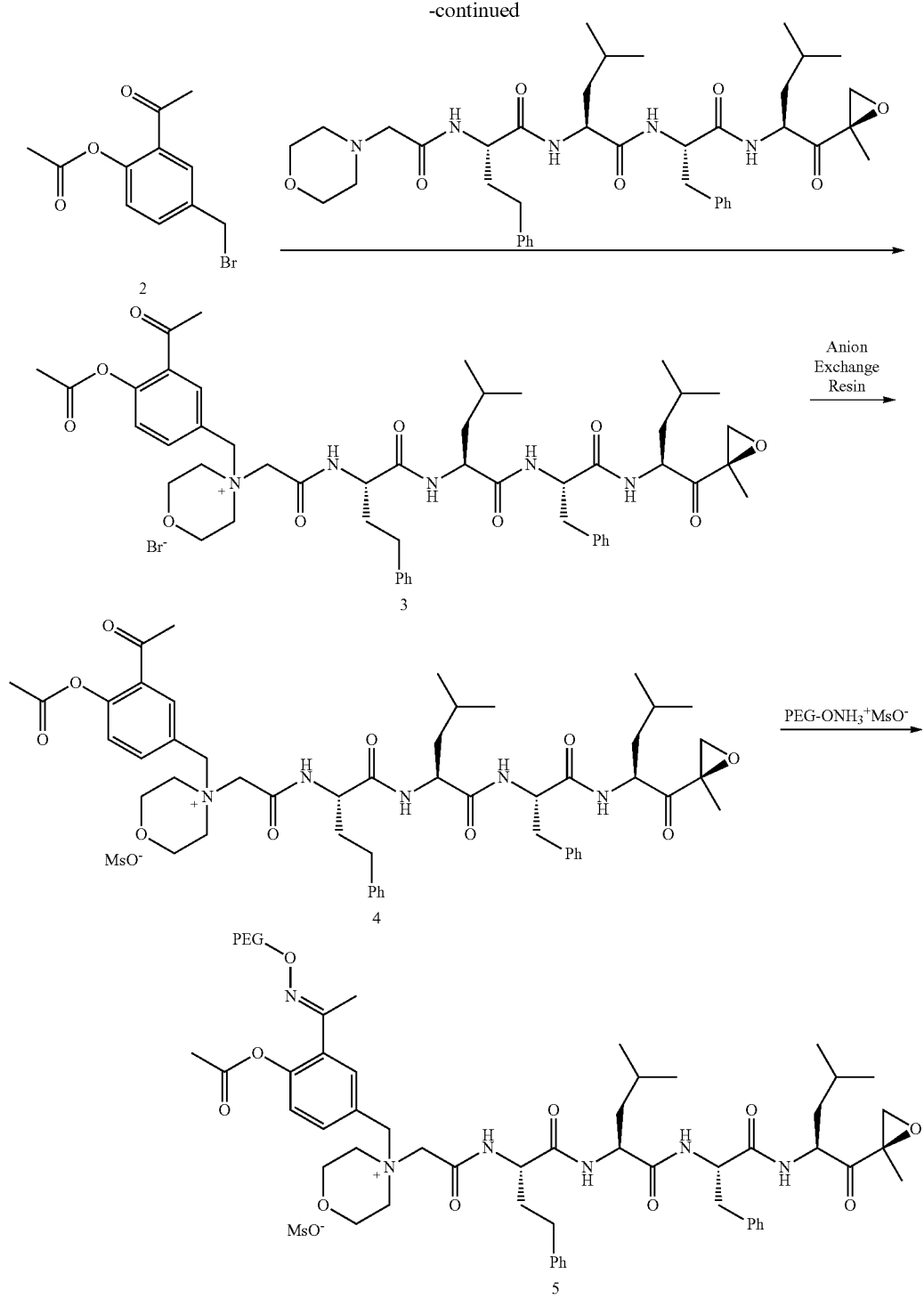

2-Acetyl-4-methylphenyl acetate (1)

To a solution of 1-(2-hydroxy-5-methylphenyl)ethanone (1.5 g, 0.01 mol) in DCM (15 mL) were added TEA (1.5 g, 0.015 mol) and acetyl chloride (0.94 g, 0.012 mol) at 0° C. The reaction mixture was stirred at RT overnight. This mixture was quenched with water (20 mL). The DCM phase was collected, washed with brine (20 mL), dried over anhydrous $MgSO_4$, and concentrated. The residue was purified by flash column chromatography on silica gel (Petroleum Ether/EtOAc=3:1) to afford compound 1 (0.9 g, 47% yield); $^1$H NMR (300 MHz, $CDCl_3$): δ 7.64 (m, 1H), 7.37 (m, 1H), 7.02 (d, J=8.1 Hz, 1H), 2.57 (s, 3H), 2.42 (s, 3H), 2.37 (s, 3H).

2-Acetyl-4-(bromomethyl)phenyl acetate (2)

To a solution of compound 1 (0.5 g, 2.6 mmol) in $CCl_4$ (20 mL) were added NBS (573 mg, 3.25 mmol) and AIBN (42.6 mg, 0.26 mmol). The reaction mixture was heated under reflux overnight. The mixture was cooled to RT and filtered. The filtrate was concentrated and the residue was purified by flash column chromatography on silica gel (Petroleum Ether/EtOAc=10:1) to afford compound 2 (160 mg, 23% yield); $^1$H NMR (300 MHz, DMSO-d6): δ8.02 (m, 1H), 7.73 (d, J=8.1 Hz, 1H), 7.25 (d, J=8.4 Hz, 1H), 4.81 (s, 2H), 2.53 (s, 3H), 2.32 (s, 3H).

4-(4-Acetoxy-3-acetylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (4)

To a solution of compound 2 (1.03 g, 3.7 mmol) in MeCN (10 mL) was added compound (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (884.7 mg, 1.23 mmol). The reaction mixture was heated at 45° C. overnight. An excess of solvent was concentrated and the residue was purified by flash column chromatography on silica gel (EtOAc/MeOH=100:3) to afford the desired compound 3, which was transformed into the corresponding mesylate (260 mg, 21% yield) by treatment with ion exchange resin; $^1$H NMR (300 MHz, CDCl$_3$): δ 9.62 (m, 1H), 8.06 (m, 1H), 7.88~7.71 (n, 2H), 7.33~7.11 (m, 11H), 6.95 (n, 1H), 6.66 (m, 1H), 5.33~4.91 (m, 2H), 4.55~3.90 (m, 11H), 3.58~2.91 (m, 4H), 2.85 (s, 3H), 2.74 (m, 2H), 2.61 (s, 3H), 2.40 (s, 3H), 2.31~1.94 (m, 7H), 1.72~1.18 (m, 8H), 0.88 (m, 12H).

Example 22 was prepared from compound 4 and PEG$_{2K}$ONH$_3^+$.MsO$^-$ following general pegylation procedure B.

Example 23: 4-(3-Acetoxy-4-((PEG$_{3K}$-imino)methyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahezadecyl)morpholin-4-ium methanesulfonate (8)

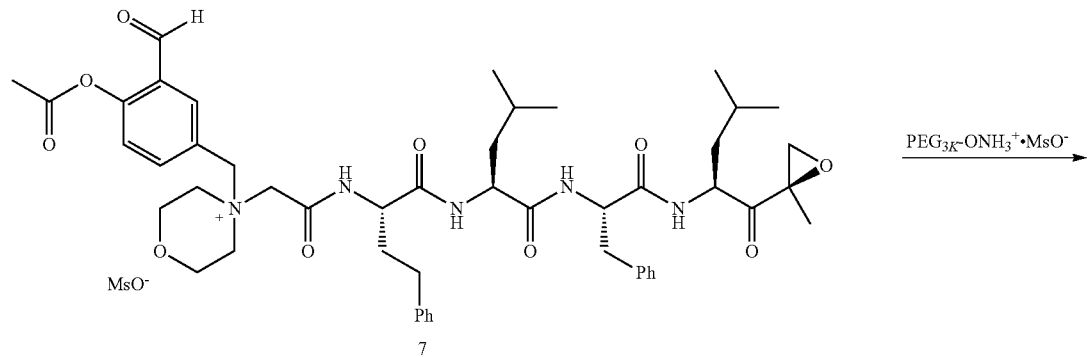

7

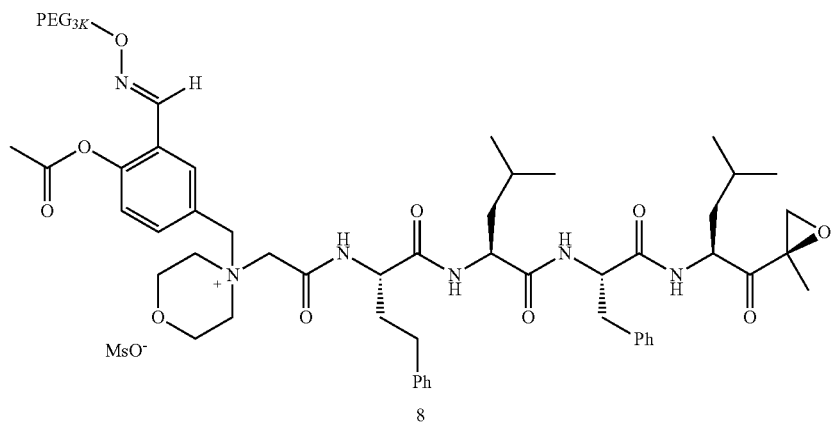

8

4-(4-Acetoxy-3-formylbenzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)

To a solution of compound 5b (380 mg, 1.48 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (532 mg, 0.74 mmol). The reaction mixture was stirred at 45° C. overnight. The solvent was removed under reduced pressure. The residue was purified by flash column chromatography on silica gel (DCM/MeOH=10:1) to afford desired compound (6), which was then transformed into the corresponding mesylate by treatment with ion exchange resin (280 mg, 39% yield); $^1$H NMR (CDCl$_3$, 400 MHz): δ 10.15 (s, 1H), 9.53 (br s, 1H), 8.03 (d, J=2.0 Hz, 1H), 7.85 (m, 1H), 7.68 (br s, 1H), 7.37 (d, J=8.0 Hz, 1H), 7.26-7.13 (m, 10H), 6.84 (br s, 1H), 6.52 (br s, 1H), 5.20 (m, 2H), 4.97 (m, 1H), 4.50-3.96 (m, 7H), 3.46-3.28 (m, 2H), 3.16 (m, 1H), 3.06-2.92 (m, 3H), 2.85-2.61 (m, 7H), 2.44 (s, 3H), 2.14 (m, 2H), 1.69-1.17 (m, 11H), 0.89-0.83 (m, 12H).

Example 23 was prepared by methods analogous to those described in Example 16, wherein the intermediates were made in similar fashion (using acetyl chloride to generate the corollary intermediate 1 shown in eg 16), and compound 7 and PEG$_{3K}$-ONH$_3^+$.MsO$^-$ following general pegylation procedure A.

Example 24: 4-(4-Acetoxy-3-(1-(PEG$_{3K}$-imino)ethyl)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (5)

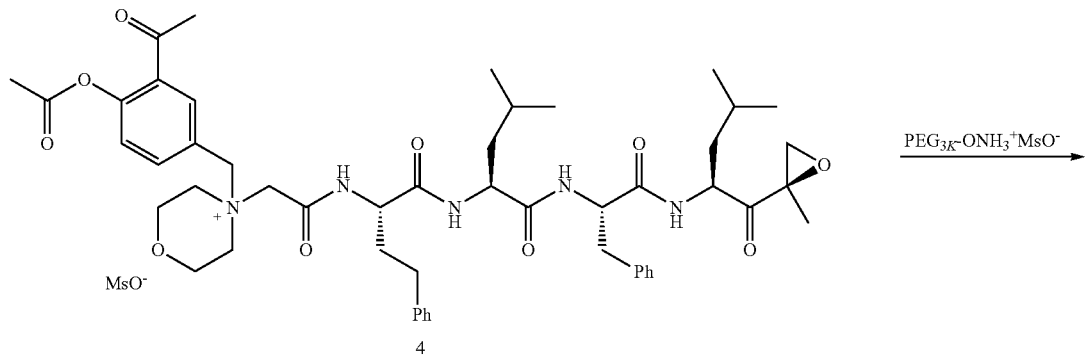

4

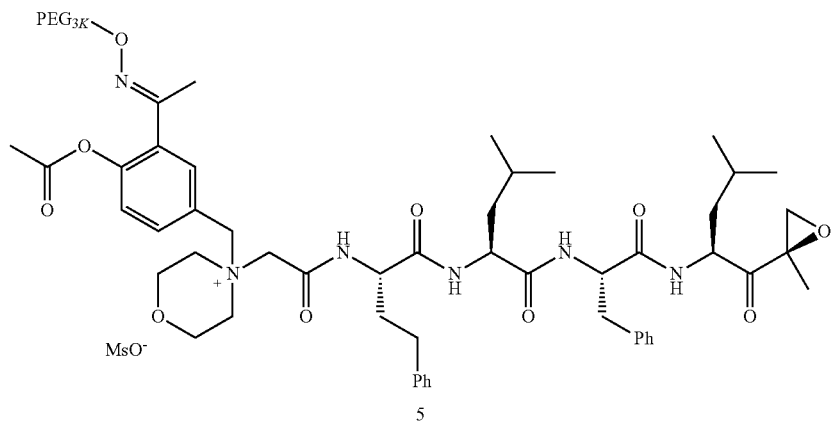

5

4-(4-Acetoxy-3-acetylbenzyl)-4-((4S,7S,10S,13S)-10-benzyl-7-isobutyl-15-methyl-3-((R)-2-methyloxirane-2-carbonyl)-2,5,8,11-tetraoxo-4-phenethyl-3,6,9,12-tetraazahexadecyl)morpholin-4-ium methanesulfonate (4)

To a solution of compound 2 (1.03 g, 3.7 mmol) in MeCN (10 mL) was added compound (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (884.7 mg, 1.23 mmol). The reaction mixture was heated at 45° C. overnight. An excess of solvent was concentrated and the residue was purified by flash column chromatography on silica gel (EtOAc/MeOH=100:3) to afford the desired compound 3, which was transformed into the corresponding mesylate (260 mg, 21% yield) by treatment with ion exchange resin: $^1$H NMR (300 MHz, CDCl$_3$): δ 9.62 (m, 1H), 8.06 (m, 1H), 7.88~7.71 (m, 2H), 7.33~7.11 (m, 11H), 6.95 (m, 1H), 6.66 (m, 1H), 5.33~4.91 (m, 2H), 4.55~3.90 (m, 11H), 3.58~2.91 (m, 4H), 2.85 (s, 3H), 2.74 (m, 2H), 2.61 (s, 3H), 2.40 (s, 3H), 2.31~1.94 (m, 7H), 1.72~1.18 (m, 8H), 0.88 (m, 12H).

Example 24 was prepared by methods analogous to those described in Example 22, wherein the intermediates were made in similar fashion and compound 4 and PEG$_{3K}$ONH$_3^+$.MsO$^-$ following general pegylation procedure B.

Example 25, 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(2-(PEG$_{20K}$-4-Arm-imino)ethoxy)-4-(pivaloyloxy)benzyl)morpholin-4-ium methanesulfonate Example 25 was prepared by methods analogous to those described in Example 17, wherein the intermediates were made in similar fashion, while using PEG$_{20K}$ONH$_3^+$.MsO$^-$ and following general pegylation procedure B.

Example 26: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((PEG$_{5K}$-imino)methyl)benzyl)morpholin-4-ium methanesulfonate (6)

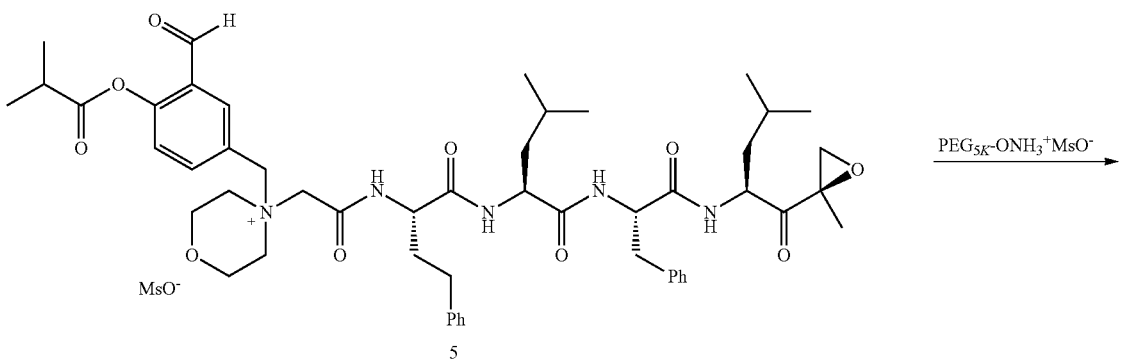

5

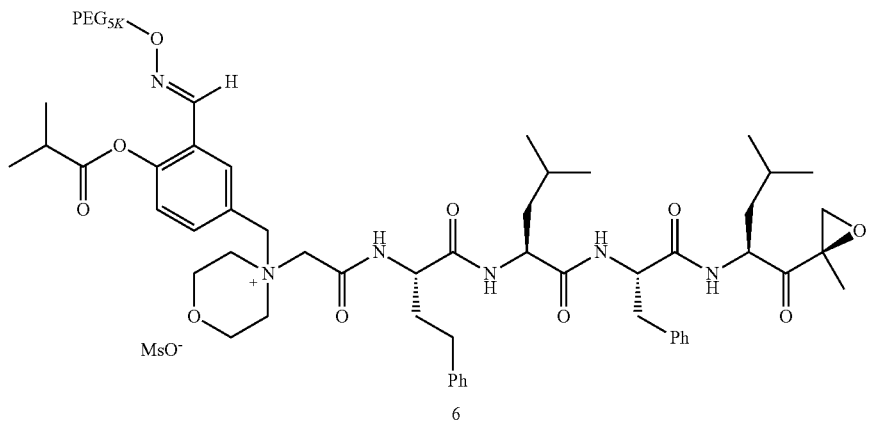

6

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(3-formyl-4-(isobutyryloxy)benzyl)morpholin-4-ium methanesulfonate (5)

To a solution of compound 3 (550 mg, 1.657 mmol) in MeCN (8 mL) was added (S)-4-methyl-N—((S)-1-(((S)-4-methyl-1-(R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (393 mg, 0.547 mmol). The reaction mixture was stirred at 40° C. overnight. An excess of solvent was concentrated and the residue was crystallized repeatedly from (EtOAc/Et$_2$O=1:5) to afford the desired compound 4, which was transformed into the corresponding mesylate 5 (115 mg, 7.5% yield) by treatment with ion exchange resin, $^1$H NMR (400 MHz, CDCl$_3$): δ 10.18 (s, 1H), 9.68 (m, 1H), 8.04 (m, 1H), 7.89 (m, 1H), 7.81 (s, 1H), 7.35 (m, 1H), 7.30 (m, 1H), 7.11-7.29 (m, 9H), 6.79 (s, 1H), 6.44 (m, 1H), 5.18 (m, 2H), 4.99 (m, 1H), 4.41 (m, 3H), 4.20 (m, 3H), 3.99 (m, 3H), 3.40 (m, 1H), 3.30 (m, 1H), 3.20 (m, 1H), 2.95 (m, 2H), 2.92 (m, 1H), 2.79 (m, 3H), 2.75 (m, 2H), 2.21 (m, 1H), 2.09 (m, 1H), 1.83 (m, 4H), 1.62 (m, 2H), 1.49 (m, 4H), 1.38 (m, 6H), 1.24 (m, 2H), 0.88 (m, 12H).

Example 26 was prepared by methods analogous to those described in Example 16, wherein the intermediates were made in similar fashion (using isopropanoyl chloride to generate the corollary intermediate 1 shown in eg 16), and compound 5 and PEG$_{5K}$ONH$_3^+$.MsO$^-$ following general pegylation procedure B.

Example 27: 4-((4S,7S,10S,13S)-1-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-((PEG$_{5K}$-imino)methyl)-4-(pivaloyloxy)benzyl)morpholin-4-ium methanesulfonate (6)

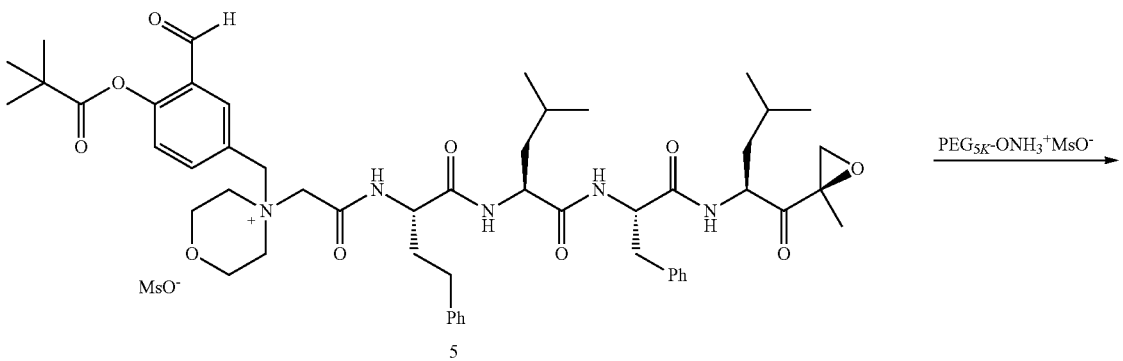

5

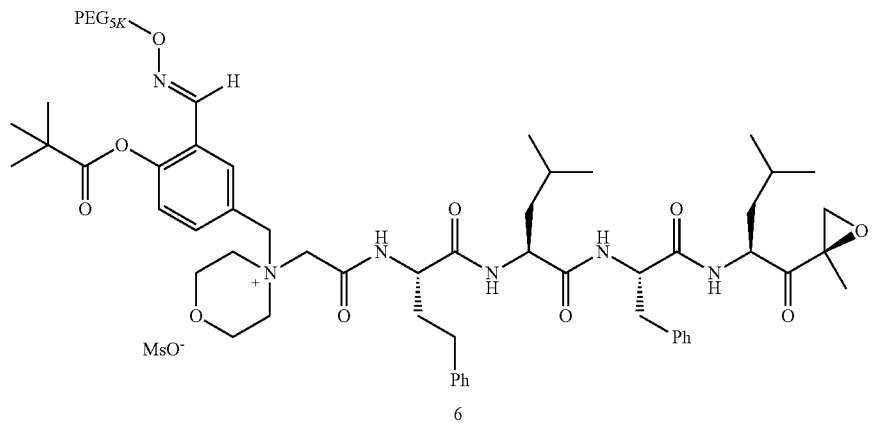

6

4-((4S,7S,10S,13S)-10-Benzyl-7-isobutyl-15-methyl-3-((R)-2-methyloxirane-2-carbonyl)-2,5,8,11-tetraoxo-4-phenethyl-3,6,9,12-tetraazahexadecyl)-4-(3-formyl-4-(pivaloyloxy)benzyl)morpholin-4-ium methanesulfonate (5)

To a solution of compound 3 (500 mg, 1.44 mmol) in MeCN (8 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (360 mg, 0.5 mmol). The reaction mixture was stirred at 40° C. overnight. An excess of solvent was concentrated and the residue was crystallized repeatedly from (EtOAc/Et$_2$O=1:5) to afford the desired compound 4, which was transformed into the corresponding mesylate 5 (130 mg, 12% yield) by treatment with ion exchange resin; $^1$H NMR (400 MHz, CDCl$_3$): δ 10.17 (s, 1H), 9.74 (m, 1H), 8.01 (m, 1H), 7.90 (m, 1H), 7.74 (m, 1H), 7.36-7.12 (m, 11H), 6.78 (m, 1H), 6.41 (m, 1H), 5.22 (m, 1H), 5.14 (m, 2H), 4.58-4.35 (m, 3H), 4.28-4.10 (m, 3H), 4.08-3.83 (m, 3H), 3.38 (m, 1H), 3.29 (m, 1H), 3.17 (m, 1H), 2.97 (m, 2H), 2.83 (s, 3H), 2.76 (m, 2H), 2.30-2.20 (m, 2H), 1.70-1.58 (m, 2H), 1.47 (m, 6H), 1.42 (s, 10H), 1.30-1.16 (m, 3H), 0.90-0.84 (m, 12H).

Example 27 was prepared by methods analogous to those described in Example 16, wherein the intermediates were made in similar fashion (using t-butanoyl chloride to generate the corollary intermediate 1 shown in eg 16), and compound 5 and PEG$_{5K}$ONH$_3^+$.MsO$^-$ following general pegylation procedure B.

Example 28: 4-(4-Acetoxy-3-(1-(PEG$_{5K}$-imino)ethyl)-5-methylbenzyl)-4-((4S,7S,10S,13S)-10-benzyl-7-isobutyl-5-methyl-13-((R)-2-methyloxirane-2-carbonyl)-2,5,8,11-tetraoxo-4-phenethyl-3,6,9,12-tetraazahexadecyl)morpholin-4-ium methanesulfonate (7)

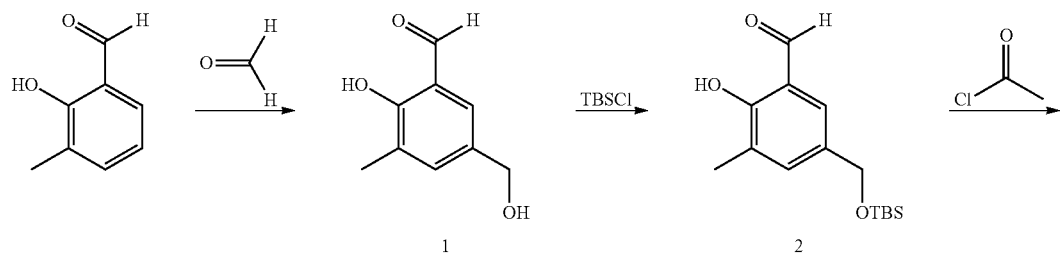

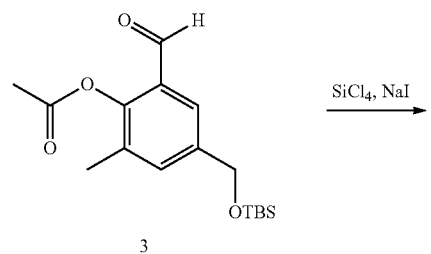

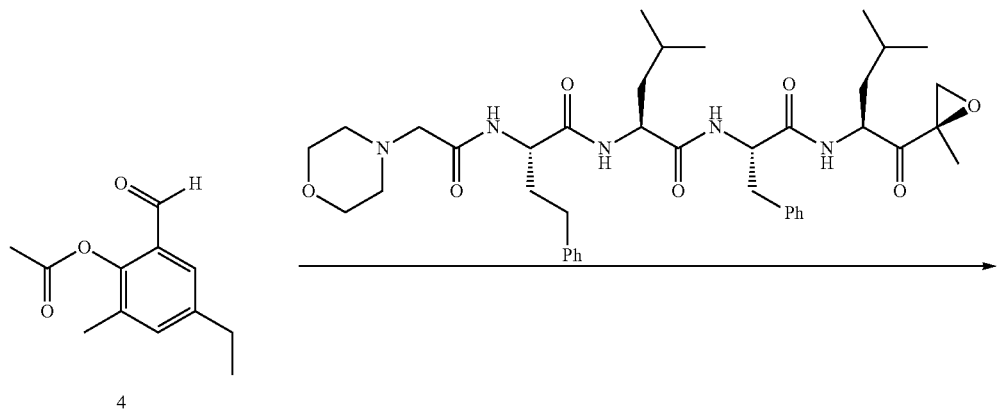

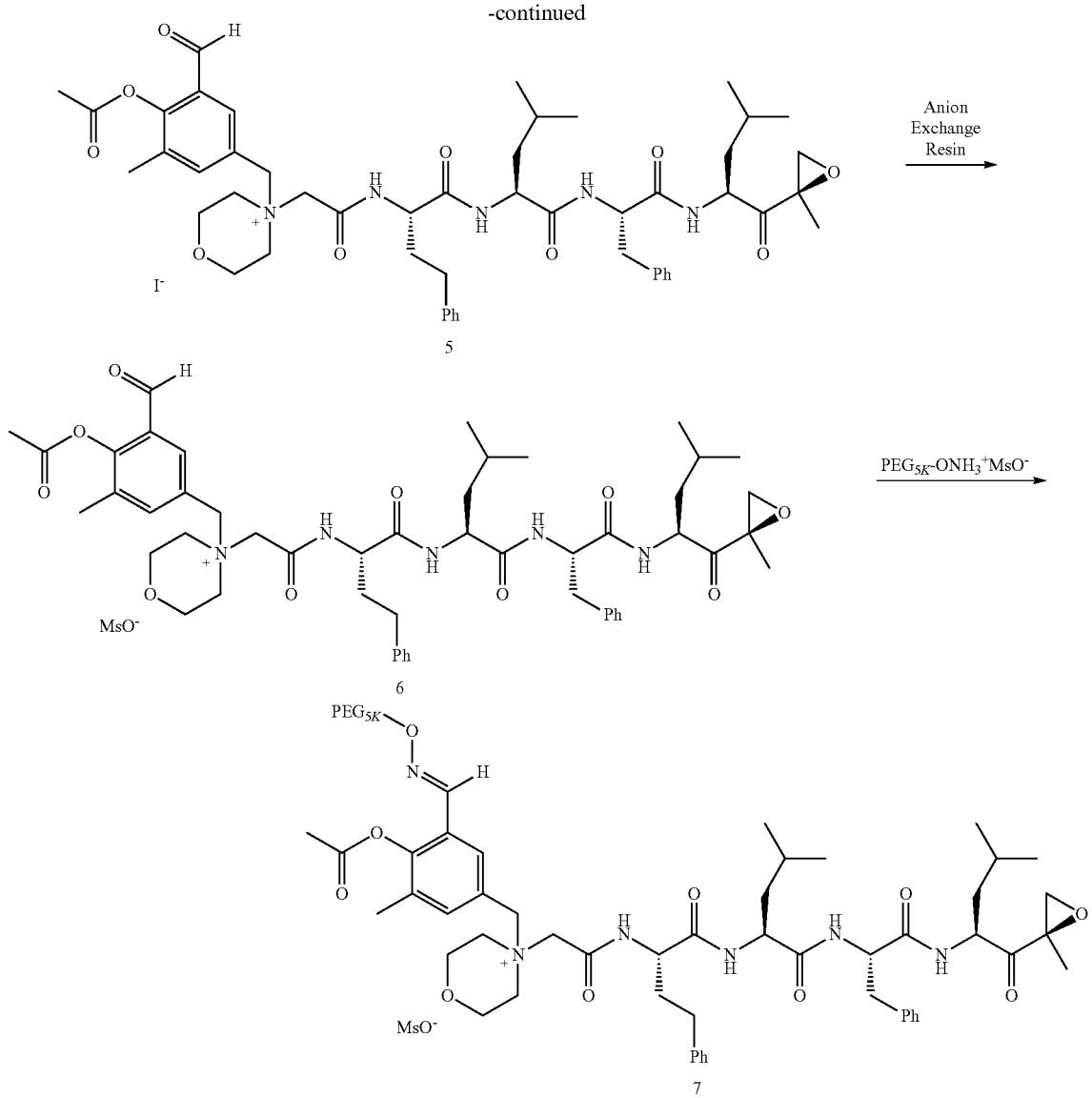

2-Hydroxy-5-(hydroxymethyl)-3-methylbenzaldehyde (1)

To a mixture of 2-hydroxy-3-methylbenzaldehyde (5.01 g, 36.84 mmol) and formaldehyde (37%, 7.01 g, 86.45 mmol) was added concentrated HCl (30 mL) at RT. The reaction mixture was heated at 80° C. for 1 h. Water (90 mL) was added and the resulting mixture was extracted with EtOAc (100 mL×3). The combined organic phases were concentrated and the residue was treated with water (150 mL, 40° C.). The solid was filtered off and the filtrate was extracted with EtOAc (100 mL×3). The combined organic phases were dried over anhydrous $MgSO_4$ and concentrated to afford compound 1 (2.60 g, 43% yield), $^1$H NMR (400 MHz, $CDCl_3$): δ 11.26 (s, 1H), 9.88 (s, 1H), 7.41 (s, 2H), 4.66 (s, 2H), 2.28 (s, 3H).

5-(((tert-Butyldimethylsilyl)oxy)methyl)-2-hydroxy-3-methylbenzaldehyde (2)

To a solution of compound 1 (2.60 g, 15.66 mmol) in DCM (50 mL) was added imidazole (2.13 g, 31.33 mmol) at 0° C. A solution of TBSCl (3.54 g, 23.50 mmol) in DCM (5 mL) was added and the reaction mixture was stirred at room temperature for 1 h. The mixture was concentrated and the residue was purified by flash column chromatography on silica gel (Hexane/EtOAc=200:1) to give compound 2 (3.90 g, 88.9% yield): $^1$H NMR (400 MHz, $CDCl_3$): δ 10.85 (br, s, 1H), 9.96 (s, 1H), 7.44 (d, J=1.6 Hz, 1H), 7.33 (d, J=1.2 Hz, 1H), 4.56 (s, 2H), 2.12 (s, 3H), 0.82 (s, 9H), 0.00 (s, 6H).

4-(((tert-Butyldimethylsilyl)oxy)methyl)-2-formyl-6-methylphenyl acetate (3)

To a solution of compound 2 (1.70 g, 6.08 mmol) in DCM (50 mL) were added TEA (1.23 g, 12.14 mmol) and acetyl chloride (715 mg, 9.11 mmol) at 0° C. The reaction mixture was stirred at RT for 20 min. The mixture was diluted with DCM (50 mL) and then poured into water (100 mL). The two phases were separated and the organic phase was washed with brine (100 mL), dried over anhydrous $MgSO_4$ and concentrated to afford crude compound 3 (1.94 g, quantitative), which was used in the next step without further purification; $^1$H NMR (400 MHz, CDCl$_3$): δ 9.90 (s, 1H), 7.52 (d, J=1.6 Hz, 1H), 7.35 (d, J=1.2 Hz, 1H), 4.63 (s, 2H), 2.30 (s, 3H), 2.11 (s, 3H), 0.83 (s, 9H), 0.00 (s, 6H).

2-Formyl-4-(iodomethyl)-6-methylphenyl acetate (4)

To a solution of NaI (4.66 g, 31.06 mmol) in MeCN (50 mL) were added compound 3 (2.01 g, 6.21 mmol) and SiCl$_4$ (1.06 g, 6.21 mmol) at 0° C. The reaction mixture was stirred for 15 min at RT. The mixture was concentrated and the residue was treated with DCM (100 mL). The resulting mixture was filtered and the filtrate was washed with saturated Na$_2$S$_2$O$_3$ (50 mL×2), dried over anhydrous MgSO$_4$ and concentrated. The residue was purified by flash column chromatography on silica gel (Hexane/EtOAc=15:1) to give compound 4 (803 mg, 41% yield); $^1$H NMR (400 MHz. CDCl$_3$): δ 10.00 (s, 1H), 7.70 (d, J=2.4 Hz, 1H), 7.52 (d, J=2.0 Hz, 1H), 4.44 (s, 2H), 2.42 (s, 3H), 2.22 (s, 3H).

4-(4-Acetoxy-3-acetyl-5-methylbenzyl)-4-((4S,7S, 10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (6)

To a solution of compound 4 (803 mg, 1.57 mmol) in MeCN (5 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (340 mg, 0.47 mmol). The reaction mixture was stirred at 40° C. overnight. An excess of solvent was concentrated and the residue was recrystallized three times from (EtOAc/Et$_2$O=1: 5) to afford the desired iodide salt 5, which was transformed into the corresponding mesylate 6 (202 mg, 47% yield) by treatment with ion exchange resin; $^1$H NMR (400 MHz, CDCl$_3$): δ 10.05 (s, 1H), 9.55 (m, 1H), 7.86 (m, 1H), 7.74 (m, 2H), 7.13-7.29 (m, 10H), 6.85 (m, 1H), 6.51 (m, 1H), 5.23 (m, 1H), 5.05 (m, 2H), 4.45 (m, 5H), 4.22 (m, 5H), 4.00 (m, 4H), 3.30-3.52 (m, 2H), 3.17 (m, 1H), 2.98 (m, 2H), 2.83 (s, 4H), 2.76 (m, 2H), 2.46 (s, 3H), 2.29 (s, 3H), 2.08-2.25 (m, 2H), 1.48-1.69 (m, 4H), 1.45 (m, 2H), 1.38 (m, 2H), 1.25 (m, 2H), 0.88 (m, 12H).

Example 28 was prepared from compound 6 and PEG$_{5K}$ONH$_3^+$.MsO$^-$ following general pegylation procedure B.

Example 29: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(((PEG$_{20K}$-4-Arm-imino)methyl)-4-(pivaloyloxy)benzyl)morpholin-4-ium methanesulfonate

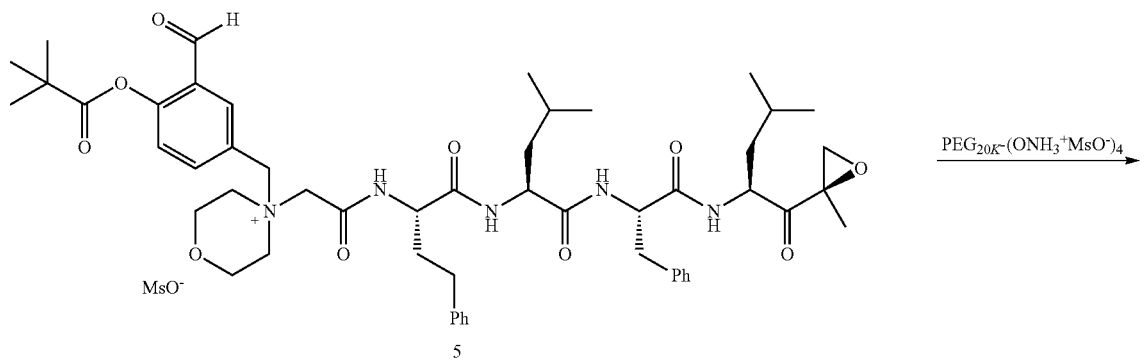

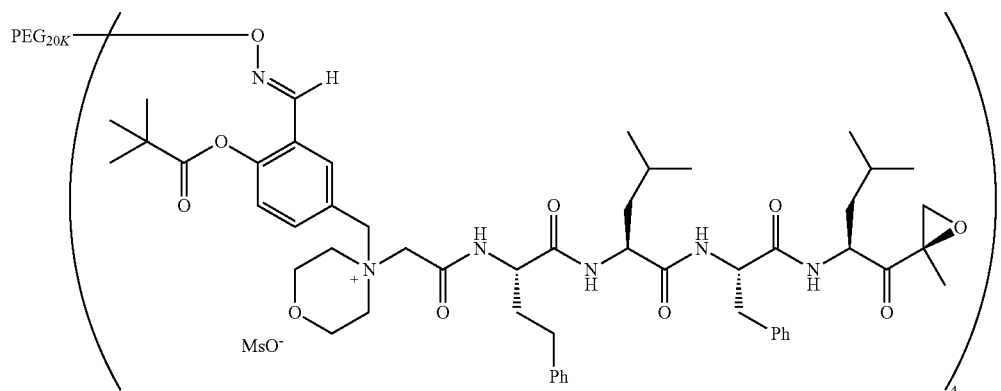

4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-formyl-4-(pivaloyloxy)benzyl)morpholin-4-ium methanesulfonate (5)

To a solution of compound 3 (500 mg, 1.44 mmol) in MeCN (8 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (360 mg, 0.5 mmol). The reaction mixture was stirred at 40° C. overnight. An excess of solvent was concentrated and the residue was crystallized repeatedly from (EtOAc/Et$_2$O=1:5) to afford the desired compound 4, which was transformed into the corresponding mesylate 5 (130 mg, 12% yield) by treatment with ion exchange resin; ° H NMR (400 MHz, CDCl$_3$): δ 10.17 (s, 1H), 9.74 (m, 1H), 8.01 (m, 1H), 7.90 (m, 1H), 7.74 (m, 1H), 7.36-7.12 (m, 11H), 6.78 (m, 1H), 6.41 (m, 1H), 5.22 (m, 1H), 5.14 (m, 2H), 4.58-4.35 (m, 3H), 4.28-4.10 (m, 3H), 4.08-3.83 (m, 3H), 3.38 (m, 1H), 3.29 (m, 1H), 3.17 (m, 1H), 2.97 (m, 2H), 2.83 (s, 3H), 2.76 (m, 2H), 2.30-2.20 (m, 2H), 1.70-1.58 (m, 2H), 1.47 (m, 6H), 1.42 (s, 10H), 1.30-1.16 (m, 3H), 0.90-0.84 (m, 12H).

Example 29 was prepared by methods analogous to those described in Example 18, wherein the intermediates were made in similar fashion (using t-butanoyl chloride to generate the corollary intermediate 1 shown in eg 18), and compound 5 and PEG$_{20K}$-(ONH$_3^+$.MsO$^-$)$_4$ following general pegylation procedure B.

Example 30: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(PEG$_{20K}$-4-Arm-imino)methyl)-5-methyl-4-(pivaloyloxy)benzyl)morpholin-4-ium methanesulfonate (6)

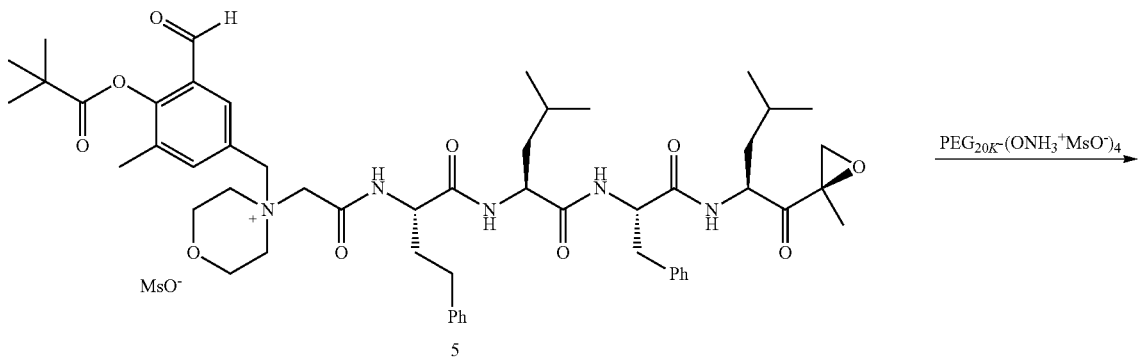

5

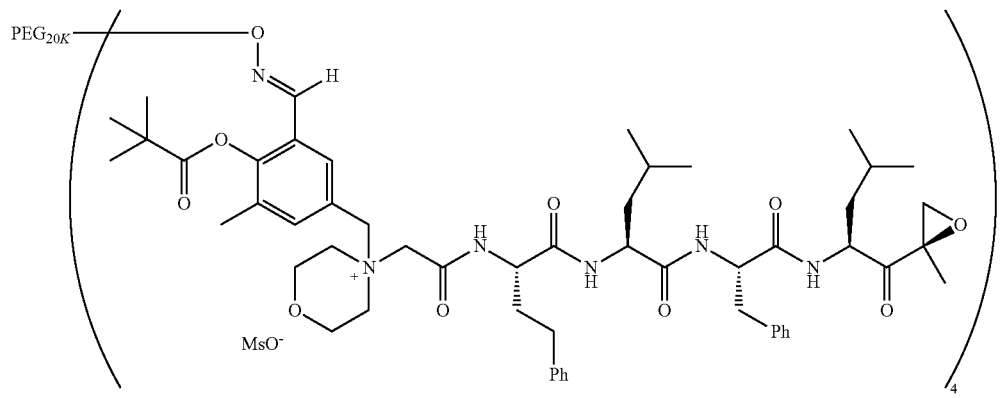

6

4-((4S,7S,10S,13S)-10-Benzyl-7-isobutyl-15-methyl-13-((R)-2-methyloxirane-2-carbonyl)-2,5,8,11-tetraoxo-1-phenethyl-3,6,9,12-tetraazahexadecyl)-4-(3-formyl-5-methyl-4-(pivaloyloxy)benzyl)morpholin-4-ium methanesulfonate (5)

To a solution of compound 3 (900 mg, 2.60 mmol) in MeCN (8 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (624 mg, 0.87 mmol). The reaction mixture was stirred at 40° C. overnight. An excess of solvent was concentrated and the residue was crystallized repeatedly from (EtOAc/Et$_2$O=1:5) to afford the desired compound 4, which was transformed into the corresponding mesylate 5 (222 mg, 9.0% yield) by treatment with ion exchange resin; $^1$H NMR (400 MHz, CDCl$_3$): δ 10.05 (s, 1H), 9.66 (m, 1H), 7.82 (m, 3H), 7.12-7.30 (m, 10H), 6.84 (m, 1H), 6.47 (m, 1H), 5.19 (m, 1H), 5.01 (m, 2H), 4.47 (m, 5H), 4.20 (m, 4H), 3.98 (m, 4H), 3.40 (m, 1H), 3.28 (m, 1H), 3.17 (m, 1H), 2.98 (m, 2H), 2.83 (m, 4H), 2.73 (m, 2H), 2.25 (m, 3H), 2.10 (m, 2H), 1.61 (m, 2H), 1.47 (m, 12H), 1.26 (m, 2H), 0.87 (m, 12H).

Example 30 was prepared by methods analogous to those described in Example 28, wherein the intermediates were made in similar fashion (using t-butanoyl chloride to generate the corollary intermediate 1 shown in eg 28), and compound 5 and PEG$_{20K}$(ONH$_3^+$.MsO$^-$)$_4$ following general pegylation procedure B.

Example 31: 4-(4-Acetoxy-3-((4-(PEG$_{5K}$-imino)methyl)benzyl)oxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium methanesulfonate (8)

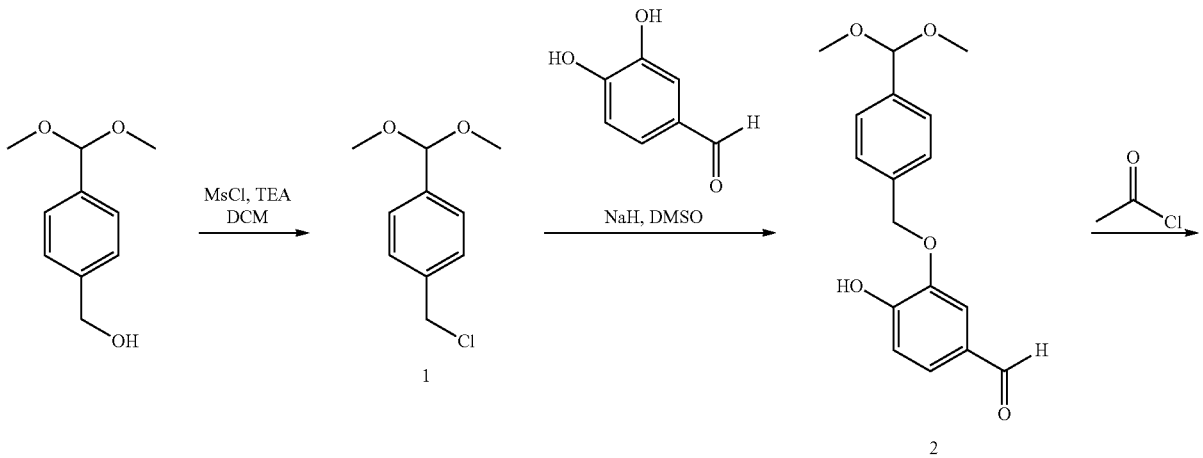

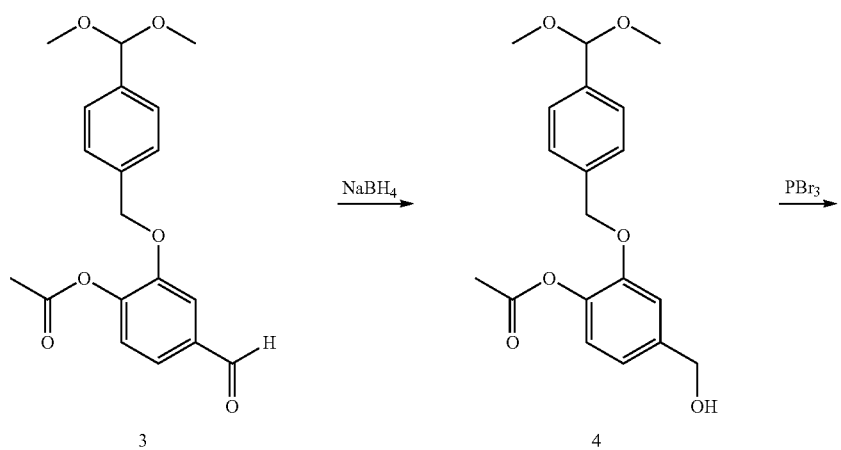

-continued
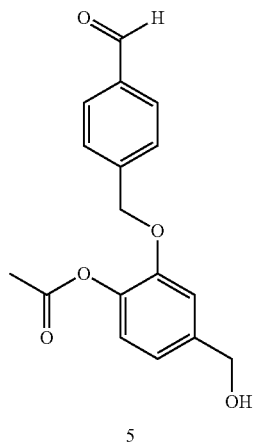
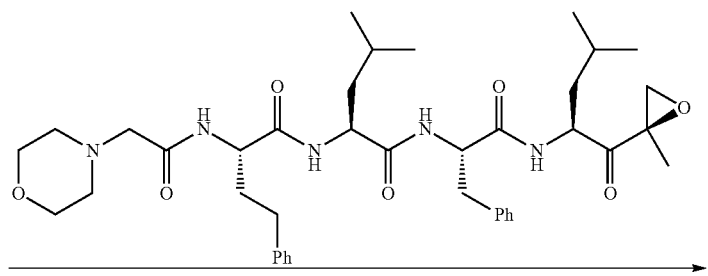
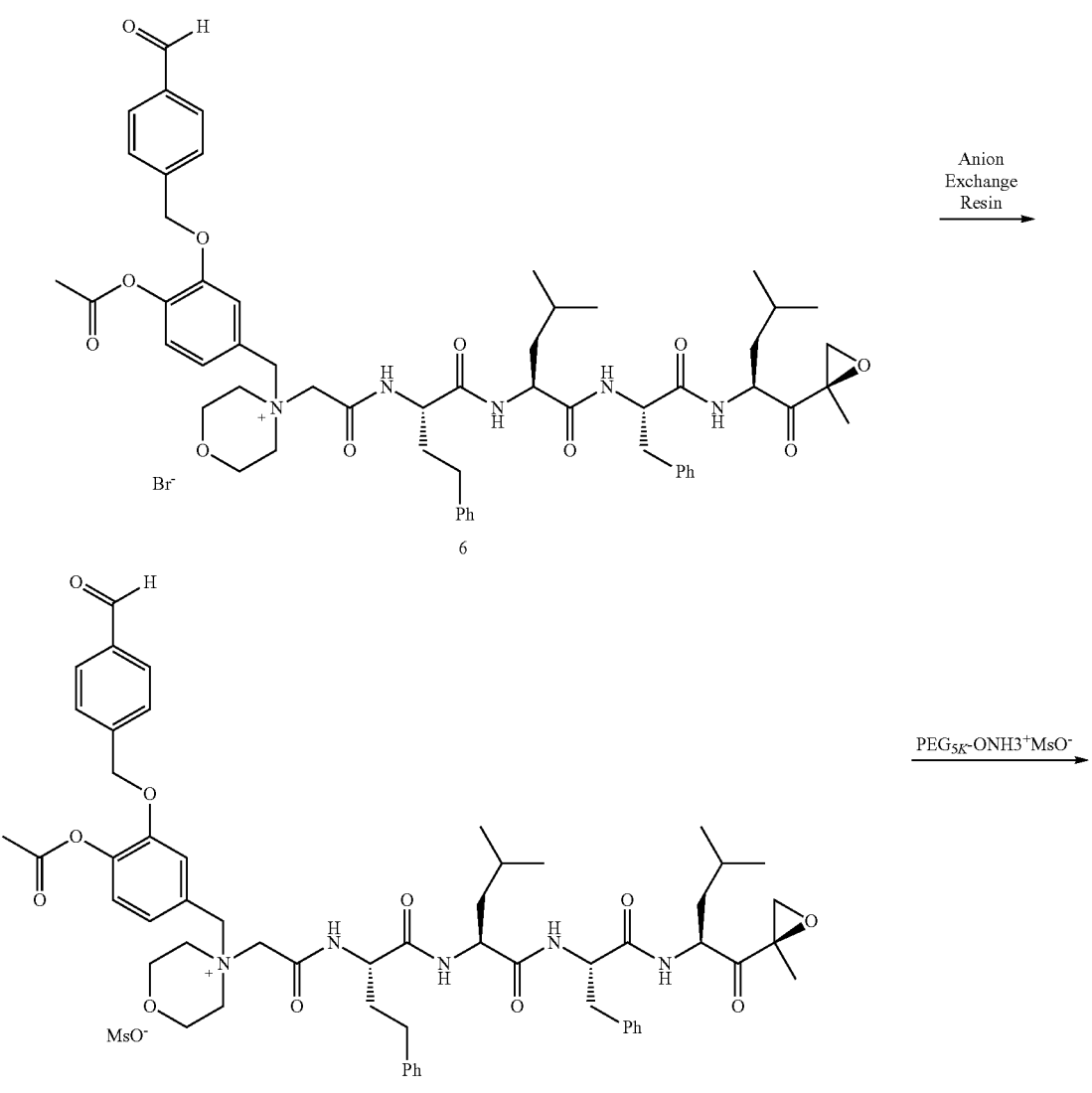

-continued

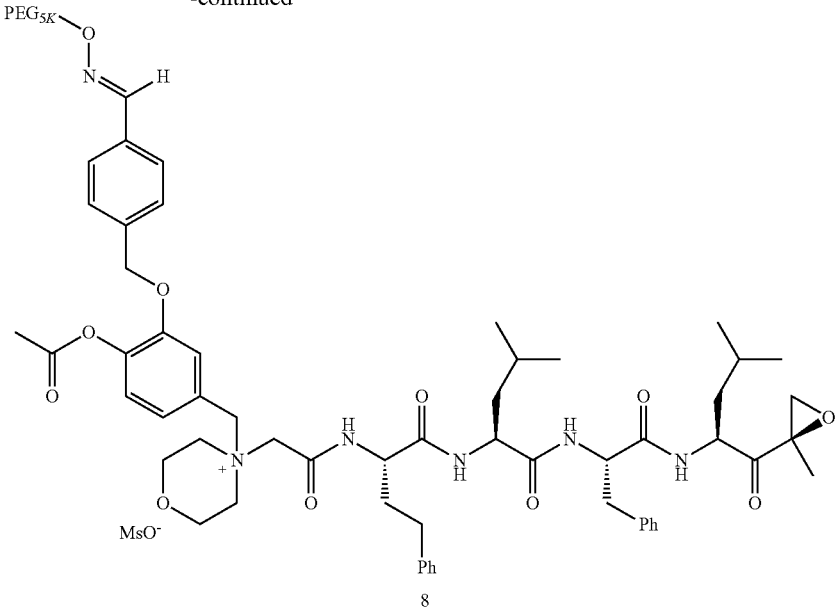

8

1-(Chloromethyl)-4-(dimethoxymethyl)benzene (1)

To a solution of (4-(dimethoxymethyl)phenyl)methanol (200 mg, 1.1 mmol) in DCM (10 ml) were added TEA (365.6 mg, 3.62 mmol) and MsCI (207.6 mg, 1.813 mmol) at 0° C. The reaction mixture was stirred at RT for 2 h, and then poured into saturated NaHCO$_3$ (10 mL). The two phases were separated, and the organic layer was dried over anhydrous Na$_2$SO$_4$ and concentrated to afford compound 1 (200 mg, 910), which was used in the next step without further purification.

4-(4-(Dimethoxymethyl)benzyloxy)-3-hydroxybenzaldehyde (2)

To a solution of compound 1 (200 mg, 0.998 mmol) in DMSO (5 mL) was added NaH (37.4 mg, 1.1 mmol) at room temperature. After 30 min of reaction, a solution of 3,4-dihydroxybenzaldehyde (137.7 mg, 0.998 mmol) in DMSO (5 mL) was added and the reaction mixture was stirred at RT overnight. The mixture was poured into saturated NaHCO$_3$ (10 mL) and the resulting mixture was extracted with DCM (10 mL 2). The combined organic layers were dried over anhydrous Na$_2$SO$_4$ and concentrated to afford compound 2 (300 mg, crude), which was used in the next step without further purification.

2-(4-(Dimethoxymethyl)benzyloxy)-4-formylphenyl acetate (3)

To a solution of compound 2 (300 mg, 1 mmol) in DCM (10 mL) were added TEA (202 mg, 2 mmol) and AcCl (102 mg, 1.3 mmol) at 0° C. The reaction mixture was stirred at r.t. for 2 h, and then poured into saturated NaHCO$_3$ (10 mL). The two phases were separated, and the organic layer was dried over anhydrous Na$_2$SO$_4$ and concentrated to afford compound 3 (200 mg, crude), which was used in the next step without further purification.

2-(4-(Dimethoxymethyl)benzyloxy)-4-(hydroxymethyl)phenyl acetate (4)

To a solution of compound 3 (200 mg, 0.58 mmol) in DCM/MeOH (10 mL/1 mL), was added NaBH$_4$ (19.8 mg, 0.58 mmol). The reaction mixture was stirred at 0° C. for 1 hour and then quenched with acetone (5 mL). The mixture was poured into saturated aq. NaHCO$_3$ (10 mL) and extracted with DCM (10 mL×2). The combined organic layers were dried over anhydrous Na$_2$SO$_4$ and concentrated to afford compound 4 (300 mg, crude), which was used in next step without further purification.

4-(Bromomethyl)-2-(4-formylbenzyloxy)phenyl acetate (5)

To a solution of compound 4 (1.8 g, 5.2 mmol) in DCM (50 nL) was added PBr$_3$ (1.41 g, 5.2 mmol). The reaction mixture was stirred at RT for 5 hours and then quenched with saturated aq. NaHCO$_3$ (60 mL). The two layers were separated and the aqueous phase was extracted with DCM (50 mL×2). The combined organic layers were dried over anhydrous Na$_2$SO$_4$ and concentrated. The residue was purified by flash column chromatography on silica gel (Petroleum Ether/EtOAc=4:1) to afford compound 5 (327 mg, 15% yield); $^1$H NMR (400 MHz, DMSO): δ 10.01 (s, 1H), 7.96~7.94 (m, 2H), 7.62~7.60 (m, 2H), 7.31 (m, 1H), 7.13~7.07 (m, 2H), 5.26 (s, 2H), 4.68 (s, 2H), 2.27 (s, 3H).

4-(4-Acetoxy-3-((4-formylbenzyl)oxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl) morpholin-4-ium methanesulfonate (7)

To a solution of compound 5 (320 mg, 0.884 mmol) in MeCN (6 mL) was added (S)-4-methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)pentanamide (254 mg, 0.354 mmol). The reaction mixture was stirred at 45° C. for 48 hours. An excessive solvent was evaporated and the residue was repeatedly crystallized from MeCN/Et$_2$O (1/5, v/v) to afford the desired product 6, which was then transformed into the corresponding mesylate compound 7 (180 mg, 47% yield) by treatment with ion exchange resin.

A solution of compound 7 (500 mg, 0.46 mmol), 2-amino-5-methoxybenzoic acid (25.5 mg, 0.14 mmol) and PEG-O—NH$_2$ (mesylate salt, 2.12 g, 0.41 mmol) in DCM was stirred at r.t. for 2 h. The reaction mixture was then concentrated and the residue was dissolved in $^i$PrOH at 40° C. The solution was cooled to RT and Et$_2$O was added to induce crystallization. The mixture was kept in ice bath for 10 min and then filtered. The filtration cake was crystallized from $^i$PrOH/Et$_2$O (5/2) to afford 8 (2.10 g, 82% yield).

Example 32: 4-((4S,7S,10S,13S)-10-Benzyl-7-isobutyl-15-methyl-13-((R)-2-methyloxirane-2-carbonyl)-2,5,8,11-tetraoxo-4-phenethyl-3,6,9,12-tetraazahexadecyl)-4-(4-(isobutyryloxy)-3-((4-(PEG$_{5K}$-imino)methyl)benzyl)oxy)benzyl)morpholin-4-ium methanesulfonate (8)

4-((4S,7S,10S,13S)-10-Benzyl-7-isobutyl-15-methyl-13-(R)-2-methyloxirane-2-carbonyl)-2,5,8,11-tetraoxo-4-phenethyl-3,6,9,12-tetraazahexadecyl)-4-(3-(4-formylbenzyloxy)-4-(isobutyryloxy)benzyl)morpholin-4-ium methanesulfonate (7)

To a solution of compound 5 (310.4 mg, 0.80 mmol) in MeCN (2 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (286 mg, 0.30 mmol). The reaction mixture was stirred at 45° C. for 48 hours. An excessive solvent was evaporated and the residue was repeatedly crystallized from MeCN/Et$_2$O (1/5, v/v) to afford the desired product 6, which was then transformed into the corresponding mesylate compound 7 (280 mg, 83% yield) by treatment with ion exchange resin.

A solution of compound 6 (280 mg, 0.25 mmol), 2-amino-5-methoxybenzoic acid (14.0 mg, 0.026 mmol) and PEG-

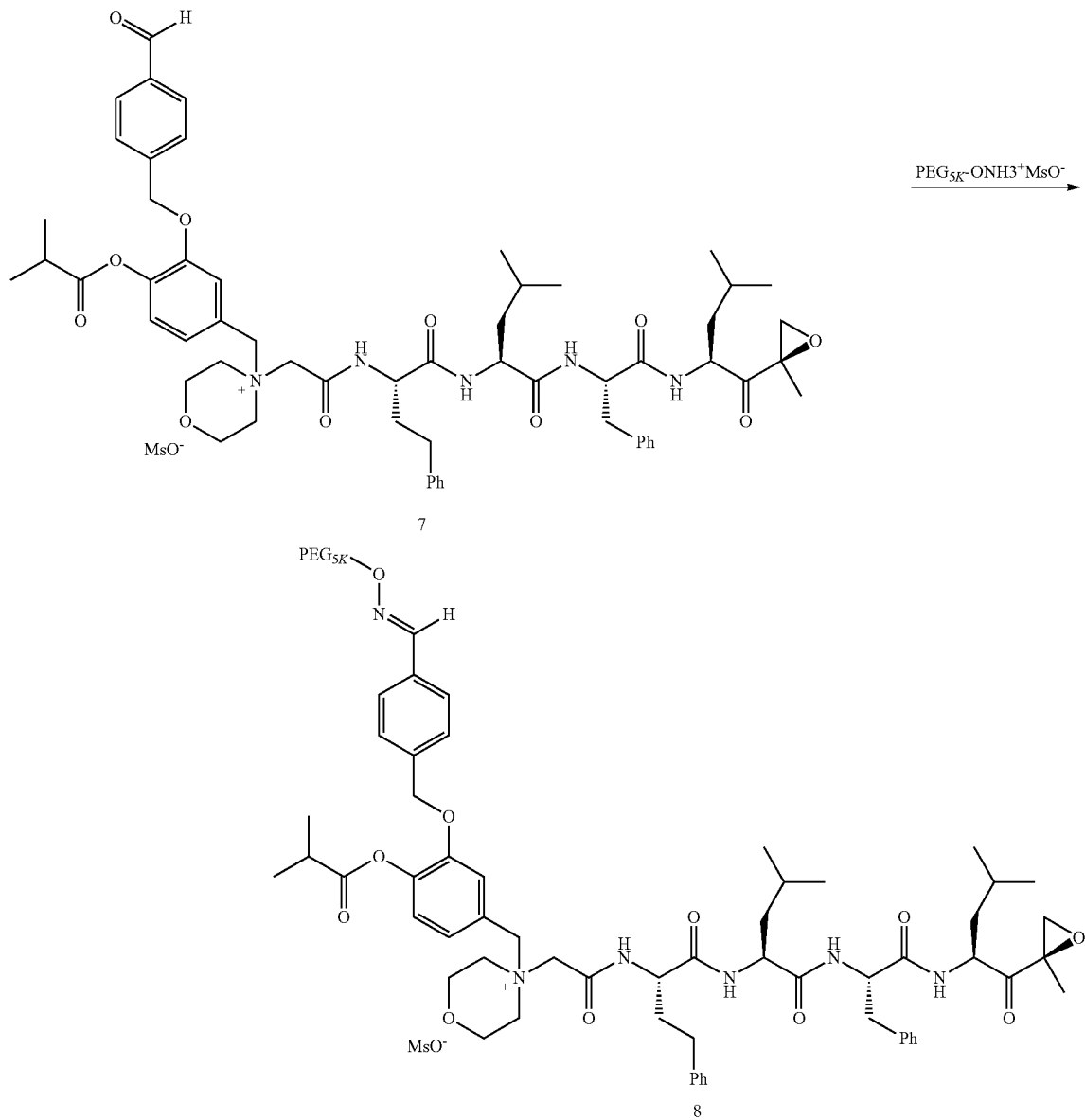

O—NH$_2$ (mesylate salt, 1.16 g, 0.227 mmol) in DCM (3 mL) was stirred at r.t. for 2 h. The reaction mixture was then concentrated and the residue was dissolved in i-PrOH at 40° C. The solution was cooled to room temperature and Et$_2$O was added to induce crystallization. The mixture was kept in ice bath for 10 min and formed solid was collected by filtration. Crystallization from i-PrOH/Et$_2$O (5:2) was repeated twice until all 7 was removed to afford 8 (1.0 g, 72% yield).

Example 33: 4-((4S,7S,10S,13S)-10-benzyl-7-isobutyl-15-methyl-13-((R)-2-methyloxirane-2-carbonyl)-2,5,8,11-tetraoxo-4-phenethyl-3,6,912-tetraazahexadecyl)-4-(3-((4-(PEG$_{5K}$-imino)methyl)benzyl)oxy)-4-(pivaloyloxy)benzyl)morpholin-4-ium methanesulfonate (8)

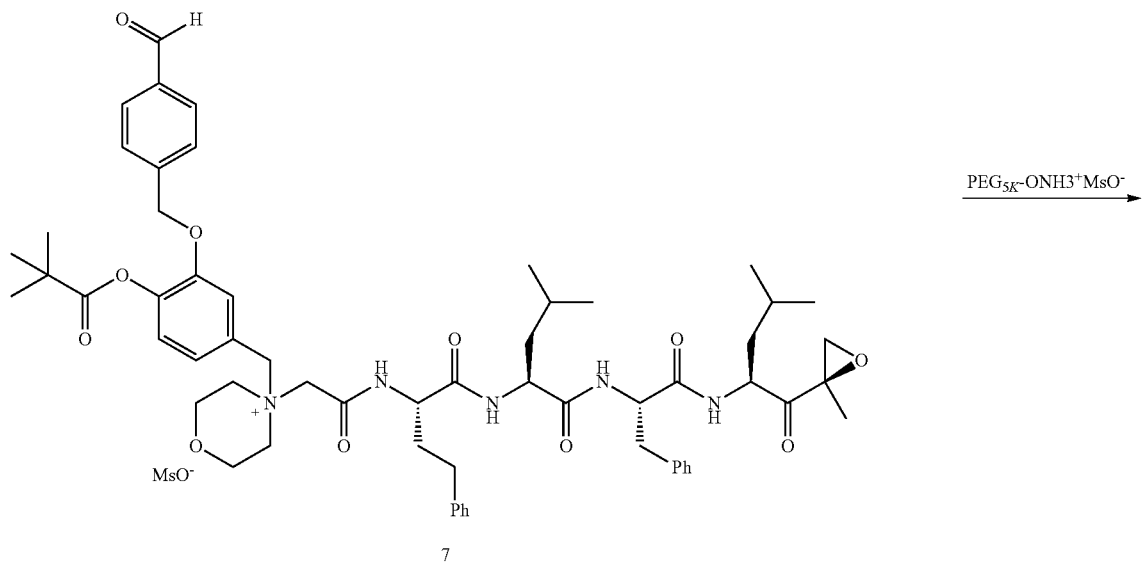

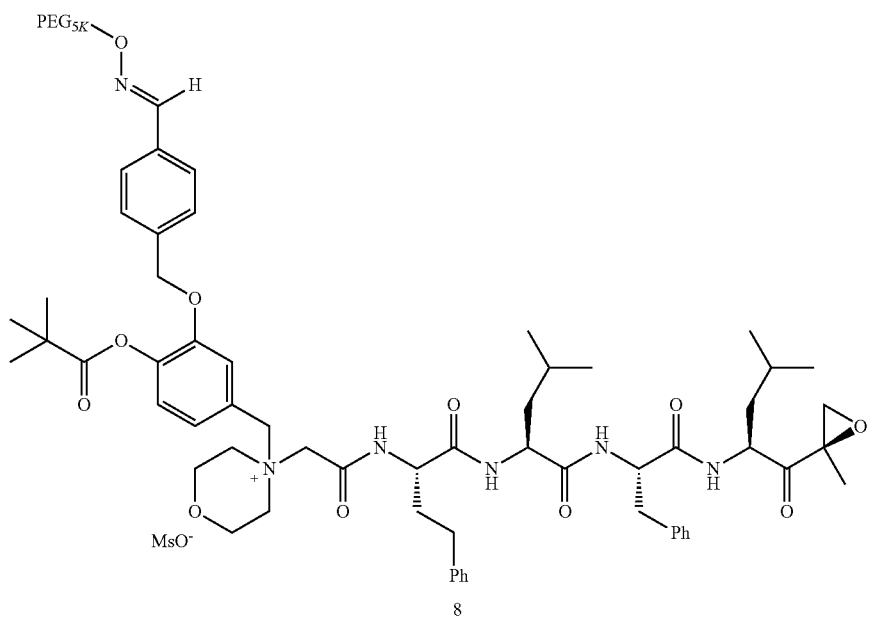

4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)-4-(3-(4-formylbenzyloxy)-4-(pivaloyloxy)benzyl)morpholin-4-ium methanesulfonate (7)

To a solution of compound 5 (t-butyl ester analog of compound 5 in example 31, 230 mg, 0.51 mmol) in MeCN (3 mL) was added (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide (184 mg, 0.25 mmol). The reaction mixture was stirred at 45° C. for 48 hours. An excessive solvent was evaporated and the residue was repeatedly crystallized from MeCN/Et$_2$O (1/5, v/v) to afford the desired product 6, which was then transformed into the corresponding mesylate salt compound 7 (170 mg, 71% yield) by treatment with ion exchange resin: $^1$H NMR (400 MHz, CDCl$_3$): δ 9.99 (s, 1H), 9.59 (m, 1H), 7.87~7.85 (m, 2H), 7.57~7.55 (m, 2H), 7.32 (m, 1H), 7.26~7.13 (m, 1H), 7.03 (m, 1H), 6.89 (m, 1H), 6.44 (m, 1H), 5.18 (m, 2H), 5.05~5.03 (m, 1H), 4.92~4.88 (m, 2H), 4.46~4.42 (m, 4H), 4.18~4.03 (m, 4H), 3.94~3.90 (m, 3H), 3.40~3.32 (m, 1H), 3.27~3.20 (m, 1H), 3.13 (m, 1H), 3.00~2.98 (m, 2H), 3.82~2.80 (m, 3H), 2.79 (m, 1H), 2.74~2.72 (m, 2H), 2.19 (m, 1H), 2.10~1.97 (m, 4H), 1.64~1.55 (m, 2H), 1.48~1.44 (m, 5H), 1.29 (m, 6H), 0.88~0.81 (m, 12H).

A solution of compound 7 (170 mg, 0.15 mmol), 2-amino-5-methoxybenzoic acid (28.2 mg, 0.016 mmol) and PEG-O—NH2 (mesylate salt, 614 mg, 0.12 mmol) in DCM was stirred at RT for 30 min. The reaction mixture was then concentrated and the residue was dissolved in $^i$PrOH at 40° C. The solution was cooled to RT and Et$_2$O was added to induce crystallization. The mixture was kept in ice bath for 10 min and then filtered. The filtration cake was crystallized from $^i$PrOH/Et$_2$O (5/2) to afford 8 (580 mg, 77%).

Representative carfilzomib prodrug examples 31-33 of the invention provide oxime linked conjugates with potentially enhanced chemical stability. In these examples the oxime linkage is spaced with an electron donating benzyloxy group to increase the overall stability of the PEG construct.

Example 34: 4-(4-Acetoxy-3-((1-PEG$_{3K}$-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,69,12-tetraazahexadecyl)morpholin-4-ium chloride

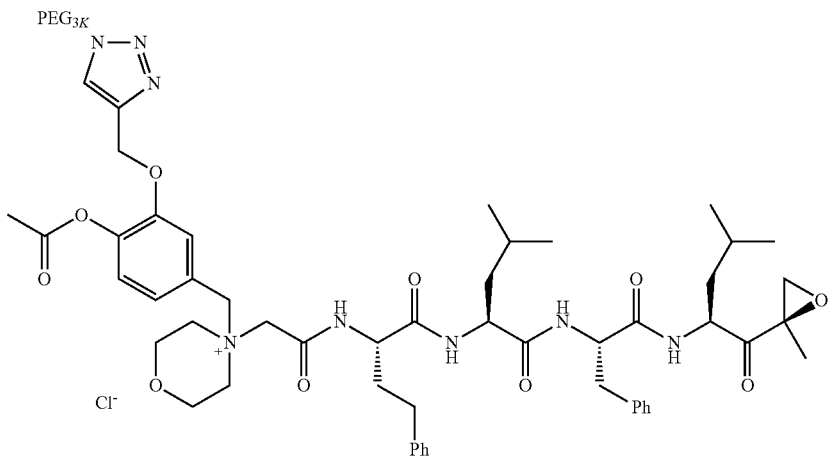

Example 34 was prepared using a method analogous to that taught in Examples 5-11 and Method A, but using the chloride salt intermediate having a chloride anion as the counter ion.

Example 35: 4-(4-Acetoxy-3-((1-PEG-1H-1,23-triazol-4-yl)methoxy)benzyl)-4-((4S,7S,10S,13S)-10-benzyl-7-isobutyl-15-methyl-13-((R)-2-methyl-oxirane-2-carbonyl)-2,5,8,11-tetraoxo-4-phenethyl-3,6,9,12-tetraazahexadecyl)morpholin-4-ium mesylate

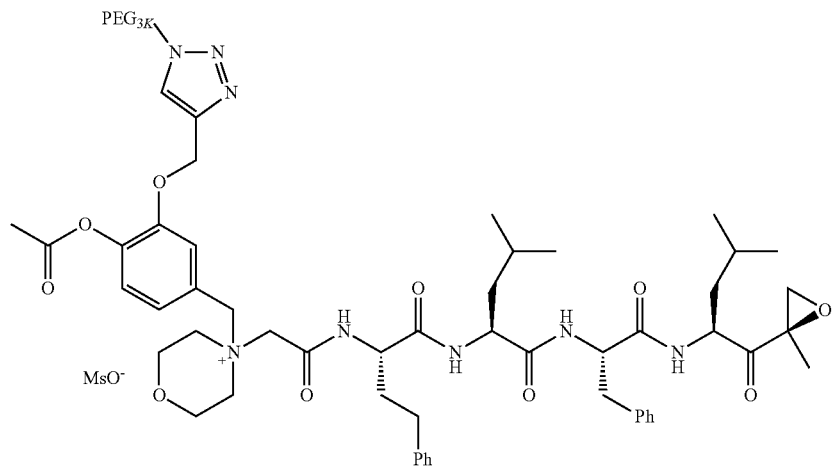

Example 35 was prepared using a method analogous to that taught in Examples 5-11 and Method A using a PEG$_{3K}$N$_3$. $^1$H NMR (DMSO-d6, 400 MHz): δ 9.19 (M, 1H), 8.24 (m, 2H), 8.12 (m, 1H), 7.90 (m, 1H), 7.62 (m, 1H), 7.22 (m, 13H), 7.0 (m, 1H), 5.26 (m, 2H), 4.88 (m, 2H), 4.53 (m, 3H), 4.37 (br s, 4H), 4.05 (m, 5H), 3.81 (m, 2H), 3.68 (m, 4H), 3.52 (br s, 339H), 3.30 (m, 4H), 3.24 (s, 4H), 2.94 (m, 2H), 2.75 (m, 1H), 2.63 (m, 2H), 2.24 (s, 3H), 1.87 (m, 2H), 1.59 (m, 2H), 1.40 (m, 7H), 0.84 (m, 12H)

Example 36: 4-(4-Acetoxy-3-((1-PEG$_{2K}$-1H-1,2,3-triazol-4-yl)methoxy)benzyl)-4-((4S,7S,10S,13S)-10-benzyl-7-isobutyl-15-methyl-13-((R)-2-methyl-oxirane-2-carbonyl)-2,5,8,11-tetraoxo-1-phenethyl-3,6,9,12-tetraazahexadecyl)morpholin-4-ium mesylate

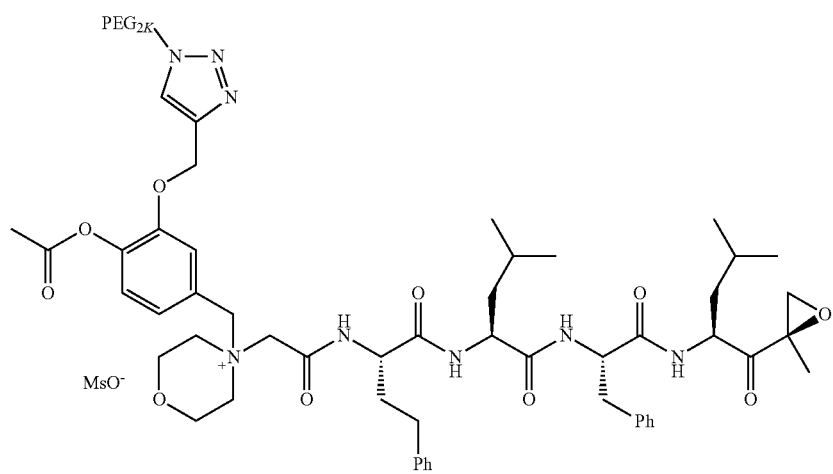

Example 36 was prepared using a method analogous to that taught in Examples 5-11 and Method A using a PEG$_{20K}$N$_3$. $^1$H NMR (DMSO-d6, 400 MHz): δ 9.44 (M, 1H), 8.26 (m, 2H), 8.16 (m, 1H), 8.00 (m, 1H), 7.62 (m, 1H), 7.22 (m, 13H), 5.26 (m, 2H), 5.00 (m, 2H), 4.54 (m, 3H), 4.37 (m, 5H), 4.09 (m, 4H), 3.81 (m, 2H), 3.68 (m, 2H), 3.50 (br s, 218H), 3.32 (m, 2H), 3.27 (s, 1H), 3.26 (s, 4H), 2.94 (m, 2H), 2.76 (m, 1H), 2.61 (m, 2H), 2.24 (s, 3H), 1.90 (m, 2H), 1.62 (m, 2H), 1.40 (m, 7H), 0.82 (m, 12H)

Example 37: 4-(4-acetoxy-3-((1-(5-((2-PEG$_{3K}$-ethyl)amino)-5-oxopentyl)-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium mesylate

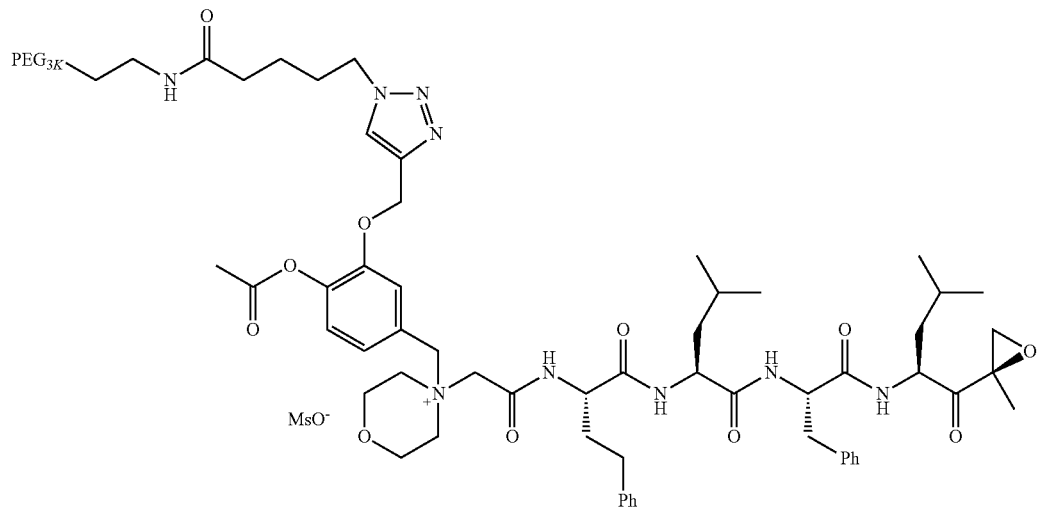

Example 37 was prepared using a method analogous to that taught in Examples 5-11 and Method A using a PEG$_{3K}$ with a linker derived from 5-azidopentanoic acid. $^1$H NMR (DMSO-d6, 400 MHz): δ 9.26 (M, 1H), 8.25 (m, 2H), 8.17 (m, 1H), 7.98 (d, 1H), 7.87 (m, 1H), 7.62 (m, 1H), 7.22 (m, 11H), 7.02 (m, 1H), 4.99 (m, 2H), 4.56 (m, 1H), 4.37 (br s, 6H), 4.11 (m, 3H), 3.71 (m, 3H), 3.52 (br s, 304H), 3.25 (br s, 7H), 2.75 (m, 1H), 2.61 (m, 2H), 2.24 (s, 3H), 2.11 (m, 1H), 1.87 (m, 2H), 1.40 (m, 5H), 0.82 (m, 12H)

Example 38: 4-(4-acetoxy-3-((1-(5-((2-PEG$_{2K}$-ethyl)amino)-5-oxopentyl)-1H-1,2,3-triazol-4-yl)methoxy)benzyl)-4-((4S,7S,10S,13S)-10-benzyl-7-isobutyl-15-methyl-13-((R)-2-methyloxirane-2-carbonyl)-2,5,8,11-tetraoxo-4-phenethyl-3,6,9,12-tetraazahexadecyl)morpholin-4-ium mesylate

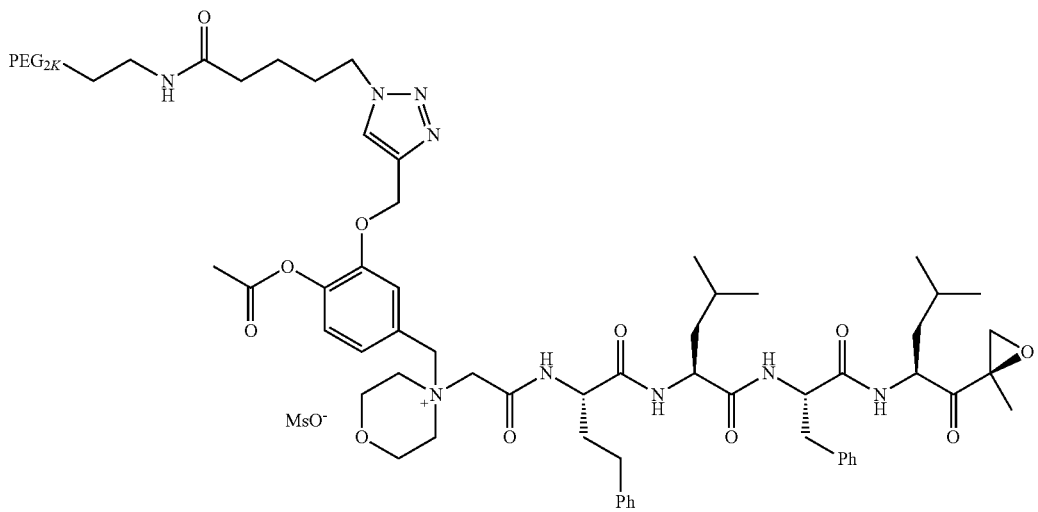

Example 38 was prepared using a method analogous to that taught in Examples 5-11 and Method A using a $PEG_{2K}$ with a linker derived from 5-azidopentanoic acid. $^1H$ NMR (DMSO-d6, 400 MHz): δ 9.56 (M, 1H), 8.29 (m, 2H), 8.18 (m, 1H), 8.04 (m, 1H), 7.92 (m, 1H), 7.62 (m, 1H), 7.22 (m, 11H), 7.0 (m, 1H), 5.38 (m, 2H), 4.99 (m, 2H), 4.56 (m, 1H), 4.37 (br s, 7H), 4.19 (m, 3H), 4.02 (m, 3H), 3.52 (br s, 179H), 3.25 (br s, 5H), 2.94 (m, 2H), 2.80 (m, 1H), 2.63 (m, 2H), 2.24 (s, 3H), 2.10 (m, 2H), 1.87 (m, 2H), 1.40 (m, 9H), 0.82 (m, 12H)

The Exemplary compounds of the present invention may be shown to be effective in treating various cancers, including without limitation, multiple myeloma, by virtue of possessing pharmacokinetic and pharmacodynamic profiles suitable and sufficient to provide such cancer treatment. The following exemplary descriptions and accompanying figures show some of these pharmacokinetic and pharmacodynamic profiles of select representative compounds of the invention.

Example 39: PEG-Carfilzomib Compound Conversion in Human Plasma

Human Plasma Conversion Protocol:

A 1 millimolar (mM) stock of the desired test compound was prepared in DMSO. 25 µM stock of the test compound was prepared in acetonitrile:water by diluting from 1 mM stock (i.e. 2.5 µL of 1 mM stock solution was added to 97.5 µL of acetonitrile:water (50:50)). The frozen human plasma (pooled from 5 males, 2KEDTA anticoagulant) was thawed at room temperature and centrifuged at 1400×RCF 4° C., for 15 minutes. Approximately 90% of the clear supernatant fraction was transferred to a separate tube and was used for the assay. For time 0 min samples, plasma was heat inactivated at 80° C. To 72 µL of heat inactivated plasma, 3 µL of 25 µM working stock was added and 50 µL of sample was crashed with 200 µL of acetonitrile containing internal standard. For assay, 1 µM incubation sample was prepared by spiking 20 µL of 25 µM working stock to 480 µL of plasma. Samples were incubated for 0.5, 1, 2, 4 and 6 h at 37° C. in shaker water bath with gentle shaking. At each time point, 50 µL sample was precipitated with 200 µL of acetonitrile containing internal standard and centrifuged at 4000×RCF, 4° C. for 20 minutes, 150 µL of supernatant was diluted with 150 µL of water and analyzed by LC-MS/MS. An 8 point calibration curve was generated using plasma with 5 µM highest concentration of carfilzomib followed by 2.5 fold dilution. The amount of carfilzomib released was quantified against the calibration curve and reported in µM.

FIG. 1 shows the rate of conversion of representative examples of PEG-carfilzomib compounds to free, non-PEG conjugated, active form of carfilzomib. As shown, the exemplified compounds of the invention provide plasma concentrations of carfilzomib beginning at time 0 and gradually increasing, for most of the examples depicted, to meaningful concentrations for as long as 2 hours and, in some instance, for longer than 2 hours. This figure shows that the half life of exemplary compounds of the present invention is projected to be at least 2 hours, and potentially longer in human plasma. Thus, FIG. 1 illustrates that PEG-carfilzomib compounds of the present invention provide a slow release of the active form of carfilzomib into the blood plasma, thereby allowing carfilzomib a potentially longer duration of action on cellular proteasome enzymes resulting in an expected prolonged inhibitory effect on proteasome activity.

Mean plasma concentration (µM) following intravenous administration of PEG-carfilzomib conjugate to female Balb/c mice (n=3). Dosage indicated is mg/kg of PEG-carfilzomib conjugate.

Example 40: PEG-Carfilzomib Mouse pK

PEG carfilzomib compounds were administered to mice (Balb/c, female, n=3 per dose group) as an intravenous (i.v.) bolus at the specified dose (dose volume 5 nL/kg) in an aqueous solution containing 10% (w/v) ethanol. Blood samples were collected at the indicated time points and plasma carfilzomib concentrations were measured in duplicate by LC/MS-MS. The control comparator profile was a carfilzomib standard formulation, i.e., an aqueous solution formulation of 10% (w/v) sulfobutylether-β-cyclodextrin and 10 mmol/L sodium citrate (pH 3.5) for administration (5 mg/kg). This standard carfilzomib represents the currently approved formulation for carfilzomib for treatment of multiple myeloma. The different doses administered to the mice for examples 13, 16 and 18 reflect an amount of carfilzomib present and dosed, and an amount calculated to be approximately the same as that amount of carfilzomib provided in the standard carfilzomib formulation.

Figure 2:
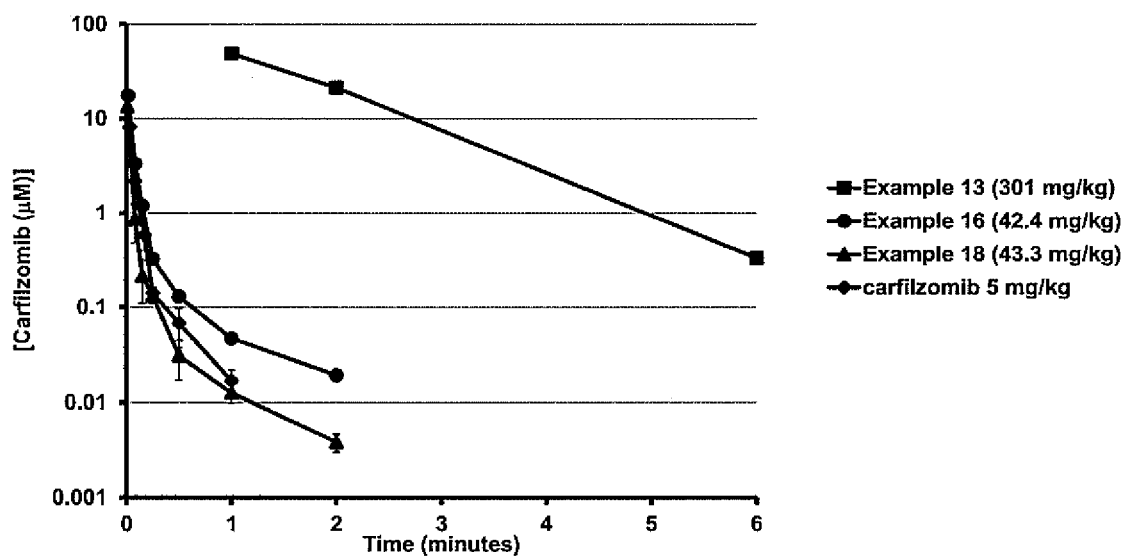
FIG. 2 is a graph reflecting the pK of representative pegylated compounds of carfilzomib in rat plasma.

As depicted in FIG. 2, while example 18 exhibited a profile similar to that of the control carfilzomib, Examples 13 and 16 exhibited extensions in their profiles. Particularly, Example 16 possessed improved availability of free, active carfilzomib over the same time period as that of the control. However, Example 13 exhibited a carfilzomib release over a far longer period of time than the control carfilzomib, which resulted in a significantly higher concentration of the carfilzomib the plasma over that longer period of time. The plasma concentration of Example 13 was multiple log-fold over that of the control.

Example 41: Proteasome Inhibition of PEG-Carfilomib Compounds Vs. Carfilzomib PEG carfilzomib compound example 1 was administered to mice (Balb/c, female, n=3 per dose group) as an intravenous (i.v.) bolus at the specified dose (dose volume 5 mL/kg) in an aqueous solution containing 10% (w/v) ethanol. Carfilzomib standard was formulated in an aqueous solution of 10% (w/v)sulfobutylether-β-cyclodextrin and 10 mmol/L sodium citrate (pH 3.5) for administration (5 mg/kg). At selected time points after i.v. drug administration, tissue samples (adrenal, heart, liver and bone marrow) were collected. Whole blood was collected by cardiac puncture into tubes containing sodium heparin.

Blood: Approximately 0.4 mL of whole blood is collected using either EDTA microcentrifuged tubes. Samples are immediately placed on ice and spun at maximum speed for 2 minutes in a microcentrifuge at room temperature (RT). Cell pellets are stored on wet ice. Whole blood cell pellets are resuspended in 1 ml of phosphate buffered saline (PBS) and centrifuged at max speed at 4° C. Supernatants are removed and the pellets are washed a second time with PBS. Samples are resuspended in 2 volumes of lysis buffer (20 mM Tris, pH 8.0, 5 mM EDTA) then frozen and stored at −80° C. until analysis.

Adrenal Glands, Heart and Liver Tissue:

Tissues (adrenal glands, heart, and liver) were collected at the graphic time points specified after dosing. Tissues were excised and placed into 15 ml tubes containing PBS at 4° C. For tissues which were homogenized, samples were minced with scissors and ~0.1-0.2 mg portions were placed into 2 mL microcentrifuge tubes. Tissue portions were frozen and stored at −80° C.

Sample Processing:

All samples were thawed on ice. All single cell pellets in lysis buffer (whole blood) were briefly vortexed then spun at 14.000 rpm in a microcentrifuge at 4° C. for 15 minutes. Supernatant was transferred at a ratio of 100 µL to 25 µL of 50% glycerol in a sample plate for a final concentration of 10% glycerol. These samples were then ready for assaying, or they may be frozen at −80° C. Approximately 2 volumes of lysis buffer and a stainless steel bead were added to the thawed tissue portions (adrenal glands, heart, and liver). Samples were homogenized at 20 mHz for 60 seconds on each side then spun at 14,000 rpm in a microcentrifuge at 4° C. for 15 minutes. Supernatant was transferred at a ratio of 100 µL to 25 µL of 50% glycerol in a sample plate for a final concentration of 10% glycerol. Care was taken to avoid the top lipid layer for tissues with high fat content (i.e. adrenal). These samples were then ready for assaying, or they may be frozen at −80° C. Samples frozen at this lysate/10% glycerol stage should be thawed on ice before assaying. The protein concentration for each sample was measured by Bradford assay. Proteasome chymotrypsin-like (CT-L) activity was quantitated by monitoring the release of free AMC from the fluorogenic peptide Suc-Leu-Leu-Val-Tyr-AMC (Boston-Biochem).

Figure 3:
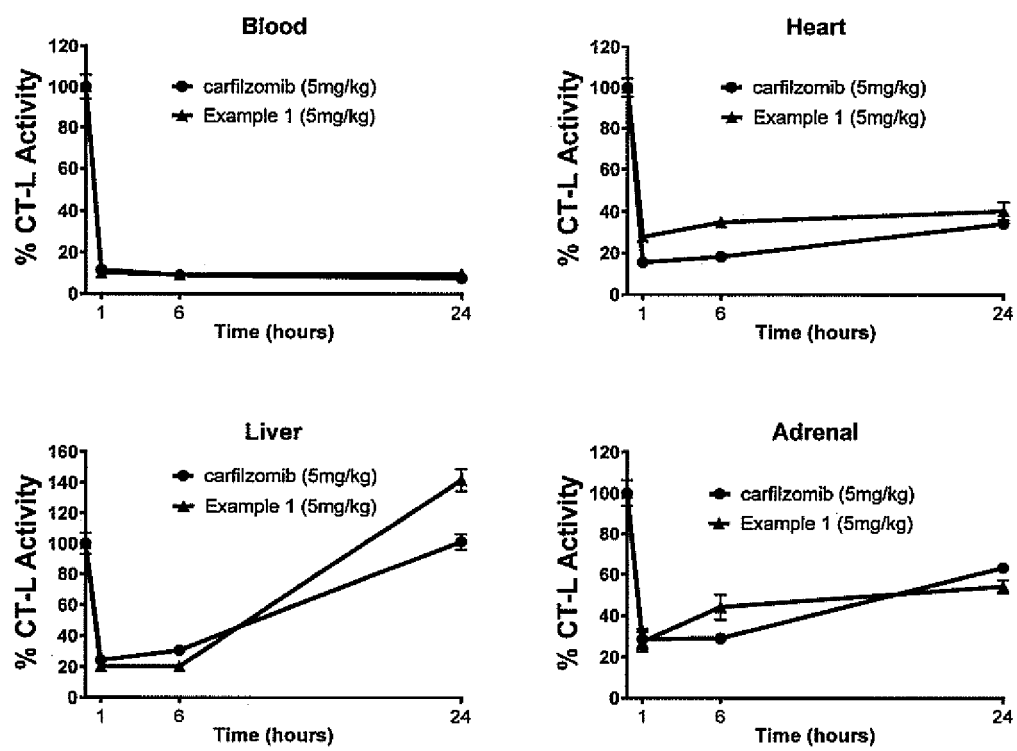
FIG. 3 is a graphic illustration of the effects of carfilzomib and compound Example 1 on chymotrypsin-like proteasome activity in the blood, adrenal gland, heart and liver tissues.

As shown in FIG. 3, the CT-L activity was comparable between the standard carfilzomib and Example conjugate 1 in the blood as well as in the tissues of the adrenal gland, the heart and of the liver, in mice.

Example 42: Mean Carfilzomib Plasma Concentration—Time Profiles for Examples 13, 26 and 34, Each Administered IV The PEG carfilzomib compounds were administered to mice (Balb/c, male, n=9 per dose group) as an intravenous (i.v.) bolus at 5 mg/kg (equivalent to carfilzomib, dose volume 1 mL/kg). Blood samples from each mouse were collected at the indicated time points (0.5, 1, 2, 4, 6, 12, 16 and 24 hours post-dose) and 25 µL of the plasma samples were extracted by protein precipitation with 125 µL of acetonitrile containing D10-CFZ as an internal standard and then centrifuged. Carfilzomib concentrations were measured in the supernatant by LC-MS/MS using multiple reaction monitoring in the positive electrospray ionization mode. The lower limit of quantitation of the assay was 0.500 ng/mL.

Figure 4:
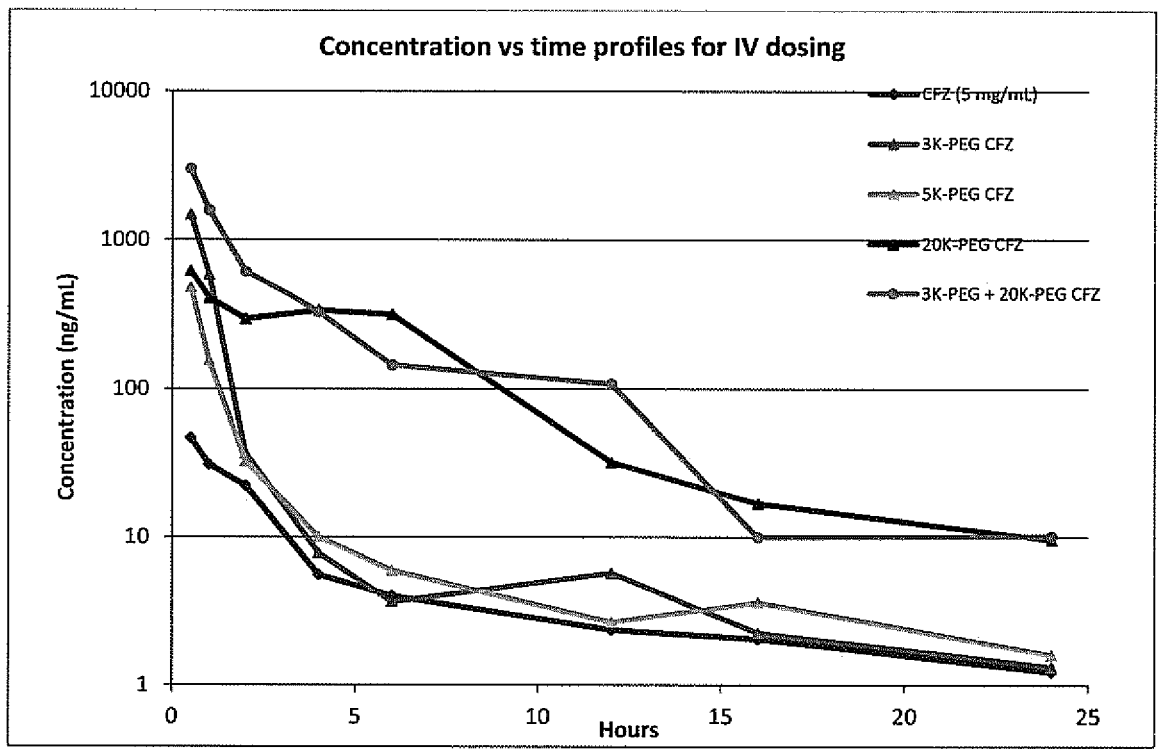
FIG. 4 is a graphic illustration of mean carfilzomib plasma concentrations over time for Examples 13, 26 and 34 of the invention.

As shown in FIG. 4, the control standard carfilzomib (CFZ) cyclodextrin formulation (5 mg/mL) in this study resulted in a plasma concentration drop over a very short period of time. The 3K-PEG CFZ (Example 34) is present in the plasma for up to between 20 and about 25 hours post initial administration of the PEG conjugate. Similarly, the 5K-PEG CFZ (Example 26) is present in the plasma, as measured in FIG. 5, at higher concentrations for practically all of the time out to about 25 hours. Finally, the 20K-PEG (Example 13) is the curve above both the 3K and 5K-PEG curves, while beginning between them, and revealing that this PEG conjugate releases carfilzomib into the plasma over the course of the 25 hours measured, while providing carfilzomib at significantly higher plasma concentrations for that lengthy duration of time. Finally, as shown in FIG. 4, the highest most curve at the starting time point, a formulation comprising a combination of both the 3K-PEG and the 20K-PEG carfilzomib compounds exhibited a plasma concentration both higher and longer than the 3K-PEG individually and comparable to the higher molecular weight 20K-PEG carfilzomib compound alone.

TABLE 4

Table 4 describes the results obtained when the representative carfilzomib compound examples were compared with standard carfilzomib and all samples were dosed IV. pK Measurements

| Example No. | $C_{max}$ (ng/mL) | $AUC_{0-24}$ (ng·h/mL) | $T_{1/2}$ (h) | CL/F (mL/kg/h) | Volume of Distribution (Vdss; mL/kg) |
|---|---|---|---|---|---|
| CFZ-IV | 46.7 | 153 | 10.9 | 29000 | 245000 |
| 34 | 1470 | 2230 | 6.09 | 2230 | 2110 |
| 26 | 472 | 847 | 8.51 | 5770 | 12800 |
| 13 | 616 | 3510 | 3.68 | 1400 | 6900 |

The PEG carfilzomib formulations dosed in Examples 39-41, were generally prepared as follows: A desired amount of the PEG-CFZ compound was weighed out into a sterile glass container using an analytical balance. A diluent volume was calculated based on the weight of the material. A diluent of 10 mM Acetate, pH 5.0, 9% sucrose was added to the glass vessel to a final volume that resulted in PEG-CFZ compounds' concentrations of 1 mg/ml, 5 mg/mL, 10 mg/mL or 20 mg/mL. Each PEG-CFZ sample was stirred for an hour at room temperature to allow for full dissolution of the material. Once the material was completely dissolved in solution, a sample was taken to measure the pH, which was consistently found to be in the desired range of 4.9-5.1. Thus, no further pH adjustments were done. Sample osmolality measurements and endotoxin testing was performed for all samples and consistently found to be within the acceptable range of 295-312 mOsm for osmolality and <1.0 EU/mL for endotoxin count. Immediately after dissolution samples were aseptically filled into 5 cc sterile glass vials, stoppered and capped. The samples were frozen at −70° C. for a period of 1 day to 2.5 weeks prior to transport and dosing in the examples 39-41 as described herein below.

Figure 5:
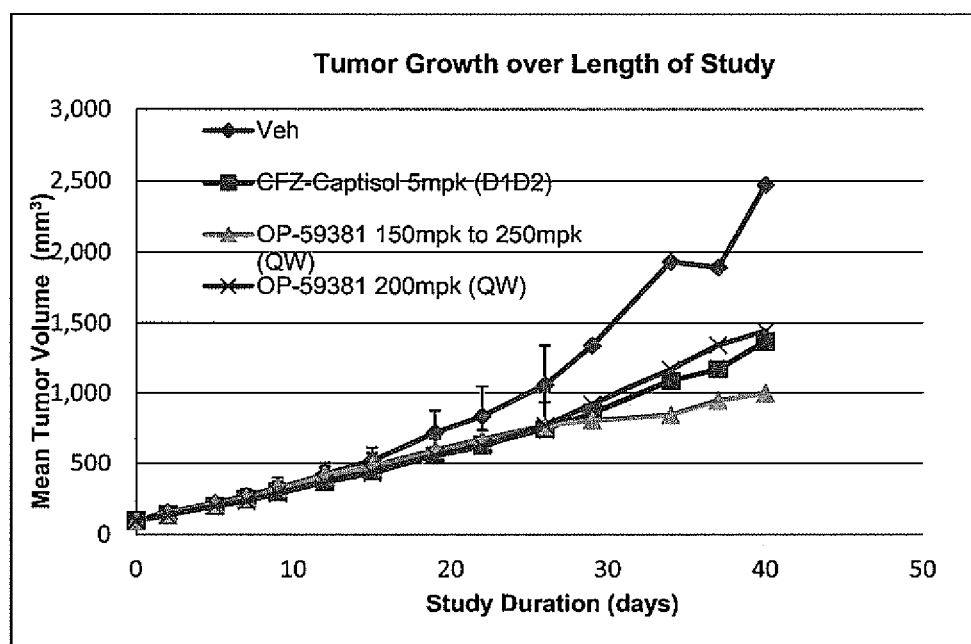
FIG. 5 is a graph illustrating the efficacy of Example 13 versus CFZ-captisol formulation in a mouse xenograph cancer model.

Example 43: Efficacy Study of Example 13 and CFZ-Captisol in HT-29 Human Colorectal Adenocarcinoma Xenograph Model in SCID Beige Mice (FIG. 5)

Procedure: Female Beige Severe Combined Immune Deficiency (SCID) mice (60 plus spares) were purchased from Harlan Laboratories (Livermore, Calif.) as 6- to 7-week-old mice. Following arrival, animals were weighed using an electronic balance (Ohaus SCOUT® PRO, Parsippany, N.J.), given a clinical examination to ensure that the animals were in good condition, and housed 5 per cage (prior to dosing). The animals were maintained in a HEPA-filtered environment in a Micro-VENT full-ventilation rodent housing system (Allentown Caging Equipment Co., Allentown, N.J.) providing at least 10 room air changes per hour. Animal room controls were set to maintain temperature and relative humidity at 20° C.±1° C., and 50%±20%, respectively. Housing rooms were on a 12:12 light/dark cycle. Cages were autoclaved, and animals were bedded on San-iChip irradiated bedding 7990.BG (Harlan Teklad; Hayward, Calif.). Water was autoclaved and supplied ad libitum to each cage via water bottles. Irradiated 2018 Teklad Global 16% Protein Rodent Diet ((Harlan Teklad) supplied ad libitum to each cage.

Compound formulation: Example 13 was prepared as generally described above. The carfilzomib comparator compound was prepared as CFZ-captisol (at 1 mg/mL). A powder sample of example 13 was diluted to 30 mg/ml (Group 3) or 50 mg/ml (Group 3 beginning fourth dose) or 40 mg/ml (Group 4) in 10% ETOH/saline. Vehicle and CFZ-captisol were stored at 4° C. throughout the study. During the study, example 13 was inspected regularly for potential changes in the quality of the suspension; none were observed Cell line: NCI-HT29 (HT-29; ATCC® HTB-38™), a human colorectal adenocarcinoma cancer cell (CA) line, was purchased from ATCC (Manassas, Va.). Following receipt at the MGI, cells were grown in-house for 7 passages in RPMI 1640 and 10% fetal bovine serum, then used to generate frozen stocks. The cells were recovered from the frozen stocks and cultured as above. Following growth, the cells were spun down and resuspended at a concentration of 5E07 cells/mL in serum-free medium without additives, then combined 1:1 with Matrigel™ (Trevigen, Gaithersburg, Md.). At the time of implant, cells corresponded to MGI Passage 7 (MGP7).

Implantation of cells: At approximately 3 weeks prior to the projected staging day, mice were implanted by subcutaneous (SC) injection into the lower left abdominal flank with 200 µL (5.0E06 cells) per mouse of the freshly prepared HT29: Matrigel mixture. All procedures were carried out in HEPA-filtered laminar-flow hoods.

Study design: Study design and treatments of all groups are shown in Table 1 (Efficacy). When the tumors reached a mean volume of approximately 200 mm$^3$ per mouse, forty animals with established tumors and moderate body weights were randomized into 4 treatment groups (n=10 mice per group). Starting on Day 0, animals were administered by once-weekly (qw) injection with vehicle (Group 1) or twice-weekly D1D2 injection (i.e., two adjacent days each week) with CFZ-captisol at 5 mpk (Group 2) or OP-59381 at 150 mg/kg (Groups 3). Starting with the fourth dose (i.e., after three week), dosing of Group 3 animals was increased to 250 mg/kg. Group 4 was dosed once-weekly (qw) injection with or OP-59381 (Example 13) at 200 mg/kg. All of these doses were administered as intravenous (IV) injections at dose volumes of 5 mL/kg. After the IV dosing for the seventh week (i.e., after Day 42 for Groups 1-4), the tumor treatment efficacy appeared to slow or cease altogether.

TABLE 5

Days 0-48

| Experiment | Group | Agent | Dose (mg/kg) | Frequency |
|---|---|---|---|---|
| 1 | 1 (n = 10) | Vehicle | — | QW × 7 weeks |
| 1 | 2 (n =10) | CFZ-captisol | 5 | QD × 2 (D1D2) × 7 weeks |
| 1 | 3 (n =10) | Example 13 | 150/250 | QW × 7 weeks |
| 1 | 4 (n = 10) | Example 13 | 200 | QW × 7 weeks |

As seen in FIG. 5, the tumors in the vehicle group (Group 1) grew linearly over the IV dosing interval, with tumors increasing to ~2,755% of initial size by Day 49. While Day 0 to Day 15 tumor sizes were unchanged vs. vehicle control in all three groups, by Day 19 tumor growth was significantly attenuated in the 200 mpk Example 13 and the 5 mpk CFZ-captisol treated animals. This significant attenuation continued to Day 29 when all three experimental groups achieved significance that continued to Day 40, demonstrating that the 3 doses were sufficient to provide anti-tumor activity.

Figure 6:
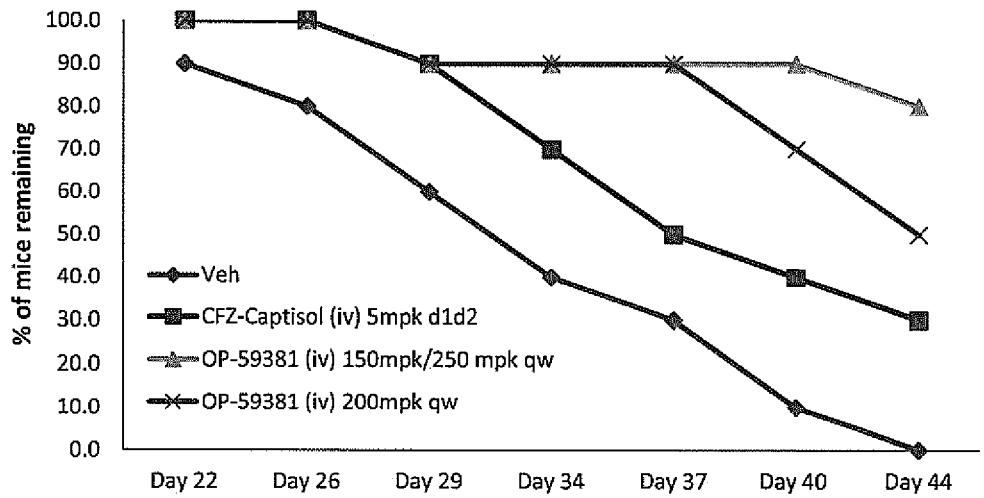
FIG. 6 is a graphic illustration of the survival of the mice from the Study illustrated in FIG. 5.

Example 44: Example 44 Reflects the Mouse Survival Data Resulting from Study of Example 41, which Data is Tabulated in Table 6 and Graphically Illustrated in FIG. 6

TABLE 6

| Group | Day 0 Tumor Vol (mm$^3$) | Day 40 Tumor Vol (mm$^3$) | % Change compared to Vehicle | # of animals at day 40 |
|---|---|---|---|---|
| 1 Vehicle | 95.8 | 2471.6 | 0 | 3 |
| 2 CFZ-Captisol 5 mpk (D1D2) | 95.6 | 1370.6 | −44.5% | 4 |
| 3 Example 13-150 mpk to 250 mpk (QW) | 95.5 | 998.5 | −59.6% | 9 |
| 4 Example 13-200 mpk (QW) | 95.9 | 1443.0 | −41.6% | 7 |

Examples 41 and 42 reveal the efficacy of carfilzomib representative compound Example 13 in a mouse xenograft model of human colorectal adenocarcinoma cancer cell. Tumors in the vehicle group grew linearly during the study. Once-weekly intravenous dosing with compound Example 13 (200 mpk, or 150 rising to 250 mpk after 3 week) or with CFZ-captisol (5 mpk) provided significant attenuation of tumor growth (compared to vehicle control) within 19 days of the first dose administration. In addition, intravenous dosing with the both formulations was associated with significant attenuation of weight gain.

Figure 7:
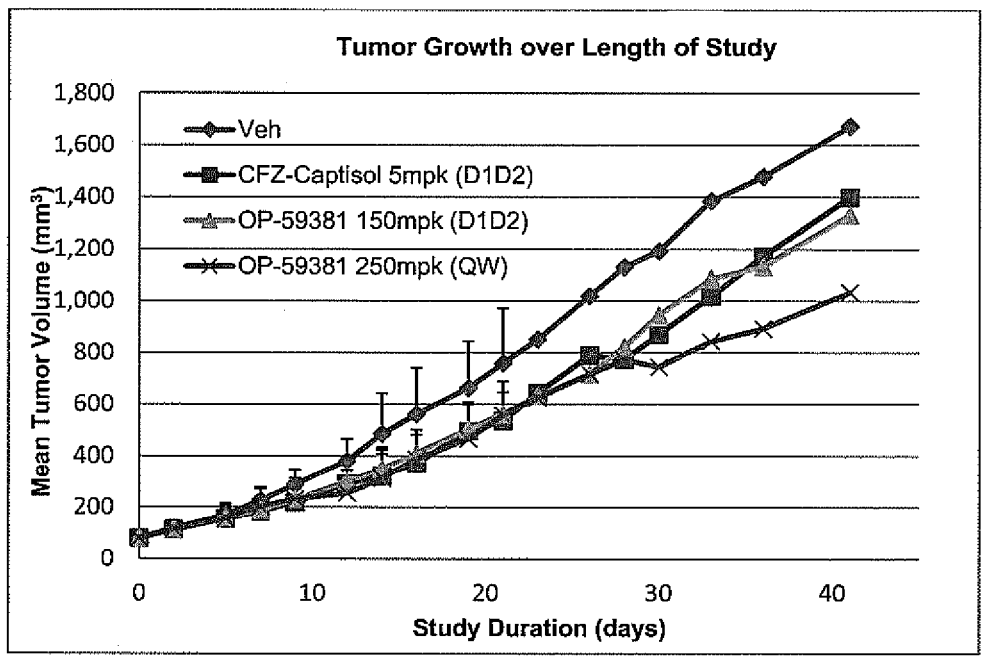
FIG. 7 is a graph illustrating a second efficacy study of Example 13 versus CFZ-captisol formulation in a mouse xenograph cancer model.
Figure 8:
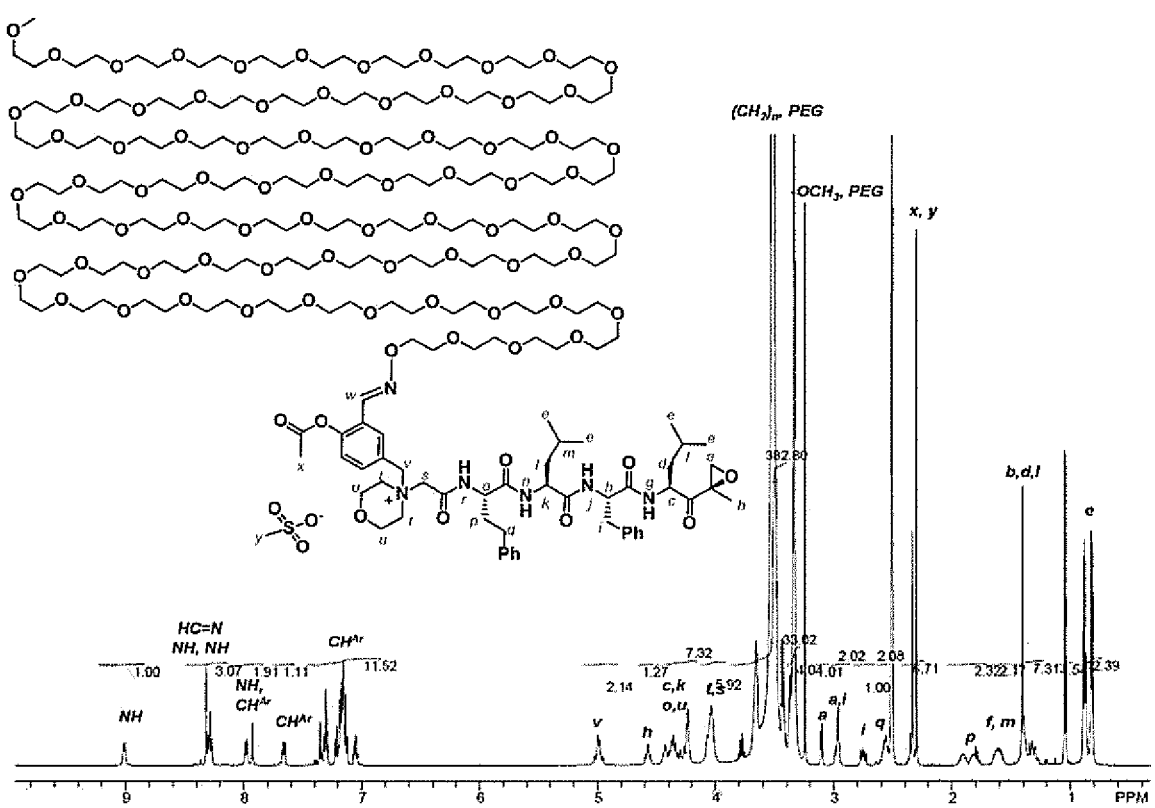
FIG. 8 is a figure of the NMR spectrum for Example 23.
Figure 9:
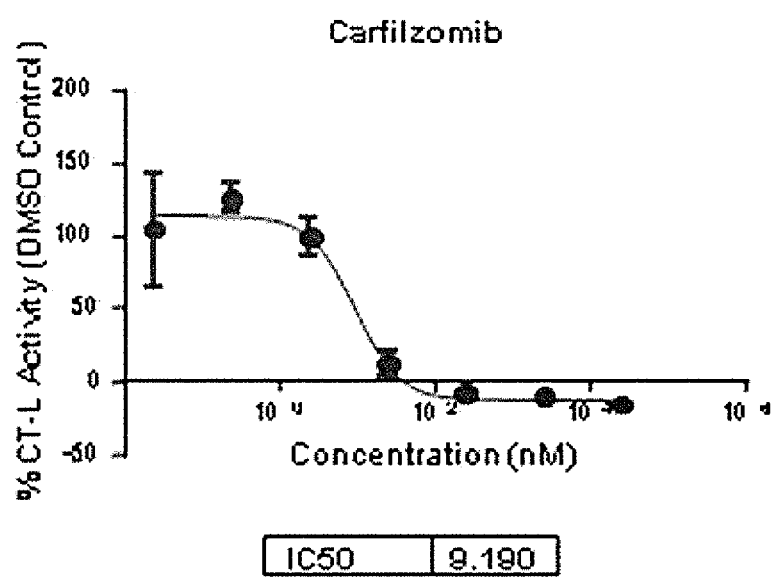
FIG. 9 is a figure of the cellular CT-L activity for carfilzomib.

Example 45: Efficacy Study of Example 13 and CFZ-Captisol in HT-29 Colorectal Adenocarcinoma Xenograph Model in SCID Beige Mice (FIG. 7)

Procedure: Female Beige Severe Combined Immune Deficiency (SCID) mice (60 plus spares) were purchased from Harlan Laboratories (Livermore, Calif.) as 6- to 7-week-old mice. Following arrival, animals were weighed using an electronic balance (Ohaus SCOUT® PRO. Parsippany, N.J.), given a clinical examination to ensure that the animals were in good condition, and housed 5 per cage (prior to dosing). The animals were maintained in a HEPA-filtered environment in a Micro-VENT full-ventilation rodent housing system (Allentown Caging Equipment Co., Allentown, N.J.) providing at least 10 room air changes per hour. Animal room controls were set to maintain temperature and relative humidity at 20° C.±1° C., and 50%±20%, respectively. Housing rooms were on a 12:12 light/dark cycle. Cages were autoclaved, and animals were bedded on SaniChip irradiated bedding 7990.BG (Harlan Teklad; Hayward, Calif.). Water was autoclaved and supplied ad libitum to each cage via water bottles. Irradiated 2018 Teklad Global 16% Protein Rodent Diet ((Harlan Teklad) supplied ad libitum to each cage.

Compound formulation: Example 13 was formulated as described herein to the desired concentration. Carfilzomib was provided as CFZ-captisol (at 1 mg/mL), a powder sample of Example 13 was diluted to 30 mg/ml (Group 3) or 50 mg/ml (Group 4) in 10% ETOH/saline. Vehicle and CFZ-captisol were stored at 4° C. throughout the study. During the study, example 13 preparations were inspected regularly for potential changes in the quality of the suspension; none were observed.

Cell line: NCI-HT29 (HT-29; ATCC® HTB-38™), a human colorectal adenocarcinoma cancer cell (CA) line, was purchased from ATCC (Manassas, Va.). Following receipt at the MGI, cells were grown in-house for 7 passages in RPMI 1640 and 10% fetal bovine serum, then used to generate frozen stocks. The cells were recovered from the frozen stocks and cultured as above. Following growth, the cells were spun down and resuspended at a concentration of 5E07 cells/mL in serum-free medium without additives, then combined 1:1 with Matrigel™ (Trevigen, Gaithersburg, Md.). At the time of implant, cells corresponded to MGI Passage 7 (MGP7).

Implantation of cells: At approximately 3 weeks prior to the projected staging day, mice were implanted by subcutaneous (SC) injection into the lower left abdominal flank with 200 µL (5.0E06 cells) per mouse of the freshly prepared HT29:Matrigel mixture. All procedures were carried out in HEPA-filtered laminar-flow hoods.

Study design: Study design and treatments of all groups are shown in Table 1 (efficacy). When the tumors reached a mean volume of approximately 200 mm$^3$ per mouse, forty animals with established tumors and moderate body weights were randomized into 4 treatment groups (n=10 mice per group). Starting on Day 0, animals were administered by once-weekly (qw) injection with vehicle (Group 1) or twice-weekly D1D2 injection (i.e., two adjacent days each week) with CFZ-captisol at 5 mpk (Group 2) or example 13 at 150 mg/kg or 250 mg/kg (Groups 3 and 4, respectively). All of these doses were administered as intravenous (IV) injections at dose volumes of 5 mL/kg. After the sixth week's dose administration(s) (i.e., after Day 35). IV dosing for efficacy ceased.

As seen in FIG. 7, tumors in the vehicle group (Group 1) grew linearly over the IV dosing interval, with tumors increasing to ~2100% of initial size by Day 41. In comparison, tumor growth was significantly attenuated in all of the experimental groups: Day −41 tumor sizes were 83.6%, 79.6%, and 61.8% of control for Groups 2, 3, and 4 respectively. This attenuation achieved significance starting at the earliest time points (9 or 12 days), demonstrating that two doses were sufficient to provide anti-tumor activity. Tumor growth resumed following the end of IV dosing (after Day 35).

TABLE 7

| | | Days 0-48 | |
|---|---|---|---|
| Group | Agent | Dose | Frequency |
| 1 (n = 10) | Vehicle | — | QW × 6 weeks |
| 2 (n = 10) | CFZ-captisol | 5 mg/kg | QD × 2 (D1D2) × 6 weeks |
| 3 (n = 10) | Example 13 | 150 mg/kg | QD × 2 (D1D2) × 6 weeks |
| 4 (n = 10) | Example 13 | 250 mg/kg | QW × 6 weeks |

Example 46: Proteosome Inhibition of Exemplary Compounds in Cells (FIGS. 9-14)

Cell line: MOLT-4 human acute lymphoblastic leukemia T lymphoblasts were grown for at least 6 passages in growth media (RPMI-1640 basal media supplemented with 10% FBS and 1×L-glutamine). Suspension cells were plated into a 96-well plate at a rate of 1-2e6 cell/mL (50 uL, ~60,000 cells/well) in duplicate.

Treatment: Preparations of carfilzomib and pegylated carfilzomib compound examples 5, 35, 36, 37, and 38 were dissolved in DMSO at a concentration of 10 mM. Serial dilutions were performed in DMSO to produce concentrations covering 7 logs, and then each serial dilution was further diluted 40× in growth media. Dilutions were then added in equal volume to wells containing cells, further diluting compound concentrations by two-fold. Cells were incubated at 37° C. (5% $CO_2$) for 1 hour, then spun at 1500 rpm for 5 mins at RT. Media was removed and the cells were washed with PBS 3 times. After the last wash, supernatant was removed and the cell pellets were frozen on dry ice.

Analysis: Cell pellets were thawed and then lysed by resuspending in 50 uL lysis buffer on ice (20 mM Tris-HCl, 5 mM EDTA, pH 8). The preparation was centrifuged at 1500 rpm for 5 mins and then utilized directly for AMC-LLVY fluorescent assay. Measurements were taken every 2 minutes for 70 minutes to generate a kinetic curve, and $IC_{50}$ values were calculated using the 5-15 minute slope (RFU/min, initial velocity).

Figure 10:
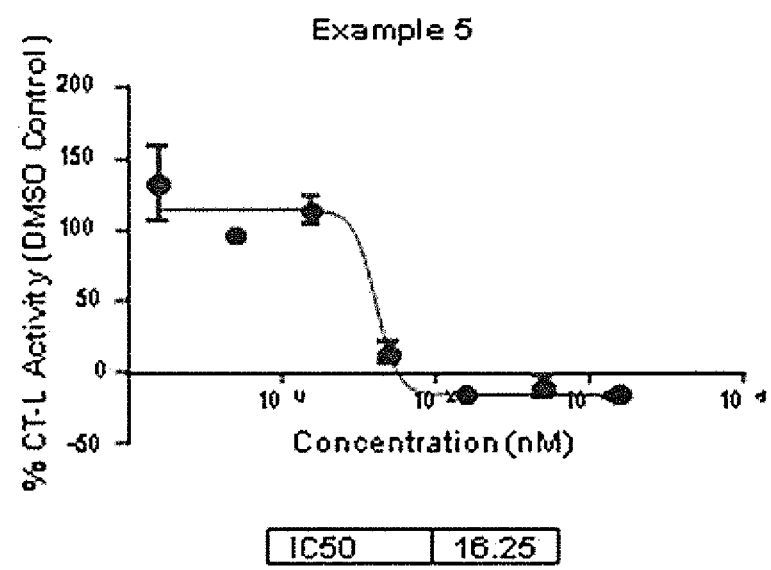
FIG. 10 is a figure of the cellular CT-L activity for compound example 5.
Figure 11:
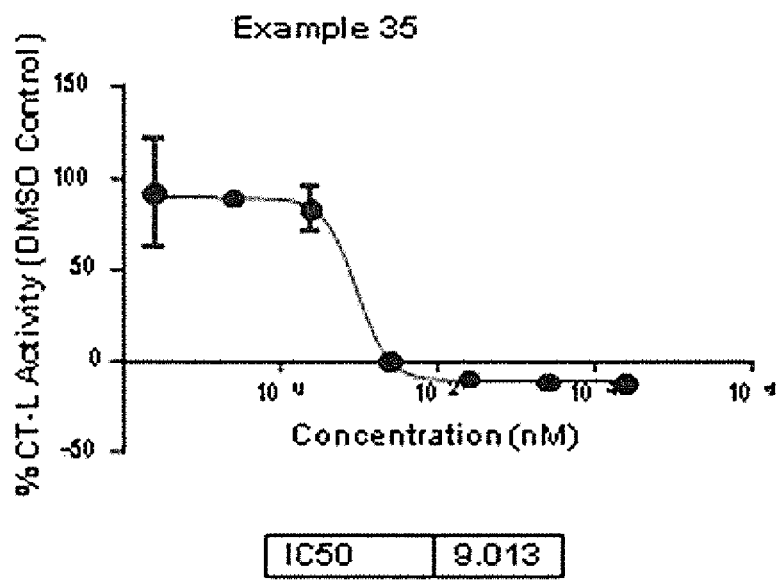
FIG. 11 is a figure of the cellular CT-L activity for compound example 35.
Figure 12:
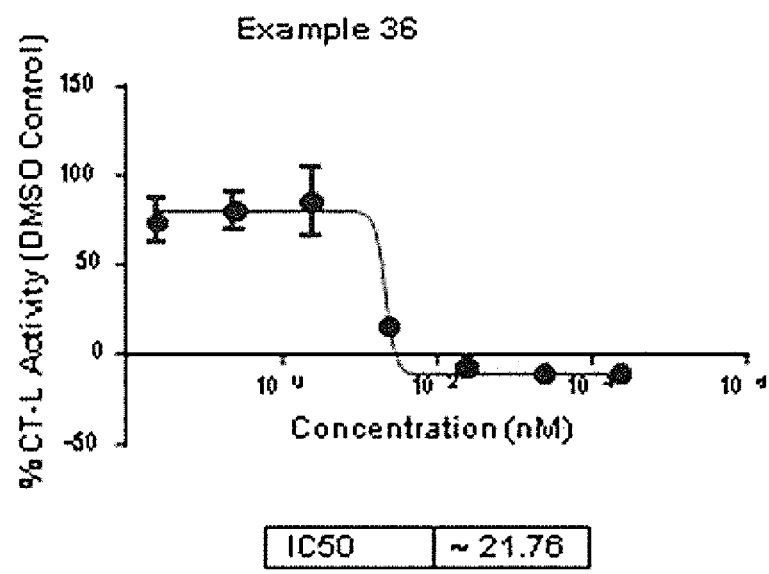
FIG. 12 is a figure of the cellular CT-L activity for compound example 36.
Figure 13:
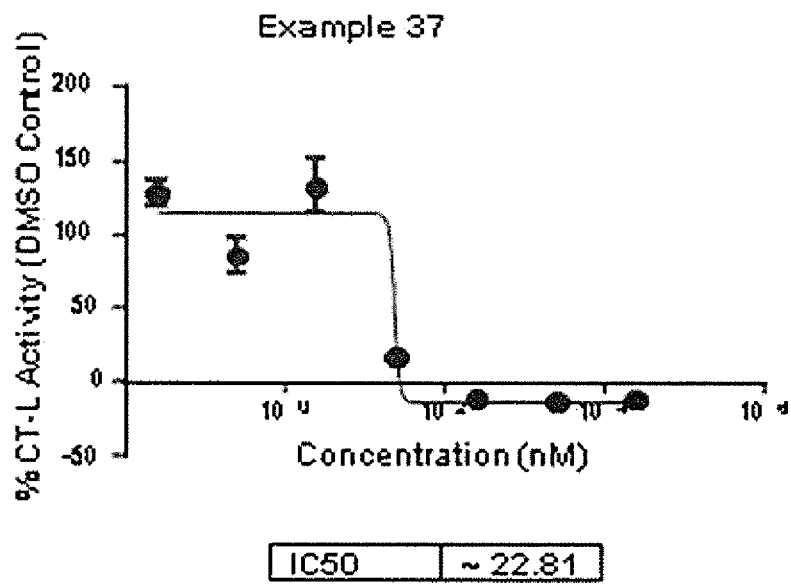
FIG. 13 is a figure of the cellular CT-L activity for compound example 37.
Figure 14:
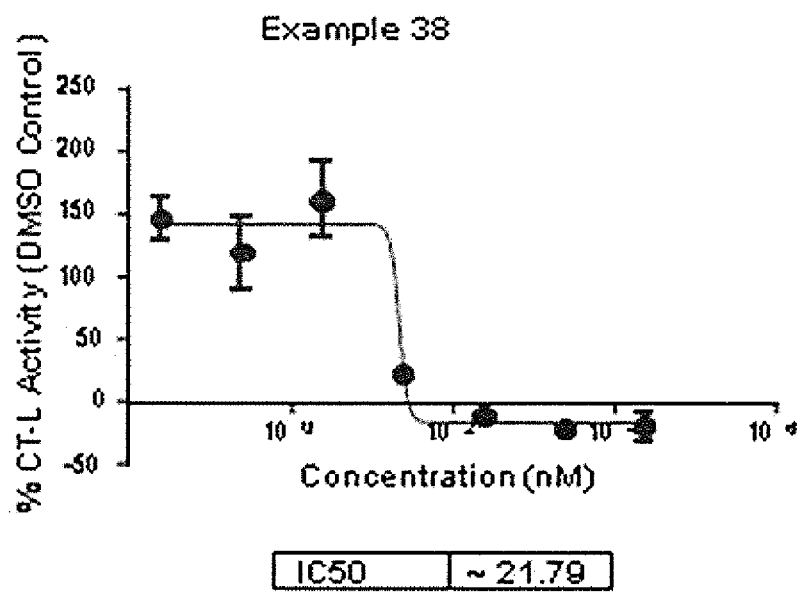
FIG. 14 is a figure of the cellular CT-L activity for compound example 38.

As shown in FIG. 10, representative exemplary compound 5 exhibited a cellular proteasome chymotrypsin-like (CT-L) $IC_{50}$ inhibitory potency of about 16.25 nM. By comparison, the control sample of carfilzomib exhibited an IC, activity of about 9.2 nM, a potency similar to that of example 5. Similarly, compound example No. 35 (FIG. 11) exhibited a cellular proteasome chymotrypsin-like (CT-L) $IC_{50}$ inhibitory potency of about 9.0 nM, compound example no. 36 (FIG. 12) exhibited a cellular proteasome chymotrypsin-like (CT-L) $IC_{50}$ inhibitory potency of about 21.8 nM, compound example no. 37 (FIG. 13) exhibited a cellular proteasome chymotrypsin-like (CT-L) $IC_{50}$ inhibitory potency of about 22.8 nM and compound example no. 38 (FIG. 14) exhibited a cellular proteasome chymotrypsin-like (CT-L) $IC_{50}$ inhibitory potency of about 21.8 nM. Some representative compounds of the present invention exhibit CT-L inhibitory activity as a pegylated carfilzomib compound.

Example 47: Proteasome Inhibition of PEG-Carfilzomib Conjugates Vs. Carfilzomib

PEG carfilzomib compound examples 35 and 36 were administered to mice (Balb/c, female, n=3 per dose group) as a subcutaneous bolus at the specified dose (dose volume 5 mL/kg) in an aqueous solution containing 10 mmol/L sodium acetate (pH 5.0) and 9% sucrose for administration (20 mg/kg). At selected time points after drug administration, blood samples were collected using tubes containing heparin. Samples are immediately placed on ice and spun at maximum speed for 2 minutes in a microcentrifuge at room temperature (RT). Cell pellets are stored on wet ice. Whole blood cell pellets are resuspended in 1 ml of phosphate buffered saline (PBS) and centrifuged at max speed at 4° C. Supernatants are removed and the pellets are washed a second time with PBS. Samples are resuspended in 2 volumes of lysis buffer (20 mM Tris, pH 8.0, 5 mM EDTA) then frozen and stored at −80° C. until analysis.

Sample Processing: All samples were thawed on ice. All single cell pellets in lysis buffer (whole blood) were briefly vortexed then spun at 14,000 rpm in a microcentrifuge at 4° C. for 15 minutes. Supernatant was transferred at a ratio of 100 µL to 25 µL of 50% glycerol in a sample plate for a final concentration of 10% glycerol. These samples were then ready for assaying, or they may be frozen at −80° C. Samples frozen at this lysate/10% glycerol stage should be thawed on ice before assaying. The protein concentration for each sample was measured by Bradford assay. Proteasome chymotrypsin-like (CT-L) activity was quantitated by monitoring the release of free AMC from the fluorogenic peptide Suc-Leu-Leu-Val-Tyr-AMC (BostonBiochem).

Figure 15:
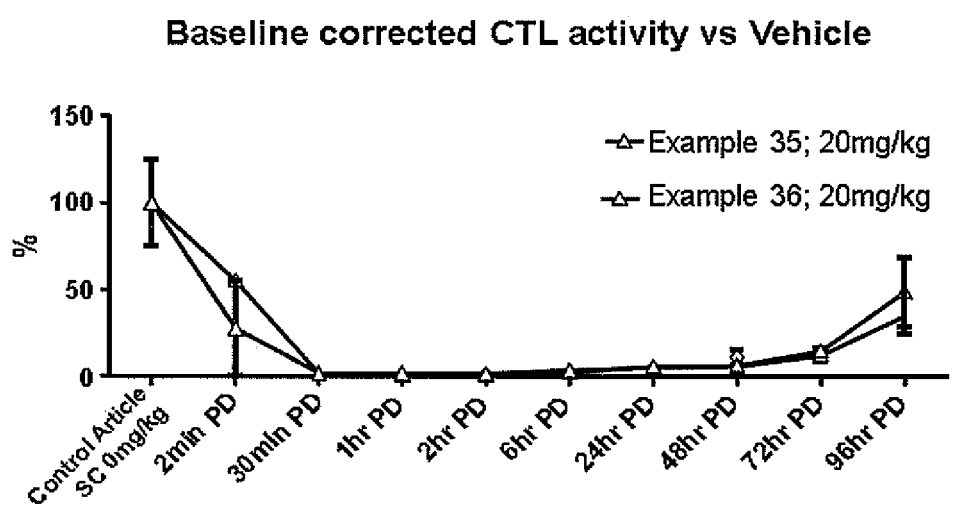
FIG. 15 is a figure of the in-vivo CT-L activity for compound examples 35 and 36.

FIG. 15 depicts the in-vivo pharmacodynamic (PD) activity of representative compound examples 35 and 36 of the present invention. As shown in FIG. 15, each of examples 35 and 36 exhibited in vivo nearly complete CT-L inhibition for over 48 h after administration in a mouse. Even over the duration of 96 hrs out, the compounds continued to exhibit CT-L inhibitory activity of about 50% or more in the mouse.

Methods of Use

The biological effects of proteasome inhibition are useful and desirable. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations comprising the PEG carfilzomib compounds of the invention in therapeutically effective dosage amounts provide a means of administering a drug to a patient and treating these conditions.

At the cellular level the accumulation of polyubiquitinated proteins, cell morphological changes, and apoptosis have been reported upon treatment of cells with various proteasome inhibitors. Proteasome inhibition has also been disclosed, and clinically and commercially proven as a useful antitumor therapeutic strategy. To this end, the compounds and compositions including the compounds of the present invention are useful for treating cancer, including without limitation, newly diagnosed and/or relapsed and refractory multiple myeloma.

Both in vitro and in vivo models have shown that malignant cells, in general, are susceptible to proteasome inhibition. In fact, proteasome inhibition has already been validated as a therapeutic strategy for the treatment of multiple myeloma. This could be due, in part, to the highly proliferative malignant cell's dependency on the proteasome system to rapidly remove proteins (Rolfe et al., *J. Mol. Med.* (1997) 75:5-17; Adams, *Nature* (2004) 4: 349-360). Provided herein is a method of treating cancer comprising administering to a patient in need of such treatment a therapeutically effective amount of a pegylated carfilzomib compound of formulas I and II, or any specifically exemplified PEG carfilzomib compound, as provided or described herein.

As used herein, the term "cancer" includes, but is not limited to, blood borne cancers and solid tumors. Cancer may afflict components of blood, bone, organs, skin tissue and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute myelogenous leukemia (AML), chronic lymphocytic leukemia (CLL), chronic myelogenous leukemia (CML), hairy cell leukemia), mature B cell neoplasms (small lymphocytic lymphoma). B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, entempathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed cellularity, lymphocyte-rich, lymphocyte depleted or not depleted, nodular lymphocyte-predominant), non-hodgkin's lymphoma, myeloma (multiple myeloma, indolent myeloma, smoldering myeloma), chronic myeloproliferative disease, myelodysplastic/myeloproliferative disease, myelodysplastic syndromes, immunodeficiency-associated lymphopoliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarconiamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

In one aspect the invention provides a pegylated carfilzomib compound as provided herein, or a pharmaceutical composition comprising the same, can be administered to treat multiple myeloma in a patient. For example, multiple myeloma can include either or both newly diagnosed or relapsed and/or refractory multiple myeloma.

Many tumors of the haematopoietic and lymphoid tissues are characterized by an increase in cell proliferation, or a particular type of cell. The chronic myeloproliferative diseases (CMPDs) are clonal haematopoietic stem cell disorders characterized by proliferation in the bone marrow of one or more of the myeloid lineages, resulting in increased numbers of granulocytes, red blood cells and/or platelets in the peripheral blood. As such, use of a proteasome inhibitor for the treatment of such diseases is attractive and being examined (Cilloni et al., *Haematologica* (2007) 92: 1124-1229). CMPD can include chronic myelogenous leukemia, chronic neutrophilic leukemia, chronic eosinophilic leukemia, polycythemia vera, chronic idiopathic myelofibrosis, essential thrombocythemia and unclassifiable chronic myeloproliferative disease. Provided herein is a method of treating CMPD comprising administering to a patient in need of such treatment an effective amount of the proteasome inhibitor compound disclosed herein.

Myelodisplastic/myeloproliferative diseases, such as chronic myelomonocytic leukemia, atypical chronic myeloid leukemia, juvenile myelomonocytic leukemia and unclassifiable myelodysplastic/myeloproliferative disease, are characterized by hypercellularity of the bone marrow due to proliferation in one or more of the myeloid lineages. Inhibiting the proteasome with a composition described herein, can serve to treat these myelodisplatic/myeloproliferative diseases by providing a patient in need of such treatment an effective amount of the composition.

Myelodysplastic syndromes (MDS) refer to a group of hematopoietic stem cell disorders characterized by dysplasia and ineffective haematopoiesis in one or more of the major myeloid cell lines. Targeting NF-kB with a proteasome inhibitor in these hematologic malignancies induces apoptosis, thereby killing the malignant cell (Braun et al. *Cell Death and Differentiation* (2006) 13:748-758). Further provided herein is a method to treat MDS comprising administering to a patient in need of such treatment an effective amount of a compound provided herein. MDS includes refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del (5q) chromosome abnormality.

Mastocytosis is a proliferation of mast cells and their subsequent accumulation in one or more organ systems. Mastocytosis includes, but is not limited to, cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extracutaneous mastocytoma. Further provided herein is a method to treat mastocytosis comprising administering an effect amount of the compound disclosed herein to a patient diagnosed with mastocytosis.

Additional embodiments include methods for affecting the proteasome-dependent regulation of oncoproteins and methods of treating or inhibiting cancer growth, each method including exposing a cell (in vivo, e.g., in a patient, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a patient an effective amount of a composition disclosed herein.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett. I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteoporosis.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds provided herein may also be useful for hair follicle growth stimulation.

Finally, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MBI subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein: exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Pharmaceutical Compositions

The present invention further provides pharmaceutical compositions to administer the treatment for cancer patients. The compositions comprise one, and in some embodiments more than one. PEG carfilzomib compound of Formulas I or II, and sub-formulas thereof, as described herein. One type of pharmaceutical composition the present invention provides is a parenterally administered pharmaceutical composition. Parenterally administrable compositions suitable for infusion, injection or sub-cutaneous administration can include sterile aqueous solutions (where water soluble) or dispersions and/or sterile powders for the extemporaneous preparation of sterile solutions or dispersions for either infusion or injection. For intravenous administration, such as by infusion, suitable carriers include sterile water for injection, sterile buffers, such as citrate buffer, bacteriostatic water, and Cremophor EL™ (BASF, Parsippany, N.J.). In all cases, the composition, particularly for human use, treatment and consumption, must be sterile and should be fluid to the extent that it is easy to add to or pull up into a syringe or infusion bag. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compounds of the invention, PEG carfilzomib compounds, in the required amount in an appropriate solvent with one or a combination of ingredients enumerated above, as required, followed by filtered sterilization. Generally, dispersions are prepared by incorporating the carfilzomib into a sterile vehicle, which contains a basic dispersion medium and the required other ingredients from those enumerated above. In the case of sterile powders for the preparation of sterile injectable solutions, a suitable method of preparation is freeze-drying (lyophilization), which provides a powder form of the carfilzomib plus any additional desired ingredient from a previously sterile-filtered solution thereof.

Systemic administration of a therapeutic compound of the invention as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds of the invention are formulated into ointments, salves, gels, or creams as generally known in the art.

In one embodiment, the therapeutic PEG carfilzomib compounds of the invention are prepared with carriers that will protect the therapeutic compounds against rapid elimination from the body, such as a controlled release formulations. Other examples include, without limitation, implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals. Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions provided by the present invention may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a PEG-carfilzomib compound of the invention as described herein in the range of 0.005% to 100% with the balance made up from non-toxic carrier may be prepared. Methods for preparation of these compositions are known to those skilled in the art. The contemplated pharmaceutical compositions of the invention may contain 0.001%-100% of the PEG carfilzomib compound provided herewith, in one embodiment 0.1-95%, and in another embodiment 75-85%. The pharmaceutical compositions can be included in a container, pack, or dispenser together with instructions for administration. In some embodiments, the PEG carfilzomib compounds provided herein may be formulated as described in U.S. Pat. No. 9,309,283.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups: or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect. More information on the dosage amounts for compounds of the invention is provided herein below. In general, compositions intended for parenteral use (e.g., intravenous, subcutaneous injection) include a solubilizing agent. The solubilizing agent may be a substituted cyclodextrin.

The precise time of administration and/or amount of the composition that will yield the most effective results in terms of efficacy of treatment in a given patient will depend upon the activity, pharmacokinetics, and bioavailability of the particular PEG carfilzomib compound, physiological condition of the patient (including age, sex, disease type and stage, general physical condition, responsiveness to a given dosage, and type of medication), route of administration, and the like. However, the above guidelines can be used as the basis for fine-tuning the treatment, e.g., determining the optimum time and/or amount of administration, which will require no more than routine experimentation consisting of monitoring the patient and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose (2) starches, such as corn starch, potato starch, and substituted or unsubstituted β-cyclodextrin; (3) cellulose, and its derivatives, such as sodium carboxymethyl cellulose, ethyl cellulose, and cellulose acetate. (4) powdered tragacanth. (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts or basic salts of the compound(s) of the invention. These salts can be prepared in situ during the final isolation and purification of the compound(s), or by separately reacting a purified PEG-carfilzomib compound in its free base form with a suitable organic or inorganic acid, and isolating the salt thus formed Representative acid addition salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, the PEG carfilzomib compounds provided herein may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of the compound. These salts can likewise be prepared in situ during the final isolation and purification of the inhibitor(s), or by separately reacting the compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative basic salts include, without limitation, alkali or alkaline earth salts such as lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of compound of the invention as an active ingredient. A composition may also be administered as a bolus, electuary, or paste.

In solid dosage forms for oral administration (capsules, tablets, pills, dragees, powders, granules, and the like), the active ingredient (compound of the invention) is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of a selected compound of the invention include powders, sprays, ointments, pastes, creams, lotions, gels, solutions, patches, and inhalants. The compound may be mixed under sterile conditions with a pharmaceutically acceptable carrier, and with any preservatives, buffers, or propellants which may be required.

The ointments, pastes, creams, and gels may contain, in addition to the compound(s) of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof. Powders and sprays can contain, in addition to compound(s) of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A PEG carfilzomib compound of the invention can be administered by aerosol. This is accomplished by preparing an aqueous aerosol, liposomal preparation, or solid particles containing the composition. A non-aqueous (e.g., fluorocarbon propellant) suspension could be used. In some embodiments, sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremorphors), pharmaceutically acceptable co-solvents such as polyethylene glycol, innocuous proteins like serum albumin. sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the compound in the proper medium. Absorption enhancers can also be used to increase the flux of the compound(s) across the skin. The rate of such flux can be controlled by either providing a rate controlling membrane or dispersing the compound(s) in a polymer matrix or gel.

Pharmaceutical compositions suitable for parenteral administration comprise one or more compound of the invention in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions provided herein include water for injection, such as by sub-cutaneous administration (e.g., sterile water for injection), ethanol, polyols (such as glycerol, propylene glycol, polyethylene glycol, and the like), buffer (such as citrate buffer), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Pharmaceutical compositions typically include a pharmaceutically acceptable carrier. As used herein the language "pharmaceutically acceptable carrier" includes a buffer, sterile water for injection, solvents, dispersion media, coatings, antibacterial and antifungal agents, isotonic and absorption delaying agents, and the like, compatible with pharmaceutical administration. In some embodiments, a pharmaceutically acceptable carrier is an acid-base buffer system, such as a citrate buffer, to maintain a stable pH for the resulting solution. In some embodiments, a pharmaceutically acceptable carrier is sterile water for injection. In some embodiments, a pharmaceutically acceptable carrier comprises citric acid.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin. In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of the compound(s) of the invention in biodegradable polymers such as polylactide-polyglycolide. Depending on the ratio, typically weight ratio, of carfilzomib to polymer, and the nature of the particular polymer employed, the rate of carfilzomib release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration." "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

The PEG-carfilzomib compounds of the invention described herein may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, a compound of the invention, which may be used in a suitable hydrated form, and/or the pharmaceutical compositions provided herein, is formulated into a pharmaceutically acceptable dosage form by conventional methods known to those of skill in the art.

As mentioned herein above, actual dosage amounts of the PEG carfilzomib compound in the pharmaceutical compositions provided by the invention may be varied so as to include an amount of the active PEG-free carfilzomib agent which is clinically proven to be effective, and/or commercially approved as effective, to achieve the desired therapeutic response for a cancer patient, including without limitation, for a multiple myeloma patient. To this end, the specific amount of and/or concentration of a pegylated carfilzomib compound of the invention in a pharmaceutically acceptable composition will vary depending on several factors, including the dosage of the compound to be administered, the pharmacokinetic characteristics of the compound(s) employed, and the route of administration. In general, the pharmaceutical compositions provided by the invention may be an aqueous solution containing about 0.1-20% w/v of a compound disclosed herein, among other substances, for parenteral administration. Typical dose ranges for the PEG carfilzomib compound active ingredients are from about 0.01 to about 50 mg/kg of body weight per day, given in 1-4 divided doses each day. Each divided dose will contain one or more of the compounds provided by the invention. The desired, specific compound dosage amount should be an amount sufficient to provide a therapeutically effective dosage of free acting carfilzomib in the plasma of the patient, the effective dosage amount being based on regulatory approved use, for regulatory approved indications. This effective amount may vary from patient to patient, and is generally dependent on several factors including the overall health of a patient, and the specific formulation composition and route of administration of the chosen compound(s).

Carfilzomib is currently approved in doses, provided once daily for the first 2 consecutive days every week for 3 consecutive weeks in a 28 day cycle, in an amount sufficient to provide a patient plasma concentration ranging from 20 $mg/m^2$ to 56 $mg/m^2$. Thus, a higher molecule weight PEG carfilzomib compound of the invention should be administered in amounts sufficient to pharmacokinetically provide amounts approximately equivalent to approved dosing ranges. For example a 2K PEG compound of the invention is approximately 24% by weight of free carfilzomib. Thus, using an average male with 1.9 m2 average body surface, to achieve about an equivalent dose of 27 $mg/m^2$, one would have to dose about 215 g of the 2 k PEG CFZ compound. Similarly, one may dose about 1100 mg of a 20K PEG CFZ compound to deliver the same amount of carfilzomib as would a 70 $mg/m^2$ dose of the currently approved formulation for carfilzomib.

In embodiment 71 of the invention, there is provided a method of treating cancer in a subject in need of treatment, the method comprising administering to the subject an effective dosage amount of a PEG carfilzomib compound of Formula I to the subject to treat the cancer. In embodiment 72, the invention provides the method of embodiment 71 wherein the cancer is multiple myeloma. In embodiment 73, the invention provides the method of any one of embodiments 71-72 wherein the effective dosage amount of PEG carfilzomib is in the range from about 100 mg to about 2000 mg. In embodiment 74, the invention provides the method of any one of embodiments 71-73 wherein the effective dosage amount is in the range from about 150 mg to about 1000 mg per day. In embodiment 75, the invention provides the method of any one of embodiments 71-74 wherein the effective dosage amount of the PEG carfilzomib compound administered is in the range from about 200 mg to about 500 mg per day. In embodiment 76, the invention provides the method of any one of embodiments 71-73 wherein the effective dosage amount of a 2K PEG carfilzomib compound administered is in the range from about 150 mg to about 600 mg per day. In embodiment 77, the invention provides the method of any one of embodiments 71-73 wherein the effective dosage amount of a 3K PEG carfilzomib compound administered is in the range from about 300 mg to about 2000 mg per day. In embodiment 78, the invention provides the method of any one of embodiments 71-73 wherein the effective dosage amount of a 5K PEG carfilzomib compound administered is in the range from about 800 mg to about 3000 mg per day. In embodiment 79, the invention provides the method of any one of embodiments 71-73 wherein the effective dosage amount of a 20K PEG carfilzomib compound administered is in the range from about 800 mg to about 3000 mg per day. In embodiment 80, the invention provides the method of any one of embodiments 71-73 wherein the effective dosage amount of a PEG carfilzomib compound administered is in the range from about 200 mg to about 1500 mg per day. In embodiment 81, the invention provides the method of any one of embodiments 71-73 wherein the effective dosage amount of the PEG carfilzomib compound administered is in the range from about 5 mg/kg to about 50 mg/kg by weight of the subject per day. In embodiment 82, the invention provides the method of any one of embodiments 71-73 wherein the effective dosage amount of a 2K, 3K or 5K PEG carfilzomib compound administered is in the range from about 200 mg to about 800 mg per day. In embodiment 83, the invention provides the method of any one of embodiments 71-73 wherein the effective dosage amount of a 2K or 3K PEG carfilzomib compound administered is in the range from about 200 mg to about 500 mg per day. In embodiment 84, the invention provides the method of any one of embodiments 71-73 wherein the effective dosage amount of a 5K or 20K PEG carfilzomib compound administered is in the range from about 400 mg to about 1000 mg per day. In embodiment 85, the invention provides the method of any one of embodiments 71-84, wherein the method further comprises administration of a steroid. In embodiment 86, the invention provides the method of embodiment 85 wherein the steroid is selected from the group consisting of dexamethasone and prednisone. In embodiment 87, the invention provides the method of any one of embodiments 85-86 wherein the steroid is dexamethasone. In embodiment 88, the invention provides the method of any one of embodiment 85-86 wherein the steroid is prednisone. In embodiment 89, the invention provides the method of any one of embodiments 71-88 wherein the method further comprises administration of an immunomodulatory agent selected from the group consisting of thalidomide, lenalidomide and pomalidomide. In embodiment 90, the invention provides the method of embodiment 89, wherein the immunomodulatory agent is lenalidomide or pomalidomide. In embodiment 91, the invention provides the method of any one of embodiments 89-90, wherein the immunomodulatory agent is lenalidomide. In embodiment 92, the invention provides the method of any one of embodiments 89-90, wherein the immunomodulatory agent is pomalidomide. In embodiment 93, the invention provides the method of any one of embodiments 71-88 wherein the method further comprises administration of a CD-38 inhibiting agent. In embodiment 94, the invention provides the method of embodiment 93, wherein the CD-38 inhibiting agent is daratumumab. In embodiment 95, the invention provides the method of any one of embodiments 71-94 wherein the cancer is relapsed or refractory multiple myeloma. In embodiment 96, the invention provides the method of any one of embodiments 71-94 wherein the cancer is new diagnosed multiple myeloma. In embodiment 97, the invention provides the method of embodiment 96 wherein the cancer is new diagnosed multiple myeloma and wherein the patient is stem cell transplant eligible, as determined by a licensed, authorized medical practitioner. In embodiment 98, the invention provides the method of embodiment 96 wherein the cancer is new diagnosed multiple myeloma and wherein the patient is not stem cell transplant eligible, as determined by a licensed, authorized medical practitioner. In embodiment 99, the invention provides the method of any one of embodiments 71-98, wherein the method comprises administering to the subject a pharmaceutical composition comprising a PEG carfilzomib compound of Formula I. In embodiment 100, the invention provides the method of embodiment 99 wherein the pharmaceutical composition is an oral solution or a parenteral solution. In embodiment 101, the invention provides the method of any one of embodiments 99-100 wherein the pharmaceutical composition is a freeze-dried preparation that can be reconstituted prior to administration. In embodiment 102, the invention provides the methods of each one of embodiments 71-98, wherein the PEG carfilzomib compound is

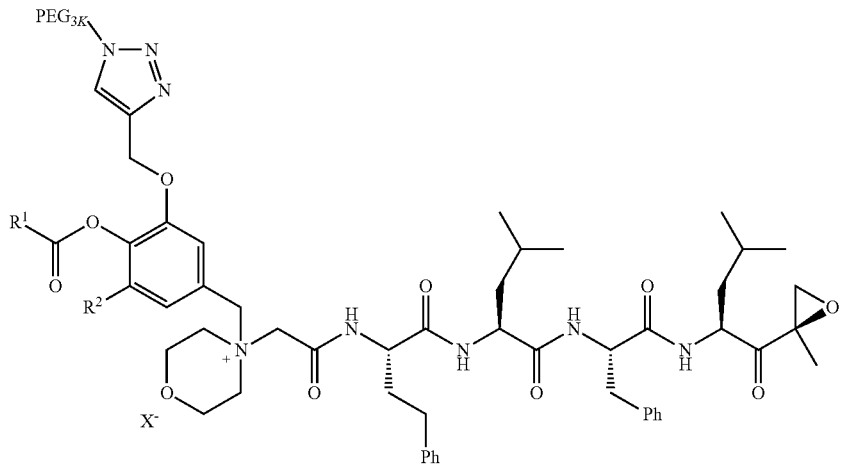

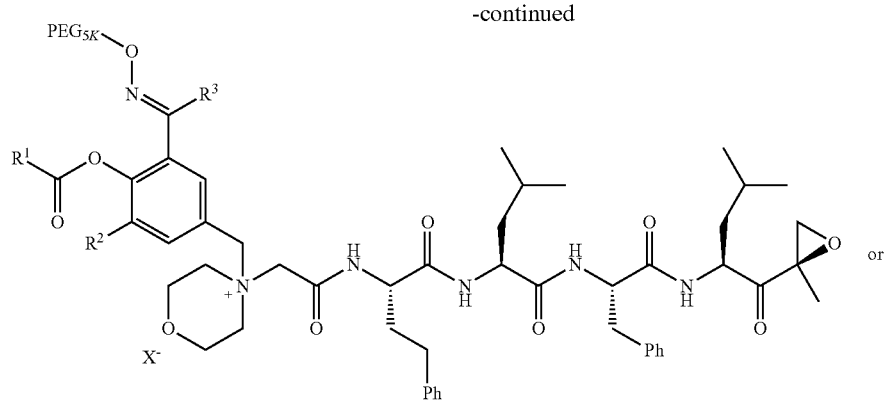
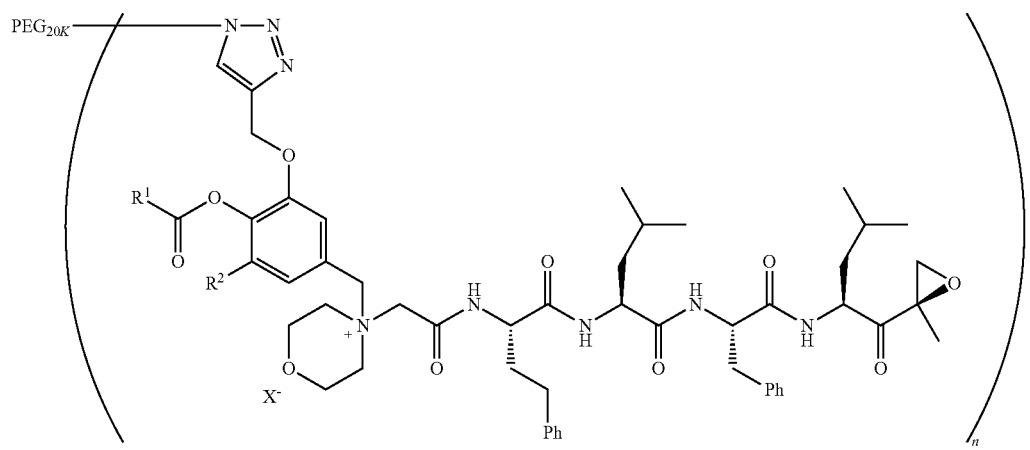
wherein $R^1$ is $C_{1-10}$alkyl;
$R^2$ is $C_{1-6}$alkyl, —$OCH_3$ or halogen;
$R^3$ is H or $CH_3$;
$X^-$ is a counter anion selected from chloride anion and a alkyl-sulfonate anion:
n is 4; and
PEG is a polyethylene glycol polymeric moiety of 3000, 5000 or 20000 dalton molecular weight.
In embodiment 103, the invention provides the methods of embodiment 71-98, wherein the PEG carfilzomib compound is
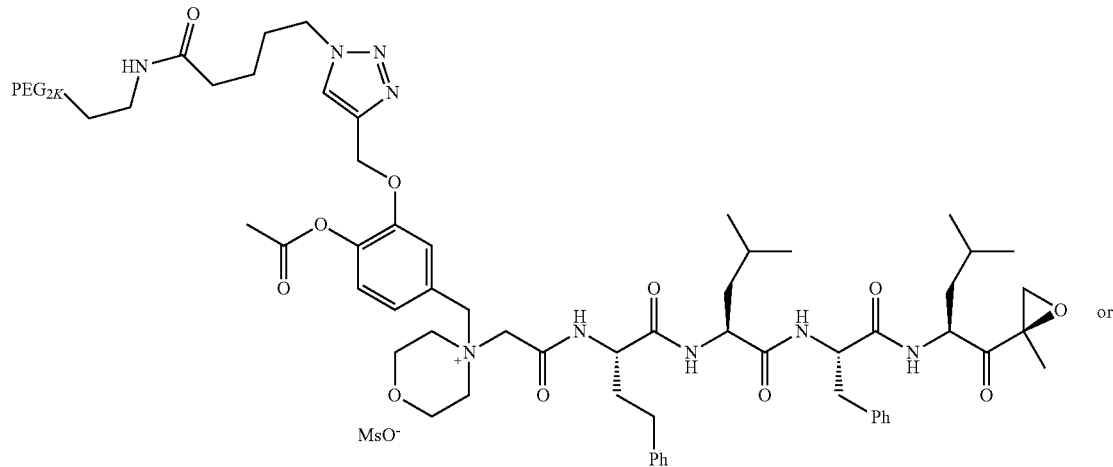

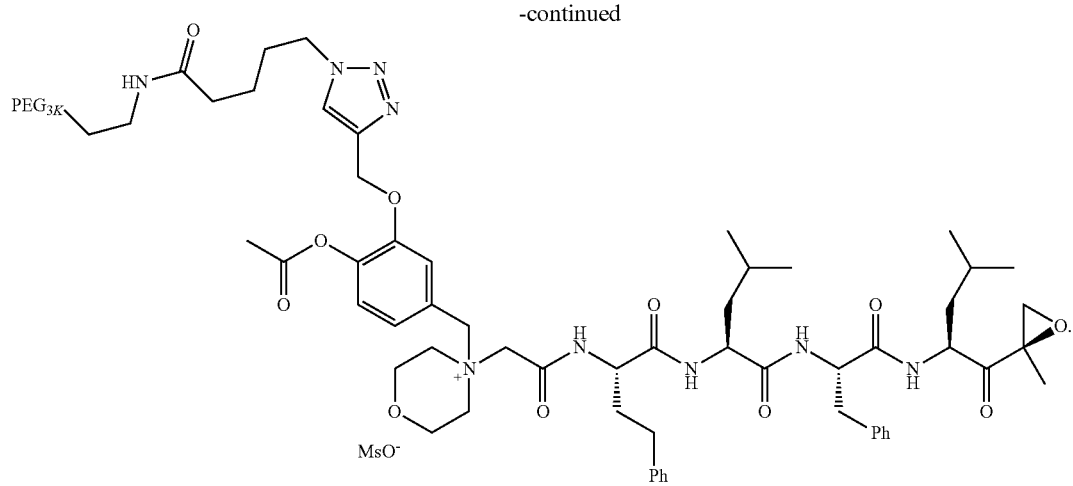
In embodiment 104, the invention provides the methods of embodiment 71-98, wherein the PEG carfilzomib compound is
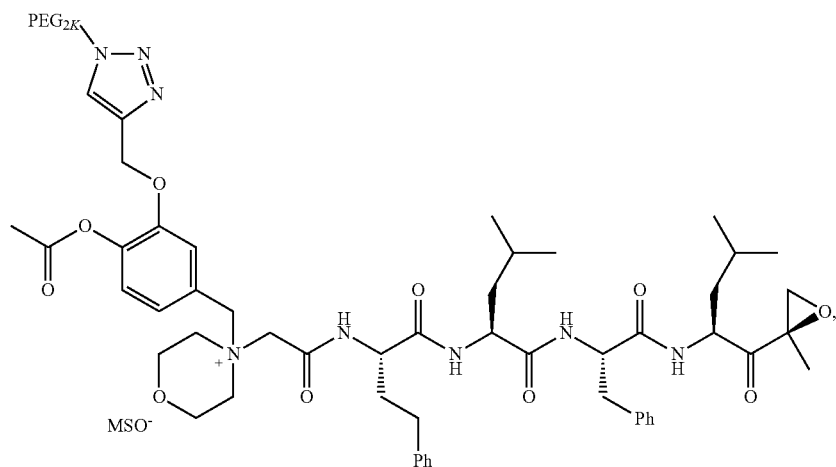
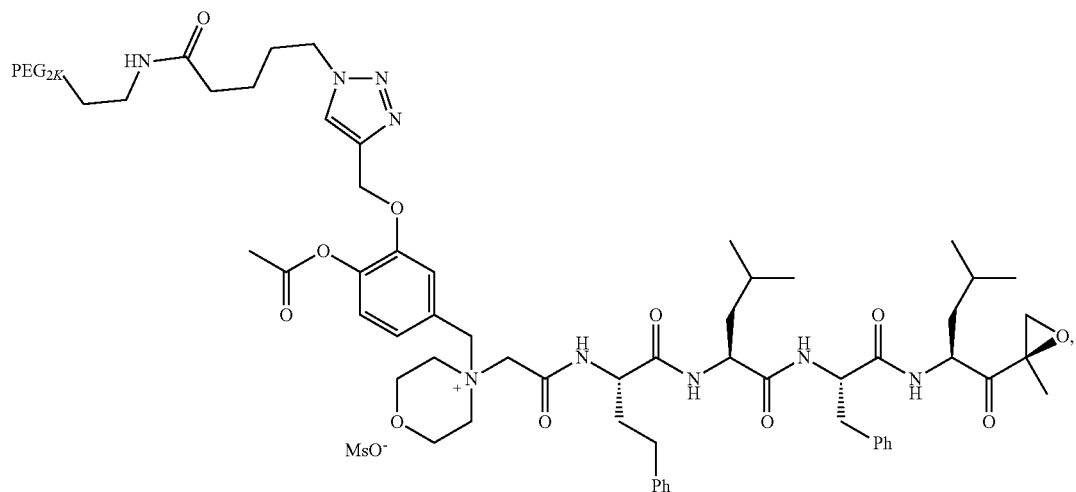

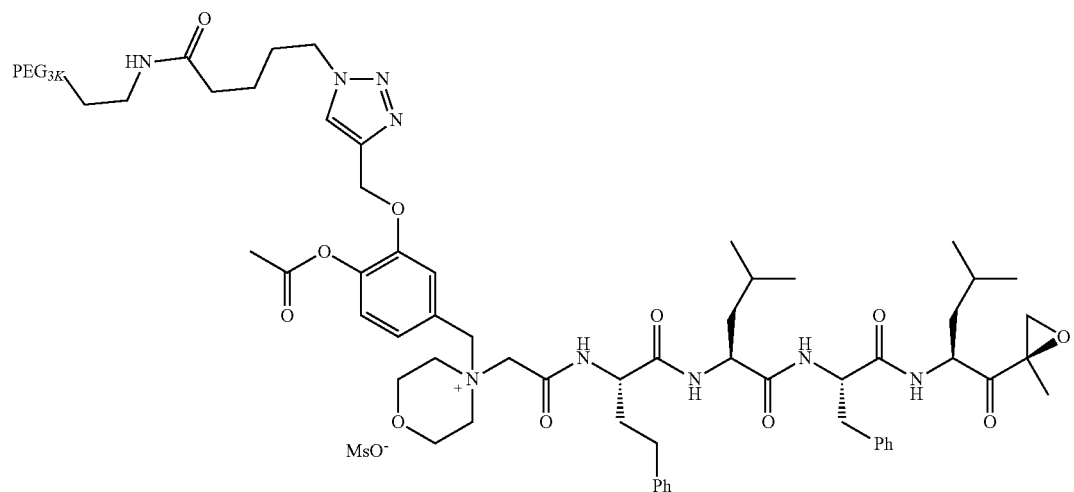
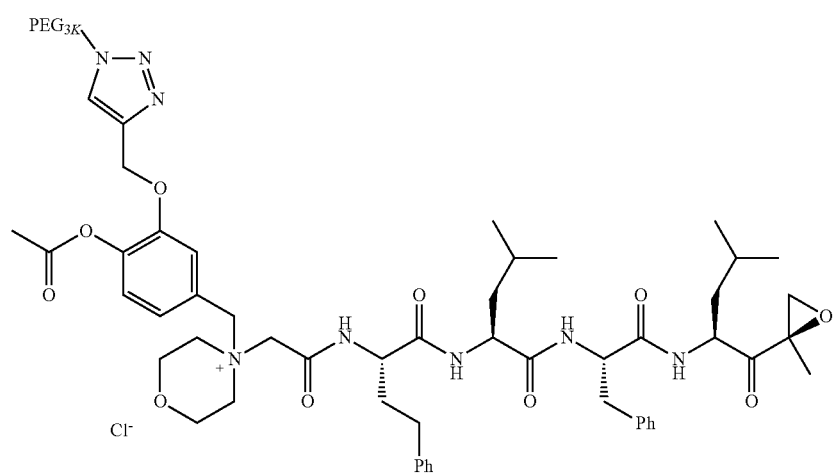
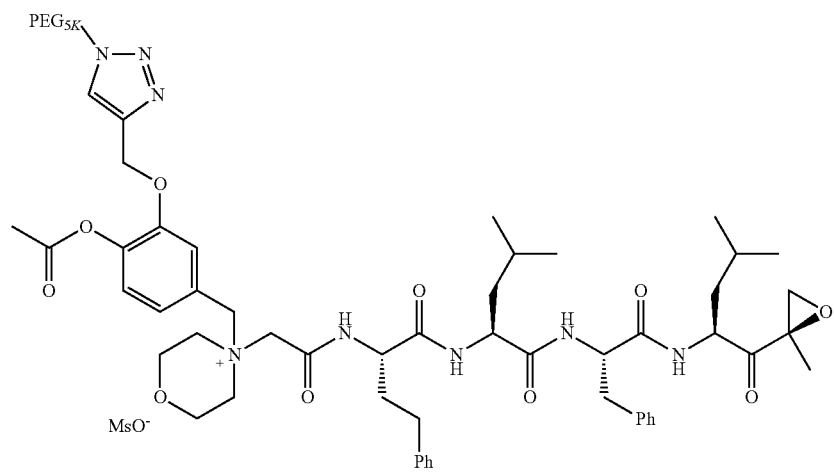

-continued
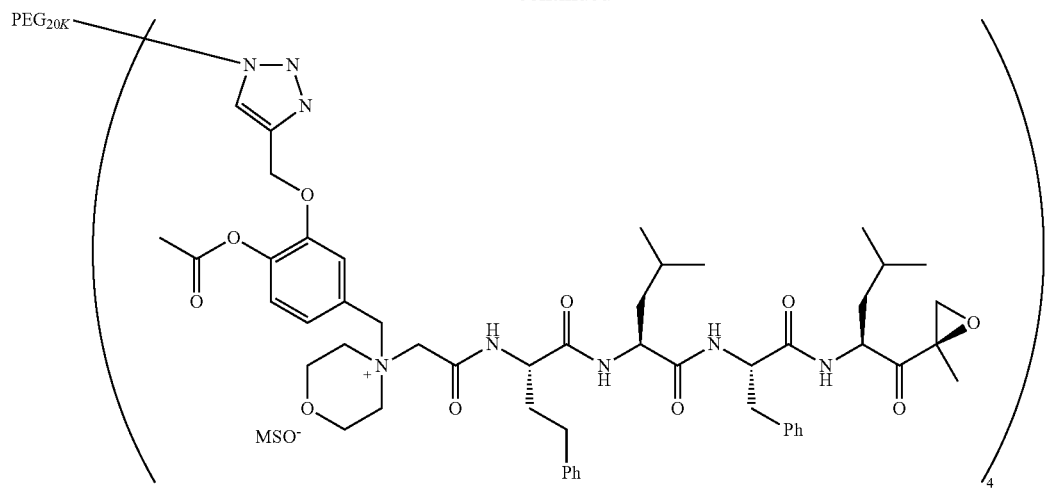
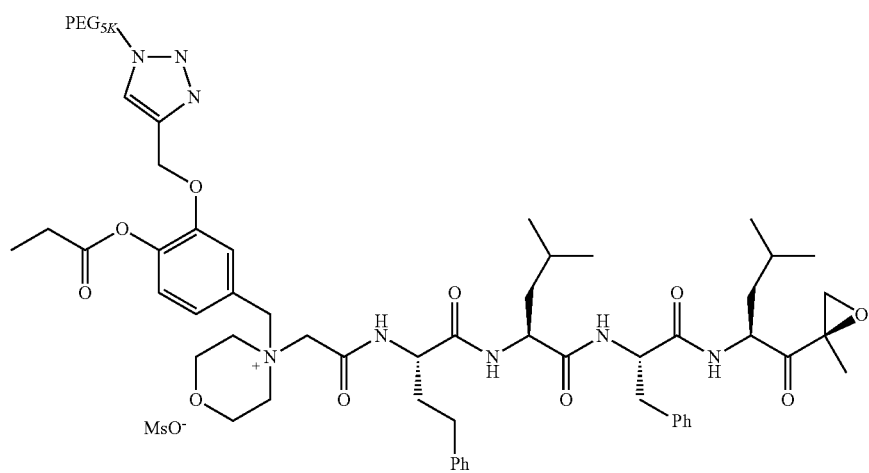
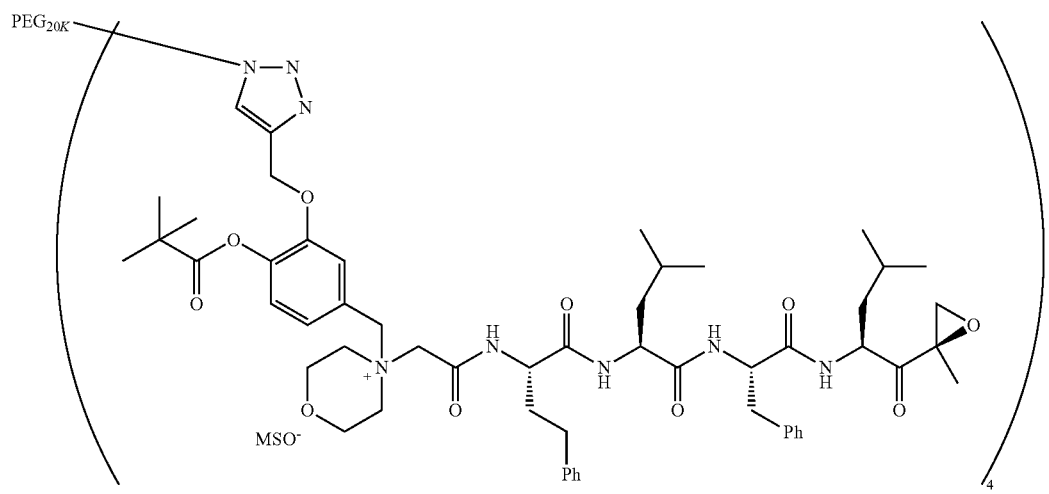

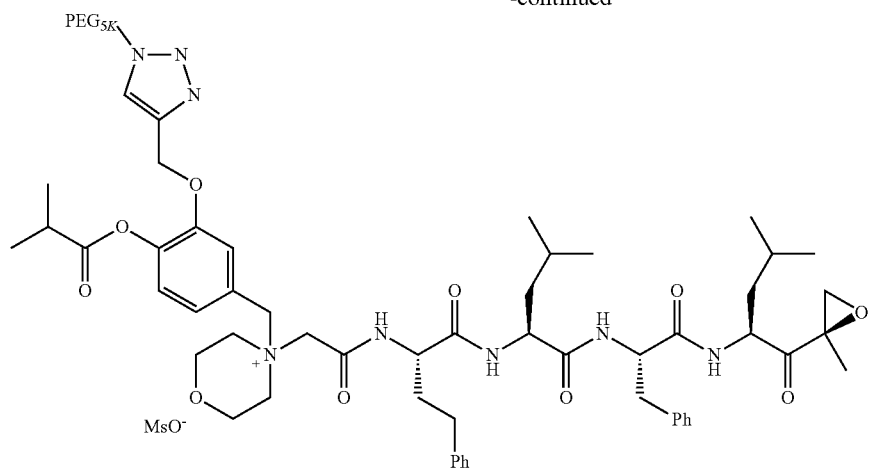
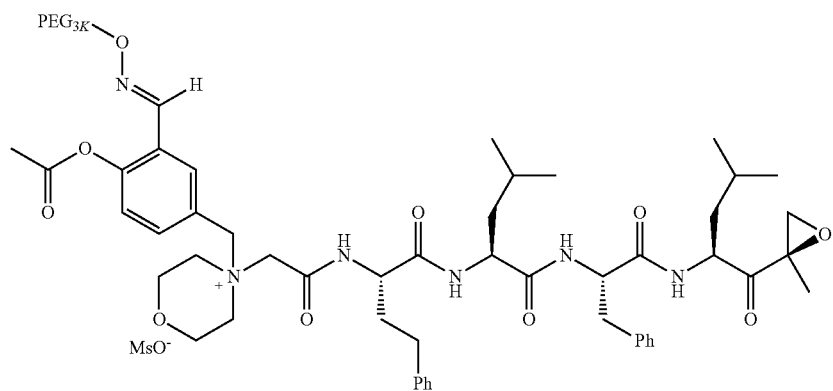
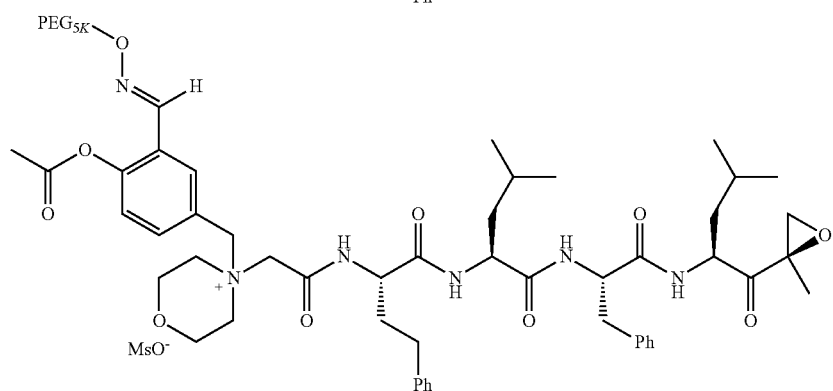
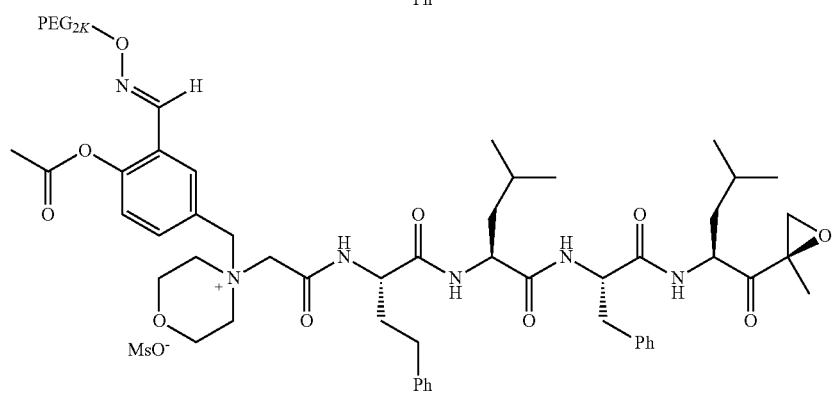

-continued

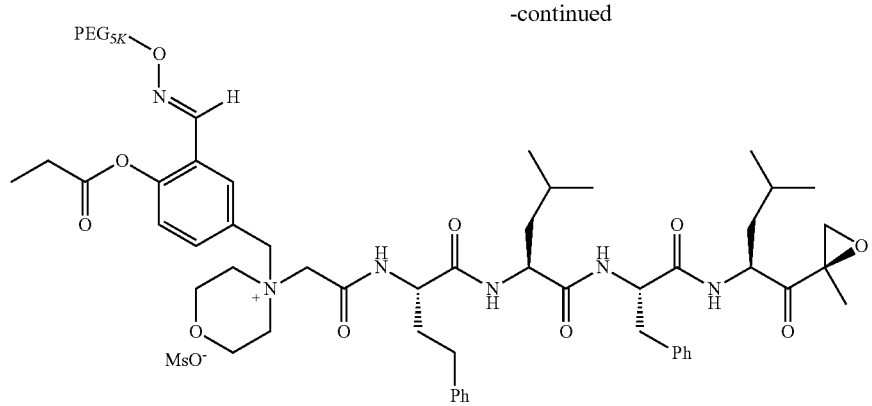

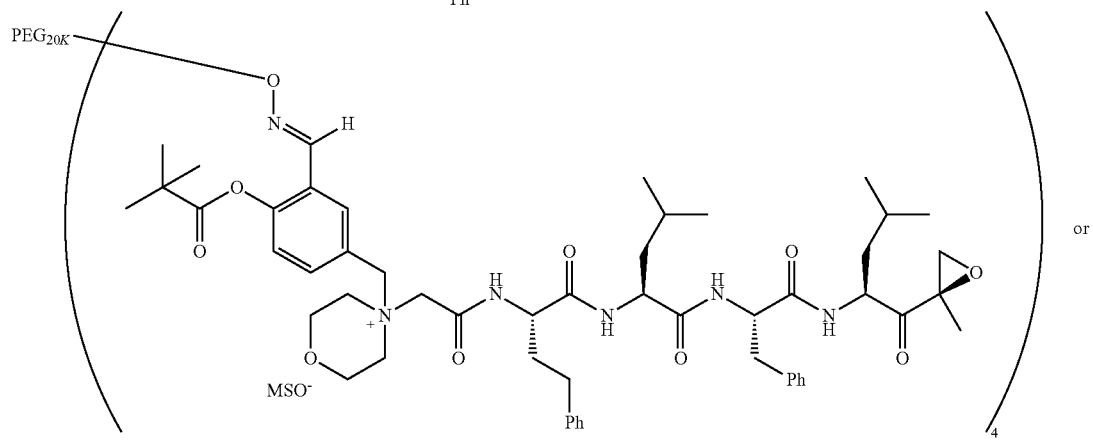

or

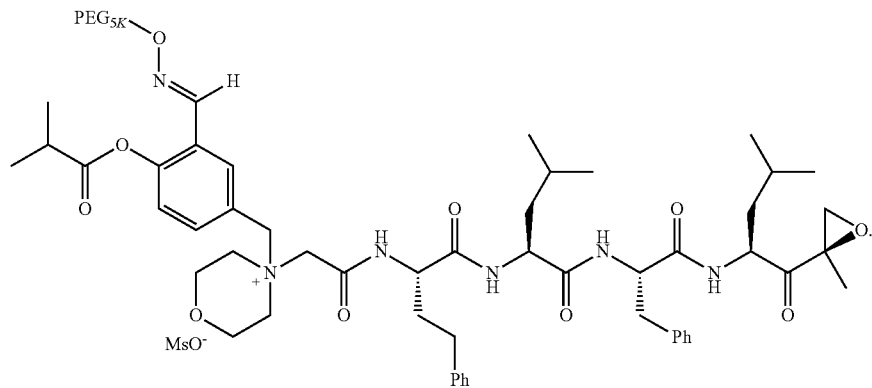

Combinations

While a PEG-carfilzomib compound of the invention can be dosed or administered as the sole active pharmaceutical agent it can also be used in combination with one or more agents, such a second anticancer agent. When administered as a combination, the PEG carfilzomib active ingredient and the other agent may be formulated as separate compositions that are administered simultaneously or sequentially at different times, or both active agents can be given as a single composition.

The phrase "co-therapy" (or "combination-therapy"), in defining the use of PEG carfilzomib compound of the present invention and another anti-cancer agent, is intended to embrace administration of each agent in a sequential manner in a regimen that will provide beneficial effects of the drug combination, and is intended as well to embrace co-administration of these agents in a substantially simultaneous manner, such as in a single dosage formulation having a fixed ratio of these active agents, or in multiple, separate dosage formulations for each active agent. Thus, the invention is not limited in the sequence of administration, i.e, the PEG carfilzomib compound(s) may be administered either prior to, simultaneous with or after administration of the other agent.

In certain embodiments, a PEG-carfilzomib compound described herein is conjointly administered with one or more other proteasome inhibitor(s). Another proteasome inhibitor may include, for example, bortezomib, oprozomib or ixazomib. In another embodiment, the PEG carfilzomib compound described herein is administered in combination with an immunomodulatory compound, including thalidomide, lenalidomide and pomalidomide. In an embodiment from the immediately preceding embodiment, the PEG carfilzomib is administered in combination with an immunomodulatory agent selected from lenalidomide and pomalidomide. In a further embodiment, the invention provides a method of treating cancer in a subject by administering to the subject a combination therapy comprising a PEG carfilzomib compound of Formula I or II and an immunomodulatory agent. In a further embodiment, the cancer is multiple myeloma.

In certain embodiments, a PEG-carfilzomib compound described herein is conjointly administered with one or more chemotherapeutics. Suitable chemotherapeutics may include, natural products such as vinca alkaloids (i.e. vinblastine, vincristine, and vinorelbine), taxanes (e.g., docetaxel, paclitaxel. e.g., docetaxel), epidipodophyllotoxins (i.e. etoposide, teniposide), antibiotics (dactinomycin (actinomycin D) daunorubicin, doxorubicin and idarubicin: e.g., doxorubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents: antiproliferative/antimitotic alkylating agents such as nitrogen mustards (mechlorethamine, ifosphamide, cyclophosphamide and analogs, melphalan, chlorambucil, e.g., melphalan), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine): aromatase inhibitors (anastrozole, exemestane, and letrozole); platinum coordination complexes (cisplatin, carboplatin), procarbazine, hydroxyurea, mitotane, aminoglutethimide; DNA binding/Cytotoxic agents (e.g., Zalypsis); histone deacetylase (HDAC) inhibitors (e.g., trichostatin, sodium butyrate, apicidan, suberoyl anilide hydroamic acid (SAHA (Vorinostat)), trichostatin A, depsipeptide, apicidin, A-161906, scriptaid, PXD-101, CHAP, butyric acid, depudecin, oxamflatin, phenylbutyrate, valproic acid, MS275 (N-(2-Aminophenyl)-4-[N-(pyridine-3-ylmethoxy-carbonyl)aminomethyl]benzamide), LAQ824/LBH589, CI994, MGCD0103, ACY-1215, Panobinostat), hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a PEG-carfilzomib compound described herein is conjointly administered with a cytokine. Cytokines include, but are not limited to, Interferon-γ, -α, and -β, Interleukins 1-8, 10 and 12. Granulocyte Monocyte Colony-Stimulating factor (GM-CSF). TNF-α and -β, and TGF-β.

In certain embodiments, a PEG-carfilzomib compound described herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difupredinate, enoxolone, fluazacort, fluclorinide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof (e.g., hydrocortisone, dexamethasone, methylprednisolone and prednisolone; e.g., dexamethasone). In certain embodiments, a PEG-carfilzomib compound described herein are conjointly administered with dexamethasone. In certain embodiments, conjoint therapy includes the dosing regimens provided on the KYPROLIS (carfilzomib) label as approved by the US FDA and by the EMA.

In some embodiments, a PEG-carfilzomib compound described herein is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

In certain embodiments, a PEG-carfilzomib compound described herein is conjointly administered with one or more histone deacetylase (HDAC) inhibitors (e.g., trichostatin, sodium butyrate, apicidan, suberoyl anilide hydroamic acid ("SAHA" (Vorinostat)), trichostatin A, depsipeptide, apicidin. A-161906, scriptaid, PXD-101. CHAP, butyric acid, depudecin, oxamflatin, phenylbutyrate, valproic acid, MS275 (N-(2-Aminophenyl)-4-[N-(pyridine-3-ylmethoxycarbonyl)aminomethyl]benzamide). LAQ824/LBH589. CI994, MGCD0103, ACY-1215, Panobinostat; e.g., SAHA, ACY-1215, Panobinostat).

In certain embodiments, a PEG-carfilzomib compound described herein is conjointly administered with one or more nitrogen mustards (mechlorethamine, ifosphamide, cyclophosphamide and analog, melphalan, chlorambucil. e.g., melphalan).

In certain embodiments, a PEG-carfilzomib compound described herein is conjointly administered with one or more DNA binding/Cytotoxic agents (e.g., Zalypsis).

In certain embodiments, a PEG-carfilzomib compound described herein is conjointly administered with one or more taxanes (e.g., docetaxel, paclitaxel, e.g., docetaxel).

In certain embodiments, a PEG-carfilzomib compound described herein is conjointly administered with one or more antibiotics (dactinomycin (actinomycin D) daunorubicin, doxorubicin and idarubicin; e.g., doxorubicin).

The foregoing is merely illustrative of the invention and is not intended to limit the invention to the disclosed uses. Variations and changes, which are routine to one skilled in the art, are intended to be within the scope and nature of the invention, which are defined in the appended claims.

What is claimed is:

1. A method of treating multiple myeloma, the method comprising: administering to a patient having multiple myeloma, a therapeutically effective amount of a compound having a structure of formula I Formula I

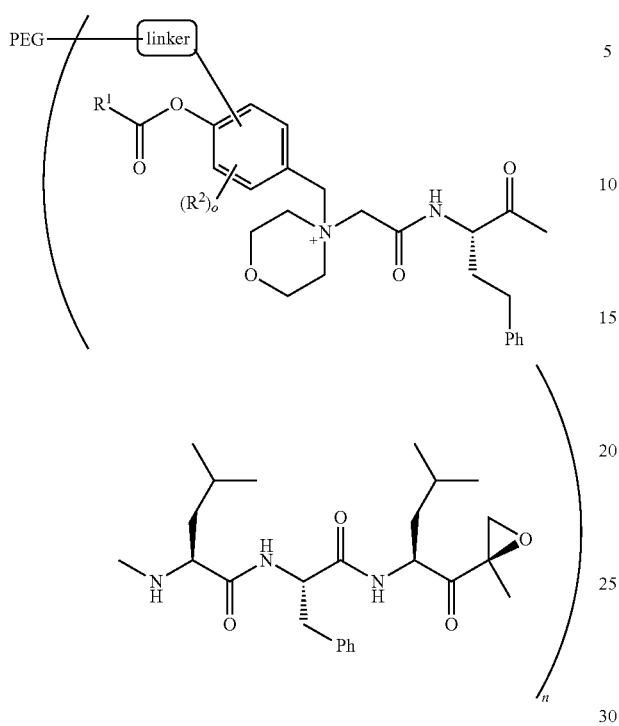

or a pharmaceutically acceptable salt thereof, wherein $R^1$ is $C_{1-10}$alkyl or $C_{3-7}$cycloalkyl;

each $R^2$, independently, is $C_{1-6}$alkyl, —$OCH_3$ or halogen;

o is an integer selected from 0, 1, 2 or 3;

linker is a moiety having the structure of

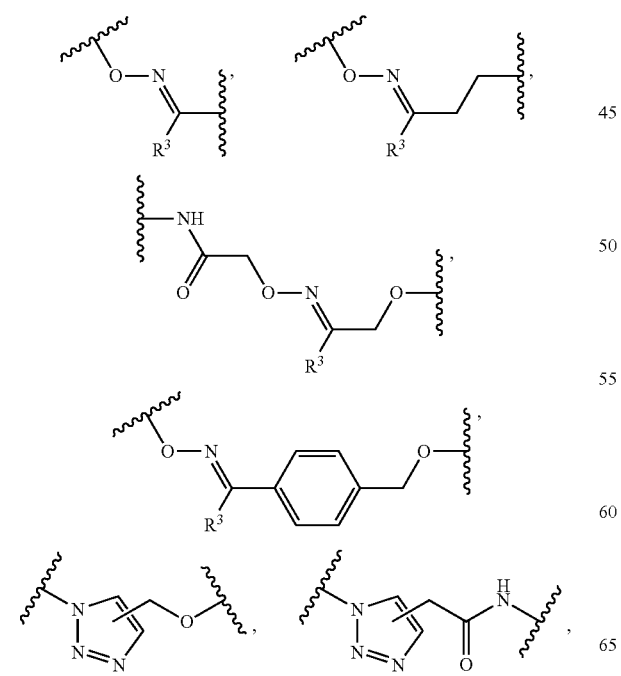

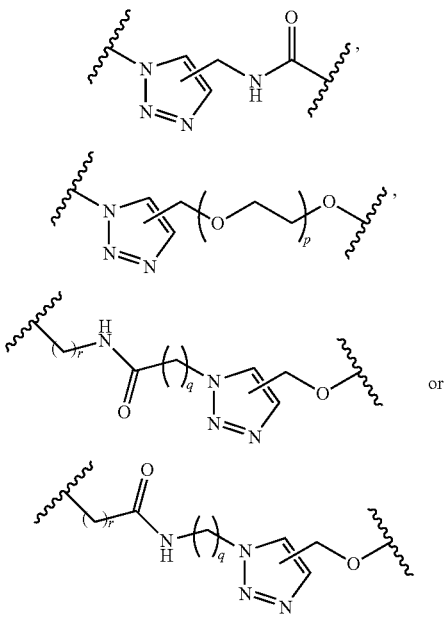

wherein $R^3$ is H or $CH_3$;

n is an integer selected from 1, 2, 3 or 4;

p is an integer selected from 0, 1, 2, 3 or 4;

q is an integer selected from 1, 2, 3, 4, 5, 6, 7, 8 or 9;

r is an integer selected from 0, 1, 2, 3, 4 or 5; and

PEG is a polyethylene glycol polymeric moiety having a molecular weight ranging from about 500 to about 20,000.

2. The method of claim 1, wherein $R^1$ is $C_{1-10}$alkyl.

3. The method of claim 1, wherein each o is 0 or 1 and $R^2$ is $CH_3$ or halogen.

4. The method of claim 1, wherein each o is 0 or 1 and $R^2$ is $CH_3$ or F.

5. The method of claim 1, wherein the linker is a moiety having the structure of

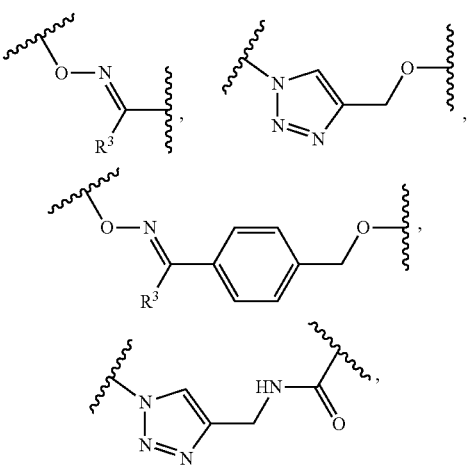

-continued

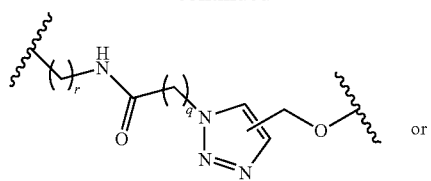

or

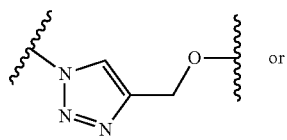

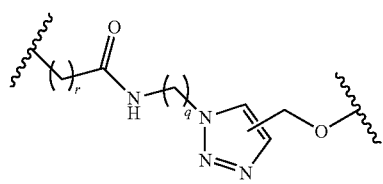

wherein R³ is H or CH₃;
q is an integer selected from 1, 2, 3, 4 or 5; and
r is an integer selected from 0, 1, 2, 3 or 4.

9. The method of claim 1, wherein the compound has a structure of Formula II

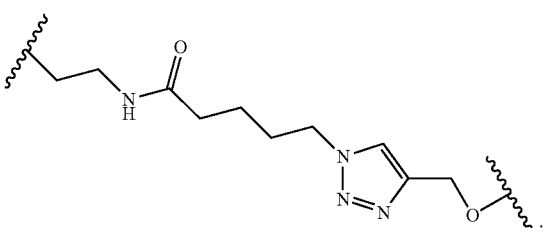

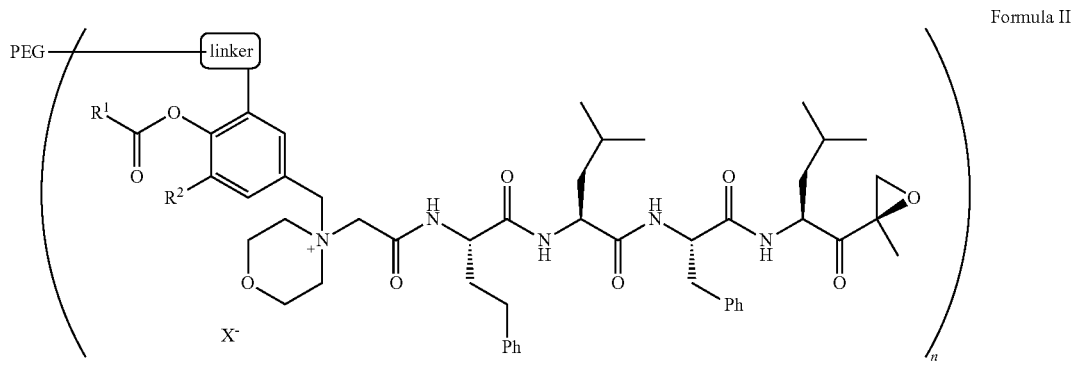

Formula II

6. The method of claim 1, wherein the linker is

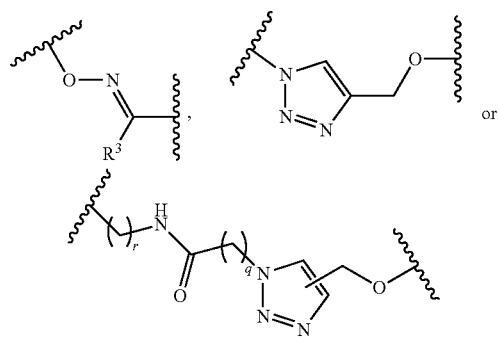

wherein R³ is H or CH₃;
q is 4; and
r is 2.

7. The method of claim 1, wherein R¹ is methyl, ethyl propyl, isopropyl, butyl, t-butyl, pentyl, hexyl or heptyl.

8. The method of claim 1, wherein R¹ is methyl, ethyl, propyl, isopropyl, butyl, t-butyl, pentyl, hexyl or heptyl; and the linker is wherein
R¹ is $C_{1-10}$alkyl or $C_{3-7}$cycloalkyl;
R² is $C_{1-6}$alkyl, —OCH₃ or halogen;
linker is a moiety having the structure of

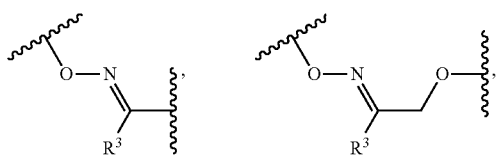

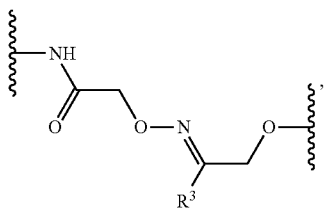

-continued

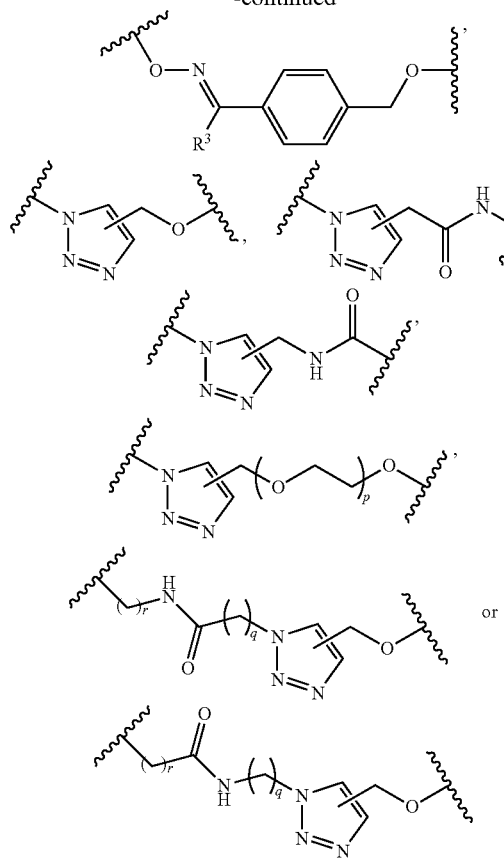

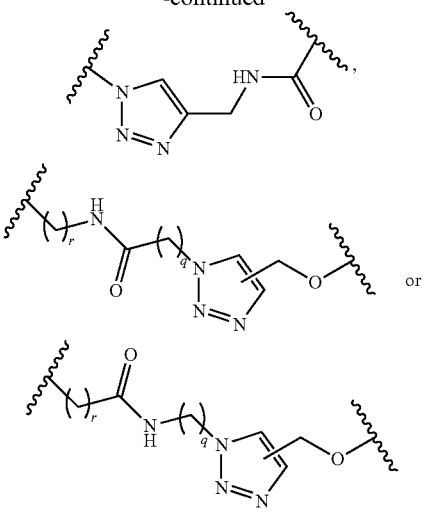

wherein $R^3$ is H or CH$_3$;
n is an integer selected from 1, 2, 3 or 4;
p is an integer selected from 0, 1, 2, 3 or 4:
q is an integer selected from 1, 2, 3, 4, 5, 6, 7, 8 or 9;
r is an integer selected from 0, 1, 2, 3, 4 or 5;
X is a counter ion salt selected from a chloride, a bisulfate, a sulfate, a nitrate, a phosphate, an alkyl-sulfonate or an aryl-sulfonate; and
PEG is a polyethylene glycol polymeric moiety having a molecular weight ranging from about 2000 to about 20,000.

10. The method of claim 9, wherein $R^1$ is C$_{1-10}$alkyl.
11. The method of claim 9, wherein $R^2$ is H, CH$_3$ or halogen.
12. The method of claim 9, wherein $R^2$ is H, CH$_3$ or F.
13. The method of claim 9, wherein the linker is a moiety having the structure of -continued wherein $R^3$ is H or CH$_3$;
q is an integer selected from 1, 2, 3, 4 or 5; and
r is an integer selected from 0, 1, 2, 3 or 4.

14. The method of claim 9, wherein the linker is

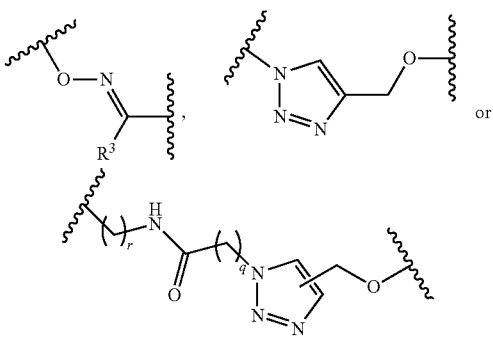

wherein $R^3$ is H or CH$_3$;
q is 4; and
r is 2.

15. The method of claim 9, wherein $R^1$ is methyl, ethyl, propyl, isopropyl, butyl, t-butyl, pentyl, hexyl or heptyl.
16. The method of claim 9, wherein $R^1$ is methyl, ethyl, propyl, isopropyl, butyl, t-butyl, pentyl, hexyl or heptyl; and the linker is

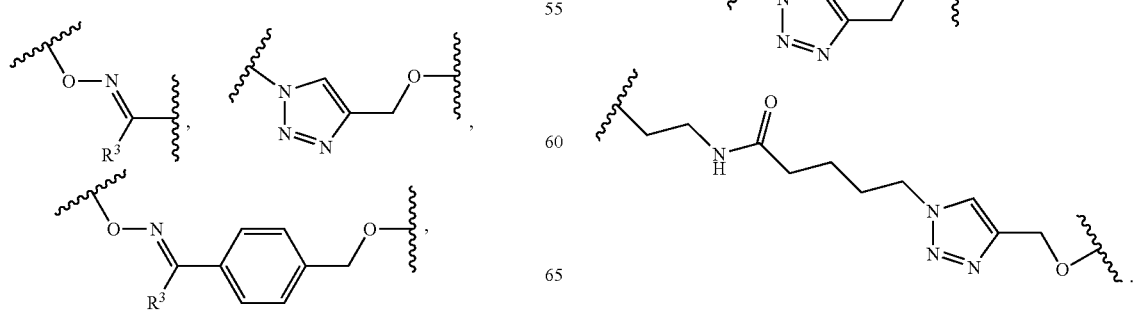

17. The method of claim 1, wherein the compound has the structure
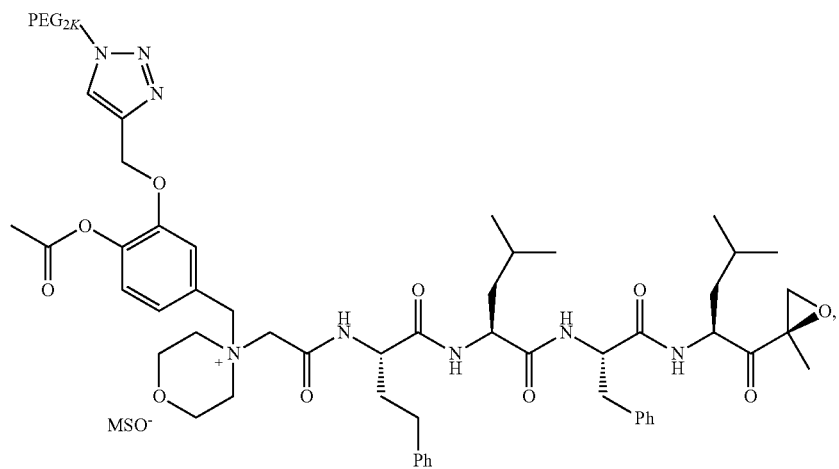
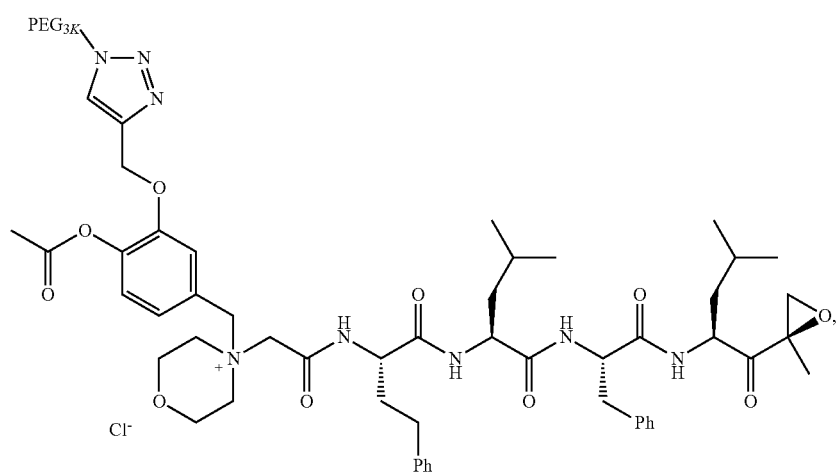
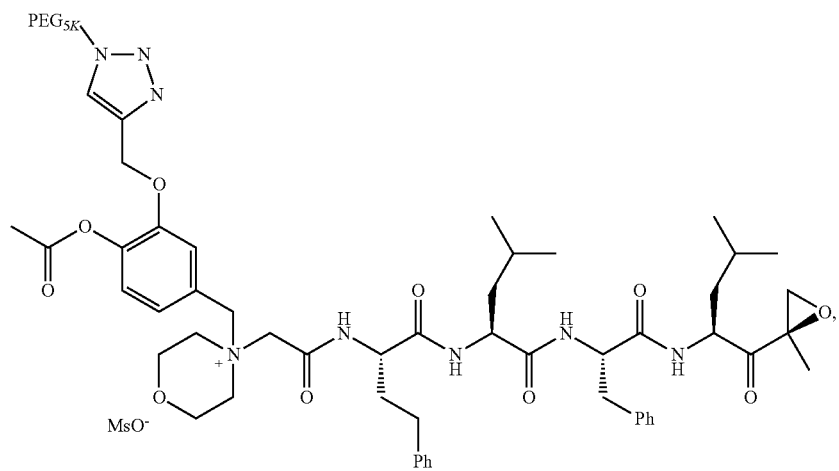

-continued
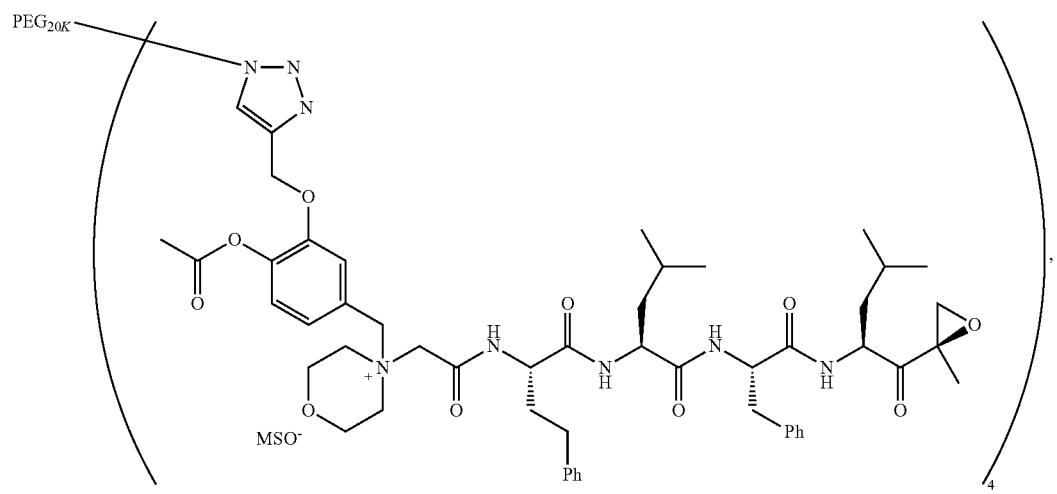
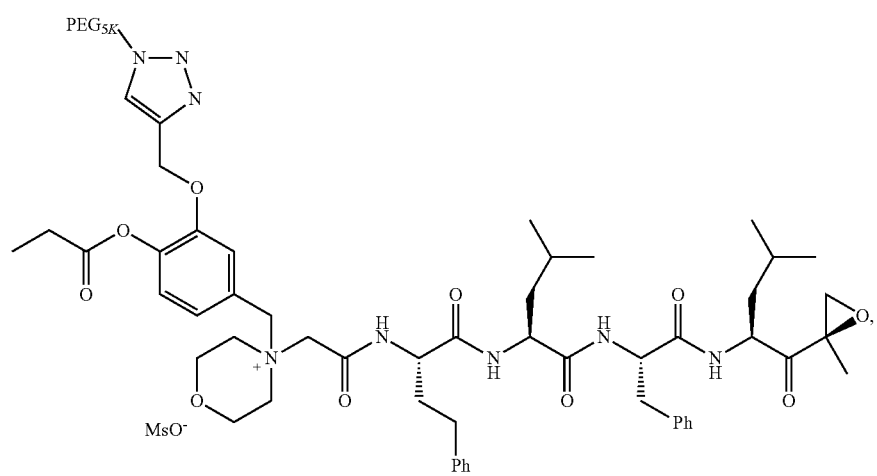
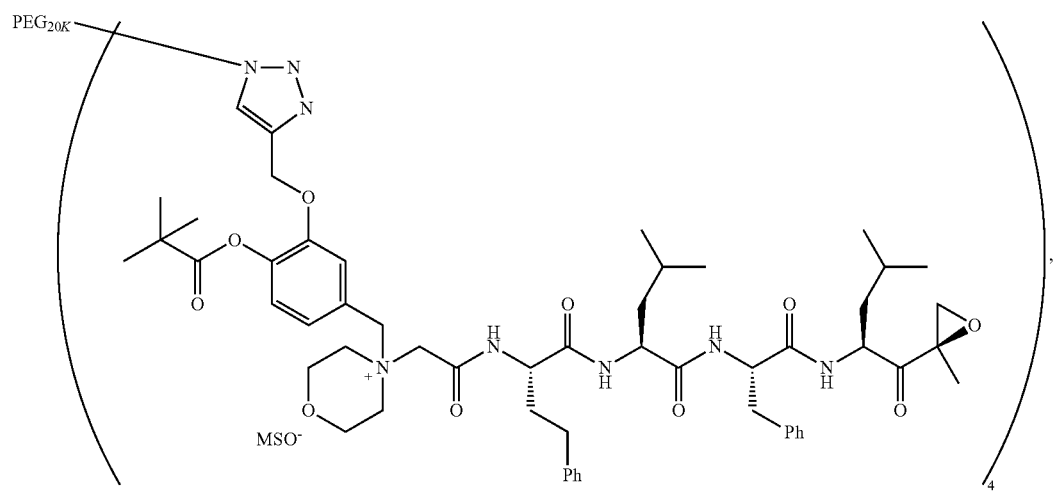

-continued
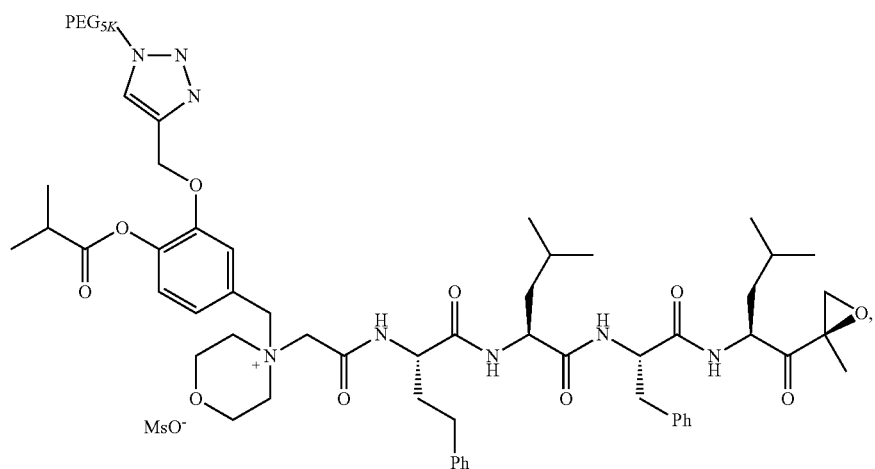
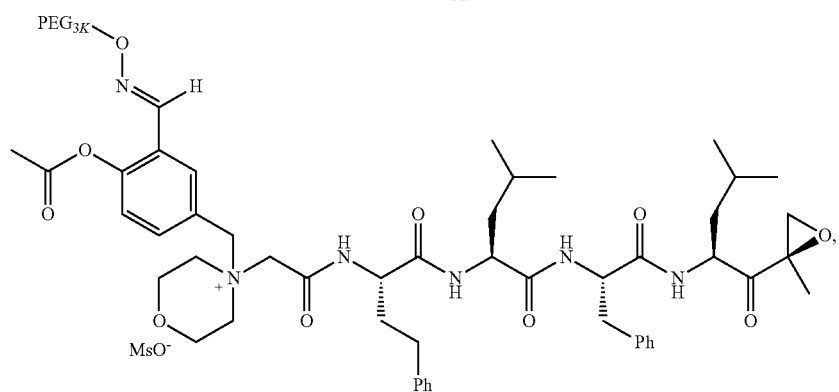
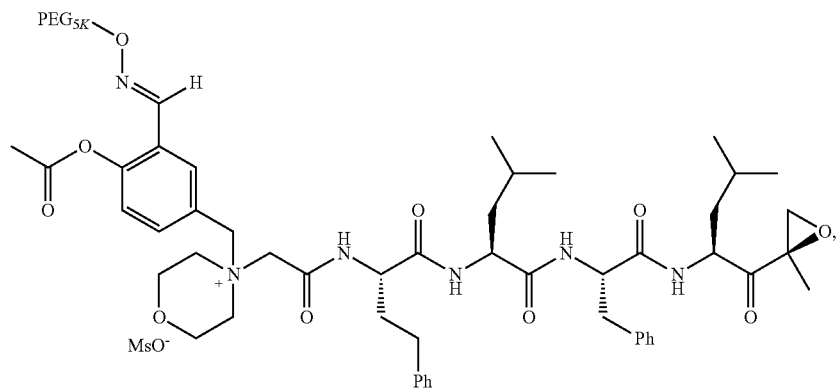
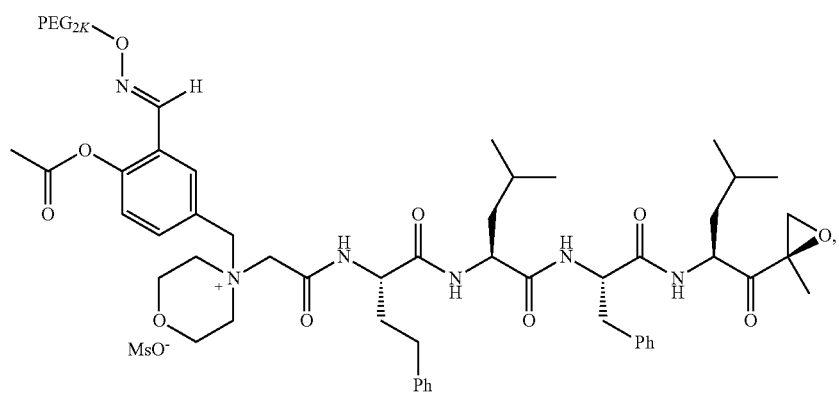

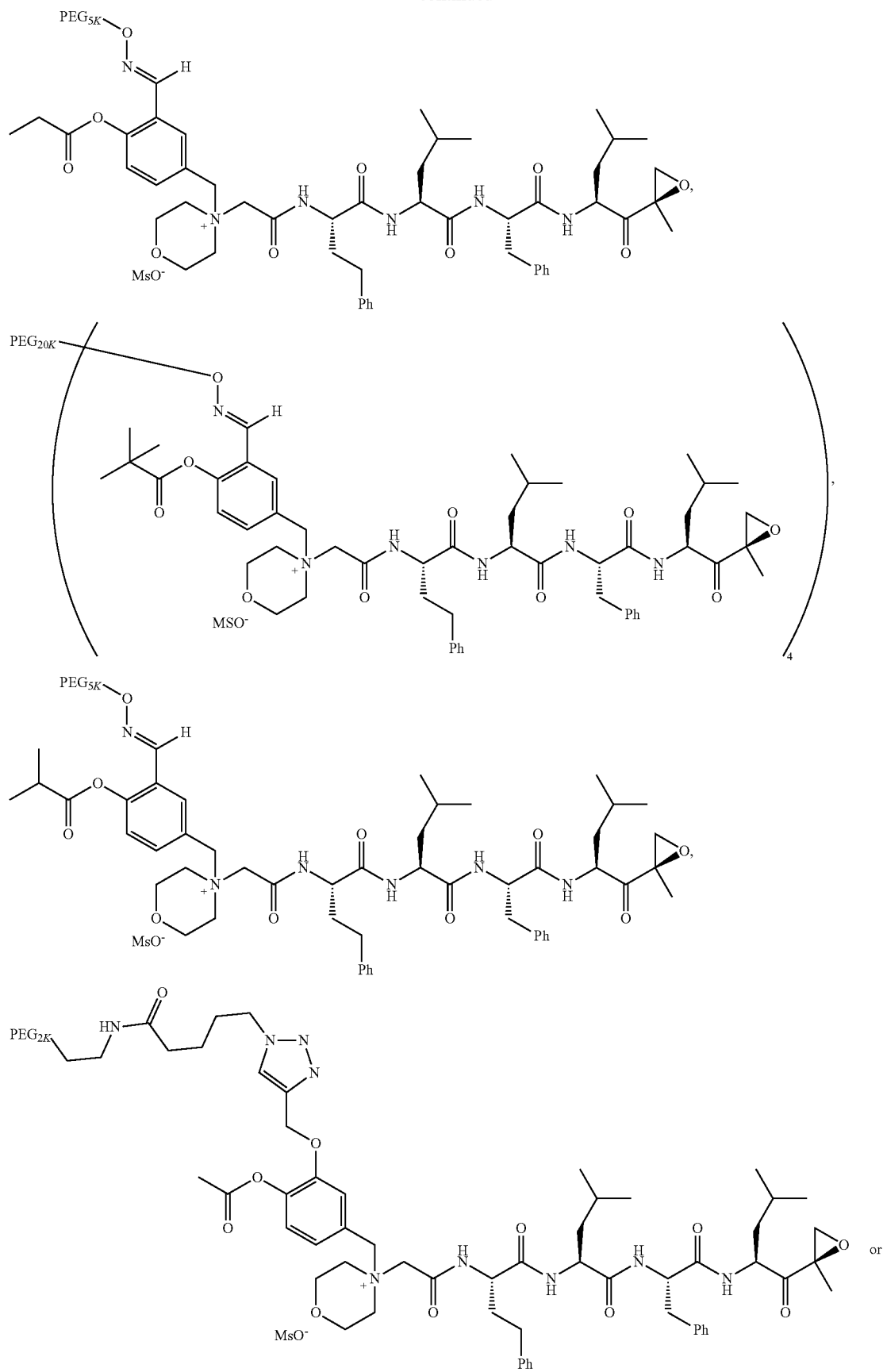

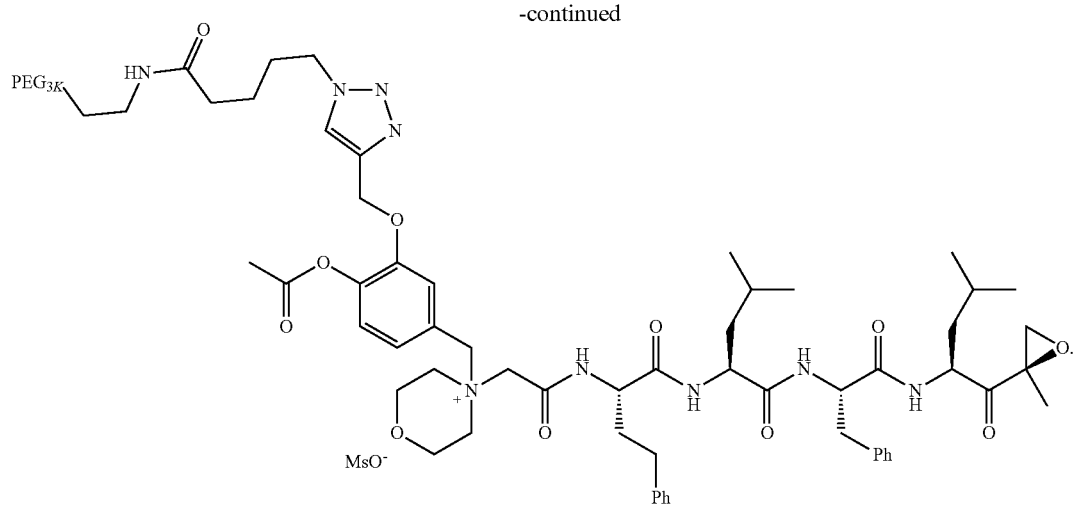

18. The method of claim 1, wherein the PEG has a weight ranging from about 2K to about 20K.

19. The method of claim 1, wherein the PEG has a weight of 2K, 3K, 5K or 20K.

20. The method of claim 1, wherein the compound is a pharmaceutically acceptable salt comprising a counter anion selected from a chloride anion, a bisulfate anion, a sulfate anion, a nitrate anion, a phosphate anion, an alky-sulfonate anion or an aryl-sulfonate anion.

21. The method of claim 20, wherein the counter anion is a chloride anion or an alky-sulfonate anion.

22. The method of claim 1, wherein the compound is in a pharmaceutical composition that further comprises a pharmaceutically acceptable excipient, carrier or diluent.

23. The method of claim 22, wherein the pharmaceutical composition is administered orally or by infusion or injection.

24. The method of claim 1 wherein the multiple myeloma is relapsed, refractory or relapsed and refractory multiple myeloma.

25. The method of claim 1 wherein the multiple myeloma is newly diagnosed multiple myeloma.

* * * * *